United States Patent
Linnanen et al.

(10) Patent No.: US 9,447,091 B2
(45) Date of Patent: Sep. 20, 2016

(54) PROTEIN KINASE INHIBITORS

(71) Applicant: Orion Corporation, Espoo (FI)

(72) Inventors: Tero Linnanen, Tuusula (FI); Gerd Wohlfahrt, Helsinki (FI); Srinivas Nanduri, Hyderabad (IN); Ravi Ujjinamatada, Karnataka (IN); Srinivasan Rajagopalan, Bangalore (IN); Subhendu Mukherjee, W. Bengal (IN)

(73) Assignee: ORION CORPORATION, Espoo (FI)

( * ) Notice: Subject to any disclaimer, the term of this patent is extended or adjusted under 35 U.S.C. 154(b) by 0 days.

(21) Appl. No.: 14/350,718

(22) PCT Filed: Oct. 9, 2012

(86) PCT No.: PCT/FI2012/000040
§ 371 (c)(1),
(2) Date: Apr. 9, 2014

(87) PCT Pub. No.: WO2013/053983
PCT Pub. Date: Apr. 18, 2013

(65) Prior Publication Data
US 2015/0011548 A1    Jan. 8, 2015

(30) Foreign Application Priority Data

Oct. 10, 2011    (IN) .......................... 1306/KOL/2011

(51) Int. Cl.
| | |
|---|---|
| C07D 471/04 | (2006.01) |
| C07D 235/20 | (2006.01) |
| C07D 401/04 | (2006.01) |
| C07D 401/14 | (2006.01) |
| C07D 403/04 | (2006.01) |
| C07D 403/14 | (2006.01) |
| C07D 405/14 | (2006.01) |
| C07D 407/14 | (2006.01) |
| C07D 413/04 | (2006.01) |
| C07D 413/14 | (2006.01) |
| C07D 417/14 | (2006.01) |

(52) U.S. Cl.
CPC ........... *C07D 471/04* (2013.01); *C07D 235/20* (2013.01); *C07D 401/04* (2013.01); *C07D 401/14* (2013.01); *C07D 403/04* (2013.01); *C07D 403/14* (2013.01); *C07D 405/14* (2013.01); *C07D 407/14* (2013.01); *C07D 413/04* (2013.01); *C07D 413/14* (2013.01); *C07D 417/14* (2013.01)

(58) Field of Classification Search
CPC .................................................... C07D 471/04
See application file for complete search history.

(56) References Cited

U.S. PATENT DOCUMENTS

| | | | |
|---|---|---|---|
| 6,162,804 A | 12/2000 | Bilodeau et al. | |
| 6,465,484 B1 | 10/2002 | Bilodeau et al. | |

FOREIGN PATENT DOCUMENTS

| | | |
|---|---|---|
| WO | WO 2005/021531 | 3/2005 |
| WO | WO 2006/050162 | 5/2006 |
| WO | WO 2006/060381 | 6/2006 |
| WO | WO 2008/078091 | 7/2008 |
| WO | WO 2008/078100 | 7/2008 |
| WO | WO 2008/138889 | 11/2008 |
| WO | WO 2009/150240 | 12/2009 |
| WO | WO 2010/119284 | 10/2010 |
| WO | WO 2010/119285 | 10/2010 |
| WO | WO 2012/088266 | 6/2012 |
| WO | WO 2012131501 A1 * | 10/2012 |

OTHER PUBLICATIONS

"Roche drug fails in lung cancer trial" PMLive Mar. 3rd 2014, "http://www.pmlive.com/pharma_news/roche_drug_fails_in_lung_cancer_trial_549919" Online accessed Nov. 9, 2015.*
Ocana, A. "Preclinical development of molecular targeted agents for cancer" Nat. Rev. Clin. Oncol. 2011, 8, 200-209.*
Sharma "Cell line-based platforms to evaluate the therapeutic efficacy of candidate anticancer agents" Nature Reviews Cancer Apr. 2010, vol. 10, 241-253.*
Simone, Oncology: Introduction, Cecil Textbook of Medicine, 20th Edition, 1996 vol. 1, pp. 1004-1010.*
Damia "Contemporary pre-clinical development of anticancer agents—What are the optimal preclinical models?" European Journal of Cancer 2009, 45, 2768-2781.*
Johnson, et. al. "Relationships between drug activity in NCI preclinical in vitro and in vivo models and early clinical trials." British Journal of Cancer 2001, 84, 1424-1431.*
Ledford "US cancer institute overhauls cell lines" Nature Feb. 25, 2016 vol. 530 p. 391.*

* cited by examiner

*Primary Examiner* — David K O Dell
(74) *Attorney, Agent, or Firm* — Finnegan, Henderson, Farabow, Garrett & Dunner, LLP

(57) ABSTRACT

A compound of formula (I), wherein $R_3$, $R_4$, G, B, M, and Z are as defined in the claims, and pharmaceutically acceptable salts thereof are disclosed. The compounds of formula (I) possess utility as FGFR inhibitors and are useful in the treatment of a condition, where FGFR kinase inhibition is desired, such as cancer.

15 Claims, No Drawings

PROTEIN KINASE INHIBITORS

This is a national stage application under §371 of International Application No. PCT/FI2012/000040, filed on Oct. 9, 2012, which claims the benefit of priority of Indian Patent Application No. 1306/KOL/2011, filed on Oct. 10, 2011, all of which are incorporated herein by reference.

TECHNICAL FIELD

The present invention relates to therapeutically active compounds and pharmaceutically acceptable salts thereof which are useful e.g. in the treatment of cancer.

BACKGROUND OF THE INVENTION

Protein kinases are a class of proteins (enzymes) that regulate a variety of cellular functions. This is accomplished by phosphorylation of specific amino acids on protein substrates resulting in conformational alteration of the substrate protein. The conformational change modulates the activity of the substrate or its ability to interact with other binding partners. Tyrosine kinases are a subset of protein kinases that catalyze the transfer of the terminal phosphate of adenosine triphosphate (ATP) to tyrosine residues on protein substrates. The human genome contains around 90 tyrosine kinases and 43 tyrosine kinase like genes, the products of which regulate cellular proliferation, survival, differentiation, function and motility.

Tyrosine kinases are of two varieties, i.e. receptor and non-receptor tyrosine kinases. Receptor tyrosine kinases (e.g., FGFR) are trans-membrane proteins with a ligand-binding extracellular domain and a catalytic intracellular kinase domain, while non-receptor tyrosine kinases (e.g., c-ABL) lack trans-membrane domains and are found in the cytosol, nucleus and inner surface of cell membrane. Kinase domains of all tyrosine kinases have bilobar architecture, with an N-terminal lobe that binds ATP and magnesium, a C-terminal lobe containing an activation loop, and a cleft between the lobes to which polypeptide substrates bind.

Receptor tyrosine kinases become activated when ligand binds to the extracellular domain, resulting in receptor oligomerization and autophosphorylation of a regulatory tyrosine within the activation loop of the kinase domain. These phenomena reorient important amino acid residues, thereby enhancing catalytic activity of the enzyme.

Fibroblast growth factor (FGF) has been recognized as an important mediator of many physiological processes, such as cell migration, proliferation, survival and differentiation during development and angiogenesis. There are currently over 25 known members of the FGF family. The fibroblast growth factor receptor (FGFR) family consists of four members with each composed of an extra cellular ligand binding domain, a single trans-membrane domain and an intracellular cytoplasmic protein tyrosine kinase domain. Upon stimulation with FGF, FGFRs undergo dimerisation and transphosphorylation. Upon dimerization, FGFRs activate range of downstream signaling pathways, such as MAPK and PKB/Akt pathways (Zhou, W. et. al. *Chemistry & Biology*, 2010, 17, 285). Abnormal FGFR signaling has been reported in many tumor types including multiple myeloma, gastric, endometrial, prostate and breast (Squires M. et. al. *Mol. Cancer Ther.*, September 2011, 10:1542-1552). FGFs also have role in tumor angiogenesis and mediate resistance to vascular endothelial growth factor receptor 2 (VEGFR2) inhibitors (Casanovas, O. et. al., *Cancer Cell*, 2005, 8, 299). Consequently, FGF and FGFRs have the potential to initiate and/or promote tumorigenesis. Due to this, the FGF signaling system happens to be an attractive therapeutic target, mainly because therapies targeting FGFRs and/or FGF signaling may affect both the tumor cells and also tumor angiogenesis (Foote, K. M. et. al., WO 2009/019518 A1). Consequently, FGF and FGFRs have the potential to initiate and/or promote tumorigenesis.

SUMMARY OF THE INVENTION

It has been found that compounds of formula (I) inhibit or modulate the activity of certain protein kinases, more specifically protein tyrosine kinases. In particular, it has been found that the compounds of formula (I) are potent and selective inhibitors of FGFR kinases. The compounds of the invention have antiproliferative activity and are particularly useful in the treatment of cancer.

The compounds of the present invention have a structure represented by formula (I)

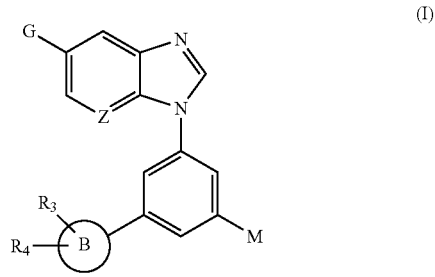

(I)

wherein
Z is CH or N;
G is cyano, —C(O)NR$_{15}$R$_{16}$, —C(O)OR$_{17}$, —C(O)R$_{21}$, —C(CH$_3$)=NOR$_{22}$ or a group of formula

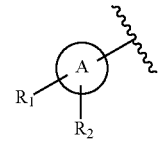

wherein A is a phenyl ring or a 5-12 membered heterocyclic ring, and
R$_1$ is H, C$_{1-7}$ alkyl, C$_{3-7}$ cycloalkyl, C$_{3-7}$ cycloalkyl C$_{1-7}$ alkyl, C$_{1-7}$ alkoxy, C$_{1-7}$ alkyl carbonyl, amino, hydroxy, hydroxy C$_{1-7}$ alkyl, C$_{1-7}$ alkylamino C$_{1-7}$ alkyl, phenyl C$_{1-7}$ alkoxy, —NHC(O)—R$_{21}$, —R$_{12}$—C(O)—R$_{13}$, —SO$_2$—R$_{14}$ or -E-R$_6$, and
R$_2$ is H, halogen, C$_{1-7}$ alkyl or oxo;
B is a 5-12 membered carbocyclic or heterocyclic ring;
R$_3$ is H, halogen, C$_{1-7}$ alkyl, C$_{1-7}$ alkoxy, cyano or an optionally substituted 5-6 membered heterocyclic ring;
R$_4$ is H, halogen, C$_{1-7}$ alkyl or oxo;
M is hydroxyl, C$_{1-7}$ alkyl or —NHR$_5$;
R$_5$ is H, —C(O)R$_7$, —SO$_2$R$_8$, —C(O)-D-R$_9$ or an optionally substituted 5-6 membered heterocyclic ring;
R$_6$ is an optionally substituted 5-6 membered heterocyclic ring;
R$_7$ is C$_{1-7}$ alkyl, C$_{2-7}$ alkenyl, C$_{3-7}$ cycloalkyl, C$_{1-7}$ alkoxy, C$_{1-7}$ alkoxy C$_{1-7}$ alkyl, carboxy C$_{1-7}$ alkyl, C$_{1-7}$ alkoxy carbonyl C$_{1-7}$ alkyl, C$_{1-7}$ alkylamino C$_{1-7}$ alkyl, —NH—R$_{10}$ or —NH—X$_1$—R$_{11}$;

R$_8$ is C$_{1-7}$ alkyl, C$_{2-7}$ alkenyl, C$_{3-7}$ cycloalkyl, hydroxy C$_{1-7}$ alkyl, —NR$_{18}$R$_{19}$, —NH—X$_2$—R$_{20}$, phenyl or an optionally substituted 5-6 membered heterocyclic ring;

R$_9$ is phenyl or an optionally substituted 5-6 membered heterocyclic ring;

R$_{10}$ is C$_{1-7}$ alkyl or C$_{3-7}$ cycloalkyl;

R$_1$ is phenyl or an optionally substituted 5-6 membered heterocyclic ring;

R$_{12}$ and R$_{21}$ are C$_{1-7}$ alkyl;

R$_{13}$ is C$_{1-7}$ alkoxy, amino or hydroxy;

R$_{14}$ is C$_{1-7}$ alkyl or C$_{3-7}$ cycloalkyl;

R$_{15}$, R$_{16}$, R$_{17}$, R$_{18}$ and R$_{19}$ are, independently, H, C$_{1-7}$ alkyl or C$_{3-7}$ cycloalkyl;

R$_{20}$ is phenyl or an optionally substituted 5-6 membered heterocyclic ring;

R$_{21}$ is an optionally substituted 5-6 membered heterocyclic ring;

R$_{22}$ is H or C$_{1-7}$ alkyl;

E is a bond or a C$_{1-7}$ alkyl;

D is a bond or a C$_{1-7}$ alkyl;

X$_1$ and X$_2$ are, independently, a bond or C$_{1-7}$ alkyl;

and pharmaceutically acceptable salts thereof.

In one class of preferred compounds are compounds of formula (I), wherein ring A is any one of the following groups or tautomers thereof:

(1')

(2')

(3')

(4')

(5')

(6')

(7')

(8')

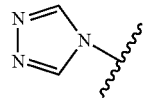

(9')

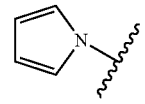

(10')

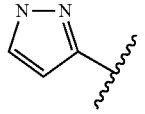

(11')

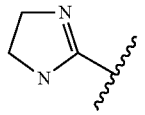

(12')

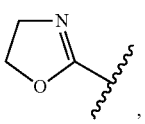

(13')

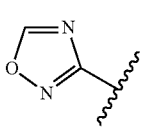

(14')

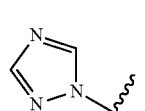

(15')

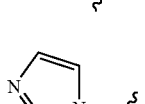

(16')

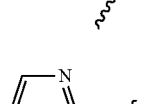

(17')

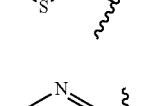

(18')

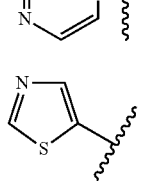

(19')

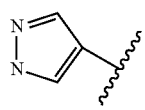
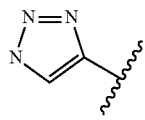
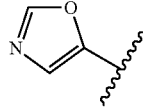
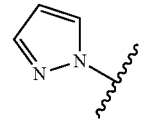
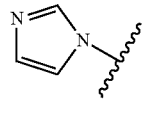
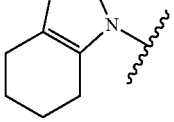
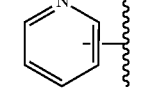

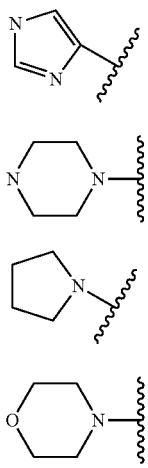

and R₁ and R₂, as defined above, are attached to the above A-rings.

In another class of preferred compounds are compounds of formula (I), wherein ring B is any one of the following groups or tautomers thereof:

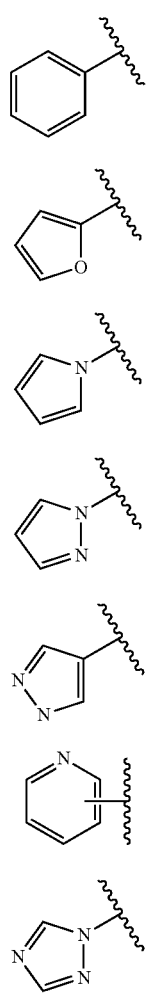

and R₃ and R₄, as defined above, are attached to the above B-rings.

In another class of preferred compounds are compounds of formula (I), wherein Z is CH. In another class of preferred compounds are compounds of formula (I), wherein Z is N.

A subclass of the above preferred classes are compounds wherein

G is a group of formula

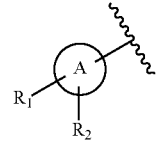

wherein A is a ring of formula (1'), (2'), (3'), (4'), (5'), (7'), (10'), (12'), (14'), (16') or (20');

$R_1$ is H, $C_{1-7}$ alkyl, $C_{1-7}$ alkoxy, hydroxy $C_{1-7}$ alkyl, $C_{1-7}$ alkylamino $C_{1-7}$ alkyl or -E-$R_6$;

$R_2$ is H;

B is a ring of formula (1"), (2"), (3"), (4") or (6");

E is a bond or $C_{1-7}$ alkyl;

$R_6$ is any of the following groups

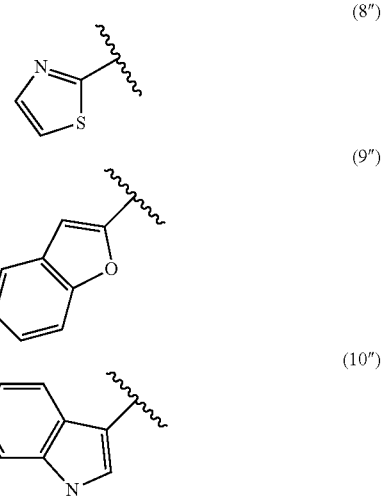

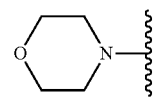

(a)

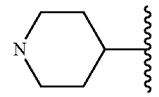

(b)

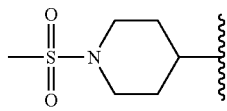

(c)

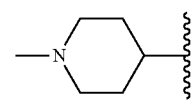

(d)

-continued
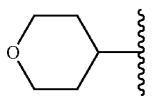 (e)
R$_3$ is H, halogen, C$_{1-7}$ alkyl, C$_{1-7}$ alkoxy;
R$_4$ is H or halogen;
M is —NHR$_5$;
R$_5$ is —C(O)R$_7$, —SO$_2$R$_8$ or —C(O)-D-R$_9$ or any one of the following groups
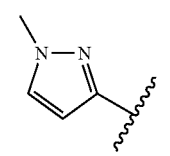 (a″)
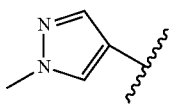 (b″)
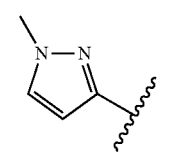 (c″)
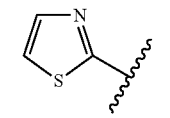 (d″)
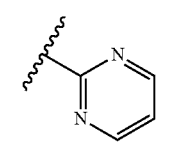 (e″)
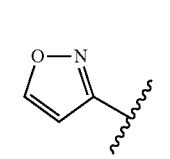 (f″)
R$_7$ is C$_{1-7}$ alkyl, C$_{2-7}$ alkenyl, —NH—R$_{10}$ or —NH—X$_1$—R$_{11}$;
R$_8$ is C$_{1-7}$ alkyl, C$_{2-7}$ alkenyl, C$_{3-7}$ cycloalkyl, hydroxy C$_{1-7}$ alkyl, —NR$_{18}$R$_{19}$, —NH—X$_2$—R$_{20}$, phenyl or a group
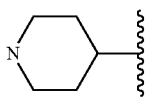 (b)
R$_9$ is phenyl or a any one of the following groups
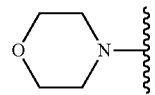 (a)
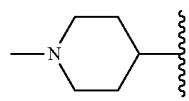 (d)
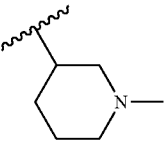 (f)
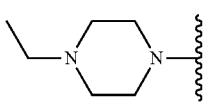 (g)
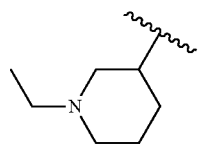 (h)
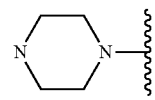 (i)
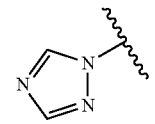 (j)
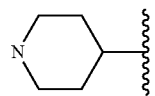 (k)
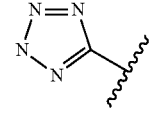 (l)
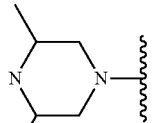 (m)
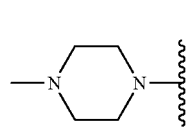 (n)
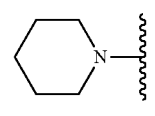 (o)

-continued (p)
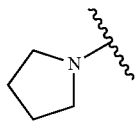

$R_{10}$ is $C_{1-7}$ alkyl or $C_{3-7}$ cycloalkyl;
$R_{11}$ is phenyl, 4-fluorophenyl, or any one of the following groups (a')
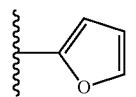

(b')
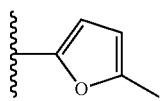

(c')
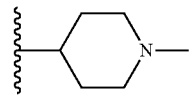

$R_{18}$ and $R_{19}$ are, independently, H, $C_{1-7}$ alkyl or $C_{3-7}$ cycloalkyl;
$R_{20}$ is a group (a')
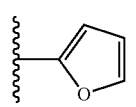

$X_1$ and $X_2$ are, independently, a bond or $C_{1-7}$ alkyl, and D is a bond or $C_{1-7}$ alkyl.

In one class are compounds of formula (I), wherein M is —NHC(O)$R_7$, wherein $R_7$ is $C_{1-7}$ alkyl, $C_{2-7}$ alkenyl, $C_{3-7}$ cycloalkyl, —NH—$R_{10}$ or —NH—$X_1$—$R_{11}$, wherein $R_{10}$ is $C_{1-7}$ alkyl or $C_{3-7}$ cycloalkyl, $X_1$ is a bond or $C_{1-7}$ alkyl, and $R_{11}$ is a 5-6 membered heterocyclic ring optionally substituted by one or two $C_{1-7}$ alkyl groups.

In another class are compounds of formula (I), wherein M is —NHSO$_2$$R_8$ wherein $R_8$ is $C_{1-7}$ alkyl, $C_{2-7}$ alkenyl, $C_{3-7}$ cycloalkyl, phenyl, or NR$_{18}$R$_{19}$ wherein $R_{18}$ and $R_{19}$ are, independently, H, $C_{1-7}$ alkyl or $C_{3-7}$ cycloalkyl.

In another class are compounds of formula (I), wherein M is —NHC(O)-D-$R_9$ wherein D is bond or $C_{1-7}$ alkyl, and $R_9$ is a 5-6 membered heterocyclic ring optionally substituted by one or two $C_{1-7}$ alkyl groups.

The present invention also provides a pharmaceutical composition comprising a compound of formula (I) or a pharmaceutically acceptable salt thereof together with a pharmaceutically acceptable carrier.

The present invention provides further a use of a compound of formula (I) or a pharmaceutically acceptable salt thereof in the manufacture of a medicament for the treatment of a condition, where FGFR kinase inhibition is desired.

The present invention provides further a use of a compound of formula (I) or a pharmaceutically acceptable salt thereof in the manufacture of a medicament for the treatment of cancer.

The present invention provides a compound of formula (I) or a pharmaceutically acceptable salt thereof for use in the treatment of a condition, where FGFR kinase inhibition is desired.

The present invention provides a compound of formula (I) or a pharmaceutically acceptable salt thereof for use in the treatment of cancer.

The present invention provides further a method for the treatment of a condition, where FGFR kinase inhibition is desired comprising administering to a subject in need thereof a therapeutically effective amount of a compound of formula (I).

The present invention provides further a method for the treatment of cancer comprising administering to a subject in need thereof a therapeutically effective amount of a compound of formula (I).

DETAILED DESCRIPTION OF THE INVENTION

The compounds of the invention can be prepared by a variety of synthetic routes analogously to the methods known in the literature using suitable starting materials. The compounds according to formula (I) can be prepared e.g. analogously or according to the following reaction Schemes. Some compounds included in the formula (I) can be obtained by converting the functional groups of the other compounds of formula (I) obtained in accordance with the following Schemes, by well known reaction steps such as oxidation, reduction, hydrolysis, acylation, alkylation, amidation, amination, sulfonation and others. It should be noted that any appropriate leaving groups, e.g. N-protecting groups, such as a t-butoxycarbonyl (t-BOC) group or a phenylsulfonyl group, can be used in well known manner during the syntheses in order to improve the selectivity of the reaction steps Compounds of formula (I), wherein G is an optionally substituted A-ring and $R_5$ is —C(O)CH$_3$ can be prepared, for example, according to Scheme 1, wherein $R_1$, $R_2$, $R_3$, $R_4$, ring A, ring B and Z, are as defined above, and R is hydrogen or alkyl. In the method of Scheme 1, the N-(3-bromo-5-nitrophenyl)acetamide [1] is coupled in a suitable solvent such as 1,2-dimethoxyethane with a boronic acid derivative [2] or a suitable ester thereof in the presence of Pd(dppf)Cl$_2$ and aqueous sodium carbonate at elevated temperature. The nitro group of the obtained compound [3] is reduced, e.g. with hydrogen and Pd/C catalyst, iron powder and aqueous calcium chloride or zinc and aqueous ammonium chloride, and the resulting amine [4] is reacted with compound [5] in a suitable solvent such as DMF in the presence of potassium fluoride at elevated temperature to obtain compound [6]. In case Z is CH in the compound [5], X" is suitably fluoro, and when Z is N, X" is suitably chloro. The nitro group in compound [6] is reduced, e.g. by using zinc and aqueous ammonium chloride or iron powder and aqueous calcium chloride, and the resulting amine [7] is heated with formic acid to produce compound [8] in a ring closure reaction. Finally, compound [10] is obtained by the Suzuki coupling between compound [8] and a boronic acid derivative [9] or a suitable ester thereof in a suitable solvent such as 1,2-dimethoxyethane in the presence of Pd(dppf)Cl$_2$ and aqueous sodium carbonate at elevated temperature.

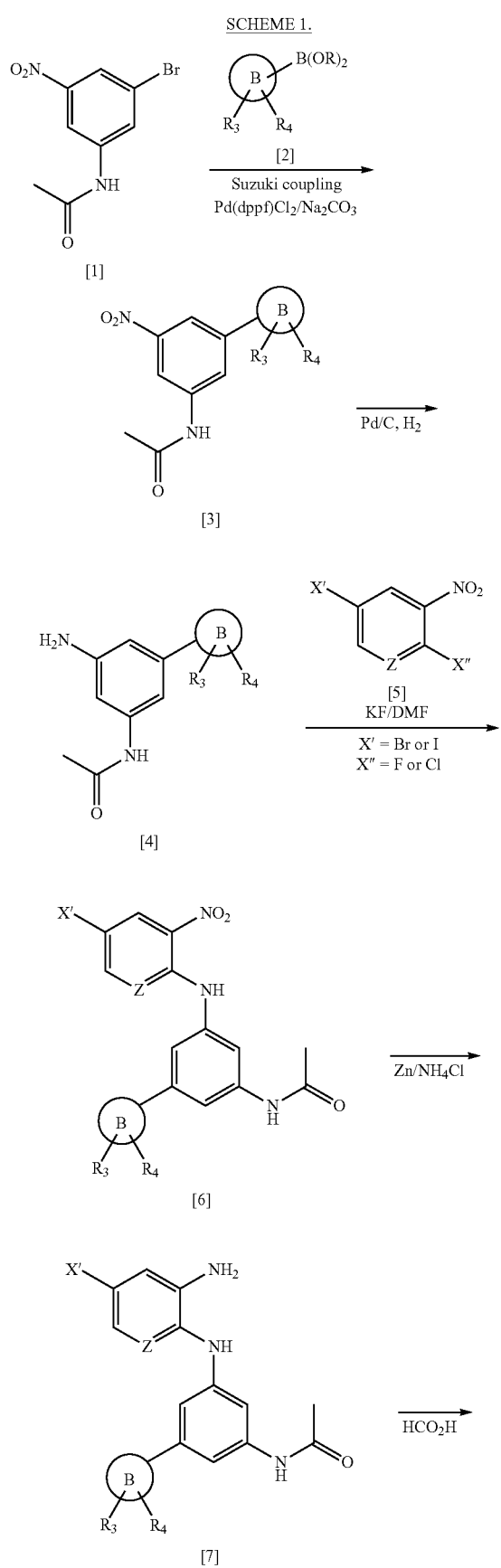

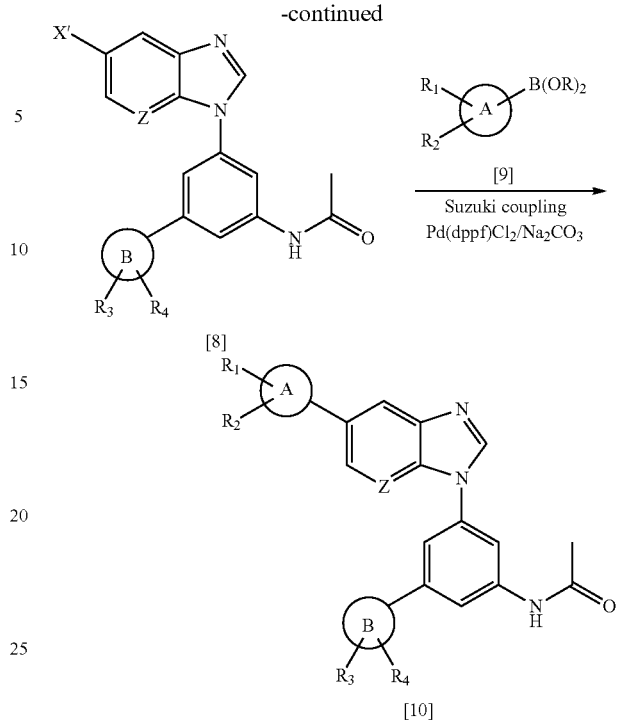

Alternatively, the compound of formula [3] can be prepared according to Scheme 2, wherein $R_3$, $R_4$, ring B and R are as defined above, using the boronic acid derivative [11] or a suitable ester thereof in the presence of Pd(dppf)Cl$_2$ and aqueous sodium carbonate. Compound [11] can be prepared, e.g. by treating N-(3-bromo-5-nitrophenyl)-acetamide with bis(pinacolato)diboron in the presence of Pd(dppf)Cl$_2$ and potassium acetate.

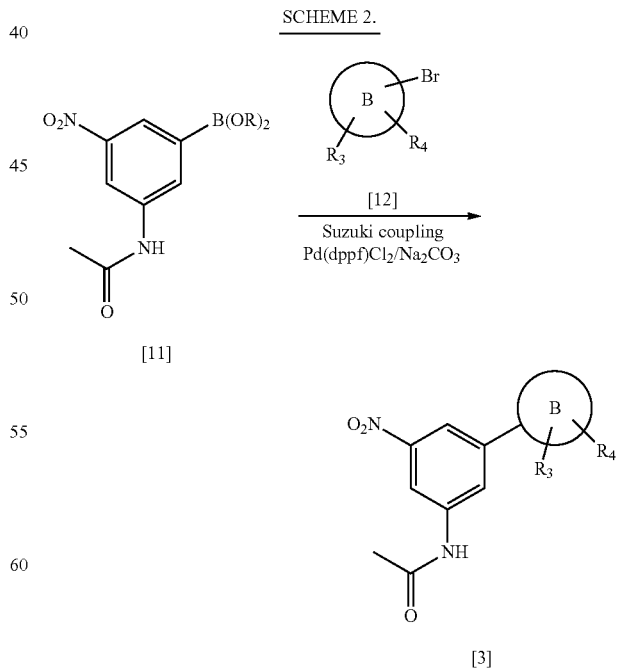

In case the B-ring in the compound [3] is a heterocycle linked to phenyl via a nitrogen heteroatom, the compound

[3] can be also prepared using a copper-catalyzed Buchwald amination in the presence of a base such cesium carbonate or potassium carbonate according to Scheme 3, wherein $R_3$ and $R_4$ are as defined above.

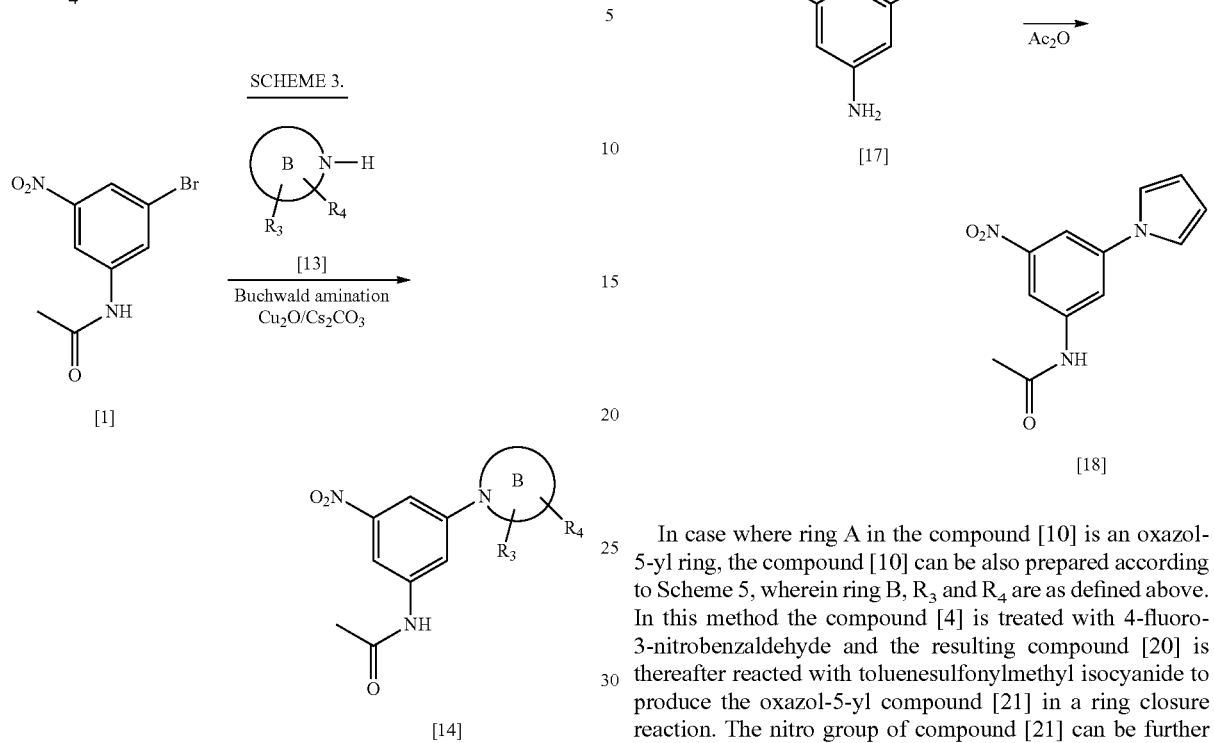

In case the B-ring in the compound [3] is pyrrole ring linked to phenyl via a nitrogen atom, the compound [3] can be also prepared from 3,5-dinitroaniline [15] and 2,5-dimethoxytetrahydrofuran according to Scheme 4. The pyrrole derivative [16] formed is reduced using ammonium sulphide to obtain compound [17], which is subsequently reacted with acetic anhydride to afford compound [18].

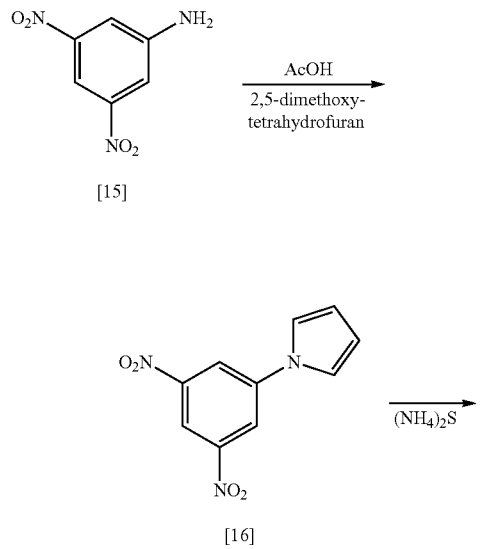

In case where ring A in the compound [10] is an oxazol-5-yl ring, the compound [10] can be also prepared according to Scheme 5, wherein ring B, $R_3$ and $R_4$ are as defined above. In this method the compound [4] is treated with 4-fluoro-3-nitrobenzaldehyde and the resulting compound [20] is thereafter reacted with toluenesulfonylmethyl isocyanide to produce the oxazol-5-yl compound [21] in a ring closure reaction. The nitro group of compound [21] can be further reduced, e.g. by hydrogenation, to produce the corresponding amine, which can be then treated with formic acid according to Scheme 1 to afford the end product in the ring closure reaction.

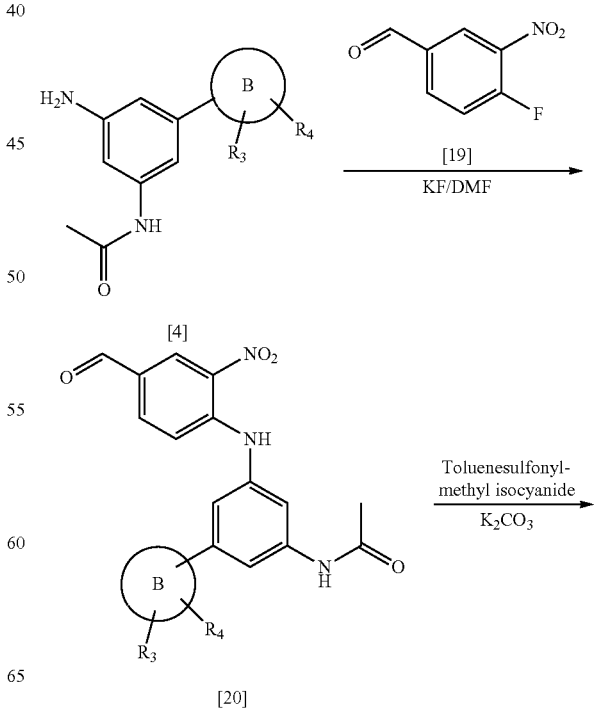

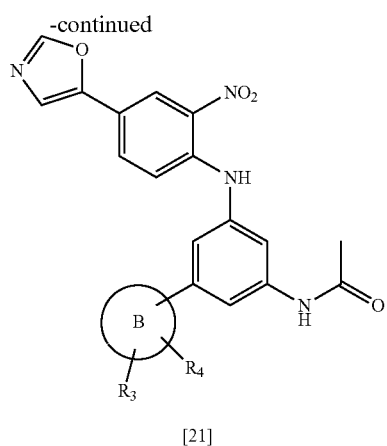

[21]

In case where ring A in the compound [10] is a heterocycle linked to the carbon atom of the bicyclic ring via a nitrogen heteroatom, the compound [10] can be also prepared using Buchwald coupling according to Scheme 6, wherein X', ring B, $R_1$, $R_2$, $R_3$, and $R_4$ are as defined above.

SCHEME 6.

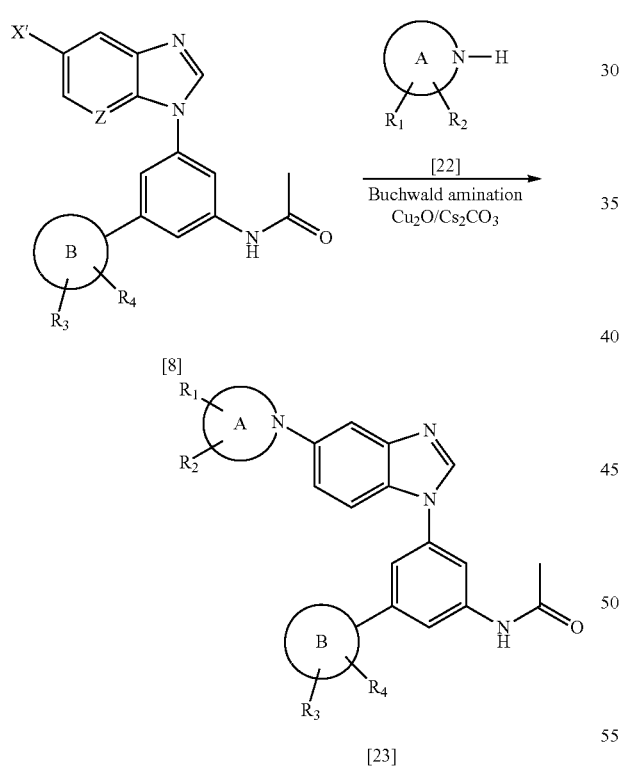

In case where ring A in the compound [10] is an 1H-1,2,3-triazol-4-yl ring and $R_2$ is hydrogen, the compound [10] can be also prepared according to Scheme 7, wherein X', Z, $R_1$, $R_3$, $R_4$ and ring B, are as defined above. The starting compound [8] is silylated by reacting with ethynyltrimethylsilane in the presence of tetrakis(triphenyl-phosphine)palladium(0) (Pd(PPh$_3$)$_4$) and Cu(I)iodide to produce compound [32]. Treatment with TBAF affords the ethynyl compound [33] which can be reacted with azido compound $R_1$—$N_3$ in a suitable solvent, such as DMSO:THF:water (1:1:1) or DMSO:DCM:water (1:1:1) to afford compound [34].

SCHEME 7.

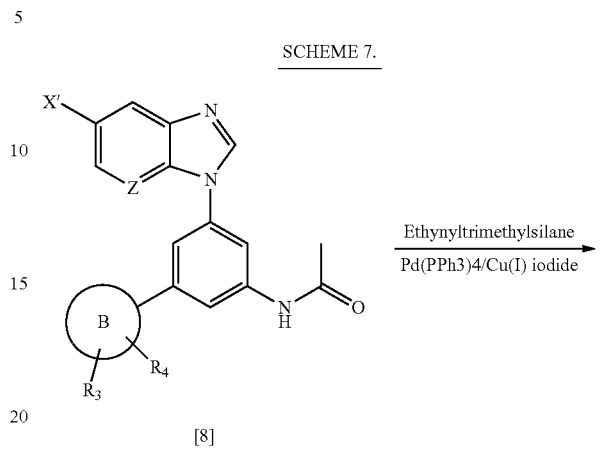

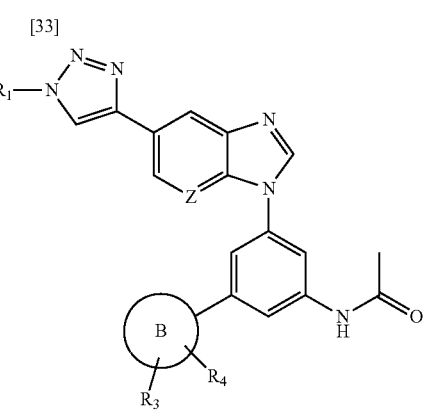

[34]

In case where ring A in the compound [10] is a 1-methyl-1H-pyrazol-3-yl ring, the compound [10] can be also prepared according to Scheme 8, wherein $R_3$, $R_4$ and ring B, are as defined above. In this method the compound [4] is treated with 1-(4-fluoro-3-nitrophenyl)ethanone and the resulting compound [36] is thereafter reacted with DMF dimethylacetal to produce the oxazol-5-yl compound [37]. Subsequent treatment with methyl hydrazine produces compound [38] in a ring closure reaction. The nitro group of compound [38] can be further reduced, e.g. by aqueous ammonium and zinc, to produce the corresponding amine, which can be then treated with formic acid according to Scheme 1 to afford the end product in the ring closure reaction.

SCHEME 8.

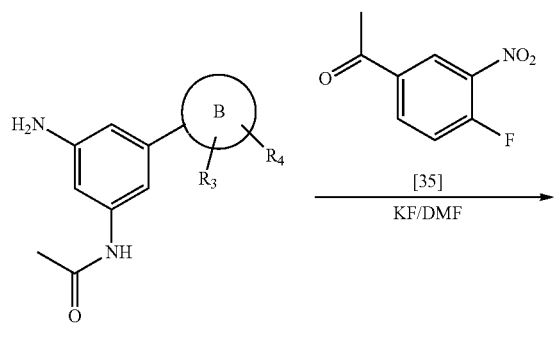

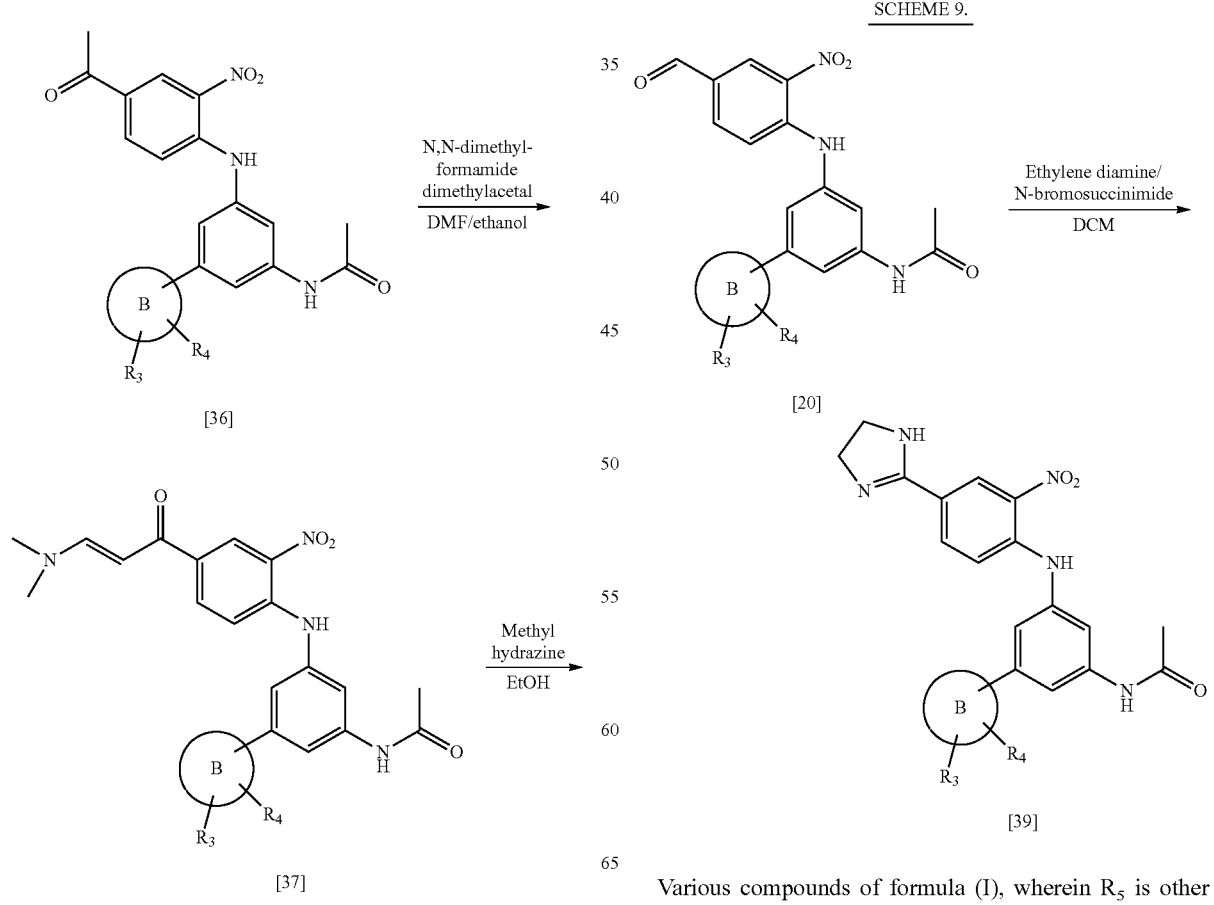

In case where ring A in the compound [10] is a 1H-imidazol-2-yl ring, the compound [10] can be also prepared according to Scheme 9, wherein $R_3$, $R_4$ and ring B, are as defined above. In this method the compound [20] of Scheme 5 is treated with ethylene diamine and N-bromosuccinimide affording compound [39] in a ring closure reaction. The nitro group of compound [39] can be further reduced, e.g. by aqueous ammonium and zinc, to produce the corresponding amine, which can be then treated with formic acid according to Scheme 1 to afford the end product in the ring closure reaction.

SCHEME 9.

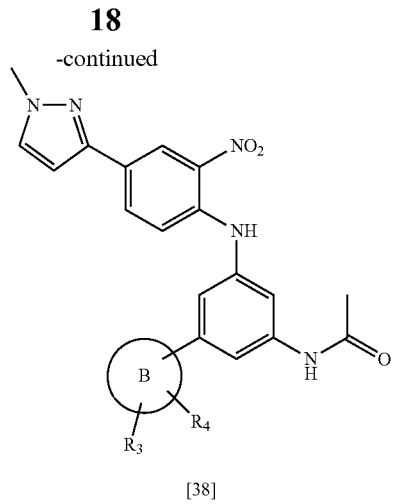

Various compounds of formula (I), wherein $R_5$ is other than —C(O)CH$_3$, can be prepared, for example, according to Scheme 10, wherein $R_1$, $R_2$, $R_3$, $R_4$, $R_7$, $R_8$, $R_9$, Z, D, ring A and ring B are as defined above. The acetamide compound [10] can be converted to its corresponding amine [24], for example, by heating in ethanol in the presence of a base, such as aqueous sodium hydroxide or potassium hydroxide, or an acid such as aqueous HCl. The obtained amine [24] can be used as a starting material for subsequent reaction steps. The compounds of formula (I), wherein $R_5$ is —$SO_2R_8$ can be prepared, for example, by treating the amine [24] with Cl—$SO_2R_8$ in suitable solvent such as DCM in the presence of pyridine. Compounds of formula (I), wherein $R_5$ is —C(O)$R_7$ and $R_7$ is $C_{1-7}$ alkyl or $C_{1-7}$ alkylamino $C_{1-7}$ alkyl, can be prepared, for example, by reacting the amine [24] with HOOC—$R_7$ in suitable solvent such as DMF in the presence of 2-(1H-7-azabenzotriazol-1-yl)-1,1,3,3-tetramethyl uronium hexafluorophosphate methanaminitim (HATU) and DIPEA. Compounds of formula (I), wherein $R_5$ is —C(O)-D-$R_9$ can be prepared, for example, by reacting the amine [24] with HOOC-D-$R_9$ in suitable solvent such as DMF in the presence of EDC, HOBt and DIPEA. Compounds of formula (I), wherein $R_5$ is —C(O)-D-$R_9$, D is a bond and $R_9$ is a heterocyclic ring linked to the carbonyl carbon atom via nitrogen heteroatom, can be prepared by reacting the amine [24] with phosgene and then with compound [29] as shown in Scheme 10.

SCHEME 10.

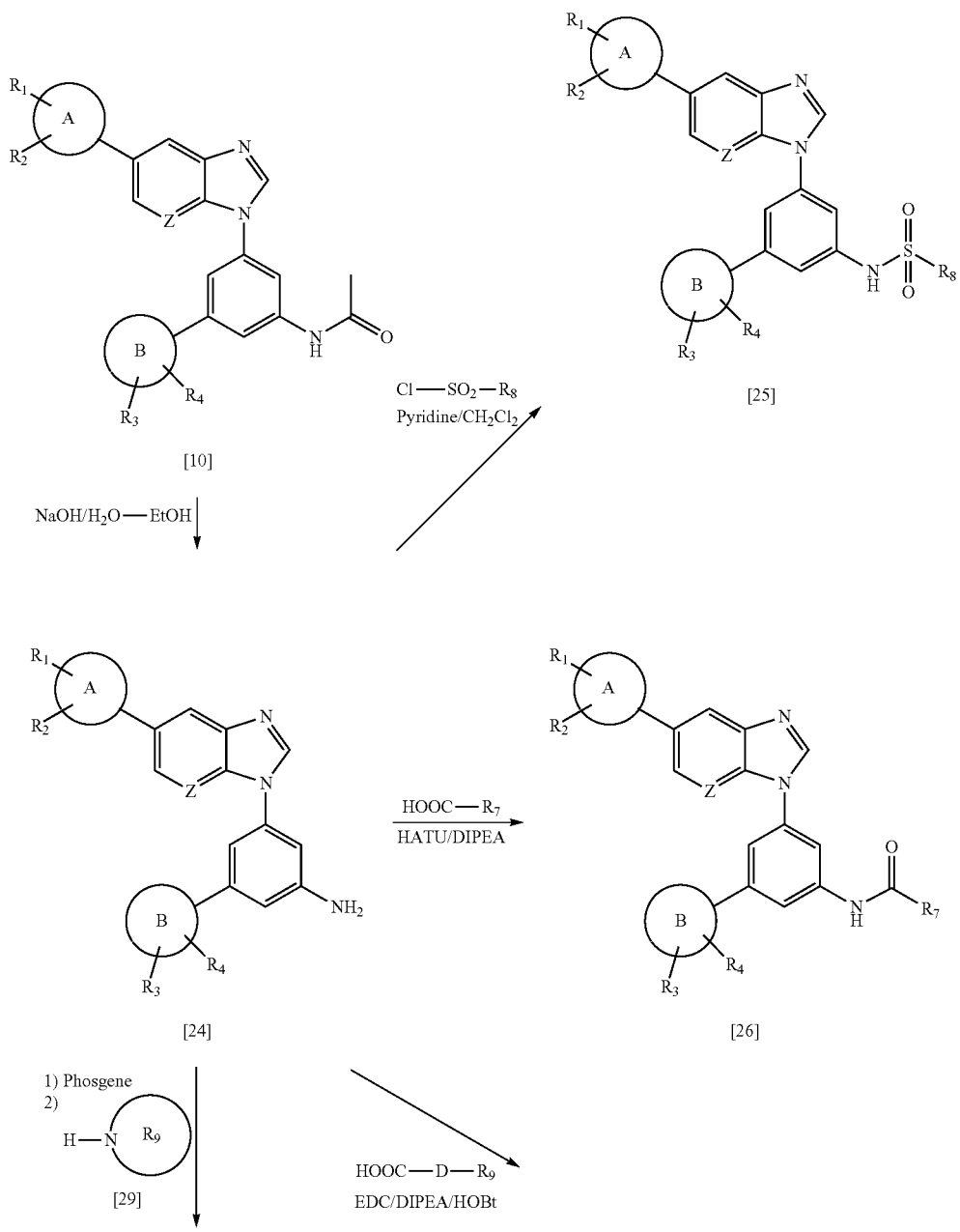

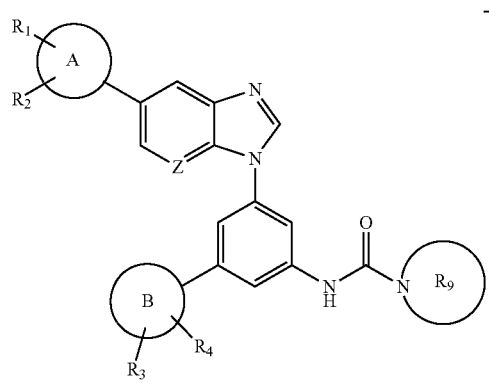

[28]

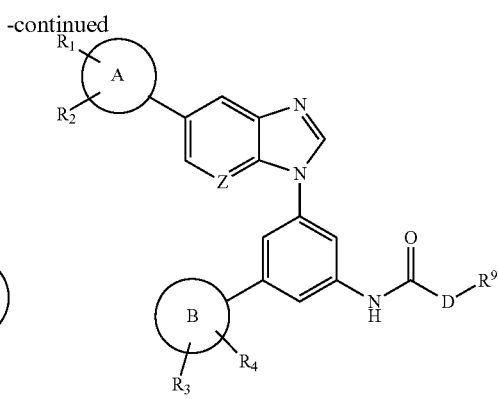

[27]

Compounds of formula (I), wherein $R_7$ is —NH—$R_{10}$ or —NH—X—$R_{11}$, can be prepared, for example, according to [24] in suitable solvent such as DCM with phosgene and then with $H_2N$—X—$R_{11}$, see Scheme 11.

SCHEME 11.

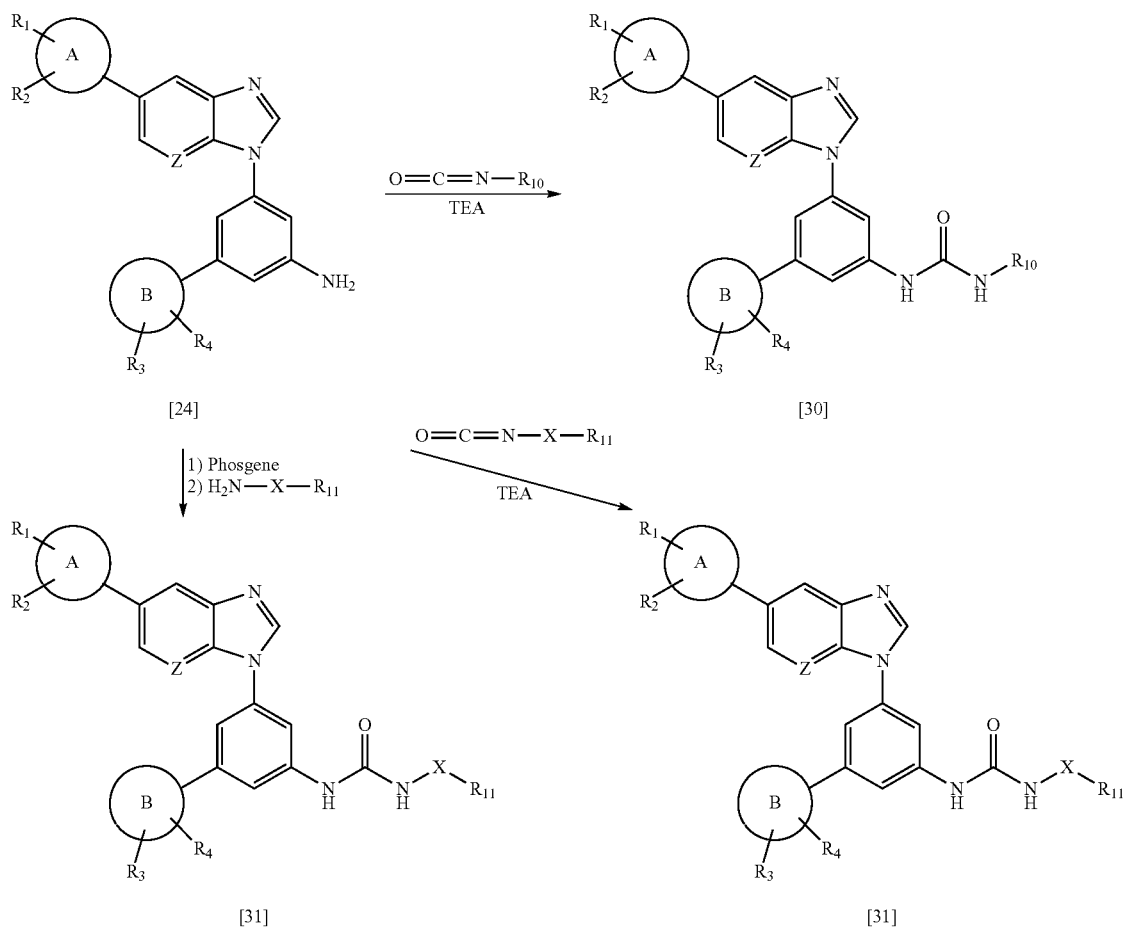

Scheme 11 by reacting the amine [24] in a suitable solvent such n-butanol with isocyanato derivatives O=C=N—$R_{10}$ or O=C=N—X—$R_{11}$ in the presence of suitable base such as triethylamine (TEA). Alternatively, compounds wherein $R_7$ is —NH—X—$R_{11}$ can be prepared by treating amine Compounds wherein G is other than optionally substituted ring A, can be prepared analogously using the methods of Scheme 1, wherein X' is replaced by G. Compounds of formula (I) wherein G is —C(O)NH$_2$ can be also prepared by heating compound [8], wherein X' is cyano, in aqueous potassium hydroxide.

Compounds wherein M is a hydroxy group can be suitably prepared from a compound of formula [42] followed by the bicyclic ring closure as in Scheme 1 and addition of the B-ring by e.g. Suzuki coupling as in Scheme 1. The alkoxy group of the obtained compound can be transformed into the hydroxy group e.g. by heating the alkoxy compound in the presence of thiourea/AlCl$_3$ reagent pair.

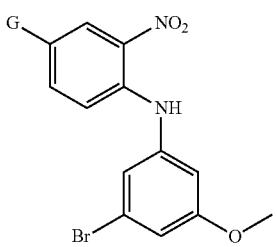

[42]

Finally, compounds wherein R$_5$ is an optionally substituted 5-6 membered heterocyclic ring can be prepared according to Scheme 12 or 13 starting from a compound [40] or [42], wherein R$_3$, R$_4$, Z, ring B and G are as defined above, using palladium (e.g. Pd$_2$(dba)$_3$) catalyzed C—N coupling in the presence of a metal chelating ligand such as Xantphos.

SCHEME 12.

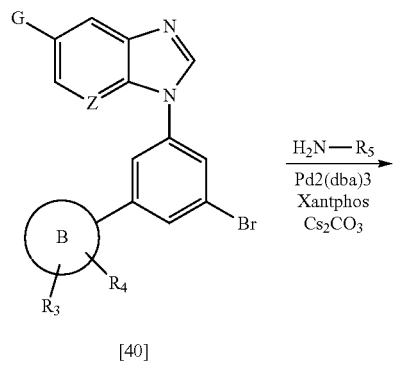

[40]

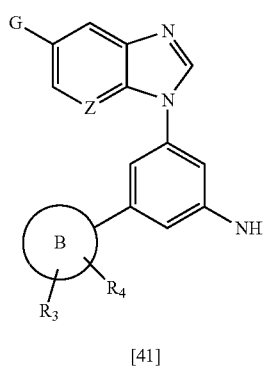

[41]

SCHEME 13.

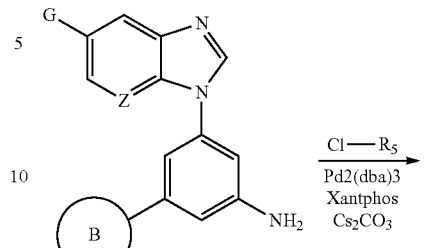

[42]

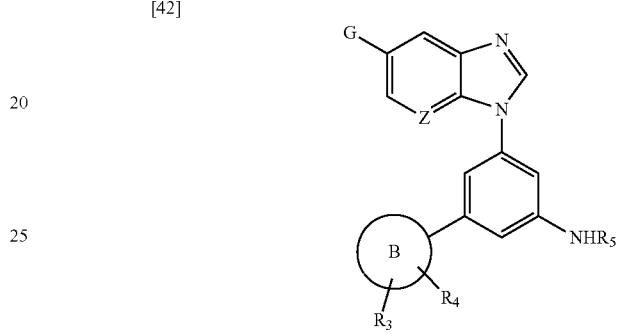

[41]

Pharmaceutically acceptable salts, e.g. acid addition salts with both organic and inorganic acids are well known in the field of pharmaceuticals. Non-limiting examples of these salts include chlorides, bromides, sulfates, nitrates, phosphates, sulfonates, formates, tartrates, maleates, citrates, benzoates, salicylates and ascorbates. Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols, e.g. methyl, ethyl, propyl, isopropyl, butyl, isobutyl, sec-butyl, tert-butyl esters. Phosphate esters and carbonate esters, are also within the scope of the invention.

The terms employed herein have the following meanings:

The term "halo" or "halogen", as employed herein as such or as part of another group, refers to chlorine, bromine, fluorine or iodine. Fluorine is a preferred halogen.

The term "C$_{1-7}$ alkyl", as employed herein as such or as part of another group, refers to a straight or branched chain saturated hydrocarbon group having 1, 2, 3, 4, 5, 6 or 7 carbon atom(s). Representative examples of C$_{1-7}$ alkyl include, but are not limited to, methyl, ethyl, n-propyl, iso-propyl, n-butyl, iso-butyl, sec-butyl, tert-butyl, n-pentyl, iso-pentyl and n-hexyl. One preferred embodiment of "C$_{1-7}$ alkyl" is C$_{1-3}$ alkyl. The term "C$_{1-3}$ alkyl" refers to an preferred embodiment of "C$_{1-7}$ alkyl" having 1, 2 or 3 carbon atoms.

The term "C$_{3-7}$ cycloalkyl", as employed herein as such or as part of another group, refers to a saturated cyclic hydrocarbon group containing 3, 4, 5, 6 or 7 carbon atoms. Representative examples of cycloalkyl include, but are not limited to, cyclopropyl, cyclobutyl, cyclopentyl and cyclohexyl.

The term "$C_{3-7}$ cycloalkyl $C_{1-7}$ alkyl", as employed herein refers to a $C_{3-7}$ cycloalkyl group, as defined herein, appended to the parent molecular moiety through a $C_{1-7}$ alkyl group, as defined herein.

The term "$C_{2-7}$ alkenyl", as employed herein as such or as part of another group, refers to an aliphatic hydrocarbon group having 2 to 7 carbon atoms and containing one or several double bonds. Representative examples include, but are not limited to, ethenyl, propenyl and cyclohexenyl.

The term "hydroxy", as employed herein as such or as part of another group, refers to an OH group. The term "cyano", as employed herein as such or as part of another group, refers to a —CN group. The term "amino", as employed herein as such or as part of another group, refers to a —NH$_2$ group. The term "carboxy", as employed herein as such or as part of another group, refers to COOH group. The term "carbonyl", as employed herein as such or as part of another group, refers to a carbon atom double-bonded to an oxygen atom (C=O). The term "oxo", as employed herein as such or as part of another group, refers to oxygen atom linked to another atom by a double bond (=O).

The term "$C_{1-7}$ alkoxy", as employed herein as such or as part of another group, refers to $C_{1-7}$ alkyl, as defined herein, appended to the parent molecular moiety through an oxygen atom. Representative examples of $C_{1-7}$ alkoxy include, but are not limited to methoxy, ethoxy, propoxy, butoxy, isobutoxy, sec-butoxy and tert-butoxy.

The term "hydroxyl $C_{1-7}$ alkyl", as employed herein, refers to at least one hydroxy group, as defined herein, appended to the parent molecular moiety through a $C_{1-7}$ alkyl group, as defined herein. Representative examples of hydroxyl $C_{1-7}$ alkyl include, but are not limited to, hydroxymethyl, 2,2-dihydroxyethyl, 1-hydroxyethyl, 3-hydroxypropyl, 1-hydroxypropyl, 1-methyl-1-hydroxyethyl and 1-methyl-1-hydroxypropyl.

The term "halo $C_{1-7}$ alkyl", as employed herein, refers to at least one halogen, as defined herein, appended to the parent molecular moiety through a $C_{1-7}$ alkyl group, as defined herein. Representative examples of halo $C_{1-7}$ alkyl include, but are not limited to, fluoromethyl, difluoromethyl, trifluoromethyl, 2-chloroethyl and 3-bromopropyl.

The term "cyano $C_{1-7}$ alkyl", as employed herein, refers to a cyano group, as defined herein, appended to the parent molecular moiety through a $C_{1-7}$ alkyl group, as defined herein. Representative examples of cyano $C_{1-7}$ alkyl include, but are not limited to, cyanomethyl, 1-cyanoethyl, 1-cyanopropyl and 2-cyanopropyl.

The term "carboxy $C_{1-7}$ alkyl", as employed herein as such or as part of another group, refers to a carboxy group, as defined herein, appended to the parent molecular moiety through a $C_{1-7}$ alkyl group, as defined herein.

The term "halogen $C_{1-7}$ alkoxy", as employed herein, refers to at least one halogen, as defined herein, appended to the parent molecular moiety through a $C_{1-7}$ alkoxy group, as defined herein.

The term "phenyl $C_{1-7}$ alkoxy", as employed herein, refers to at least one phenyl group appended to the parent molecular moiety through a $C_{1-7}$ alkoxy group, as defined herein.

The term "$C_{1-7}$ alkylcarbonyl", as employed herein as such or as part of another group, refers to a $C_{1-7}$ alkyl group, as defined herein, appended to the parent molecular moiety through a carbonyl group, as defined herein.

The term "$C_{1-7}$ alkoxycarbonyl", as employed herein as such or as part of another group, refers to a $C_{1-7}$ alkoxy group, as defined herein, appended to the parent molecular moiety through a carbonyl group, as defined herein.

The term "$C_{1-7}$ alkoxycarbonyl $C_{1-7}$ alkyl", as employed herein as such or as part of another group, refers to a $C_{1-7}$ alkoxycarbonyl group, as defined herein, appended to the parent molecular moiety through a $C_{1-7}$ alkyl group, as defined herein.

The term "aminocarbonyl", as employed herein as such or as part of another group, refers to an amino group, as defined herein, appended to the parent molecular moiety through a carbonyl group, as defined herein.

The term "amino $C_{1-7}$ alkyl", as employed herein, refers to at least one amino group, as defined herein, appended to the parent molecular moiety through a $C_{1-7}$ alkyl group, as defined herein. Representative examples of amino $C_{1-7}$ alkyl include, but are not limited to, aminomethyl, 2-aminoethyl, 1-aminoethyl, 2,2-diaminoethyl, 3-aminopropyl, 2-aminopropyl, 4-aminobutyl and 1-methyl-1-aminoethyl.

The term "$C_{1-7}$ alkylamino", as employed herein as such or as part of another group, refers to at least one $C_{1-7}$ alkyl group, as defined herein, appended to the parent molecular moiety through an amino group, as defined herein. Representative examples of $C_{1-7}$ alkylamino include, but are not limited to methylamino, ethylamino, propylamino, butylamino, dimethylamino, diethylamino and N-ethyl-N-methylamino.

The term "$C_{1-7}$ alkylamino $C_{1-7}$ alkyl", as employed herein as such or as part of another group, refers to at least one $C_{1-7}$ alkylamino group, as defined herein, appended to the parent molecular moiety through an $C_{1-7}$ alkyl group, as defined herein.

The term "carboxy $C_{1-7}$ alkylamino", as employed herein as such or as part of another group, refers to at least one carboxy group, as defined herein, appended to the parent molecular moiety through an $C_{1-7}$ alkylamino group, as defined herein The term "$C_{1-7}$ alkoxy $C_{1-7}$ alkyl", as employed herein, refers to at least one $C_{1-7}$ alkoxy group, as defined herein, appended to the parent molecular moiety through an $C_{1-7}$ alkyl group, as defined herein.

The term "$C_{1-7}$ alkoxycarbonyl $C_{1-7}$ alkyl", as employed herein, refers to at least one $C_{1-7}$ alkoxycarbonyl group, as defined herein, appended to the parent molecular moiety through an $C_{1-7}$alkyl group, as defined herein.

The term "substituted" as used herein in connection with various residues refers to halogen substituents, such as fluorine, chlorine, bromine, iodine, or $C_{1-7}$ alkyl, $C_{3-7}$ cycloalkyl, halo $C_{1-7}$ alkyl, hydroxy, amino, $C_{1-7}$ alkoxy, $C_{1-7}$ acyl $C_{1-7}$alkylamino, amino $C_{1-7}$ alkyl, nitro, cyano, thiol or methylsulfonyl substituents. Preferred are halogen, $C_{1-7}$ alkyl, halo $C_{1-7}$ alkyl, hydroxy, amino, $C_{1-7}$ alkoxy and methylsulfonyl substituents. In one group of preferred substituents are one or two $C_{1-7}$ alkyl substituents, particularly one or two $C_{1-3}$ alkyl substituents, particularly selected from methyl and ethyl substituents.

The "substituted" groups may contain 1 to 3, preferably 1 or 2, of the above mentioned substituents.

The term "5-6 membered heterocyclic ring" as employed herein, refers to a saturated, partially saturated or aromatic ring with 5 or 6 ring atoms, of which 1-4 atoms are heteroatoms selected from a group consisting of N, O and S. Representative examples of 5-6-membered heterocyclic ring include, but are not limited to, pyrazolyl, 1,2,4-triazol-1-yl, 1,2,3-triazol-1-yl, pyrimidinyl, pyridinyl, tetrazolyl, piperazinyl, furanyl, morpholinyl, piperidinyl, pyrrolidinyl, thiazolyl, isoxazolyl, pyrazinyl tetrahydropyranyl, 1,2,4-oxadiazolyl, oxazolyl, imidazolyl, indolyl and 4,5-dihydroimidazolyl rings.

The term "5-12 membered heterocyclic ring" as employed herein, refers to a monocyclic or bicyclic saturated, partially saturated or aromatic ring with 5 to 12 ring atoms, of which 1-5 atoms are heteroatoms selected from a group consisting of N, O and S. Representative examples of 5-12 membered heterocyclic ring include the examples given above and additionally, but not limited to, indazolyl, pyrazolo[1,5-a]pyrimidinyl, benzo[d]imidazolyl, imidazo[4,5-b]pyridinyl, 4,5,6,7-tetrahydrobenzo[d]imidazolyl and benzofuranyl rings.

The term "5-12 membered carbocyclic ring" as employed herein, refers to a saturated, partially saturated or aromatic ring with 5 to 12 ring atoms consisting of carbon atoms only. Representative examples of 5-12 membered carbocyclic ring include, but are not limited to, phenyl, naphtyl and cyclohexyl rings.

The definition of formula (I) above is inclusive of all the possible stereoisomers of the compounds, including geometric isomers, e.g. Z and E isomers (cis and trans isomers), and optical isomers, e.g. diastereomers and enantiomers, and all prodrug esters, e.g. phosphate esters and carbonate esters, and isotopes. Furthermore, the invention includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of optical isomers, e.g. enantiomers, from the mixture thereof the conventional resolution methods, e.g. fractional crystallisation, may be used.

Compounds of the invention may be administered to a patient in therapeutically effective amounts which range usually from about 0.1 to about 2000 mg per day depending on the age, weight, ethnic group, condition of the patient, condition to be treated, administration route and the active ingredient used. The compounds of the invention can be formulated into dosage forms using the principles known in the art. The compound can be given to a patient as such or in combination with suitable pharmaceutical excipients in the form of tablets, granules, capsules, suppositories, emulsions, suspensions or solutions. Choosing suitable ingredients for the composition is a routine for those of ordinary skill in the art. Suitable carriers, solvents, gel forming ingredients, dispersion forming ingredients, antioxidants, colours, sweeteners, wetting compounds and other ingredients normally used in this field of technology may be also used. The compositions containing the active compound can be given enterally or parenterally, the oral route being the preferred way. The contents of the active compound in the composition is from about 0.5 to 100%, preferably from about 0.5 to about 20%, per weight of the total composition.

The compounds of the invention can be given to the subject as the sole active ingredient or in combination with one of more other active ingredients for treatment of a particular disease, for example cancer.

The present invention will be explained in more detail by the following experiments and examples. The experiments and examples are meant only for illustrating purposes and do not limit the scope of the invention defined in claims.

Experiments

1. Inhibition of FGFR1 and Other Kinases

Methods

FGFR1 Assay

Compounds were screened in the TR-FRET assay with FGFR1 kinase. 5 ng of FGFR1 [Upstate, USA] kinase was used for assay. The compound was incubated with the kinase for 30 minutes at RT. After the incubation, substrate mix [40 nM Ultra light poly GT (Perkin Elmer, USA) and 13 µM ATP (Sigma)] was added. The above reaction was stopped by the addition of 40 mM EDTA after the 30 mM kinase reaction. The Eu-labelled antiphospho-tyrosine antibody [Perkin Elmer, USA] was added at 0.5 nM and the fluorescence emission at 615 nm/665 nm [excitation at 340 nm] was measured. The compounds were initially screened at 100 nM and 1 µM concentrations. The compounds with >50% inhibition at 100 nM of FGFR1 were taken for the full dose response studies. The final DMSO concentration in the assay was 1%. For $IC_{50}$ determination, $\frac{1}{3}^{rd}$ serial dilution was made from the 20 mM DMSO stock solution. 2 µl of these were transferred to the test wells containing 20 µl of the reaction mixture [total reaction volume 20 µl]. The fluorescence was measured in Perkin Elmer Wallac 1420 Multilabel Counter Victor 3. The $IC_{50}$ was determined by fitting the dose response data to sigmoidal curve fitting equation using GraphPad Prism software V5.

c-Met Assay

Compounds were screened in the TR-FRET assay with c-Met kinase. 0.1 ng of c-Met [expressed in-house] kinase was used for assay. The compound was incubated with the kinase for 60 min at RT. After the incubation, substrate mix [40 nM Ultra light poly GT (Perkin Elmer, USA) and 10 µM ATP (Sigma)] was added. The above reaction was stopped by the addition of 40 mM EDTA after the 30 min kinase reaction. The Eu-labelled antiphospho-tyrosine antibody [Perkin Elmer, USA] was added at 0.5 nM and the fluorescence emission at 615 nm/665 nm [excitation at 340 nm] was measured. The compounds were initially screened at 100 nM and 1 µM concentrations. The compounds with >50% inhibition at 100 nM of c-Met were taken for the full dose response studies. The final DMSO concentration in the assay was 1%. For $IC_{50}$ determination, ⅓rd serial dilution was made from the 20 mM DMSO stock solution. 2 µl of these were transferred to the test wells containing 20 µl reaction mixture [total reaction volume 20 µl]. The fluorescence was measured in Perkin Elmer Wallac 1420 Multilabel Counter Victor 3. The IC50 was determined by fitting the dose response data to sigmoidal curve fitting equation using GraphPad Prism software V5.

Results

Enzymatic activity and selectivity of selected compounds of the invention on different kinases is presented in Table 1. The compounds of the invention were found to be potent and selective FGFR kinase inhibitors.

TABLE 1

Inhibition of FGFR1 and c-Met kinase

| Compound | Inhibition (%) of FGFR1 at 1000 nM | $IC_{50}$ of FGFR1 inhibition (nM) | Inhibition (%) of c-Met at 1000 nM |
|---|---|---|---|
| Example 5 | 95 | 12 | 7 |
| Example 22 | 99 | 3.8 | 5 |
| Example 25 | 93 | 34 | 12 |
| Example 26 | 93 | 21 | 2 |

TABLE 1-continued

Inhibition of FGFR1 and c-Met kinase

| Compound | Inhibition (%) of FGFR1 at 1000 nM | IC$_{50}$ of FGFR1 inhibition (nM) | Inhibition (%) of c-Met at 1000 nM |
|---|---|---|---|
| Example 30 | 94 | 16 | 1 |
| Example 38 | 88 | 33 | 0 |
| Example 47 | 99 | 7 | 10 |
| Example 49 | 98 | 3.4 | 9 |
| Example 69 | 87 | 22 | −2 |
| Example 70 | 99 | 10 | 0 |
| Example 72 | 98 | 32 | 11 |
| Example 82 | 96 | 16 | 15 |
| Example 83 | 95 | 37 | 5 |
| Example 112 | 97 | 1.8 | 0 |
| Example 119 | 94 | 83 | 23 |
| Example 123 | 94 | 61 | 0 |
| Example 127 | 91 | 62 | 10 |
| Example 131 | 99 | 1.3 | 15 |
| Example 133 | 97 | 14 | 0 |
| Example 134 | 92 | 98 | 0 |
| Example 142 | 91 | 48 | 0 |
| Example 152 | 79 | 7.3 | 0 |
| Example 155 | 89 | 62 | 1 |
| Example 158 | 95 | 22 | 12 |
| Example 169 | 89 | 94 | nd |
| Example 170 | 92 | 59 | nd |
| Example 178 | 86 | 14.9 | nd |
| Example 190 | 96 | 4.3 | nd |
| Example 204 | 98 | 20 | nd |
| Example 217 | 91 | 10.4 | nd |
| Example 241 | 97 | 2.9 | nd |
| Example 244 | 98 | 14 | nd |
| Example 280 | 80 | 90 | nd |
| Example 281 | 96 | 9 | nd |
| Example 220 | 97 | 3.4 | nd |
| Example 289 | 94 | 32 | nd |
| Example 294 | 99 | 9.3 | nd |
| Example 319 | 97 | 18 | nd |
| Example 322 | 92 | 65.8 | nd |
| Example 259 | 92 | 45 | nd | nd = not determined

The preparation of the compounds of the invention is illustrated by the following Examples.

EXAMPLES

LCMS data has been recorded in +ve mode unless otherwise mentioned.

Intermediate Example 1

N,N-dimethyl-2-(4-(4,4,5,5-tetramethyl-1,3,2-dioxaborolan-2-yl)-1H-pyrazol-1-yl)ethanamine a) 2-(4-Bromo-1H-pyrazol-1-yl)-N,N-dimethylethanamine

To a solution of 4-bromo-1H-pyrazole (5 g, 34 mmol) in DMF were added K$_2$CO$_3$ (11.75 g, 85.03 mmol, 2.5 eq.) and 2-chloro-N,N-dimethylethanamine HCl (7.35 g, 51 mmol, 1.5 eq) and the mixture was stirred at RT for 12 h. The mixture was quenched with water and extracted with DCM (3×150 ml). The combined organic layer was washed with water, brine and dried over sodium sulphate. The solvent was distilled off to afford the crude residue which was purified by column chromatography (60-120 silica gel, 1% methanol in DCM) to give the product in 86% yield (6.4 g). $^1$H NMR (300 MHz, DMSO-d$_6$): δ 7.95 (s, 1H), 7.25 (s, 1H), 4.18 (t, 2H), 2.61 (t, 2H), 2.15 (s, 6H); LC-MS (ESI): Calculated mass: 218.09; Observed mass: 219.8[M+H]$^+$ (RT: 0.439 min).

b) N,N-dimethyl-2-(4-(4,4,5,5-tetramethyl-1,3,2-dioxaborolan-2-yl)-1H-pyrazol-1-yl)ethanamine To a degassed (N$_2$ bubbling) solution of the compound of Intermediate Example 1(a) (10 g, 45.85 mmol) in 1,4-dioxane (50 ml) were added 4,4,4',4',5,5,5',5'-octamethyl-2,2'-bi(1,3,2-dioxaborolane) (17.47 g, 68.78 mmol, 1.5 eq.), Pd(dppf)Cl$_2$ (1.87 g, 2.29 mmol, 0.05 eq.) and potassium acetate (11.23 g, 114.6 mmol, 2.5 eq.). The mixture was heated at 100° C. in a sealed tube for 12 h. The mixture was diluted with ethyl acetate and filtered over a pad of celite. The solvent was distilled off to give the product (7.0 g). LC-MS (ESI): Calculated mass: 265.16; Observed mass: 266.2 [M+H]$^+$ (RT: 0.09 min).

Intermediate Example 2

4-(2-(4-(4,4,5,5-Tetramethyl-1,3,2-dioxaborolan-2-yl)-1H-pyrazol-1-yl)ethyl)-morpholine The compound was synthesized using the procedure described in Example 1. LC-MS (ESI): Calculated mass: 307.2; Observed mass: 308.1 [M+H]$^+$ (RT: 0.11 min).

Intermediate Example 3

1-Fluoro-4-iodo-2-nitrobenzene

To a solution of 1-fluoro-2-nitrobenzene (5 g, 35.43 mmol) in triflic acid (15.6 ml, 177.15 mmol, 5 eq.) at 0° C. was added N-iodosuccinimide (9.57 g, 42.5 mmol, 1.2 eq.) portionwise and the mixture was stirred at RT for 1 h. The mixture was quenched by the addition of water and extracted with diethylether (3×150 ml). The combined organic layer was washed with water, aqueous sodium thiosulfate, brine and dried over sodium sulphate. The solvent was distilled off and the crude residue was purified by column chromatography (60-120 silica gel, 5% ethyl acetate in hexane) to afford the compound in 66% yield (6.2 g). $^1$H NMR (300 MHz, DMSO-d$_6$): δ 8.42 (dd, 1H), 8.18-8.13 (m, 1H), 7.46-7.39 (m, 1H).

Intermediate Example 4

4-Fluoro-3-nitrobenzaldehyde

Nitration mixture (sulfuric acid 40 ml+nitric acid 5.5 ml) was added dropwise to 4-fluorobenzaldehyde (10 g, 80.57 mmol) at 0° C. and the mixture was stirred at 5° C. for 20 min and at RT for 1 h. The mixture was quenched by the addition of crushed ice. The precipitate formed was filtered and was washed repeatedly with water to give white solid. The solid was dried under vacuum to give the product in 77% yield (10.5 g). $^1$H NMR (300 MHz, CDCl$_3$): δ 10.04 (s, 1H), 8.58 (dd, 1H), 8.22-8.18 (m, 1H), 7.5 (t, 1H).

Intermediate Example 5 tert-Butyl 4-(4-(4,4,5,5-tetramethyl-1,3,2-dioxaborolan-2-yl)-1H-pyrazol-1-yl)-piperidine-1-carboxylate a) tert-Butyl 4-hydroxypiperidine-1-carboxylate

To a solution of piperidin-4-ol (3.5 g, 34.6 mmol) in CH$_2$Cl$_2$ (50 ml) at 0° C. were added Boc$_2$O (11.3 g, 51.9 mmol, 1.5 eq) and Et$_3$N (7.2 ml, 51.9 mmol, 1.5 eq). The mixture was stirred at RT for 1 h and quenched and extracted as in Intermediate Example 1(a). The solvent was distilled off to give the crude product (7.0 g).

b) tert-Butyl 4-(methylsulfonyloxy)piperidine-1-carboxylate

The compound of the Intermediate Example 5(a) (7 g, 34.7 mmol) was dissolved in $CH_2Cl_2$ (70 ml) at 0° C. $Et_3N$ (10 ml, 69.4 mmol, 2 eq.) and methanesulfonyl chloride (2.7 ml, 34.7 mmol, 1 eq.) were added. The mixture was stirred at RT for 3 h and quenched and extracted as in previous example. The solvent was distilled off to afford the crude product (6.7 g).

c) tert-Butyl 4-(4-bromo-1H-pyrazol-1-yl)piperidine-1-carboxylate

To a cooled solution of the compound of Intermediate Example 5(b) (6.7 g, 23.9 mmol) in DMF (50 ml) was added NaH (2.8 g, 119 mmol, 5 eq.) and 4-bromo-1H-pyrazole (2.8 g, 19.1 mmol, 0.8 eq.) and stirred at 80° C. for 12 h. The mixture was quenched and extracted with ethyl acetate (3×100 ml). The combined organic layer was washed with water, brine and dried over sodium sulphate. The solvent was distilled off to afford the crude product (8.0 g).

d) tert-Butyl 4-(4-(4,4,5,5-tetramethyl-1,3,2-dioxaborolan-2-yl)-1H-pyrazol-1-yl)piperidine-1-carboxylate To a ($N_2$ bubbling) solution of the compound of Intermediate Example 5(c) (8 g, 24.2 mmol) in 1,4-dioxane (100 ml) were added 4,4,4',4',5,5,5',5'-octamethyl-2,2'-bi-(1,3,2-dioxaborolane) (7.36 g, 29 mmol, 1.2 eq.), $Pd(dppf)Cl_2$ (2 g, 2.42 mmol, 0.1 eq.) and potassium acetate (8 g, 82.4 mmol, 3.4 eq.) using the procedure of Intermediate Example 1(b). The solvent was distilled off and the residue was purified by column chromatography (60-120 silica gel, 10% ethyl acetate in hexane) to give the product in 59% yield (5.4 g). LC-MS (ESI): Calculated mass: 377.29; Observed mass: 378.3 [(M+H)]$^+$ (RT: 1.83 min).

Intermediate Example 6

4-Azido-2-methylbutan-2-ol a) 4-Bromo-2-methylbutan-2-ol

To a cooled solution of ethyl 3-bromopropanoate (0.5 g, 2.8 mmol) in diethyl ether (50 ml) at 0° C. was added methyl magnesium bromide (0.98 g, 8.3 mmol, 3 eq.) dropwise over 5 min and the mixture was allowed to stir until TLC showed complete absence of the starting material. The mixture was quenched and extracted as in Intermediate Example 5(c). The solvent was distilled off to give the crude product (0.4 g).

b) 4-Azido-2-methylbutan-2-ol

To a mixture of 4-bromo-2-methylbutan-2-ol (0.4 g, 2.4 mmol) and triethylamine (1 ml, 7 mmol, 3 eq.) in $CH_2Cl_2$ (15 ml) was added sodium azide (0.47 g, 7 mmol, 3 eq.) in $H_2O$ (5 ml) and the mixture was allowed to stir overnight. The mixture was quenched with water and extracted with $CH_2Cl_2$ (3×50 ml). The combined organic layer was washed with water, brine and dried over sodium sulphate. The solvent was distilled off to afford the product in 65% yield (0.2 g). $^1H$ NMR (300 MHz, DMSO-$d_6$): δ 4.39 (br s, 1H), 3.40-3.32 (m, 2H), 1.15 (t, 2H), 1.23-1.04 (m, 6H).

Intermediate Example 7

Azidocyclopentane

To a solution of iodocyclopentane (0.5 g, 2.55 mmol) in DMF (2 ml) was added aqueous sodium azide (0.33 g, 5.1 mmol). The mixture stirred at RT for 10 min, and then stirred at 80° C. overnight. The mixture was extracted with diethyl ether (3×50 ml) and the combined organic layer was washed with water, brine and dried over sodium sulphate. The solvent was distilled off to afford the product in 64% yield (0.18 g) which was directly used for the next step. FTIR (neat): v 3448, 2471, 2100, 1671, 1498, 1438, 1383, 1256, 1094, 865 cm$^{-1}$.

Intermediate Example 8

(Azidomethyl)Cyclobutane

To a solution of (bromomethyl)cyclobutane (0.5 g, 3.35 mmol) in DMF (2 ml) was added aqueous sodium azide (0.43 g, 6.7 mmol). The mixture was stirred at RT for 10 min, followed by stirring at 80° C. overnight. The mixture was extracted as in the previous example. The solvent was distilled off to give the product in 54% yield (0.2 g). $^1H$ NMR (300 MHz, DMSO-$d_6$): δ 3.66-3.53 (m, 2H), 2.66-2.21 (m, 1H), 2.06-2.00 (m, 2H), 1.84-1.66 (m, 4H).

Intermediate Example 9

1-(Cyclopropylmethyl)-4-(4,4,5,5-tetramethyl-1,3,2-dioxaborolan-2-yl)-1H-pyrazole a) 4-Bromo-1-(cyclopropylmethyl)-1H-pyrazole To a solution of 4-bromo-1H-pyrazole (0.1 g, 0.68 mmol) in DMF (20 ml) were added $K_2CO_3$ (0.19 g, 1.36 mmol, 2 eq.) and (bromomethyl)cyclopropane (92 mg, 0.68 mmol, 1 eq.). The mixture was stirred at RT for 4 h. The mixture was quenched and extracted as in Intermediate Example 5(c). The solvent was distilled off to afford the crude product (0.15 g).

b) 1-(Cyclopropylmethyl)-4-(4,4,5,5-tetramethyl-1,3,2-dioxaborolan-2-yl)-1H-pyrazole To a degassed ($N_2$ bubbling) solution of the compound of Intermediate Example 9(a) (0.15 g, 0.75 mmol) in 1,4-dioxane (10 ml) were added 4,4,4',4',5,5,5',5'-octamethyl-2,2'-bi(1,3,2-dioxaborolane) (0.23 g, 0.9 mmol, 1.2 eq.), $Pd(dppf)Cl_2$ (0.12 g, 0.15 mmol, 0.2 eq.) and potassium acetate (0.25 g, 2.55 mmol, 3.4 eq.). using the procedure of Intermediate Example 1(b). The solvent was distilled off to afford the crude residue which was purified by column chromatography (60-120 silica gel, 30% ethyl acetate in hexane) to give the product in 81% yield (0.15 g). LC-MS (ESI): Calculated mass: 248.13; Observed mass: 249.2 [(M+H)]$^+$ (rt: 1.58 min).

Intermediate Example 10

2-Morpholinoacetic acid a) Ethyl 2-morpholinoacetate

To a solution of ethyl 2-chloroacetate (0.5 g, 5.74 mmol) in DMF (70 ml) at 10° C. were added $K_2CO_3$ (1.98 g, 14.34 mmol, 2.5 eq.) and 1-methylpiperazine (1.05 g, 8.6 mmol, 1.5 eq.) and the mixture was stirred at RT for 2 h. The mixture was quenched and extracted as in Intermediate Example 5(c). The solvent was distilled off and the crude residue was purified by column chromatography (60-120 silica gel, 40% ethyl acetate in hexane) to afford the product in 74% yield (0.74 g). LC-MS (ESI): Calculated mass: 173.2, Observed mass: 174.0 [M+H]$^+$ (rt: 0.20 min).

b) 2-Morpholinoacetic Acid

A solution of ethyl 2-morpholinoacetate (1.8 g, 11.44 mmol) in 8 N HCl (5 ml) was heated at 90° C. for 12 h. The mixture was concentrated to give the product in 64% yield (0.9 g). LC-MS (ESI): Calculated mass: 145.16; Observed mass: 146.3 [M+H]$^+$ (rt: 0.21 min).

Intermediate Example 11

4-Azido-1-methylpiperidine a) 1-Methylpiperidin-4-yl methanesulfonate

1-Methylpiperidin-4-ol (4 g, 34.7 mmol) was dissolved in CH$_2$Cl$_2$ (70 ml) at 0° C. followed by the addition of Et$_3$N (10 ml, 69.4 mmol, 2 eq.) and methanesulfonyl chloride (2.7 ml, 34.7 mmol, 1 eq.). The mixture was stirred at RT for 3 h and quenched and extracted as in Intermediate Example 5(a). The solvent was distilled off to afford the crude product (6.7 g).

b) 4-Azido-1-methylpiperidine

To a solution of the compound of Intermediate Example 11(a) (2.1 g, 10.9 mmol) in DMF (30 ml) was added sodium azide (1 g, 16.32 mmol, 1.5 eq.) The mixture was stirred at 60° C. for 12 h. The mixture was then quenched with water and extracted with diethylether (3×100 ml). The combined organic layer was washed with water, brine and dried over sodium sulphate. The solvent was distilled off to give the product (1.3 g). $^1$H NMR (300 MHz, CDCl$_3$): δ 3.49-3.37 (m, 1H), 2.71-2.67 (m, 2H) 2.24 (s, 3H) 2.18-2.09 (m, 2H) 1.93-1.85 (m, 2H) 1.72-1.60 (m, 2H); LC-MS (ESI); Calculated mass: 140.1: Observed mass: 141.1 [M+H]$^+$ (rt: 0.13 min).

Intermediate Example 12

1-Isopropyl-4-(4,4,5,5-tetramethyl-1,3,2-dioxaborolan-2-yl)-1H-pyrazole a) 4-Bromo-1-isopropyl-1H-pyrazole To a solution of 4-bromo-1H-pyrazole (5 g, 34 mmol) in DMF (70 ml) were added K$_2$CO$_3$ (11.83 g, 85.6 mmol, 2.5 eq.) and 2-bromopropane (6.3 g, 51.36 mmol, 1.5 eq.) and the mixture was stirred at RT for 12 h. The mixture was quenched and extracted as in Intermediate Example 5(a). The solvent was distilled off and the crude residue was purified by column chromatography (60-120 silica gel, 20% ethyl acetate in hexane) to afford the product in 89% yield (5.8 g). $^1$H NMR (300 MHz, DMSO-d$_6$): δ 8.01 (s, 1H), 7.50 (s, 1H), 4.49-4.43 (m, 1H), 1.38 (d, 6H).

b) 1-Isopropyl-4-(4,4,5,5-tetramethyl-1,3,2-dioxaborolan-2-yl)-1H-pyrazole

To a degassed (N$_2$ bubbling) solution of the compound of Intermediate Example 12(a) 4-bromo-1-isopropyl-1H-pyrazole (1.5 g, 7.9 mmol) in 1,4-dioxane (30 ml) were added 4,4,4',4',5,5,5',5'-octamethyl-2,2'-bi(1,3,2-dioxaborolane) (3 g, 11.84 mmol, 1.5 eq.), Pd(dppf)Cl$_2$ (0.64 g, 0.79 mmol, 0.1 eq.) and potassium acetate (1.93 g, 19.74 mmol, 2.5 eq.) using the procedure of Intermediate Example 1(b). The solvent was distilled off to afford the product in 67% yield (1.2 g). LC-MS (ESI): Calculated mass: 236.12; Observed mass: 237.1 [M+H]$^+$ (rt: 1.41 min).

Intermediate Example 13

1-Ethyl-4-(4,4,5,5-tetramethyl-1,3,2-dioxaborolan-2-yl)-1H-pyrazole a) 4-Bromo-1-ethyl-1H-pyrazole To a solution of 4-bromo-1H-pyrazole (5 g, 34 mmol) in DMF were added K$_2$CO$_3$ (11.75 g, 85.03 mmol, 2.5 eq.) and iodoethane (8 g, 51 mmol, 1.5 eq.) and the mixture was stirred at RT for 12 h. The mixture was quenched and extracted as in Intermediate Example 5(c). The solvent was distilled off and the crude residue was purified by column chromatography (60-120 silica gel, 40% ethyl acetate in hexane) to yield the product in 84% yield (5 g). $^1$H NMR (300 MHz, DMSO-d$_6$): δ 8.02 (s, 1H), 7.55 (s, 1H), 4.15 (q, 2H), 1.37 (t, 3H); LC-MS (ESI): Calculated mass: 175.03; Observed mass: 177.0 [M+H]$^+$ (rt: 0.56 min).

b) 1-Ethyl-4-(4,4,5,5-tetramethyl-1,3,2-dioxaborolan-2-yl)-1H-pyrazole

To a degassed (N$_2$ bubbling) solution of 4-bromo-1-ethyl-1H-pyrazole (2 g, 11.42 mmol) in 1,4-dioxane (30 ml) were added 4,4,4',4',5,5,5',5'-octamethyl-2,2'-bi-(1,3,2-dioxaborolane) (4.35 g, 17.14 mmol, 1.5 eq.), Pd(dppf)Cl$_2$ (0.93 g, 1.14 mmol, 0.1 eq.) and potassium acetate (2.79 g, 28.55 mmol, 2.5 eq.) using the procedure of Intermediate Example 1(b). The solvent was distilled off to give the product in 88% yield (2.2 g). LC-MS (ESI): Calculated mass: 222.09; Observed mass: 223.3 [M+H]$^+$ (rt: 0.83 min).

Intermediate Example 14

2-Chloro-5-iodo-3-nitropyridine a) 5-Iodo-3-nitropyridin-2-amine

To a solution of 3-nitropyridin-2-amine (1.2 g, 8.63 mmol) in acetic acid (5 ml), water (1 ml) and sulfuric acid (0.2 ml) was added periodic acid (0.4 g, 1.72 mmol, 0.2 eq.) and the mixture was stirred at 90° C. for 15 min. Iodine (0.87 g, 3.45 mmol, 0.4 eq.) was added portionwise and the mixture was heated at 90° C. for 1 h. The mixture was quenched by the addition of water and extracted with ethylacetate (3×150 ml). The combined organic layer was washed with water, aqueous sodium thiosulfate, brine and dried over sodium sulphate. The solvent was distilled off to give the product in 57% yield (1.3 g). $^1$H NMR (300 MHz, DMSO-d$_6$): δ 8.58 (d, 1H), 8.54 (d, 1H) 8.04 (br s, 2H); LC-MS (ESI); Calculated mass: 265.01: Observed mass: 265.9 [M+H]$^+$ (rt: 1.36 min).

b) 2-Chloro-5-iodo-3-nitropyridine

To a solution of 5-iodo-3-nitropyridin-2-amine (1.3 g, 4.9 mmol) in concentrated HCl at 0° C. was added sodium nitrite (6.73 g, 97.13 mmol, 20 eq.) stepwise followed by the addition of copper(I) chloride (0.5 g, 4.9 mmol, 1 eq.) and the mixture was stirred at RT for 12 h. The mixture was then poured in to a mixture of ammonium hydroxide and water (1:1) and extracted with ethylacetate (3×150 ml). The combined organic layer was washed with water, aqueous sodium thiosulfate, brine and dried over sodium sulphate. The solvent was distilled off to afford the product in 43% yield (0.6 g).

Intermediate Example 15

2-(4-Ethylpiperazin-1-yl)acetic acid a) Ethyl 2-(4-methylpiperazin-1-yl)acetate

To a solution of 1-methylpiperazine (1 g, 8.771 mmol, 1.0 eq) in DMF were added $K_2CO_3$ (265 m g, 21.927 mmol, 2.5 eq) and ethyl 2-bromoacetate (167 mg, 13.15 mmol, 1.5 eq). The mixture was stirred at RT for 16 h and quenched and extracted as in Intermediate Example 5(a). The solvent was distilled off to afford the product in 76.4% yield. (1.3 g).

b) 2-(4-Ethylpiperazin-1-yl)acetic acid

The solution of methyl 2-(4-ethylpiperazin-1-yl)acetate (1.3 g, 6.50 mmol, 1.0 eq) in 8 N HCl was stirred at 95° C. for 16 h and concentrated on vacuum pump. The mixture was quenched with sodium bicarbonate solution and extracted with ethyl acetate (3×150 ml). The combined organic layer was washed with water, brine and dried over sodium sulphate. The solvent was distilled off to give the product in 54.5% yield (0.6 g). LC-MS (ESI): Calculated mass: 158.0; Observed mass: 159.1 $[M+H]^+$ (rt: 0.102 min).

Intermediate Example 16

N-cyclopropyl-2-oxooxazolidine-3-sulfonamide

To a solution of bromoethanol (1 g, 8.06 mmol) in DCM was added chloro sulfonyl isocyanate (1.13 g, 8.06 mmol) in DCM and this solution added over 2 min, dropwise, to cyclopropyl amine (0.552 g, 0.009 mmol) and triethylamine (1 ml, 0.007 mmol) in DCM and stirred at RT for 1 h. The mixture was quenched with 0.2 M HCl solution and extracted with DCM (3×150 ml). The combined organic layer was washed with water, brine and dried over sodium sulphate. The solvent was distilled off to afford the product in 48% yield (0.8 g). $^1$H NMR (400 MHz, DMSO-$d_6$): δ 8.15-8.14 (d, 1H), 4.42 (t, 2H), 3.70 (t, 2H), 2.35 (m, 1H), 0.58-0.53 (m, 4H).

Intermediate Example 17

N-(1H-pyrazol-4-yl)acetamide

Acetic anhydride (0.7 ml, 8.433 mmol) was added dropwise at 0° C. to 1H-pyrazol-4-amine (0.7 g, 8.433 mmol). The mixture was stirred for 30 min at RT and quenched by the addition of crushed ice. The mixture was extracted with ethyl acetate The combined organic layer was washed with water, brine and dried over sodium sulphate. The solvent was distilled off to afford the product in 54% yield. (0.6 g). LC-MS (ESI): Calculated mass: 125.0; Observed mass 126.0 $[M+H]^+$ (rt: 0.115 min).

Intermediate Example 18

2-(1H-1,2,4-triazol-1-yl)acetic acid a) Ethyl 2-(1H-1,2,4-triazol-1-yl)acetate

To a solution of 1H-1,2,4-triazol (2 g, 29.9 mmol, 1.0 eq) in DMF were added $K_2CO_3$ (12.3 g, 88.9 mmol, 3 eq.) and ethyl 2-bromoacetate (4.8 g, 29.9 mmol, 1 eq). The mixture was stirred at RT for 16 h. The mixture was quenched and extracted as in Intermediate Example 5(a). The solvent was distilled off to give the product in 65% yield (3 g). LC-MS (ESI): Calculated mass: 155.0; Observed mass: 156.1 $[M+H]^+$ (rt: 0.113 min).

b) 2-(1H-1,2,4-triazol-1-yl)acetic acid

The solution of the compound of Intermediate Example 18(a) (3 g, 19.35 mmol, 1.0 eq) in 8 N HCl was stirred at 95° C. for 16 h and concentrated on vacuum pump. The mixture was quenched and extracted as in Intermediate Example 15(b). The solvent was distilled off to afford desired product in 62% yield (1.5 g). LC-MS (ESI): Calculated mass: 127.0; Observed mass: 128.0 $[M+H]^+$ (rt: 0.24 min).

Intermediate Example 19 a) Ethyl 2-(pyrrolidin-1-yl)acetate

To a solution of pyrrolidine (1.2 g, 16.3 mmol, 1.0 eq) in DMF were added $K_2CO_3$ (5.63 g, 40.7 mmol, 2.5 eq.) and ethyl 2-bromoacetate (1.73 g, 24.4 mmol, 1.5 eq.). The mixture was stirred at RT for 16 h and quenched and extracted as in Intermediate Example 5(a). The solvent was distilled off to afford the product in 80% yield (2 g). LC-MS (ESI): Calculated mass: 157.2; Observed mass 158.1 $[M+H]^+$ (rt: 0.2 min).

b) 2-(Pyrrolidin-1-yl)acetic acid

The solution of ethyl 2-(pyrrolidin-1-yl)acetate (2 g, 12.7 mmol, 1.0 eq) in 8 N HCl was stirred at 95° C. for 16 h. The mixture was concentrated and quenched and extracted as in Intermediate Example 15(b). The solvent was distilled off to afford the product in 91% yield (1.5 g). LC-MS (ESI): Calculated mass: 129.1; Observed mass 130.1 $[M+H^+]$ (rt: 0.26 min).

Intermediate Example 20

2-Morpholinoacetic Acid a) Ethyl 2-morpholinoacetate

To a solution of morpholine (1.4 g, 16.3 mmol, 1.0 eq) in DMF were added $K_2CO_3$ (5.63 g, 40.7 mmol, 2.5 eq.) and ethyl 2-bromoacetate (4.07 g, 24.4 mmol, 1.5 eq.). The mixture was stirred at RT for 16 h and quenched and extracted as in Intermediate Example 5(a). The solvent was distilled off to afford the product in 71.4% yield (2 g). LC-MS (ESI): Calculated mass: 173.2; Observed mass: 174.0 $[M+H]^+$ (rt: 0.20 min).

b) 2-Morpholinoacetic Acid

The solution of ethyl 2-morpholinoacetate (1 g, 57.8 mmol, 1.0 eq) in 8 N HCl was stirred at 95° C. for 16 h. The mixture was concentrated and quenched and extracted as in Intermediate Example 15(b). The solvent was distilled off to afford the product in 96.3% yield (0.8 g). LC-MS (ESI): Calculated mass: 145.16; Observed mass: 146.3 [M+H]$^+$ (rt: 0.21 min).

Intermediate Example 21

2-(Piperidin-1-yl)acetic acid a) Ethyl 2-(piperidin-1-yl)acetate

To a solution of piperidine (3.4 g, 40.7 mmol, 1.0 eq) in DMF were added K$_2$CO$_3$ (14 g, 101.0 mmol, 2.5 eq.) and ethyl 2-chloroacetate (4.83 ml, 48.9 mmol, 1.2 eq). The mixture was stirred at RT for 16 h. The mixture was quenched and extracted as in Intermediate Example 5(a). The solvent was distilled off to give the product in 72% yield (5 g). LC-MS (ESI): Calculated mass: 171.1; Observed mass 172.3 [M+H]$^+$ (rt: 0.1 min).

b) 2-(Piperidin-1-yl)acetic acid

The solution of ethyl 2-(piperidin-1-yl)acetate (1 g, 5.84 mmol, 1.0 eq) in 8 N HCl was stirred at 95° C. for 16 h. The mixture was concentrated and quenched and extracted as in Intermediate Example 15(b). The solvent was distilled off to afford the product in 95% yield (0.8 g). LC-MS (ESI): Calculated mass: 143.1; Observed mass 144.4 [M+H]$^+$ (rt: 0.21 min).

Intermediate Example 22

2-(3,5-Dimethylpiperazin-1-yl)acetic acid a) Ethyl 2-(3,5-dimethylpiperazin-1-yl)acetate To a solution of 2,6-dimethylpiperazine (500 mg, 4.378 mmol, 1.0 eq) in THF were added K$_2$CO$_3$ (1.2 g, 8.75 mmol, 2.2 eq.) and ethyl 2-bromoacetate (731 mg, 4.378 mmol, 1 eq). The mixture was stirred at RT for 4 h and then quenched and extracted as in Intermediate Example 5(a). The solvent was distilled off to afford the product in 34% yield (0.3 g). LC-MS (ESI): Calculated mass: 200.0; Observed mass: 201.0 [M+H]$^+$ (rt: 0.102 min).

b) 2-(3,5-Dimethylpiperazin-1-yl)acetic acid

The solution of the compound of Intermediate Example 22(a) (300 mg, 1.5 mmol, 1.0 eq) in 8 N HCl was stirred at 95° C. for 16 h. The mixture was concentrated and quenched and extracted as in Intermediate Example 15(b). The solvent was distilled off to afford the product in 96% yield (250 mg). LC-MS (ESI): Calculated mass: 172.0; Observed mass: 173.1 [M+H]$^+$ (rt: 0.094 min).

Intermediate Example 23

2-(4-(tert-Butoxycarbonyl) piperazin-1-yl) acetic acid a) tert-Butyl 4-(2-ethoxy-2-oxoethyl) piperazine-1-carboxylate To a solution of tert-butyl piperazine-1-carboxylate (2.9 g, 10.7 mmol, 1.0 eq) in THF were added potassium carbonate (2.96 g, 21.0 mmol, 2 eq) and ethyl 2-bromoacetate (1.58 g, 10.7 mmol, 1 eq). The mixture was stirred at RT for 16 h. The mixture was quenched and extracted as in Intermediate Example 5(a). The solvent was distilled off to afford the product in 51% yield (1.5 g).

b) 2-(4-(tert-Butoxycarbonyl) piperazin-1-yl) acetic acid

To a solution of the compound of Intermediate Example 23(a) (1.5 g, 5.51 mmol) in methanol (10 ml) was added aqueous solution of NaOH (0.8 g, 22.0 mmol, 4 eq). The mixture was stirred at RT for 2 h. The mixture was concentrated and extracted as in Intermediate Example 5(c). The solvent was distilled off to give the product in 76% yield (1 g). LC-MS (ESI): Calculated mass: 244.29; Observed mass: 145.1 [M-Boc+H]$^+$ (rt: 0.102 min).

Intermediate Example 24 a) Ethyl 2-(4-ethylpiperazin-1-yl)acetate

To a solution of 1-ethylpiperazine (1 g, 8.771 mmol, 1.0 eq) in DMF were added K$_2$CO$_3$ (3 g, 21.927 mmol, 2.5 eq.) and ethyl 2-bromoacetate (2.19 g, 13.156 mmol, 1.5 eq.). The mixture was stirred at RT for 16 h. The mixture was quenched and extracted as in Intermediate Example 5(a). The solvent was distilled off to afford the product in 76.4% yield (1.3 g).

b) 2-(4-Ethylpiperazin-1-yl)acetic acid

The solution of ethyl 2-(4-ethylpiperazin-1-yl)acetate (1.3 g, 6.50 mmol, 1.0 eq) in 8 N HCl stirred at 95° C. for 16 h. The mixture was concentrated on vacuum pump, and quenched and extracted as in Intermediate Example 15(b). The solvent was distilled off to afford the product in 54.5% yield (0.6 g).

Intermediate Example 25

1-Isopropyl-4-(4,4,5,5-tetramethyl-1,3,2-dioxaborolan-2-yl)-1H-pyrazole a) 4-Bromo-1-isopropyl-1H-pyrazole To a solution of 4-bromo-1H-pyrazole (5 g, 34.24 mmol, 1.0 eq) in DMF were added K$_2$CO$_3$ (11.83 g, 85.60 mmol, 2.5 eq.) and 2-bromopropane (6.31 g, 51.36 mmol, 1.5 eq.) The mixture was stirred at RT for 12 h. The mixture was quenched and extracted as in Intermediate Example 5(a). The solvent was distilled off to afford the product in 76.9% yield (5.0 g).

b) 1-Isopropyl-4-(4,4,5,5-tetramethyl-1,3,2-dioxaborolan-2-yl)-1H-pyrazole

To a (N$_2$ bubbling) solution of 4-bromo-1-isopropyl-1H-pyrazole (1.5 g, 7.894 mmol) in 1,4 dioxane (15 ml) were added 4,4,4',4',5,5,5',5'-octamethyl-2,2'-bi(1,3,2-dioxaborolane) (3.0 g, 11.84 mmol, 1.5 eq.), Pd(dppf)Cl$_2$ (0.644 g, 0.784 mmol, 0.1 eq.) and potassium acetate (1.93 g, 19.73 mmol, 2.5 eq.) using the procedure of Intermediate Example 1(b). The solvent was distilled off and the residue was purified by column chromatography (60-120 silica gel, 15% ethyl acetate in hexane) to yield the product in 66.6% yield (1.2 g). LC-MS (ESI): Calculated mass: 236.17; Observed mass: 237.1 [M+H]+ (rt: 1.4 min).

Intermediate Example 26

2-(Piperidin-1-yl) acetic acid a) Ethyl 2-(piperidin-1-yl) acetate

To a solution of piperidine (1.5 g, 17.61 mmol, 1.0 eq) in DMF were added $K_2CO_3$ (6.08 g, 44.02 mmol, 2.5 eq.) and ethyl 2-chloroacetate (3.23 g, 26.42 mmol, 1.5 eq.). The mixture was stirred at RT for 12 h and quenched and extracted as in Intermediate Example 5(a). The solvent was distilled off to afford the product in 80% yield (2.4 g). LC-MS (ESI): Calculated mass: 171.1; Observed mass 172.3 [M+H]+ (rt: 0.1-0.2 min).

b) 2-(Piperidin-1-yl) acetic acid

The solution of ethyl 2-(piperidin-1-yl)acetate (2.4 g, 14.0 mmol, 1.0 eq) in 8 N HCl was stirred at 95° C. for 16 h. The mixture was concentrated on vacuum pump and quenched and extracted as in Intermediate Example 15(b). The solvent was distilled off to afford the product in 60% yield (1.2 g). LC-MS (ESI): Calculated mass: 143.1; Observed mass 144.4 [M+H]+ (rt: 0.21 min).

Intermediate Example 27

2-Morpholinoacetic acid a) Ethyl 2-morpholinoacetate

To a solution of morpholine (0.5 g, 5.739 mmol, 1.0 eq) in DMF were added $K_2CO_3$ (1.98 g, 14.34 mmol, 2.5 eq.) and ethyl 2-chloroacetate (1.05 g, 8.60 mmol, 1.5 eq.). The mixture was stirred at RT for 12 h. The mixture was quenched and extracted as in Intermediate Example 5(a). The solvent was distilled off to afford the product in 73.9% yield (0.735 g). LC-MS (ESI): Calculated mass: 173.21; Observed mass 174.0 [M+H]+ (rt: 0.1-0.4 min).

b) 2-Morpholinoacetic Acid

The solution of ethyl 2-morpholinoacetate (0.73 g, 4.24 mmol, 1.0 eq) in 8 N HCl was stirred at 95° C. for 16 h. The mixture was concentrated on vacuum pump and quenched and extracted as in Intermediate Example 15(b). The solvent was distilled off to afford the product in 60% yield (0.37 g). LC-MS (ESI): Calculated mass: 145.1; Observed mass 146.3 [M+H]+ (rt: 0.28 min).

Intermediate Example 28

2-(Pyrrolidin-1-yl) acetic acid a) Ethyl 2-(pyrrolidin-1-yl) acetate

To a solution of pyrrolidine (0.9 g, 12.65 mmol, 1.0 eq) in DMF were added $K_2CO_3$ (4.37 g, 31.62 mmol, 2.5 eq.) and ethyl 2-chloroacetate (2.32 g, 18.98 mmol, 1.5 eq.). The mixture was stirred at RT for 12 h. The mixture was quenched and extracted as in Intermediate Example 5(a). The solvent was distilled off to afford the product in 94.7% yield (1.8 g). LC-MS (ESI): Calculated mass: 157.2; Observed mass 158.1 [M+H]+ (rt: 0.2-0.3 min).

b) 2-(Pyrrolidin-1-yl) acetic acid

The solution of ethyl 2-(pyrrolidin-1-yl)acetate (1.8 g, 11.95 mmol, 1.0 eq) in 8 N HCl was stirred at 95° C. for 16 h. The mixture was concentrated on vacuum pump and quenched and extracted as in Intermediate Example 15(b). The solvent was distilled off to afford the product in 54% yield (1.4 g). LC-MS (ESI): Calculated mass: 129.1; Observed mass 130.1 [M+H]+ (rt: 0.26 min).

Intermediate Example 29

2-Methyl-4-(4-(4,4,5,5-tetramethyl-1,3,2-dioxaborolan-2-yl)-1H-pyrazol-1-yl) butan-2-ol a) 4-Bromo-2-methylbutan-2-ol To a solution of methyl 3-bromopropanoate (5.0 g, 29.94 mmol, and 1.0 eq) in dry THF was added methyl magnesium bromide at 0° C. The mixture was stirred at RT for 16 h and quenched and extracted as in Intermediate Example 5(c). The solvent was distilled off to afford the crude residue which was purified by column chromatography (60-120 silica gel, 50% ethyl acetate in hexane). Yield 48.9% (2.4 g). LC-MS (ESI): Calculated mass: 167.0; Observed mass 167.1[M+H]+ (rt: 0.8-1.0 min).

b) 4-(4-Bromo-1H-pyrazol-1-yl)-2-methylbutan-2-ol

To a solution of 4-bromo-1H-pyrazole (1 g, 6.84 mmol, 1.0 eq) in DMF were added $K_2CO_3$ (2.3 g, 17.1 mmol, 2.5 eq.) and 4-bromo-2-methylbutan-2-ol (1.7 g, 10.27 mmol, 1.5 eq.). The mixture was stirred at RT for 16 h. The mixture was quenched and extracted as in Intermediate Example 5(a). The solvent was distilled off to afford the product in 60% yield (0.9 g). LC-MS (ESI): Calculated mass 233.0; Observed mass 235.0. [M+H]+ (rt: 0.64 min).

c) 2-Methyl-4-(4-(4,4,5,5-tetramethyl-1,3,2-dioxaborolan-2-yl)-1H-pyrazol-1-yl) butan-2-ol To a degassed ($N_2$ bubbling) solution of the compound of Intermediate Example 29(b) (0.5 g, 2.16 mmol) in 1,4-dioxane (5 ml) were added 4,4,4',4',5,5,5',5'-octamethyl-2,2'-bi(1,3,2-dioxaborolane) (0.824 g, 3.24 mmol, 1.5 eq.), Pd(dppf)Cl$_2$ (0.1766 g, 0.216 mmol, 0.1 eq.) and potassium acetate (0.529 g, 5.40 mmol, 2.5 eq.) using the procedure of Intermediate Example 1(b). The solvent was distilled off which was purified by column chromatography (60-120 silica gel, 15% ethyl acetate in hexane) to yield the product in 49.6% yield (0.3 g). LC-MS (ESI): Calculated mass: 280.1; Observed mass: 281.2 [M+H]+ (rt: 0.8 min).

Intermediate Example 30 tert-Butyl 3-(4-(4,4,5,5-tetramethyl-1,3,2-dioxaborolan-2-yl)-1H-pyrazol-1-yl) pyrrolidine-1-carboxylate a) tert-Butyl 3-(methylsulfonyl) pyrrolidine-1-carboxylate To a solution of tert-butyl 3-hydroxypyrrolidine-1-carboxylate (1.0 g, 5.34 mmol, 1.0 eq) in DCM (10 ml) were added TEA (1.08 g, 10.68 mmol, 2.0 eq) and DMAP (65 mg, 0.53 mmol). The mixture was stirred at RT for 15 min. Then methanesulfonyl chloride (0.730 g 6.41 mmol 1.2 eq) was added and the mixture was stirred for overnight. The mixture was quenched and extracted as in Intermediate Example 5(a). The solvent was distilled off to afford the product in 71.4% yield (1.0 g).

b) tert-Butyl 3-(4-bromo-1H-pyrazol-1-yl) pyrrolidine-1-carboxylate

To a solution of 4-bromo-1H-pyrazole (0.65 g, 4.42 mmol) in DMF were added sodium hydride at 0° C. (0.159 g, 6.6 mmol, 1.5 eq.) and the compound of Intermediate Example 30(a) (1.1 g, 4.42 mmol, 1.0 eq.). The mixture was stirred at RT for 16 h and quenched and extracted as in Intermediate Example 5(a). The solvent was distilled off to afford the crude residue which was purified by column chromatography (60-120 silica gel, 1% methanol in DCM) to yield the product in 61.5% yield (0.85 g).

c) tert-Butyl 3-(4-(4,4,5,5-tetramethyl-1,3,2-dioxaborolan-2-yl)-1H-pyrazol-1-yl) pyrrolidine-1-carboxylate To a degassed ($N_2$ bubbling) solution of the compound of Intermediate Example 30(b) (0.850 g, 2.68 mmol) in 1,4-dioxane (10 ml) were added 4,4,4',4',5,5,5',5'-octamethyl-2,2'-bi(1,3,2-dioxaborolane) (0.819 g, 3.22 mmol, 1.2 eq.), Pd(dppf)Cl$_2$ (0.218 g, 0.268 mmol, 0.1 eq.) and potassium acetate (0.788 g, 8.04 mmol, 3.0 eq.) using the procedure of Intermediate Example 1(b). The solvent was distilled off to give the product in 84.5% yield (0.82 g). LC-MS (ESI): Calculated mass: 363.2; Observed mass: 364.2 [M+H]$^+$ (rt: 1.73 min).

Intermediate Example 31

4-(4-Fluoro-3-nitrophenyl)-1-methyl-1H-pyrazol

A solution of 4-bromo-1-fluoro-2-nitrobenzene (2 g, 9.095 mmol) in 1,4-dioxane (20 ml) was degassed by $N_2$ bubbling for 5 min. 1-Methyl-4-(4,4,5,5-tetramethyl-1,3,2-dioxaborolan-2-yl)-1H-pyrazole (2.27 g, 10.91 mmol, 1.2 eq.) and aqueous sodium carbonate (2.89 g, 27.27 mmol, 3.0 eq.) were added and the mixture was degassed for another 15 min. Pd(PPh$_3$)$_2$Cl$_2$ (0.638 g, 0.909 mmol, 0.1 eq.) was added sequentially and the mixture was further degassed for 15 min and then heated at 90° C. for 2 h. The mixture was quenched and extracted as in Intermediate Example 5(c). The solvent was distilled off to afford the crude residue which was purified by column chromatography (60-120 silica gel, 40-50% ethyl acetate in hexane) to yield the product in 79% yield (1.6 g). $^1$H NMR (300 MHz, DMSO-d$_6$): δ 8.32-8.26 (m, 2H), 8.0-7.97 (m, 2H), 7.62-7.55 (m, 1H).

Intermediate Example 32

1-Cyclopentyl-4-(4,4,5,5-tetramethyl-1,3,2-dioxaborolan-2-yl)-1H-pyrazole a) 1-Cyclopentyl-4-iodo-1H-pyrazole

To a solution of 4-iodo-1H-pyrazole (5 g, 25.78 mmol, 1.0 eq.) in DMF (25 ml) were added K$_2$CO$_3$ (8.908 g, 64.45 mmol, 2.5 eq.) and bromocyclopentane (4.96 g, 33.51 mmol, 1.3 eq.). The mixture was stirred at RT for 12 h. The mixture was quenched and extracted as in Intermediate Example 5(a). The solvent was distilled off to give the product in 89.5% yield. $^1$H NMR (300 MHz, CDCl$_3$): δ 7.49 (s, 1H), 7.45 (s, 1H), 4.66-4.62 (m, 1H), 2.17-2.02 (m, 1H), 2.00-1.96 (m, 2H), 1.93-1.78 (m, 2H), 1.73-1.67 (m, 2H). LC-MS (ESI): Calculated mass: 262; Observed mass: 263 [M+H]$^+$ (rt: 1.57 min).

b) 1-Cyclopentyl-4-(4,4,5,5-tetramethyl-1,3,2-dioxaborolan-2-yl)-1H-pyrazole To a degassed ($N_2$ bubbling) solution of 1-cyclopentyl-4-iodo-1H-pyrazole (6.0 g, 22.90 mmol) in DMSO (60 ml) were added 4,4,4',4',5,5,5',5'-octamethyl-2,2'-bi(1,3,2-dioxaborolane) (8.312 g, 34.35 mmol, 1.5 eq.), Pd(dppf)Cl$_2$ (0.529 g, 0.45 mmol, 0.02 eq.) and potassium acetate (4.494 g, 45.80 mmol, 2.0 eq.) using the procedure of Intermediate Example 1(b). The solvent was distilled off which was purified by column chromatography (60-120 silica gel, 15% ethyl acetate in hexane) to yield the product in 48% yield (2.89 g). $^1$H NMR (300 MHz, CDCl$_3$): δ 7.77 (s, 1H), 7.72 (s, 1H), 4.65 (m, 1H), 2.17-2.02 (m, 1H), 2.00-1.96 (m, 2H), 1.93-1.78 (m, 2H), 1.73-1.67 (m, 2H), 1.30-1.24 (m, 12H). LC-MS (ESI): Calculated mass: 262; Observed mass: 262.92 [M+H]$^+$ (rt: 1.54 min).

Intermediate Example 33 tert-Butyl(5-(4,4,5,5-tetramethyl-1,3,2-dioxaborolan-2-yl)pyridin-2-yl)-carbamate To a solution of 5-(4,4,5,5-tetramethyl-1,3,2-dioxaborolan-2-yl)pyridin-2-amine (0.33 g, 1.5 mmol) in CH$_2$Cl$_2$ (5 ml) at 0° C. were added Boc$_2$O (0.33 g, 1.5 mmol, 1 eq) and Et$_3$N (0.62 ml, 4.5 mmol, 3 eq.). The mixture was stirred at RT for 1 h and then quenched and extracted as in Intermediate Example 5(a). The solvent was distilled off to afford the crude product (0.48 g).

Example 1

N-(2',4'-difluoro-5-(5-(1-methyl-1H-pyrazol-4-yl)-1H-benzo[d]imidazol-1-yl)-biphenyl-3-yl)acetamide a) 1-Bromo-3,5-dinitrobenzene

To a solution of 1,3-dinitrobenzene (25 g, 0.149 mol) in concentrated sulfuric acid (100 ml) at 0° C. was added 1,3-dibromo-5,5-dimethylhydantoin (31.75 g, 0.111 mol, 0.75 eq) portionwise over a period of 30 min. The mixture was stirred for 12 at RT and quenched by the addition of crushed ice. The precipitate formed was filtered and was washed repeatedly with water to obtain white solid. The solid was dried under vacuum to give the product in 87% yield (32 g).

b) 3-Bromo-5-nitroaniline

To a solution of 1-bromo-3,5-dinitrobenzene (20 g, 80.97 mmol) in acetic acid (120 ml) at 90° C. was added iron powder (11.3 g, 202.4 mmol, 2.5 eq) slowly portionwise over a period of 30 min (caution: highly exothermic reaction). After completion of the addition, the mixture was quenched by the addition of crushed ice. The precipitate formed was filtered and was washed with cold water to obtain orange solid. The solid was dried under vacuum to give the product in 80% yield (14 g). $^1$H NMR (300 MHz, CDCl$_3$): δ 10.55 (br s, 2H), 8.46 (s, 1H), 8.19 (s, 1H), 8.02 (s, 1H).

c) N-(3-Bromo-5-nitrophenyl)acetamide

Acetic anhydride (14 ml) was added dropwise at 0° C. to 3-bromo-5-nitroaniline (14 g, 64.5 mmol). The mixture was stirred for 30 min at RT and then quenched by the addition of crushed ice. The precipitate formed was filtered and washed with cold water to obtain off-white solid. The solid was dried under vacuum to give the product in 78% yield (13 g). $^1$H NMR (300 MHz, DMSO-d$_6$): δ 10.54 (br s, 1H), 8.45 (s, 1H), 8.2 (s, 1H), 8.03 (s, 1H), 2.11 (s, 3H).

d) N-(2',4'-difluoro-5-nitrobiphenyl-3-yl)acetamide

A solution of N-(3-bromo-5-nitrophenyl)acetamide (1 g, 3.86 mmol) in 1,2-dimethoxyethane (15 ml) was degassed by N$_2$ bubbling for 5 min. 2,4-Difluorophenylboronic acid (0.727 g, 4.63 mmol, 1.2 eq.) was added and the mixture was degassed for another 5 min. Pd(dppf)Cl$_2$ (0.627 g, 0.769 mmol, 0.2 eq.) and aqueous sodium carbonate (1.22 g, 11.5 mmol, 3.0 eq.) were added sequentially and the mixture was further degassed for 5 min and then heated at 90° C. for 2 h. The mixture was quenched with water and extracted with ethyl acetate (3×50 ml). The combined organic layer was washed with water, brine and dried over sodium sulphate. The solvent was distilled off under reduced pressure and the crude residue was purified by column chromatography (60-120 silica gel, 30% ethyl acetate in hexane) to give the product in 80% yield (0.9 g). $^1$H NMR (300 MHz, DMSO-d$_6$): δ 10.63 (s, 1H), 8.7-8.69 (m, 1H), 8.16 (d, 1H), 8.04 (s, 1H), 7.8-7.67 (m, 1H), 7.53 (m, 1H), 7.34 (m, 1H), 2.19 (s, 3H).

e) N-(5-amino-2',4'-difluorobiphenyl-3-yl)acetamide

To a solution of N-(2',4'-difluoro-5-nitrobiphenyl-3-yl) acetamide (4 g, 13.7 mmol) in methanol (30 ml) and ethyl acetate (15 ml) was added 10% Pd/C (400 mg, 0.1 eq.) and the reaction vessel was purged with nitrogen gas for 5 min. The mixture was then hydrogenated with H$_2$ balloon for 12 h. The mixture was filtered through a pad of celite and the filtrate was concentrated under reduced pressure to afford the compound in 89% yield (3.2 g). $^1$H NMR (300 MHz, DMSO-d$_6$): δ 9.77 (br s, 1H), 7.46-7.42 (m, 1H), 7.35-7.28 (m, 1H), 7.2-7.15 (m, 1H), 6.99 (br s, 1H), 8.86 (d, 1H), 6.39 (d, 1H), 5.45 (br s, 2H), 2.02 (s, 3H).

f) N-(5-(4-bromo-2-nitrophenylamino)-2',4'-difluorobiphenyl-3-yl)acetamide

A solution of N-(5-amino-2',4'-difluorobiphenyl-3-yl)acetamide (3.0 g, 11.44 mmol), 4-bromo-1-fluoro-2-nitrobenzene (2.52 g, 11.44 mmol, 1.0 eq.) and potassium fluoride (0.663 g, 11.44 mmol, 1.0 eq.) in DMF was heated at 130° C. for 5 h. The mixture was quenched and extracted as in Example 1(d). The solvent was distilled off under reduced pressure and the crude residue was purified by column chromatography (60-120 silica gel, 40% ethyl acetate in hexane) to afford the product in 45% yield (2.4 g).

g) N-(5-(2-amino-4-bromophenylamino)-2',4'-difluorobiphenyl-3-yl)acetamide

To a solution of N-(5-(4-bromo-2-nitrophenylamino)-2',4'-difluorobiphenyl-3-yl)acetamide (3.2 g, 6.92 mmol) in THF (30 ml) were added a solution of ammonium chloride (3.7 g, 69.22 mmol, 10 eq.) in water (15 ml) and zinc (4.53 g, 69.22 mmol, 10 eq.). The mixture was stirred at RT for 6 h and filtered. The filtrate was diluted with water and extracted as in Example 1(d). The solvent was distilled off under reduced pressure to afford the product in 87% yield (2.6 g).

h) N-(5-(5-bromo-1H-benzo[d]imidazol-1-yl)-2',4'-difluorobiphenyl-3-yl)-acetamide A mixture of the compound of Example 1(g) (2.6 g, 6.01 mmol) and formic acid (10 ml) was heated at 100° C. for 30 min. The formic acid was distilled off under reduced pressure and the crude was dissolved in ethyl acetate. The ethyl acetate layer was washed with water, brine and dried over sodium sulphate. The solvent was distilled off under reduced pressure to afford the product in 60% yield (1.6 g). $^1$H NMR (300 MHz, DMSO-d$_6$): δ 10.41 (s, 1H), 8.72 (s, 1H), 8.02 (d, 2H), 7.82 (s, 1H), 7.75-7.66 (m, 2H), 7.53-7.41 (m, 3H), 7.27 (m, 1H), 2.11 (s, 3H).

i) N-(2',4'-difluoro-5-(5-(1-methyl-1H-pyrazol-4-yl)-1H-benzo[d]imidazol-1-yl)-biphenyl-3-yl)acetamide A solution of the compound of Example 1(h) (1.5 g, 3.39 mmol) in 1,2-dimethoxyethane (15 ml) was degassed by N$_2$ bubbling for 5 min. 1-Methyl-4-(4,4,5,5-tetramethyl-1,3,2-dioxaborolan-2-yl)-1H-pyrazole (0.847 g, 4.07 mmol, 1.2 eq.) was added and the mixture was degassed for another 5 min. Pd(dppf)Cl$_2$ (0.553 g, 0.678 mmol, 0.2 eq.) and aqueous sodium carbonate (1.08 g, 10.18 mmol, 3.0 eq.) were added following the procedure described in Example 1(d). The crude residue of the product was purified by column chromatography (60-120 silica gel, 80% ethyl acetate in hexane) to afford the product in 67% yield (1.0 g). $^1$H NMR (300 MHz, DMSO-d$_6$): δ 10.4 (s, 1H), 8.64 (s, 1H), 8.2 (1H, s), 8.07 (s, 1H), 7.99 (s, 1H), 7.94 (s, 1H), 7.8-7.68 (m, 2H), 7.6-7.45 (m, 4H), 7.27 (t, 1H), 3.88 (s, 3H), 2.12 (s, 3H); LC-MS (ESI): Calculated mass: 443.45; Observed mass: 444.1 [M+H]$^+$ (rt: 1.2 min).

Example 2

N-(2',4'-difluoro-5-(5-(1-methyl-1H-pyrazol-4-yl)-1H-benzo[d]imidazol-1-yl)-biphenyl-3-yl)methanesulfonamide a) 2',4'-Difluoro-5-(5-(1-methyl-1H-pyrazol-4-yl)-1H-benzo[d]imidazol-1-yl)-biphenyl-3-amine To a solution of N-(2',4'-difluoro-5-(5-(1-methyl-1H-pyrazol-4-yl)-1H-benzo-[d]imidazol-1-yl)biphenyl-3-yl)acetamide of Example 1 (1.0 g, 2.26 mmol) in ethanol (10 ml) was added aqueous solution of NaOH (800 mg, 20 mmol, 8.9 eq.) and the mixture was heated at 85° C. for 5 h. The mixture was quenched and extracted as in Example 1(d). The solvent was distilled off under reduced pressure to afford the product in 66% yield (0.6 g). LC-MS (ESI): Calculated mass: 401.41; Observed mass: 402.1 [M+H]$^+$ (rt: 1.198 min).

b) N-(2',4'-difluoro-5-(5-(1-methyl-1H-pyrazol-4-yl)-1H-benzo[d]imidazol-1-yl)-biphenyl-3-yl)methanesulfonamide To a solution of the compound of Example 2(a) (50 mg, 0.125 mmol) in DCM was added pyridine (20 mg, 0.249 mmol, 2.0 eq.) followed by methanesulfonyl chloride (17 mg, 0.15 mmol, 1.2 eq.). The mixture was stirred for 1 h, quenched with water and extracted with DCM (3×50 ml). The combined organic layer was washed with water, brine and dried over sodium sulphate. The solvent was distilled off under reduced pressure and the crude residue was purified by preparative HPLC to give the product in 33% yield (20 mg). $^1$H NMR (300 MHz, DMSO-$d_6$): δ 10.26 (s, 1H), 8.66 (s, 1H), 8.2 (s, 1H), 7.98 (s, 1H), 7.94 (s, 1H), 7.75-7.67 (m, 2H), 7.57 (t, 3H), 7.45-7.43 (m, 2H), 7.29-7.25 (m, 1H), 3.87 (s, 3H), 3.17 (s, 3H); LC-MS (ESI): Calculated mass: 479.5; Observed mass: 480.2 [M+H]$^+$ (rt: 1.34 min).

Example 3

N-(2',4'-difluoro-5-(5-(1-methyl-1H-pyrazol-4-yl)-1H-benzo[d]imidazol-1-yl)-biphenyl-3-yl)ethanesulfonamide The compound was prepared from the compound of Example 1 using the procedures of Example 2. $^1$H NMR (300 MHz, DMSO-$d_6$): δ 10.29 (s, 1H), 8.84 (s, 1H), 8.22 (s, 1H), 7.99 (s, 1H), 7.96 (s, 1H), 7.78-7.62 (m, 3H), 7.57 (br s, 2H), 7.48-7.43 (m, 2H), 7.29-7.25 (m, 1H), 3.88 (s, 3H), 3.29 (quartet, 2H), 1.25 (t, 3H); LC-MS (ESI): Calculated mass: 493.53; Observed mass: 494.2 [M+H]$^+$ (rt: 1.41 min).

Example 4

N-(2',4'-difluoro-5-(5-(1-methyl-1H-pyrazol-4-yl)-1H-benzo[d]imidazol-1-yl)-biphenyl-3-yl)propane-2-sulfonamide The compound was prepared from the compound of Example 1 using the procedures of Example 2. $^1$H NMR (300 MHz, DMSO-$d_6$): δ 10.29 (s, 1H), 8.81 (s, 1H), 8.22 (s, 1H), 7.99 (s, 1H), 7.95 (s, 1H), 7.75-7.56 (m, 5H), 7.48-7.43 (m, 2H), 7.27 (m, 1H), 3.88 (s, 3H), 3.48-3.44 (m, 1H), 1.3 (d, 6H); LC-MS (ESI): Calculated mass: 507.55; Observed mass: 508.2 [M+H]$^+$ (rt: 1.47 min).

Example 5

N-(2',4'-difluoro-5-(5-(1-methyl-1H-pyrazol-4-yl)-1H-benzo[d]imidazol-1-yl)-biphenyl-3-yl)cyclopropanesulfonamide The compound was prepared from the compound of Example 1 using the procedures of Example 2 and cyclopropane sulfonyl chloride. $^1$H NMR (300 MHz, DMSO-$d_6$): δ 10.29 (s, 1H), 8.88 (s, 1H), 8.23 (s, 1H), 8.0 (s, 1H), 7.96 (s, 1H), 7.76-7.64 (m, 3H), 7.6 (s, 2H), 7.5-7.46 (m, 2H), 7.3-7.25 (m, 1H), 3.88 (s, 3H), 2.88-2.85 (m, 1H), 1.02-1.0 (m, 4H); LC-MS (ESI): Calculated mass: 505.54; Observed mass: 506.1 [M+H]$^+$ (rt: 1.517 min).

Example 6

N-(2',4'-difluoro-5-(5-(1-methyl-1H-pyrazol-4-yl)-1H-benzo[d]imidazol-1-yl)-biphenyl-3-yl)cyclopentanesulfonamide The compound was prepared from the compound of Example 1 using the procedures of Example 2. $^1$H NMR (300 MHz, DMSO-$d_6$): δ 10.25 (s, 1H), 8.96 (s, 1H), 8.24 (s, 1H), 8.0 (s, 1H), 7.97 (s, 1H), 7.77-7.66 (m, 3H), 7.6-7.59 (m, 2H), 7.49 (m, 1H), 7.46-7.43 (m, 1H), 7.3-7.25 (m, 1H), 3.88 (s, 3H), 3.83-3.78 (m, 1H), 1.99-1.93 (m, 4H), 1.69-1.64 (m, 2H), 1.63-1.52 (m, 2H); LC-MS (ESI): Calculated mass: 533.59; Observed mass: 534.3 [M+H]$^+$ (rt: 1.57 min).

Example 7

N-(2',4'-difluoro-5-(5-(1-methyl-1H-pyrazol-4-yl)-1H-benzo[d]imidazol-1-yl)-biphenyl-3-yl)benzenesulfonamide The compound was prepared from the compound of Example 1 using the procedures of Example 2. $^1$H NMR (300 MHz, DMSO-$d_6$): δ 8.57 (s, 1H), 8.21 (s, 1H), 7.96-7.95 (m, 2H), 7.88-7.86 (m, 2H), 7.72-7.61 (m, 4H), 7.57-7.55 (m, 2H), 7.5 (br s, 1H), 7.45-7.32 (m, 4H), 7.26-7.22 (m, 1H), 3.88 (s, 3H); LC-MS (ESI): Calculated mass: 541.57; Observed mass: 542.1 [M+H]$^+$ (rt: 1.642 min).

Example 8

N-(5-(5-(1-(2-(dimethylamino)ethyl)-1H-pyrazol-4-yl)-1H-benzo[d]imidazol-1-yl)-2',4'-difluorobiphenyl-3-yl)acetamide A solution of compound of Example 1(h) (7 g, 15.83 mmol) in 1,2-dimethoxyethane (200 ml) was degassed by N$_2$ bubbling for 5 min. N,N-dimethyl-2-(4-(4,4,5,5-tetramethyl-1,3,2-dioxaborolan-2-yl)-1H-pyrazol-1-yl)ethanamine of Intermediate Example 1 (6.3 g, 23.74 mmol, 1.5 eq.) was added and the mixture was degassed for another 5 min. Pd(PPh$_3$)$_4$ (1.83 g, 1.583 mmol, 0.1 eq.) and aqueous sodium carbonate (5.03 g, 47.5 mmol, 3.0 eq.) were added following the procedure of Example 1(d). The crude residue of the product was purified by column chromatography (neutral alumina, 80% ethyl acetate in hexane) to give the product in 19% yield (1.5 g). $^1$H NMR (300 MHz, DMSO-$d_6$): δ; 10.45 (s, 1H), 8.8 (s, 1H), 8.35 (s, 1H), 8.15 (s, 2H), 8.05 (s, 1H), 7.6-7.7 (m, 4H), 7.4-7.55 (m, 2H), 7.2-7.3 (m, 1H), 4.56 (t, 2H), 3.65-3.63 (m, 2H), 2.85 (s, 6H), 2.12 (s, 3H); LC-MS (ESI): Calculated mass: 500.54; Observed mass: 501.2 [M+H]$^+$ (rt: 0.277 min).

Example 9

N-(5-(5-(1-(2-(dimethylamino)ethyl)-1H-pyrazol-4-yl)-1H-benzo[d]imidazol-1-yl)-2',4'-difluorobiphenyl-3-yl)methanesulfonamide a) 5-(5-(1-(2-(dimethylamino)ethyl)-1H-pyrazol-4-yl)-1H-benzo[d]imidazol-1-yl)-2',4'-difluorobiphenyl-3-amine To a solution of the compound of Example 8 (1.5 g, 3.0 mmol) in ethanol (30 ml) was added aqueous solution of NaOH (1.5 g, 37.5 mmol, 12.5 eq.) and the mixture was heated at 100° C. for 4 h. The mixture was quenched and extracted as in Example 1(d). The solvent was distilled off to afford the product in 58% yield (0.8 g).

b) N-(5-(5-(1-(2-(dimethylamino)ethyl)-1H-pyrazol-4-yl)-1H-benzo[d]imidazol-1-yl)-2',4'-difluorobiphenyl-3-yl)methanesulfonamide To a solution of the compound of Example 9(a) (200 mg, 0.436 mmol) in DCM was added pyridine (69 mg, 0.872 mmol, 2.0 eq.) followed by methanesulfonyl chloride (75 mg, 0.654 mmol, 1.5 eq.). The mixture was stirred for 1 h and quenched and extracted as in Example 2(b). The solvent was distilled off and the crude residue was purified by preparative HPLC to give the product in 13% yield (30 mg). $^1$H NMR (300 MHz, DMSO-$d_6$): δ 8.66 (s, 1H), 8.26 (s, 1H), 7.99 (d, 1H), 7.96 (s, 1H), 7.81-7.7 (m, 2H), 7.68 (s, 1H), 7.62-7.57 (m, 3H), 7.5-7.44 (m, 2H), 7.3-7.25 (m, 1H), 4.23 (t, 2H), 3.18 (s, 3H), 2.75-2.73 (m, 2H), 2.12 (s, 6H); LC-MS (ESI): Calculated mass: 536.6; Observed mass: 537.3 [M+H]$^+$ (rt: 0.26 min).

Example 10

N-(5-(5-(1-(2-(dimethylamino)ethyl)-1H-pyrazol-4-yl)-1H-benzo[d]imidazol-1-yl)-2',4'-difluorobiphenyl-3-yl)ethanesulfonamide The compound was prepared from the compound of Example 8 using the procedures of Example 9. $^1$H NMR (300 MHz, DMSO-$d_6$): δ 10.35 (s, 1H), 9.2-9.4 (br s, 1H), 8.8 (s, 1H), 8.4 (s, 1H), 8.15 (s, 1H), 8.0 (s, 1H), 7.6-7.8 (m, 2H), 7.6 (s, 2H), 7.4-7.5 (m, 2H), 7.2-7.3 (m, 1H), 4.55 (t, 2H), 3.65-3.63 (m, 2H), 3.3 (quartet, 2H), 2.85 (s, 6H), 1.26 (t, 3H); LC-MS (ESI): Calculated mass: 550.62; Observed mass: 551.2 [M+H]$^+$ (rt: 0.365 min).

Example 11

N-(5-(5-(1-(2-(dimethylamino)ethyl)-1H-pyrazol-4-yl)-1H-benzo[d]imidazol-1-yl)-2',4'-difluorobiphenyl-3-yl)propane-2-sulfonamide The compound was prepared from the compound of Example 8 using the procedures of Example 9. $^1$H NMR (300 MHz, CD$_3$OD): δ 8.5 (s, 1H), 8.1 (s, 1H), 7.9-7.95 (d, 2H), 7.55-7.7 (m, 5H), 7.45-7.5 (m, 2H), 7.05-7.1 (m, 2H), 4.32 (t, 2H), 3.44-3.39 (m, 1H), 2.85 (t, 2H), 2.3 (s, 6H), 1.4 (d, 6H); LC-MS (ESI): Calculated mass: 564.65; Observed mass: 565.2 [M+H]$^+$ (rt: 0.507 min).

Example 12

N-(2',4'-difluoro-5-(5-(1-(2-morpholinoethyl)-1H-pyrazol-4-yl)-1H-benzo[d]-imidazol-1-yl)biphenyl-3-yl)acetamide The compound was prepared using the procedures of Example 8 using the compound of Intermediate Example 2. $^1$H NMR (300 MHz, DMSO-$d_6$): δ 10.43 (s, 1H), 8.82 (s, 1H), 8.35 (s, 1H), 8.13 (s, 2H), 8.05 (s, 1H), 7.79-7.73 (m, 3H), 7.67-7.63 (m, 1H), 7.51-7.44 (m, 2H), 7.31-7.27 (m, 1H), 4.6 (t, 2H), 3.93-3.88 (m, 4H), 3.67-3.63 (m, 4H), 3.82-3.78 (m, 2H), 2.1 (s, 3H); LC-MS (ESI): Calculated mass: 542.58; Observed mass: 543.2 [M+H]$^+$ (rt: 0.24 min).

Example 13

N-(2',4'-difluoro-5-(5-(1-(2-morpholinoethyl)-1H-pyrazol-4-yl)-1H-benzo[d]-imidazol-1-yl)biphenyl-3-yl)methanesulfonamide The compound was prepared from the compound of Example 12 using the procedures of Example 9. $^1$H NMR (300 MHz, DMSO-$d_6$): δ 10.3 (s, 1H), 8.8 (s, 1H), 8.35 (s, 1H), 8.15 (s, 1H), 8.05 (s, 1H), 7.7-7.8 (m, 2H), 7.6-7.7 (m, 1H), 7.55-7.6 (m, 2H), 7.4-7.5 (m, 2H), 7.25-7.35 (m, 1H), 4.59 (t, 2H), 4.0 (m, 4H), 3.82-3.78 (m, 2H), 3.5 (m, 4H), 3.18 (s, 3H); LC-MS (ESI): Calculated mass: 578.63; Observed mass: 579.2 [M+H]$^+$ (rt: 0.383 min).

Example 14

N-(2',4'-difluoro-5-(5-(1-(2-morpholinoethyl)-1H-pyrazol-4-yl)-1H-benzo[d]-imidazol-1-yl)biphenyl-3-yl)ethanesulfonamide The compound was prepared from the compound of Example 12 using the procedures of Example 9. $^1$H NMR (300 MHz, DMSO-$d_6$): δ 10.35 (s, 1H), 8.85 (s, 1H), 8.35 (s, 1H), 8.15 (s, 1H), 8.05 (s, 1H), 7.77-7.68 (m, 3H), 7.58 (s, 2H), 7.48-7.45 (m, 2H), 7.31-7.27 (m, 1H), 4.59 (t, 2H), 4.0-3.92 (m, 4H), 3.82-3.78 (m, 2H), 3.5-3.41 (m, 4H), 3.29 (quartet, 2H), 1.25 (t, 3H); LC-MS (ESI): Calculated mass: 592.66; Observed mass: 593.2 [M+H]$^+$ (rt: 0.419 min).

Example 15

N-(2',4'-difluoro-5-(5-(1-(2-morpholinoethyl)-1H-pyrazol-4-yl)-1H-benzo[d]-imidazol-1-yl)biphenyl-3-yl)propane-2-sulfonamide The compound was prepared from the compound of Example 12 using the procedures of Example 9. $^1$H NMR (300 MHz, CD$_3$OD): δ 8.5 (s, 1H), 8.1 (s, 1H), 7.93 (s, 1H), 7.9 (s, 1H), 7.6-7.7 (m, 4H), 7.5 (s, 2H), 7.1-7.15 (m, 2H), 4.33 (t, 2H), 3.67 (t, 4H), 3.46-3.39 (m, 1H), 2.85 (t, 2H), 2.52 (t, 4H), 1.4 (d, 6H); LC-MS (ESI): Calculated mass: 606.69; Observed mass: 607.3 [M+H]$^+$ (rt: 0.62 min).

Example 16

N-(2',4'-difluoro-5-(5-(1-(2-morpholinoethyl)-1H-pyrazol-4-yl)-1H-benzo[d]-imidazol-1-yl)biphenyl-3-yl)cyclopropanesulfonamide The compound was prepared from the compound of Example 12 using the procedures of Example 9 and cyclopropane sulfonyl chloride. $^1$H NMR (300 MHz, DMSO-$d_6$): δ 8.6 (s, 1H), 8.25 (s, 1H), 7.98 (s, 1H), 7.95 (s, 7.74-7.65 (m, 2H), 7.59-7.55 (m, 1H), 7.45-7.38 (m, 2H), 7.28-7.24 (m, 4H), 4.24 (t, 2H), 3.56 (t, 4H), 2.75 (t, 2H), 2.67-2.64 (m, 1H), 2.42 (t, 4H), 0.91-0.88 (m, 4H); LC-MS (ESI): Calculated mass: 604.67; Observed mass: 605.4 [M+H]$^+$ (rt: 0.68 min).

Example 17

N-(2',4'-difluoro-5-(5-(1-methyl-1H-1,2,3-triazol-4-yl)-1H-benzo[d]imidazol-1-yl)biphenyl-3-yl)acetamide a) N-(2',4'-difluoro-5-(4-iodo-2-nitrophenylamino)biphenyl-3-yl)acetamide A solution of the compound of Example 1(e) (4.6 g, 17.54 mmol), 1-fluoro-4-iodo-2-nitrobenzene of Intermediate Example 3 (4.683 g, 17.54 mmol, 1.0 eq.) and potassium fluoride (1.22 g, 21.05 mmol, 1.2 eq.) in DMF was heated at 130° C. for 5 h. The mixture was quenched and extracted as in Example 1(d). The solvent was distilled off and the crude residue was purified by column chromatography (60-120 silica gel, 50% ethyl acetate in hexane) to give the product in 76% yield (6.8 g). $^1$H NMR (300 MHz, DMSO-$d_6$): δ

10.15 (br s, 1H), 9.41 (s, 1H), 8.35 (d, 1H), 7.78 (dd, 1H), 7.66-7.54 (m, 3H), 7.39 (m, 1H), 7.22 (m, 1H), 7.14-7.11 (m, 2H), 2.06 (s, 3H).

b) N-(5-(2-amino-4-iodophenylamino)-2',4'-difluorobiphenyl-3-yl)acetamide

To a solution of the compound of Example 17(a) (3.0 g, 5.89 mmol) in THF (30 ml) were added a solution of ammonium chloride (1.26 g, 23.56 mmol, 4 eq.) in water (5 ml) and zinc (1.54 g, 23.56 mmol, 4 eq.). The mixture was stirred at RT for 0.5 h and filtered. The filtrate was diluted with water and extracted as in Example 1(d). The solvent was distilled off to afford the product in 77% yield (2.18 g). $^1$H NMR (300 MHz, DMSO-$d_6$): δ 9.85 (br s, 1H), 7.44 (quartet, 1H), 7.36-7.31 (m, 2H), 7.19-7.14 (m, 2H), 7.07 (s, 1H), 7.02 (s, 1H), 6.82 (s, 2H), 6.53 (br s, 1H), 5.03 (br s, 2H), 2.0 (s, 3H).

c) N-(2',4'-difluoro-5-(5-iodo-1H-benzo[d]imidazol-1-yl)biphenyl-3-yl)acetamide A mixture of the compound of Example 17(b) (2.18 g, 4.55 mmol) and formic acid (10 ml) was heated at 100° C. for 30 min. The formic acid was distilled off and the crude was dissolved in ethyl acetate. The ethyl acetate layer was washed with water, brine and dried over sodium sulphate. The solvent was distilled off to afford the product in 47% yield (1.05 g).

d) N-(2',4'-difluoro-5-(5-((trimethylsilyl)ethynyl)-1H-benzo[d]imidazol-1-yl)-biphenyl-3-yl)acetamide A solution of the compound of Example 17(c) (0.7 g, 1.43 mmol) in DMF-Et$_3$N (1:1; 20 ml) was degassed by N$_2$ bubbling for 15 min. Pd(PPh$_3$)$_4$ (0.165 g, 0.143 mmol, 0.1 eq.), copper(I) iodide (0.027 g, 0.143 mmol, 0.1 eq.) and ethynyltrimethylsilane (0.4 ml, 2.86 mmol, 2 eq.) were added sequentially and the mixture was stirred for 12 h at RT. The mixture was quenched and extracted as in Example 1(d). The solvent was distilled off and the crude residue was purified by column chromatography (60-120 silica gel, 60% ethyl acetate in hexane) to give the product in 68% yield (0.45 g). $^1$H NMR (300 MHz, DMSO-$d_6$): δ 10.42 (s, 1H), 8.79 (br s, 1H), 8.03 (s, 1H), 7.89-7.84 (m, 2H), 7.78-7.7 (m, 2H), 7.51-7.41 (m, 3H), 7.29-7.24 (m, 1H), 2.12 (s, 3H), 0.23 (s, 9H).

e) N-(5-(5-ethynyl-1H-benzo[d]imidazol-1-yl)-2',4'-difluorobiphenyl-3-yl)-acetamide To a solution of the compound of Example 17(d) (0.41 g, 0.9 mmol) in THF at 0° C. was added TBAF (1M in THF; 0.28 ml, 1.07 mmol, 1.2 eq.) and the mixture was stirred for 0.5 h. The mixture was filtered over a pad of silica and distilled to give the product in 89% yield (0.31 g). $^1$H NMR (300 MHz, DMSO-$d_6$): δ 10.3 (br s, 1H), 8.79 (s, 1H), 8.1 (s, 1H), 7.96 (s, 1H), 7.88 (s, 1H), 7.82-7.73 (m, 2H), 7.54-7.45 (m, 3H), 7.34-7.27 (m, 1H), 4.2 (s, 1H), 2.16 (s, 3H).

f) N-(2',4'-difluoro-5-(5-(1-methyl-1H-1,2,3-triazol-4-yl)-1H-benzo[d]imidazol-1-yl)biphenyl-3-yl)acetamide A mixture of the compound of Example 17(e) (115 mg, 0.297 mmol), sodium azide (19 mg, 0.297 mmol, 1.0 eq.), methyl iodide (42 mg, 0.297 mmol, 1.0 eq.), sodium ascorbate (59 mg, 0.297 mmol, 1.0 eq.) and copper sulfate pentahydrate (37 mg, 0.149 mmol, 0.5 eq.) in DMSO, THF and water (1:1:1, 3 ml) was stirred for 12 h at RT. The mixture was quenched with water and the precipitate formed was filtered and dried. The crude product was purified by preparative HPLC to give the product in 15% yield (20 mg). $^1$H NMR (300 MHz, DMSO-$d_6$): δ 10.4 (s, 1H), 8.7 (s, 1H), 8.6 (s, 1H), 8.25 (s, 1H), 8.05 (s, 1H), 7.7-7.95 (m, 4H), 7.4-7.55 (m, 2H), 7.2-7.3 (m, 1H), 4.1 (s, 3H), 2.1 (s, 3H); LC-MS (ESI): Calculated mass: 444.44; Observed mass: 445.1 [M+H]$^+$ (rt: 1.039 min).

Example 18

N-(2',4'-difluoro-5-(5-(1-methyl-1H-1,2,3-triazol-4-yl)-1H-benzo[d]imidazol-1-yl)biphenyl-3-yl)methanesulfonamide a) 2',4'-difluoro-5-(5-(1-methyl-1H-1,2,3-triazol-4-yl)-1H-benzo[d]imidazol-1-yl)biphenyl-3-amine To a solution of the compound of Example 17 (300 mg, 0.675 mmol) in ethanol (10 ml) was added aqueous solution of NaOH (338 mg, 8.44 mmol, 12.5 eq.) and the mixture was heated at 85° C. for 5 h. The mixture was quenched and extracted as in Example 1(d). The solvent was distilled off to afford the product in 44% yield (0.12 g). LC-MS (ESI): Calculated mass: 402.4; Observed mass: 403.4 [M+H]$^+$ (rt: 1.03 min).

b) N-(2',4'-difluoro-5-(5-(2-methyl-2H-1,2,3-triazol-4-yl)-1H-benzo[d]imidazol-1-yl)biphenyl-3-yl)methanesulfonamide To a solution of the compound of Example 18(a) (90 mg, 0.224 mmol) in DCM was added pyridine (35 mg, 0.447 mmol, 2.0 eq.) followed by methanesulfonyl chloride (26 mg, 0.224 mmol, 1.0 eq.). The reaction was monitored by LCMS. After completion of the reaction the solvent was removed and the crude product was purified by preparative HPLC to give the product in 13% yield (14 mg). $^1$H NMR (300 MHz, DMSO-$d_6$): δ 10.31 (s, 1H), 8.84 (br s, 1H), 8.61 (s, 1H), 8.25 (s, 1H), 7.92 (d, 1H), 7.8-7.74 (m, 2H), 7.59 (d, 2H), 7.49-7.43 (m, 2H), 7.31-7.26 (m, 1H), 4.11 (s, 3H), 3.18 (s, 3H); LC-MS (ESI): Calculated mass: 480.49; Observed mass: 481.1 [M+H]$^+$ (rt: 1.357 min).

Example 19

N-(2',4'-difluoro-5-(5-(2-methyl-2H-1,2,3-triazol-4-yl)-1H-benzo[d]imidazol-1-yl)biphenyl-3-yl)benzenesulfonamide The compound was prepared from the compound of Example 17 using the procedures of Example 18. $^1$H NMR (300 MHz, DMSO-$d_6$): δ 10.9 (s, 1H), 8.73 (s, 1H), 8.62 (s, 1H), 8.22 (s, 1H), 7.9-7.87 (m, 3H), 7.71-7.62 (m, 4H), 7.55 (s, 1H), 7.47-7.39 (m, 4H), 7.28-7.24 (m, 1H), 4.12 (s, 3H); LC-MS (ESI): Calculated mass: 542.56; Observed mass: 543.2 [M+H]$^+$ (rt: 1.52 min).

Example 20

N-(5-(5-(1-(2-(dimethylamino)ethyl)-1H-1,2,3-triazol-4-yl)-1H-benzo[d]-imidazol-1-yl)-2',4'-difluorobiphenyl-3-yl)acetamide A mixture of the compound of Example 17(e) (115 mg, 0.297 mmol), 2-azido-N,N-dimethylethanamine (34 mg, 0.297 mmol, 1.0 eq.), sodium ascorbate (59 mg, 0.297 mmol, 1.0 eq.) and copper sulfate pentahydrate (37 mg, 0.149 mmol, 0.5 eq.) in DMSO, THF and water (1:1:1, 3 ml) was stirred for 12 h at RT. The mixture was quenched with water and the precipitate formed was filtered and dried. The crude product was purified by preparative HPLC to give the product in 27% yield (40 mg). $^1$H NMR (300 MHz, DMSO-$d_6$): δ 10.45 (s, 1H), 8.71 (s, 2H), 8.25 (s, 1H), 8.1 (s, 1H), 7.9 (d, 1H), 7.81-7.72 (m, 3H), 7.52 (s, 1H), 7.48-7.42 (m, 1H), 7.3-7.25 (m, 1H), 4.82 (br s, 2H), 3.59 (br s, 2H), 2.78 (br s, 6H), 2.1 (s, 3H); LC-MS (ESI): Calculated mass: 501.53; Observed mass: 502.2 [M+H]$^+$ (rt: 0.259 min).

Example 21

N-(2',4'-difluoro-5-(5-(1-(2-morpholinoethyl)-1H-1, 2,3-triazol-4-yl)-1H-benzo-[d]imidazol-1-yl)biphenyl-3-yl)acetamide The compound was prepared from the compound of Example 17(e) using the procedures of Example 20. $^1$H NMR (300 MHz, DMSO-$d_6$): δ 10.42 (s, 1H), 8.79 (s, 1H), 8.72 (s, 1H), 8.27 (s, 1H), 8.12 (s, 1H), 7.94-7.92 (m, 1H), 7.82-7.72 (m, 3H), 7.54 (s, 1H), 7.48-7.42 (m, 1H), 7.3-7.25 (m, 1H), 4.89 (t, 2H), 4.09 (m, 4H), 3.76 (m, 2H), 2.54-2.46 (m, 4H), 2.1 (s, 3H); LC-MS (ESI): Calculated mass: 543.57; Observed mass: 544.2 [M+H]$^+$ (rt: 0.277 min).

Example 22

N-(2',4'-difluoro-5-(5-(oxazol-5-yl)-1H-benzo[d] imidazol-1-yl)biphenyl-3-yl)-acetamide a) N-(2',4'-difluoro-5-(4-formyl-2-nitrophenylamino) biphenyl-3-yl)acetamide A solution of the compound of Example 1(e) (4.3 g, 16.4 mmol), 4-fluoro-3-nitrobenzaldehyde of the Intermediate Example 4 (2.46 g, 16.4 mmol, 1.0 eq.) and potassium fluoride (0.95 g, 16.4 mmol, 1.0 eq.) in DMF was heated at 130° C. for 5 h. The mixture was quenched and extracted as in Example 1(d). The solvent was distilled off and the crude residue was purified by column chromatography (60-120 silica gel, 50% ethyl acetate in hexane) to yield the product in 45% yield (3.0 g). $^1$H NMR (300 MHz, DMSO-$d_6$): δ 10.22 (s, 1H), 9.85 (s, 1H), 8.7 (s, 1H), 7.93-7.9 (m, 1H), 7.73-7.58 (m, 3H), 7.43-7.2 (m, 5H), 2.07 (s, 3H).

b) N-(2',4'-difluoro-5-(2-nitro-4-(oxazol-5-yl)phenylamino)biphenyl-3-yl)-acetamide To a solution of the compound of Example 22(a) (2.0 g, 4.86 mmol) in methanol was added potassium carbonate (0.74 g, 5.35 mmol, 1.1 eq.) and the mixture was stirred for 10 min at RT. Toluenesulfonylmethyl isocyanide (1.044 g, 5.35 mmol, 1.1 eq.) was added and the mixture was refluxed for 4 h. The methanol was distilled off and water was added to the crude. The mixture was extracted as in Example 1(d). The solvent was distilled off and the residue was purified by column chromatography (60-120 silica gel, 40% ethyl acetate in hexane) to give the product in 64% yield (1.4 g). $^1$H NMR (300 MHz, DMSO-$d_6$): δ 10.17 (s, 1H), 9.59 (s, 1H), 8.45 (s, 1H), 8.4 (d, 1H), 7.91-7.87 (m, 1H), 7.71 (s, 2H), 7.61-7.56 (m, 2H), 7.44-7.37 (m, 2H), 7.23-7.17 (m, 2H), 2.07 (s, 3H).

c) N-(5-(2-amino-4-(oxazol-5-yl)phenylamino)-2',4'-difluorobiphenyl-3-yl)-acetamide To a solution of the compound of Example 22(b) (1 g, 2.22 mmol) in methanol (35 ml) and ethyl acetate (15 ml) was added 10% Pd/C (200 mg, 0.2 eq.) and the reaction vessel was purged with nitrogen gas for 5 min. The mixture was then hydrogenated with $H_2$ balloon for 12 h. The mixture was filtered through a pad of celite and the filtrate was concentrated to afford the compound in 86% yield (0.8 g).

d) N-(2',4'-difluoro-5-(5-(oxazol-5-yl)-1H-benzo[d] imidazol-1-yl)biphenyl-3-yl)acetamide A mixture of the compound of Example 22(c) (1.5 g, 3.57 mmol) and formic acid (6 ml) was heated at 100° C. for 30 min. The formic acid was distilled off and the crude was dissolved in ethyl acetate. The ethyl acetate layer was washed with water, brine and dried over sodium sulphate. The solvent was distilled off to afford the product in 52% yield (0.8 g). $^1$H NMR (300 MHz, DMSO-$d_6$): δ 10.44 (s, 1H), 8.74 (s, 1H), 8.45 (s, 1H), 8.15 (s, 1H), 8.07 (s, 1H), 7.82-7.73 (m, 5H), 7.52 (s, 1H), 7.5-7.2 (m, 1H), 7.27-7.23 (m, 1H), 2.11 (s, 3H); LC-MS (ESI): Calculated mass: 430.41; Observed mass: 431.2 [M+H]$^+$ (rt: 1.42 min).

Example 23

N-(2',4'-difluoro-5-(5-(oxazol-5-yl)-1H-benzo[d] imidazol-1-yl)biphenyl-3-yl)-methanesulfonamide a) 2',4'-difluoro-5-(5-(oxazol-5-yl)-1H-benzo[d]imidazol-1-yl)biphenyl-3-amine To a solution of the compound of Example 22 (800 mg, 1.86 mmol) in ethanol (10 ml) was added aqueous solution of NaOH (640 mg, 16 mmol, 8.6 eq.) and the mixture was heated at 85° C. for 5 h. The mixture was quenched and extracted as in Example 1(d). The solvent was distilled off to afford the product in 69% yield (0.5 g). LC-MS (ESI): Calculated mass: 388.37; Observed mass: 389.1 [M+H]$^+$ (rt: 1.517 min).

b) N-(2',4'-difluoro-5-(5-(oxazol-5-yl)-1H-benzo[d] imidazol-1-yl)biphenyl-3-yl)methanesulfonamide To a solution of the compound of Example 23(a) (100 mg, 0.258 mmol) in DCM was added pyridine (40 mg, 0.515 mmol, 2.0 eq.) followed by methanesulfonyl chloride (35 mg, 0.309 mmol, 1.2 eq.). The reaction was stirred for 1 h and quenched and extracted as in Example 2(b). The solvent was distilled off and the crude residue was purified by preparative HPLC to give the product in 10% yield (12 mg). $^1$H NMR (300 MHz, DMSO-$d_6$): δ 10.3 (s, 1H), 8.78 (s, 1H), 8.46 (s, 1H), 8.16 (s, 1H), 7.8-7.76 (m, 4H), 7.6-7.56 (m, 2H), 7.46 (m, 2H), 7.34-7.27 (m, 1H), 3.18 (s, 3H); LC-MS (ESI): Calculated mass: 466.46; Observed mass: 467 [M+H]$^+$ (rt: 1.553 min).

Example 24

N-(2',4'-difluoro-5-(5-(oxazol-5-yl)-1H-benzo[d] imidazol-1-yl)biphenyl-3-yl)-ethanesulfonamide The compound was prepared from the compound of Example 22 using the procedures of Example 23. $^1$H NMR (300 MHz, DMSO-$d_6$): δ 10.33 (s, 1H), 8.78 (s, 1H), 8.46 (s, 1H), 8.15 (s, 1H), 7.8-7.73 (m, 4H), 7.58-7.55 (m, 2H), 7.48-7.43 (m, 2H), 7.29-7.25 (m, 1H), 3.29 (quartet, 2H), 1.25 (t, 3H); LC-MS (ESI): Calculated mass: 480.49; Observed mass: 481.1 [M+H]+ (rt: 1.517 min).

Example 25

N-(2',4'-difluoro-5-(5-(oxazol-5-yl)-1H-benzo[d]imidazol-1-yl)biphenyl-3-yl)-propane-2-sulfonamide The compound was prepared from the compound of Example 22 using the procedures of Example 23. 1H NMR (300 MHz, DMSO-$d_6$): δ 10.31 (s, 1H), 8.8 (s, 1H), 8.46 (s, 1H), 8.16 (s, 1H), 7.78 (d, 4H), 7.58 (m, 2H), 7.5-7.43 (m, 2H), 7.3-7.25 (m, 1H), 3.49-3.47 (m, 1H), 1.3 (d, 6H); LC-MS (ESI): Calculated mass: 495.41; Observed mass: 496.1 [M+H]+ (rt: 1.66 min).

Example 26

N-(2',4'-difluoro-5-(5-(oxazol-5-yl)-1H-benzo[d]imidazol-1-yl)biphenyl-3-yl)-benzenesulfonamide The compound was prepared from the compound of Example 22 using the procedures of Example 23. 1H NMR (300 MHz, DMSO-$d_6$): δ 10.9 (s, 1H), 8.77 (s, 1H), 8.47 (s, 1H), 8.14 (s, 1H), 7.88 (d, 2H), 7.78-7.74 (m, 2H), 7.72-7.61 (m, 4H), 7.54 (s, 1H), 7.49-7.45 (m, 1H), 7.43-7.39 (m, 3H), 7.27-7.22 (m, 1H); LC-MS (ESI): Calculated mass: 528.53; Observed mass: 529.1 [M+H]+ (rt: 1.641 min).

Example 27

N-(5-(5-(3,5-dimethylisoxazol-4-yl)-1H-benzo[d]imidazol-1-yl)-2',4'-difluorobiphenyl-3-yl)acetamide The compound was prepared from the compound of Example 1(h) using the procedures of Example 1. 1H NMR (300 MHz, DMSO-$d_6$): δ 12.15 (br s, 1H), 10.24 (s, 1H), 8.67 (s, 1H), 8.08 (s, 1H), 7.82 (s, 1H), 7.78-7.73 (m, 2H), 7.65 (s, 1H), 7.53 (s, 1H), 7.48-7.43 (m, 1H), 7.3-7.25 (m, 2H), 2.23 (s, 6H), 2.12 (s, 3H); LC-MS (ESI): Calculated mass: 457.47; Observed mass: 458 [M+H]+ (rt: 0.75 min).

Example 28

N-(5-(5-(1H-pyrazol-1-yl)-1H-benzo[d]imidazol-1-yl)-2',4'-difluorobiphenyl-3-yl)acetamide To a solution of the compound of Example 1(h) (5 g, 11.31 mmol) in DMF (20 ml) were added pyrazole (5 g, 73.49 mmol, 6.5 eq.), copper(I) oxide (4.86 g, 33.92 mmol, 3.0 eq.) and cesium carbonate (14.73 g, 45.22 mmol, 4.0 eq.) and the mixture was heated at 90° C. for 48 h. The mixture was quenched and extracted as in Example 1(d). The solvent was distilled off and the crude residue was purified by column chromatography (neutral alumina, 1% methanol in DCM) to give the product in 49% yield (2.4 g). 1H NMR (300 MHz, DMSO-$d_6$): δ 10.43 (s, 1H), 8.8 (s, 1H), 8.6 (d, 1H), 8.25 (s, 1H), 8.1 (s, 1H), 7.9-8.0 (m, 1H), 7.7-7.9 (m, 4H), 7.4-7.6 (m, 2H), 7.2-7.3 (m, 1H), 6.6 (m, 1H), 2.1 (s, 3H); LC-MS (ESI): Calculated mass: 429.42; Observed mass: 430.4 [M+H]+ (rt: 1.46 min).

Example 29

N-(5-(5-(1H-pyrazol-1-yl)-1H-benzo[d]imidazol-1-yl)-2',4'-difluorobiphenyl-3-yl)methanesulfonamide a) 5-(5-(1H-pyrazol-1-yl)-1H-benzo[d]imidazol-1-yl)-2',4'-difluorobiphenyl-3-amine To a solution of the compound of Example 28 (2.4 g, 5.59 mmol) in ethanol (40 ml) was added aqueous solution of NaOH (2.4 g, 60 mmol, 10.7 eq.) and the mixture was heated at 85° C. for 5 h. The mixture was quenched and extracted as in Example 1(d). The solvent was distilled off to afford the product in 69% yield (1.5 g).

b) N-(5-(5-(1H-pyrazol-1-yl)-1H-benzo[d]imidazol-1-yl)-2',4'-difluorobiphenyl-3-yl)methanesulfonamide To a solution of the compound of Example 29(a) (250 mg, 0.645 mmol) in DCM was added pyridine (102 mg, 1.29 mmol, 2.0 eq.) followed by methanesulfonyl chloride (100 mg, 0.877 mmol, 1.4 eq.). The mixture was stirred for 1 h and quenched and extracted as in Example 2(b). The solvent was distilled off and the residue was purified by preparative HPLC to give the product in 33% yield (100 mg). 1H NMR (300 MHz, DMSO-$d_6$): δ 10.31 (s, 1H), 8.85 (s, 1H), 8.62 (d, 1H), 8.25 (d, 2H), 7.95-7.92 (m, 1H), 7.84-7.77 (m, 3H), 7.62 (s, 1H), 7.58 (s, 1H), 7.51-7.44 (m, 2H), 7.33-7.27 (m, 1H), 3.19 (s, 3H); LC-MS (ESI): Calculated mass: 465.48; Observed mass: 466.1 [M+H]+ (rt: 1.606 min).

Example 30

N-(5-(5-(1H-pyrazol-1-yl)-1H-benzo[d]imidazol-1-yl)-2',4'-difluorobiphenyl-3-yl)ethanesulfonamide The compound was prepared from the compound of Example 28 using the procedures of Example 29. 1H NMR (300 MHz, DMSO-$d_6$): δ 10.3-10.4 (Br s, 1H), 8.75 (s, 1H), 8.6 (d, 1H), 8.25 (d, 1H), 7.9-7.95 (dd, 1H), 7.7-7.8 (m, 3H), 7.55 (m, 2H), 7.4-7.5 (m, 2H), 7.3 (m, 1H), 6.55 (m, 1H), 4.1 (q, 2H), 1.2-1.3 (t, 3H); LC-MS (ESI): Calculated mass: 479.5; Observed mass: 480.1 [M+H]+ (rt: 1.641 min).

Example 31

N-(5-(5-(1H-pyrazol-1-yl)-1H-benzo[d]imidazol-1-yl)-2',4'-difluorobiphenyl-3-yl)propane-2-sulfonamide The compound was prepared from the compound of Example 28 using the procedures of Example 29. 1H NMR (300 MHz, DMSO-$d_6$): δ 10.3 (s, 1H), 8.78 (s, 1H), 8.61 (d, 1H), 8.25 (d, 1H), 7.94 (dd, 1H), 7.78-7.75 (m, 3H), 7.61-7.57 (m, 2H), 7.5-7.48 (m, 1H), 7.46-7.43 (m, 1H), 7.29-7.25 (m, 1H), 6.6 (s, 1H), 3.5-3.46 (m, 1H), 1.31 (d, 6H); LC-MS (ESI): Calculated mass: 493.53; Observed mass: 494.1 [M+H]+ (rt: 1.61 min).

Example 32

N-(5-(5-(1H-pyrazol-1-yl)-1H-benzo[d]imidazol-1-yl)-2',4'-difluorobiphenyl-3-yl)cyclopropanesulfonamide The compound was prepared from the compound of Example 28 using the procedures of Example 29 and cyclopropane sulfonyl chloride. $^1$H NMR (300 MHz, DMSO-d$_6$): δ 10.34 (s, 1H), 9.0 (s, 1H), 8.64 (d, 1H), 8.27 (d, 1H), 7.99 (dd, 1H), 7.85-7.76 (m, 3H), 7.65-7.62 (m, 2H), 7.54-7.45 (m, 2H), 7.33-7.27 (m, 1H), 6.59-6.57 (m, 1H), 2.95-2.93 (m, 1H), 1.04-1.02 (m, 4H); LC-MS (ESI): Calculated mass: 491.51; Observed mass: 492.1 [M+H]$^+$ (rt: 1.659 min).

Example 33

1-(5-(5-(1H-pyrazol-1-yl)-1H-benzo[d]imidazol-1-yl)-2',4'-difluorobiphenyl-3-yl)-3-(furan-2-ylmethyl)urea To a solution of the compound of Example 29(a) (250 mg, 0.645 mmol) in n-butanol was added TEA (200 mg, 1.98 mmol, 3.05 eq.) followed by 2-(isocyanatomethyl) furan (160 mg, 1.3 mmol, 2.0 eq.). The mixture was stirred for 1 h and then quenched and extracted as in Example 1(d). The solvent was distilled off and the residue was purified by preparative HPLC to give the product in 18% yield (60 mg). $^1$H NMR (300 MHz, DMSO-d$_6$): δ 9.07 (s, 1H), 8.84 (s, 1H), 8.61 (d, 1H), 8.24 (d, 1H), 7.96-7.93 (m, 2H), 7.84-7.71 (m, 3H), 7.64-7.6 (m, 2H), 7.46-7.41 (m, 2H), 7.27-7.23 (m, 1H), 6.82 (t, 1H), 6.58-6.56 (m, 1H), 6.41-6.4 (m, 1H), 6.28-6.27 (m, 1H), 4.32 (d, 2H); LC-MS (ESI): Calculated mass: 510.49; Observed mass: 511.1 [M+H]$^+$ (rt: 1.59 min).

Example 34

N-(5-(5-(1H-imidazol-1-yl)-1H-benzo[d]imidazol-1-yl)-2',4'-difluorobiphenyl-3-yl)acetamide The compound was prepared from the compound of Example 1(h) using the procedures of Example 28. $^1$H NMR (300 MHz, DMSO-d$_6$): δ; 10.44 (s, 1H), 8.86 (s, 1H), 8.29 (s, 2H), 8.14 (s, 1H), 7.92 (d, 2H), 7.79-7.71 (m, 4H), 7.55 (s, 1H), 7.47-7.43 (m, 1H), 7.29-7.26 (m, 1H), 2.1 (s, 3H); LC-MS (ESI): Calculated mass: 429.42; Observed mass: 430.2 [M+H]$^+$ (rt: 0.21 min).

Example 35

N-(2',4'-difluoro-5-(4,5,6,7-tetrahydro-1'H-1,5'-bibenzo[d]imidazol-1'-yl)biphenyl-3-yl)acetamide The compound was prepared from the compound of Example 1(h) using the procedures of Example 28. $^1$H NMR (300 MHz, CD$_3$OD): δ 8.66 (s, 1H), 8.15 (t, 1H), 7.86-7.75 (m, 4H), 7.69-7.62 (m, 1H), 7.55 (d, 1H), 7.43 (dd, 1H), 7.18-7.1 (m, 2H), 2.67-2.57 (m, 4H), 2.2 (s, 3H), 1.91-1.85 (m, 4H); LC-MS (ESI): Calculated mass: 483.51; Observed mass: 484.2 [M+H]$^+$ (rt: 0.632 min).

Example 36

N-(5-(5-(1-cyclopentyl-1H-pyrazol-4-yl)-1H-benzo[d]imidazol-1-yl)-2',4'-difluorobiphenyl-3-yl)acetamide A solution of the compound of Example 17(c) (60 mg, 0.123 mmol) in 1,2-dimethoxyethane (10 ml) was degassed by N$_2$ bubbling for 5 min. 1-Cyclopentyl-4-(4,4,5,5-tetramethyl-1,3,2-dioxaborolan-2-yl)-1H-pyrazole (35 mg, 0.135 mmol, 1.1 eq.) was added and the mixture was degassed for another 5 min. Pd(dppf)Cl$_2$ (20 mg, 0.025 mmol, 0.2 eq.) and aqueous sodium carbonate (39 mg, 0.369 mmol, 3.0 eq.) were added and the procedure of Example 1(d) was followed. The crude residue of the product was purified by preparative HPLC to give the product in 25% yield (15 mg). $^1$H NMR (300 MHz, DMSO-d$_6$): δ 10.4 (s, 1H), 8.63 (s, 1H), 8.30 (s, 1H), 8.07 (s, 1H), 8.02 (s, 1H), 7.95 (s, 1H), 7.8 (s, 1H), 7.78-7.76 (m, 2H), 7.63-7.61 (m, 1H), 7.51 (s, 1H), 7.45-7.40 (m, 1H); 7.27 (dt, 1H), 4.73-4.69 (m, 1H), 2.12-2.01 (m, 5H), 2.01-1.96 (m, 2H), 1.85-1.81 (m, 2H), 1.69-1.66 (m, 2H); LC-MS (ESI): Calculated mass: 497.54; Observed mass: 498.5 [M+H]$^+$ (rt: 1.59 min).

Example 37

N-(2',4'-difluoro-5-(5-(1-(piperidin-4-yl)-1H-pyrazol-4-yl)-1H-benzo[d]-imidazol-1-yl)biphenyl-3-yl) acetamide a) tert-butyl 4-(4-(1-(5-acetamido-2',4'-difluorobiphenyl-3-yl)-1H-benzo[d]-imidazol-5-yl)-1H-pyrazol-1-yl)piperidine-1-carboxylate A solution of the compound of Example 17(c) (150 mg, 0.306 mmol) in 1,2-dimethoxyethane (5 ml) was degassed by N$_2$ bubbling for 5 min. tert-Butyl 4-(4(4,4,5,5-tetramethyl-1,3,2-dioxaborolan-2-yl)-1H-pyrazol-1-yl)piperidine-1-carboxylate of the Intermediate Example 5 (173 mg, 0.460 mmol, 1.5 eq.) was added and the mixture was degassed for another 5 min. Pd(PPh$_3$)$_4$ (50 mg, 0.0613 mmol, 0.2 eq.) and aqueous sodium carbonate (97 mg, 0.92 mmol, 3.0 eq.) were added and the procedure of Example 1(d) was followed. The crude residue of the product was obtained in 64% yield (120 mg).

b) N-(2',4'-difluoro-5-(5-(1-(piperidin-4-yl)-1H-pyrazol-4-yl)-1H-benzo[d]-imidazol-1-yl)biphenyl-3-yl)acetamide To a solution of the compound of Example 37(a) (120 mg, 0.2 mmol) in 1,4-dioxane (8 ml) at 0° C. was added HCl in dioxane and stirred at RT for 30 min. The solvent was distilled off and the residue was purified by preparative HPLC to give the product in 24% yield (25 mg). $^1$H NMR (300 MHz, DMSO-d$_6$): δ 10.42 (s, 1H), 8.83 (br s, 1H), 8.70-8.68 (m, 1H), 8.45-8.43 (m, 1H) 8.34 (s, 1H), 8.14-8.13 (m, 1H), 8.06 (s, 2H), 7.78 (m, 1H), 7.76-7.72 (m, 2H), 7.68 (dd, 1H), 7.53 (s, 1H), 7.43-7.40 (m, 1H), 7.27 (dt, 1H), 4.55-4.45 (m, 1H), 3.17-3.08 (m, 4H), 2.28-2.17 (m, 4H), 2.12 (s, 3H); LC-MS (ESI): Calculated mass: 512.55; Observed mass: 513.2 [M+H]$^+$ (rt: 0.22 min).

Example 38

1-(5-(5-(1H-pyrazol-1-yl)-1H-benzo[d]imidazol-1-yl)-2',4'-difluorobiphenyl-3-yl)-3-cyclopentylurea To a solution of the compound of Example 29(a) (200 mg, 0.52 mmol) in n-butanol (10 ml) was added triethylamine (157 mg, 1.56 mmol, 3 eq.) followed by iso-cyanatocyclopentane (115 mg, 1.3 mmol, 1.04 eq.). The mixture was stirred for 1 h and then quenched and extracted as in Example 1(d). The solvent was distilled off and the residue was purified by preparative HPLC to give the product in 15% yield (39 mg). $^1$H NMR (300 MHz, DMSO-d$_6$): δ 8.83 (s, 1H), 8.72 (s, 1H), 8.60 (d, 1H), 8.23 (d, 1H), 7.90 (dd, 2H), 7.82-7.70 (m, 3H), 7.60 (d, 1H), 7.45 (dt, 1H), 7.34 (br s, 1H), 7.25 (dt, 1H), 6.57-6.56 (m, 1H), 6.46 (d, 1H), 4.0-3.93 (m, 1H), 1.87-1.82 (m, 2H), 1.65-1.54 (m, 4H), 1.43-1.39 (m, 2H); LC-MS (ESI): Calculated mass: 498.53; Observed mass: 499.3 [M+H]$^+$ (rt: 1.66 min).

Example 39

N-(5-(5-(1-(2-(dimethylamino)ethyl)-1H-1,2,3-triazol-4-yl)-1H-benzo[d]-imidazol-1-yl)-2',4'-difluorobiphenyl-3-yl)methanesulfonamide a) 5-(5-(1-(2-(dimethylamino)ethyl)-1H-1,2,3-triazol-4-yl)-1H-benzo[d]-imidazol-1-yl)-2',4'-difluorobiphenyl-3-amine To a solution of the compound of Example 20 (450 mg, 0.9 mmol) in ethanol (10 ml) was added aqueous solution of NaOH (450 mg, 11.25 mmol, 12.5 eq.) and the mixture was heated at 85° C. for 2 h. The mixture was quenched and extracted as in Example 1(d). The solvent was distilled off to afford the product in 77% yield (0.32 g).

b) N-(5-(5-(1-(2-(dimethylamino)ethyl)-1H-1,2,3-triazol-4-yl)-1H-benzo[d]-imidazol-1-yl)-2',4'-difluorobiphenyl-3-yl)methanesulfonamide To a solution of the compound of Example 39(a) (80 mg, 0.174 mmol) in DCM (10 ml) was added pyridine (28 mg, 0.35 mmol, 2 eq.) followed by methanesulfonyl chloride (22 mg, 0.19 mmol, 1.1 eq.). The mixture was stirred for 2 h and quenched and extracted as in Example 2(b). The solvent was distilled off and the residue was purified by preparative HPLC to give the product in 11% yield (10 mg). $^1$H NMR (300 MHz, DMSO-d$_6$): δ 10.32 (s, 1H), 8.79 (s, 1H), 8.73 (s, 1H), 8.27 (s, 1H), 7.92 (dd, 1H), 7.82-7.77 (m, 2H), 7.60 (d, 2H), 7.49-7.44 (m, 2H), 7.30-7.27 (m, 1H), 4.88 (t, 2H), 3.73 (m, 2H), 3.19 (s, 3H), 2.89 (s, 6H); LC-MS (ESI): Calculated mass: 537.58; Observed mass: 538.2 [M+H]$^+$ (rt: 0.243 min).

Example 40

N-(5-(5-(1-(2-(dimethylamino)ethyl)-1H-1,2,3-triazol-4-yl)-1H-benzo[d]-imidazol-1-yl)-2',4'-difluorobiphenyl-3-yl)ethanesulfonamide The compound was prepared from the compound of Example 20 using the procedures of Example 39. $^1$H NMR (300 MHz, DMSO-d$_6$): δ 10.37 (s, 1H), 8.85 (s, 1H), 8.73 (s, 1H), 8.28 (s, 1H), 8.83 (d, 1H), 7.82-7.76 (m, 2H), 7.59 (s, 2H), 7.48-7.47 (m, 2H), 7.29 (dt, 1H), 4.89-4.86 (m, 2H), 3.73 (m, 2H), 3.30 (quartet, 2H), 2.90 (s, 6H), 1.26 (t, 3H); LC-MS (ESI): Calculated mass: 551.61; Observed mass: 552.2 [M+H]$^+$ (rt: 0.282 min).

Example 41

N-(5-(5-(1-(2-(dimethylamino)ethyl)-1H-1,2,3-triazol-4-yl)-1H-benzo[d]-imidazol-1-yl)-2',4'-difluorobiphenyl-3-yl)propane-2-sulfonamide The compound was prepared from the compound of Example 20 using the procedures of Example 39. $^1$H NMR (300 MHz, DMSO-d$_6$): δ 10.32 (s, 1H), 8.79 (s, 1H), 8.73 (s, 1H), 8.27 (s, 1H), 7.93 (d, 1H), 7.80-7.75 (m, 2H), 7.59 (d, 2H), 7.50-7.47 (m, 2H), 7.29 (dt, 1H), 4.88 (t, 2H), 3.74 (m, 2H), 3.50-3.46 (m, 1H), 2.89 (s, 6H), 1.31 (d, 6H); LC-MS (ESI): Calculated mass: 565.64; Observed mass: 566.2 [M+H]$^+$ (rt: 0.402 min).

Example 42

N-(5-(5-(1-(2-(dimethylamino)ethyl)-1H-1,2,3-triazol-4-yl)-1H-benzo[d]-imidazol-1-yl)-2',4'-difluorobiphenyl-3-yl)cyclopropanesulfonamide The compound was prepared from the compound of Example 20 using the procedures of Example 39 and cyclopropane sulfonyl chloride. $^1$H NMR (400 MHz, CD$_3$OD): δ 8.93 (s, 1H), 8.53 (s, 1H), 8.32 (s, 1H), 7.80 (d, 1H), 7.82 (d, 1H), 7.68-7.58 (m, 4H), 7.17-7.10 (m, 2H), 4.95 (t, 2H), 3.85 (t, 2H), 3.02 (s, 6H), 2.78-2.71 (m, 1H), 1.16-1.09 (m, 2H), 1.05-1.01 (m, 2H); LC-MS (ESI): Calculated mass: 563.62; Observed mass: 564.2 [M+H]$^+$ (rt: 0.412 min).

Example 43

N-(5-(5-(1-(2-(dimethylamino)ethyl)-1H-1,2,3-triazol-4-yl)-1H-benzo[d]-imidazol-1-yl)-2',4'-difluorobiphenyl-3-yl)benzenesulfonamide The compound was prepared from the compound of Example 20 using the procedures of Example 39. $^1$H NMR (300 MHz, DMSO-d$_6$): δ 10.92 (s, 1H), 8.73 (d, 2H), 8.25 (s, 1H), 7.90-7.88 (m, 3H), 7.70-7.62 (m, 4H), 7.55-7.38 (m, 5H), 7.26-7.20 (m, 1H), 4.90-4.87 (m, 2H), 3.73 (t, 2H), 2.89 (s, 6H); LC-MS (ESI): Calculated mass: 599.65; Observed mass: 600.2 [M+H]$^+$ (rt: 0.75 min).

Example 44

N-(2',4'-difluoro-5-(5-(1-(3-hydroxy-3-methylbutyl)-1H-1,2,3-triazol-4-yl)-1H-benzo[d]imidazol-1-yl)biphenyl-3-yl)acetamide A mixture of the compound of Example 17(e), 4-azido-2-methylbutan-2-ol of Intermediate Example 6 (0.16 g, 1.25 mmol, 1.0 eq.), sodium ascorbate (0.25 g, 1.25 mmol, 1.0 eq.) and copper sulfate pentahydrate (0.155 g, 0.62 mmol, 0.5 eq.) in CH$_2$Cl$_2$ (5 ml), DMSO (2 ml) and water (2 ml) was stirred for 12 h at RT. The mixture was quenched with water and the precipitate formed was filtered and dried. The crude product was purified by preparative HPLC to give the product in 62% yield (0.4 g). $^1$H NMR (300 MHz, DMSO-d$_6$): δ 10.43 (s, 1H), 8.86 (s, 1H), 8.70 (s, 1H), 8.25 (s, 1H), 8.09 (s, 1H), 7.93 (d, 1H), 7.84-7.81 (m, 3H), 7.55 (s, 1H), 7.50-7.43 (m, 1H), 7.30-7.25 (m, 1H), 4.51-4.56 (m, 2H), 2.13 (s, 3H), 2.05-1.99 (t, 2H), 1.18 (s, 6H); LC-MS (ESI): Calculated mass: 516.54; Observed mass: 517.2 [M+H]$^+$ (rt: 1.226 min).

Example 45

N-(2',4'-difluoro-5-(5-(1-(3-hydroxy-3-methylbutyl)-1H-1,2,3-triazol-4-yl)-1H-benzo[d]imidazol-1-yl)biphenyl-3-yl)methanesulfonamide a) 4-(4-(1-(5-amino-2',4'-difluorobiphenyl-3-yl)-1H-benzo[d]imidazol-5-yl)-1H-1,2,3-triazol-1-yl)-2-methylbutan-2-ol To a solution of the compound of Example 44 (400 mg, 0.77 mmol) in ethanol (20 ml) was added aqueous solution of NaOH (385 mg, 9.63 mmol, 12.5 eq.) and the mixture was heated at 90° C. for 3 h. The mixture was quenched and extracted as in Example 1(d). The solvent was distilled off to give the product in 38% yield (140 mg).

b) N-(2',4'-difluoro-5-(5-(1-(3-hydroxy-3-methylbutyl)-1H-1,2,3-triazol-4-yl)-1H-benzo[d]imidazol-1-yl)biphenyl-3-yl)methanesulfonamide To a solution of the compound of Example 45(a) (70 mg, 0.15 mmol) in DCM (10 ml) was added pyridine (24 mg, 0.3 mmol, 2 eq.) followed by methanesulfonyl chloride (19 mg, 0.165 mmol, 1.1 eq.). The mixture was stirred for 2 h, and quenched and extracted as in Example 2(b). The solvent was distilled off and the residue was purified by preparative HPLC to give the product in 1.2% yield (1 mg). $^1$H NMR (300 MHz, DMSO-$d_6$): δ 10.30 (s, 1H), 8.83 (s, 1H), 8.30 (s, 1H), 8.25 (s, 1H), 7.92 (d, 1H), 7.82-7.80 (m, 2H), 7.60 (d, 2H), 7.47 (s, 2H), 7.29-7.21 (m, 1H), 4.49 (m, 2H), 3.19 (s, 3H), 2.02 (m, 2H), 1.18 (s, 6H); LC-MS (ESI): Calculated mass: 552.60; Observed mass: 553.1 [M+H]$^+$ (rt: 1.352 min).

Example 46

N-(2',4'-difluoro-5-(5-(1-(3-hydroxy-3-methylbutyl)-1H-1,2,3-triazol-4-yl)-1H-benzo[d]imidazol-1-yl)biphenyl-3-yl)ethanesulfonamide The compound was prepared from the compound of Example 44 using the procedures of Example 45. $^1$H NMR (300 MHz, DMSO-$d_6$): δ 10.34 (s, 1H), 8.87 (s, 1H), 8.70 (s, 1H), 8.25 (s, 1H), 7.93 (dd, 1H), 7.84-7.80 (m, 2H), 7.59 (s, 2H), 7.49-7.44 (m, 2H), 7.29 (dt, 1H), 4.51-4.47 (m, 2H), 3.30 (quartet, 2H), 2.04-2.00 (m, 2H), 1.26 (t, 3H), 1.16 (s, 6H); LC-MS (ESI): Calculated mass: 566.62; Observed mass: 567.2 [M+H]$^+$ (rt: 1.42 min).

Example 47

N-(2',4'-difluoro-5-(5-(1-(3-hydroxy-3-methylbutyl)-1H-1,2,3-triazol-4-yl)-1H-benzo[d]imidazol-1-yl)biphenyl-3-yl)cyclopropanesulfonamide The compound was prepared from the compound of Example 44 using the procedures of Example 45 and cyclopropane sulfonyl chloride. $^1$H NMR (400 MHz, CD$_3$OD): δ 9.09 (s, 1H), 8.47 (s, 1H), 8.30 (s, 1H), 8.0 (d, 1H), 7.83 (d, 1H), 7.69-7.60 (m, 4H), 7.17-7.10 (m, 2H), 4.62-4.58 (m, 2H), 2.78-2.69 (m, 1H), 2.17-2.13 (m, 2H), 1.29-1.15 (m, 8H), 1.10-1.02 (m, 2H); LC-MS (ESI): Calculated mass: 578.63; Observed mass: 579.2 [M+H]$^+$ (rt: 1.449 min).

Example 48

N-(2',4'-difluoro-5-(5-(1-(2-morpholinoethyl)-1H-1,2,3-triazol-4-yl)-1H-benzo[d]imidazol-1-yl)biphenyl-3-yl)methanesulfonamide a) 2',4'-difluoro-5-(5-(1-(2-morpholinoethyl)-1H-1,2,3-triazol-4-yl)-1H-benzo[d]imidazol-1-yl)biphenyl-3-amine To a solution of the compound of Example 21 (1 g, 1.9 mmol) in ethanol (15 ml) was added aqueous solution of NaOH (0.95 g, 23.8 mmol, 12.5 eq.) and the mixture was heated at 90° C. for 4 h. The mixture was quenched and extracted as in Example 1(d). The solvent was distilled off to afford the product in 63% yield (600 mg).

b) N-(2',4'-difluoro-5-(5-(1-(2-morpholinoethyl)-1H-1,2,3-triazol-4-yl)-1H-benzo[d]imidazol-1-yl)biphenyl-3-yl)methanesulfonamide To a solution of the compound of Example 48(a) (80 mg, 0.159 mmol) in DCM (10 ml) was added pyridine (25 mg, 0.318 mmol, 2 eq.) followed by methanesulfonyl chloride (21 mg, 0.191 mmol, 1.2 eq.). The mixture was stirred for 2 h and quenched and extracted as in Example 2(b). The solvent was distilled off and the residue was purified by preparative HPLC to give the product in 13% yield (12 mg). $^1$H NMR (300 MHz, DMSO-$d_6$): δ 10.32 (s, 1H), 8.80 (s, 1H), 8.73 (s, 1H), 8.28 (s, 1H), 7.94-7.92 (d, 1H), 7.82-7.72 (m, 2H), 7.60 (d, 2H), 7.46-7.40 (m, 2H), 7.27 (dt, 1H), 4.89 (m, 2H), 3.96-3.94 (m, 6H), 3.77 (m, 4H), 3.19 (s, 3H); LC-MS (ESI): Calculated mass: 579.62; Observed mass: 580.2 [M+H]$^+$ (rt: 0.29 min).

Example 49

N-(2',4'-difluoro-5-(5-(1-(2-morpholinoethyl)-1H-1,2,3-triazol-4-yl)-1H-benzo[d]imidazol-1-yl)biphenyl-3-yl)ethanesulfonamide The compound was prepared from the compound of Example 21 using the procedures of Example 48. $^1$H NMR (300 MHz, DMSO-$d_6$): δ 10.41 (s, 1H), 8.83 (s, 1H), 8.80 (s, 1H), 8.32 (s, 1H), 7.97 (d, 1H), 7.85-7.80 (m, 2H), 7.63 (s, 2H), 7.52-7.50 (m, 2H), 7.33 (d, 1H), 4.93 (m, 2H), 4.0 (m, 6H), 3.70 (m, 4H), 3.34 (quartet, 2H), 1.30 (t, 3H); LC-MS (ESI): Calculated mass: 593.65; Observed mass: 594.2 [M+H]$^+$ (rt: 0.36 min).

Example 50

N-(2',4'-difluoro-5-(5-(1-(2-morpholinoethyl)-1H-1,2,3-triazol-4-yl)-1H-benzo[d]imidazol-1-yl)biphenyl-3-yl)cyclopropanesulfonamide The compound was prepared from the compound of Example 21 using the procedures of Example 48 and cyclopropane sulfonyl chloride. $^1$H NMR (300 MHz, DMSO-$d_6$): δ 10.9 (s, 1H), 8.73 (s, 1H), 8.62 (s, 1H), 8.22 (s, 1H), 7.9-7.87 (m, 3H), 7.71-7.62 (m, 4H), 7.55 (s, 1H), 7.47-7.39 (m, 4H), 7.28-7.24 (m, 1H), 4.12 (s, 3H); LC-MS (ESI): Calculated mass: 605.6; Observed mass: 606.2 [M+H]$^+$ (rt: 0.367 min).

Example 51

N-(5-(5-(1-cyclopentyl-1H-1,2,3-triazol-4-yl)-1H-benzo[d]imidazol-1-yl)-2',4'-difluorobiphenyl-3-yl)acetamide A solution of the compound of Example 17(e) (100 mg, 0.258 mmol) in dry DMF (10 ml) in a sealed tube was purged with N$_2$ for 20 min, followed by the addition of azidocyclopentane of Intermediate Example 7 (34 mg, 0.3 mmol, 1.2 eq.) and copper iodide (5 mg, 0.0258 mmol, 0.1 eq.) and stirred at 90° C. for 12 h. The solvent was distilled off and the residue was purified by preparative HPLC to give the product in 14% yield (18 mg). $^1$H NMR (400 MHz, CD$_3$OD): δ 8.55 (s, 1H), 8.43 (s, 1H), 8.36 (s, 1H), 8.23 (br s, 1H), 8.10 (s, 1H), 7.92-7.88 (m, 1H), 7.74 (d, 2H), 7.68-7.61 (m, 1H), 7.52 (s, 1H), 7.15-7.09 (m, 1H), 5.09-5.03 (m, 1H), 2.35-2.30 (m, 2H), 2.19-2.12 (m, 5H), 1.96-1.90 (m, 4H); LC-MS (ESI): Calculated mass: 498.53; Observed mass: 499.2 [M+H]$^+$ (rt: 1.55 min).

Example 52

N-(5-(5-(1-(cyclobutylmethyl)-1H-1,2,3-triazol-4-yl)-1H-benzo[d]imidazol-1-yl)-2',4'-difluorobiphenyl-3-yl)acetamide The compound was prepared from the compound of Example 17(e) using the compound of Intermediate Example 8 and the procedure of Example 51. $^1$H NMR (300 MHz, DMSO-d$_6$): δ 10.34 (s, 1H), 8.13 (s, 1H), 8.61 (s, 1H), 8.24 (s, 1H), 8.07 (s, 1H), 7.92-7.90 (d, 1H), 7.82-7.71 (m, 3H), 7.52 (s, 1H), 7.42 (m, 1H), 7.24-7.20 (m, 1H), 4.42 (d, 2H), 2.10 (s, 3H), 2.05 (m, 3H), 1.90-1.83 (m, 4H); LC-MS (ESI): Calculated mass: 498.53; Observed mass: 499.2 [M+H]$^+$ (rt: 1.55 min).

Example 53

N-(4'-fluoro-5-(5-(1-methyl-1H-pyrazol-4-yl)-1H-benzo[d]imidazol-1-yl)biphenyl-3-yl)acetamide a) N-(4'-fluoro-5-nitrobiphenyl-3-yl)acetamide The compound was prepared from the compound of Example 1(c) (10.0 g, 38.6 mmol) using the procedure of Example 1(d) and 4-fluorophenylboronic acid (6.48 g, 46.3 mmol, 1.2 eq.) to give the product in 86% yield (9.1 g). $^1$H NMR (300 MHz, DMSO-d$_6$): δ 10.53 (s, 1H), 8.57 (t, 1H), 8.17 (s, 1H), 8.09 (t, 1H), 7.86-7.74 (m, 2H), 7.41 (t, 2H), 7.15 (t, 1H), 2.13 (s, 3H); LC-MS (ESI): Calculated mass: 274.25; Observed mass: 274.8 [M+H]$^+$ (rt: 1.52 min).

b) N-(5-amino-4'-fluorobiphenyl-3-yl)acetamide

The compound was prepared from the compound of Example 53(a) (11.0 g, 40.1 mmol) using the procedure of Example 1(e) to afford the compound in 92% yield (9.0 g). $^1$H NMR (300 MHz, DMSO-d$_6$): δ 9.73 (s, 1H), 8.11 (s, 1H), 7.53-7.48 (m, 2H), 7.26 (t, 1H), 6.94-6.92 (m, 2H), 6.47 (s, 1H), 5.22 (s, 2H), 2.02 (s, 3H); LC-MS (ESI): Calculated mass: 244.26; Observed mass: 245.1 [M+H]$^+$ (rt: 0.312 min).

c) N-(5-(4-bromo-2-nitrophenylamino)-4'-fluorobiphenyl-3-yl)acetamide

The compound was prepared from the compound of Example 53(b) (9.0 g, 36.85 mmol) using the procedure of Example 1(f). The reaction was quenched with water. The precipitate formed was filtered, washed with cold water and hexane and dried under high vacuum to give the product as orange solid in 92% yield (15.0 g). $^1$H NMR (300 MHz, DMSO-d$_6$): δ 10.14 (s, 1H), 9.45 (s, 1H), 8.25 (d, 1H), 7.69-7.62 (m, 5H), 7.35-7.24 (m, 4H), 2.07 (s, 3H); LC-MS (ESI): Calculated mass: 444.25; Observed mass: 446.1 [M+H]$^+$ (rt: 1.84 min).

d) N-(5-(2-amino-4-bromophenylamino)-4'-fluorobiphenyl-3-yl)acetamide

The compound was prepared from the compound of Example 53(c) (15 g, 33.77 mmol) using the procedure of Example 1(g) to afford the product in 93% yield (13.0 g). $^1$H NMR (300 MHz, DMSO-d$_6$): δ 9.84 (1H, s), 7.53-7.49 (m, 3H), 7.31-7.25 (m, 4H), 6.98-6.91 (m, 2H), 6.88-6.62 (m, 2H), 5.11 (s, 2H), 2.01 (s, 3H); LC-MS (ESI): Calculated mass: 414.27; Observed mass: 416 [M+H]$^+$ (rt: 1.73 min).

e) N-(5-(5-bromo-1H-benzo[d]imidazol-1-yl)-4'-fluorobiphenyl-3-yl)acetamide

The compound was prepared from the compound of Example 53(d) (13.0 g, 31.38 mmol) using the procedure of Example 1(h) to afford the product in 68% yield (9.0 g). $^1$H NMR (300 MHz, DMSO-d$_6$): δ 10.38 (s, 1H), 8.77 (s, 1H), 8.14 (s, 1H), 8.02-7.97 (m, 1H), 7.9 (s, 1H), 7.82-7.77 (m, 2H), 7.7-7.67 (m, 1H), 7.63-7.62 (m, 1H), 7.54-7.5 (m, 1H), 7.36 (t, 2H), 2.12 (s, 3H); LC-MS (ESI): Calculated mass: 424.27; Observed mass: 425.1 [M+H]$^+$ (rt: 1.925 min).

f) N-(4'-fluoro-5-(5-(1-methyl-1H-pyrazol-4-yl)-1H-benzo[d]imidazol-1-yl)-biphenyl-3-yl)acetamide The compound was prepared from the compound of Example 53(e) (1.3 g, 3.06 mmol) using the procedure of Example 1(i) and 1-methyl-4-(4,4,5,5-tetramethyl-1,3,2-dioxaborolan-2-yl)-1H-pyrazole (0.765 g, 3.68 mmol, 1.2 eq.) to give the product in 46% yield (0.6 g). $^1$H NMR (300 MHz, DMSO-d$_6$): δ 10.4 (s, 1H), 9.0 (s, 1H), 8.25 (s, 1H), 8.08 (s, 1H), 8.0 (d, 2H), 7.90 (s, 1H), 7.8 (m, 3H), 7.65 (m, 2H), 7.4 (t, 2H), 3.9 (s, 3H), 2.1 (s, 3H); LC-MS (ESI): Calculated mass: 425.46; Observed mass: 425.9 [M+H]$^+$ (rt: 1.13 min).

Example 54

N-(4'-fluoro-5-(5-(1-methyl-1H-pyrazol-4-yl)-1H-benzo[d]imidazol-1-yl)biphenyl-3-yl)methanesulfonamide a) 4'-fluoro-5-(5-(1-methyl-1H-pyrazol-4-yl)-1H-benzo[d]imidazol-1-yl)biphenyl-3-amine To a solution of the compound of Example 53 (0.6 g, 1.41 mmol) in ethanol (20 ml) was added aqueous solution of NaOH (451 mg, 11.3 mmol, 8.0 eq.) and the mixture was heated at 85° C. for 4 h. The mixture was quenched and extracted as in Example 1(d). The solvent was distilled off to afford the product in 44% yield (0.24 g). LC-MS (ESI): Calculated mass: 383.42; Observed mass: 384.1 [M+H]$^+$ (rt: 1.004 min).

b) N-(4'-fluoro-5-(5-(1-methyl-1H-pyrazol-4-yl)-1H-benzo[d]imidazol-1-yl)biphenyl-3-yl)methanesulfonamide To a solution of the compound of Example 54(a) (50 mg, 0.125 mmol) in DCM was added pyridine (20 mg, 0.249 mmol, 2.0 eq.) followed by methanesulfonyl chloride (17 mg, 0.15 mmol, 1.2 eq.). The mixture was stirred for 1 h quenched and extracted as in Example 2(b). The solvent was distilled off and the residue was purified by preparative HPLC to give the product in 33% yield (20 mg). $^1$H NMR (300 MHz, DMSO-d$_6$): δ 10.23 (br s, 1H), 8.71 (s, 1H), 7.97 (d, 2H), 7.85-7.8 (m, 2H), 7.69 (m, 2H), 7.61-7.58 (m, 2H), 7.52 (d, 2H), 7.38 (t, 2H), 3.89 (s, 3H), 3.19 (s, 3H); LC-MS (ESI): Calculated mass: 461.51; Observed mass: 461.9 [M+H]$^+$ (rt: 1.3 min).

Example 55

N-(4'-fluoro-5-(5-(1-methyl-1H-pyrazol-4-yl)-1H-benzo[d]imidazol-1-yl)biphenyl-3-yl)ethanesulfonamide The compound was prepared from the compound of Example 53 using the procedures of Example 54. $^1$H NMR (300 MHz, DMSO-$d_6$): δ 10.36 (br s, 1H), 9.35 (br s, 1H), 8.28 (s, 1H), 8.02 (d, 2H), 7.85-7.79 (m, 2H), 7.76-7.7 (m, 3H), 7.6-7.57 (m, 2H), 7.39 (t, 2H), 3.89 (s, 3H), 3.31 (quartet, 2H), 1.27 (t, 3H); LC-MS (ESI): Calculated mass: 475.54; Observed mass: 475.9 [M+H]$^+$ (rt: 1.38 min).

Example 56

N-(4'-fluoro-5-(5-(1-methyl-1H-pyrazol-4-yl)-1H-benzo[d]imidazol-1-yl)-biphenyl-3-yl)propane-2-sulfonamide The compound was prepared from the compound of Example 53 using the procedures of Example 54. $^1$H NMR (300 MHz, DMSO-$d_6$): δ 10.28 (br s, 1H), 8.92 (br s, 1H), 8.24 (s, 1H), 7.99 (d, 2H), 7.83-7.78 (m, 2H), 7.71-7.67 (m, 3H), 7.56 (d, 2H), 7.38 (t, 2H), 3.88 (s, 3H), 3.52-3.48 (m, 1H), 1.31 (d, 6H); LC-MS (ESI): Calculated mass: 489.56; Observed mass: 490.2 [M+H]$^+$ (rt: 1.46 min).

Example 57

N-(4'-fluoro-5-(5-(1-methyl-1H-pyrazol-4-yl)-1H-benzo[d]imidazol-1-yl)biphenyl-3-yl)cyclopropanesulfonamide The compound was prepared from the compound of Example 53 using the procedures of Example 54 and cyclopropane sulfonyl chloride. $^1$H NMR (300 MHz, DMSO-$d_6$): δ 10.28 (s, 1H), 9.1 (br s, 1H), 8.26 (s, 1H), 8.01 (d, 2H), 7.84-7.81 (m, 2H), 7.74-7.71 (m, 3H), 7.59 (s, 2H), 7.39 (t, 2H), 3.89 (s, 3H), 2.91-2.89 (m, 1H), 1.03 (d, 4H); LC-MS (ESI): Calculated mass: 487.55; Observed mass: 488.1 [M+H]$^+$ (rt: 1.42 min).

Example 58

1-cyclopentyl-3-(4'-fluoro-5-(5-(1-methyl-1H-pyrazol-4-yl)-1H-benzo[d]imidazol-1-yl)biphenyl-3-yl)urea To a solution of the compound of Example 54(a) (100 mg, 0.261 mmol) in n-butanol was added triethylamine (79 mg, 0.783 mmol, 3.0 eq.) followed by isocyanato-cyclopentane (58 mg, 0.522 mmol, 2.0 eq.). The mixture was stirred for 1 h and then quenched and extracted as in Example 1(d). The solvent was distilled off and the residue was purified by preparative HPLC to give the product in 31% yield (40 mg). $^1$H NMR (300 MHz, DMSO-$d_6$): δ 8.84 (br s, 1H), 8.71 (s, 1H), 8.22 (s, 1H), 7.99 (d, 2H), 7.88 (s, 1H), 7.82-7.78 (m, 2H), 7.73 (d, 1H), 7.68-7.63 (m, 2H), 7.48 (s, 1H), 7.36 (t, 2H), 6.4 (d, 1H), 4.1-3.8 (m, 1H), 3.88 (s, 3H), 1.89-1.83 (m, 2H), 1.69-1.5 (m, 4H), 1.45-1.38 (m, 2H); LC-MS (ESI): Calculated mass: 494.56; Observed mass: 494.8 [M+H]$^+$ (rt: 1.51 min).

Example 59

1-(4'-fluoro-5-(5-(1-methyl-1H-pyrazol-4-yl)-1H-benzo[d]imidazol-1-yl)biphenyl-3-yl)-3-(1-methylpiperidin-4-yl)urea To a solution of the compound of Example 54(a) (50 mg, 0.13 mmol) in DCM at 0° C. was added phosgene (20% in toluene) (0.1 ml, 0.195 mmol, 1.5 eq.) and the mixture was stirred for 15 min at 0° C. and 30 min at RT. 1-Methylpiperidin-4-amine (18 mg, 0.156 mmol, 1.2 eq.) was added and the mixture was stirred for 16 h. The mixture was quenched by the addition of water and extracted with 8% methanol/DCM (3×50 ml). The combined organic layer was washed with water, brine and dried over sodium sulphate. The solvent was distilled off and the residue was purified by preparative HPLC to give the product in 44% yield (30 mg). $^1$H NMR (300 MHz, DMSO-$d_6$): δ 8.48 (s, 1H), 7.98 (s, 1H), 7.89-7.85 (m, 4H), 7.72-7.55 (m, 6H), 7.39 (s, 1H), 7.2 (t, 2H), 3.94 (s, 3H), 3.89-3.84 (m, 1H), 3.42-3.33 (m, 2H), 3.05-3.0 (m, 2H), 2.78 (s, 3H), 2.17-2.13 (m, 2H), 1.85-1.81 (m, 2H); LC-MS (ESI): Calculated mass: 523.6; Observed mass: 524 [M+H]$^+$ (rt: 0.2 min).

Example 60

1-(4'-fluoro-5-(5-(1-methyl-1H-pyrazol-4-yl)-1H-benzo[d]imidazol-1-yl)biphenyl-3-yl)-3-(furan-2-ylmethyl)urea The compound was prepared from the compound of Example 54(a) using the procedures of Example 58. $^1$H NMR (300 MHz, CD$_3$OD): δδ 9.1 (s, 1H), 8.1 (s, 1H), 8.02 (s, 2H), 7.93 (s, 1H), 7.85-7.81 (m, 2H), 7.74-7.67 (m, 3H), 7.53 (d, 1H), 7.44 (d, 1H), 7.22 (t, 2H), 6.37-6.34 (m, 1H), 6.3-6.29 (m, 1H), 4.42 (s, 2H), 3.95 (s, 3H); LC-MS (ESI): Calculated mass: 506.53; Observed mass: 507.1 [M+H]$^+$ (rt: 1.44 min).

Example 61

1-(4'-fluoro-5-(5-(1-methyl-1H-pyrazol-4-yl)-1H-benzo[d]imidazol-1-yl)biphenyl-3-yl)-3-((5-methylfuran-2-yl)methyl)urea The compound was prepared from the compound of Example 54(a) using the procedures of Example 58. $^1$H NMR (300 MHz, CD$_3$OD): δ 9.51 (s, 1H), 8.1 (s, 1H), 8.02 (s, 2H), 7.93 (s, 1H), 7.85-7.73 (m, 4H), 7.65 (m, 1H), 7.53 (s, 1H), 7.22 (t, 2H), 6.2-6.14 (m, 1H), 5.9-5.81 (m, 1H), 4.38 (s, 2H), 3.95 (s, 3H), 2.26 (s, 3H); LC-MS (ESI): Calculated mass: 520.56; Observed mass: 521.1 [M+H]$^+$ (rt: 1.51 min).

Example 62

N-(5-(5-(1-(2-(dimethylamino)ethyl)-1H-pyrazol-4-yl)-1H-benzo[d]imidazol-1-yl)-4'-fluorobiphenyl-3-yl)acetamide The compound was prepared from the compound of Example 53(e) using the procedures of Example 53. $^1$H NMR (300 MHz, DMSO-$d_6$): δ 10.42 (s, 1H), 8.98 (s, 1H), 8.37 (s, 1H), 8.14-8.06 (m, 3H), 7.85-7.75 (m, 4H), 7.68-7.66 (m, 2H), 7.38 (t, 2H), 4.57 (t, 2H), 3.65-3.63 (m, 2H), 2.85 (d, 6H), 2.13 (s, 3H); LC-MS (ESI): Calculated mass: 482.55; Observed mass: 483.1 [M+H]⁺ (rt: 0.19 min).

Example 63

N-(5-(5-(1-(2-(dimethylamino)ethyl)-1H-pyrazol-4-yl)-1H-benzo[d]imidazol-1-yl)-4'-fluorobiphenyl-3-yl)methanesulfonamide The compound was prepared from the compound of Example 62 using the procedures of Example 54. $^1$H NMR (300 MHz, DMSO-d$_6$): δ 10.27 (s, 1H), 8.87 (s, 1H), 8.37 (s, 1H), 8.14 (s, 1H), 8.06 (s, 1H), 7.84-7.8 (m, 2H), 7.76-7.64 (m, 3H), 7.55-7.52 (m, 2H), 7.38 (t, 2H), 4.57 (t, 2H), 3.65-3.62 (m, 2H), 3.19 (s, 3H), 2.86 (d, 6H); LC-MS (ESI): Calculated mass: 518.61; Observed mass: 519 [M+H]⁺ (rt: 0.22 min).

Example 64

N-(5-(5-(1-(2-(dimethylamino)ethyl)-1H-pyrazol-4-yl)-1H-benzo[d]imidazol-1-yl)-4'-fluorobiphenyl-3-yl)ethanesulfonamide The compound was prepared from the compound of Example 62 using the procedures of Example 54. $^1$H NMR (300 MHz, DMSO-d$_6$): δ 10.29 (s, 1H), 8.77 (s, 1H), 8.35 (s, 1H), 8.13 (s, 1H), 8.06 (s, 1H), 7.83-7.78 (m, 2H), 7.72-7.63 (m, 3H), 7.54-7.51 (m, 2H), 7.38 (t, 2H), 4.57 (t, 2H), 0.65-3.62 (m, 2H), 3.3 (quartet, 2H), 2.86 (d, 6H), 1.27 (t, 3H); LC-MS (ESI): Calculated mass: 532.63; Observed mass: 533 [M+H]⁺ (rt: 0.25 min).

Example 65

N-(5-(5-(1-(2-(dimethylamino)ethyl)-1H-pyrazol-4-yl)-1H-benzo[d]imidazol-1-yl)-4'-fluorobiphenyl-3-yl)propane-2-sulfonamide The compound was prepared from the compound of Example 62 using the procedures of Example 54. $^1$H NMR (300 MHz, DMSO-d$_6$): δ 10.27 (s, 1H), 8.82 (s 1H), 8.36 (s, 1H), 8.14 (s, 1H), 8.06 (s, 1H), 7.83-7.79 (m, 2H), 7.71-7.65 (m, 3H), 7.56-7.53 (m, 2H), 7.38 (t, 2H), 4.57 (t, 2H), 3.67-3.64 (m, 2H), 3.52-3.49 (m, 1H), 2.85 (d, 6H), 1.32 (d, 6H); LC-MS (ESI): Calculated mass: 546.66; Observed mass: 547.2 [M+H]⁺ (rt: 0.507 min).

Example 66

N-(5-(5-(1-(2-(dimethylamino)ethyl)-1H-pyrazol-4-yl)-1H-benzo[d]imidazol-1-yl)-4'-fluorobiphenyl-3-yl)cyclopropanesulfonamide The compound was prepared from the compound of Example 62 using the procedures of Example 54 and cyclopropane sulfonyl chloride. $^1$H NMR (300 MHz, DMSO-d$_6$): δ 10.26 (s, 1H), 8.84 (s, 1H), 8.36 (s, 1H), 8.14 (s, 1H), 8.06 (s, 1H), 7.82-7.79 (m, 2H), 7.73-7.67 (m, 3H), 7.56 (d, 2H), 7.39 (t, 2H), 4.57 (t, 2H), 3.65-3.62 (m, 2H), 2.9-2.87 (m, 1H), 2.86 (d, 6H), 1.02 (d, 4H); LC-MS (ESI): Calculated mass: 544.64; Observed mass: 546.2 [M+H]⁺ (rt: 0.401 min).

Example 67

N-(5-(5-(1-(2-(dimethylamino)ethyl)-1H-pyrazol-4-yl)-1H-benzo[d]imidazol-1-yl)-4'-fluorobiphenyl-3-yl)benzenesulfonamide The compound was prepared from the compound of Example 62 using the procedures of Example 54. $^1$H NMR (300 MHz, DMSO-d$_6$): δ 10.9 (s, 1H), 8.78 (s, 1H), 8.37 (s, 1H), 8.14 (s, 1H), 8.03 (s, 1H), 7.89 (d, 2H), 7.72-7.68 (m, 3H), 7.66-7.61 (m, 4H), 7.41-7.33 (m, 5H), 4.57 (t, 2H), 3.66-3.63 (m, 2H), 2.85 (d, 6H); LC-MS (ESI): Calculated mass: 580.68; Observed mass: 581.1 [M+H]⁺ (rt: 0.781 min).

Example 68

1-cyclopentyl-3-(5-(5-(1-(2-(dimethylamino)ethyl)-1H-pyrazol-4-yl)-1H-benzo[d]imidazol-1-yl)-4'-fluorobiphenyl-3-yl)urea The compound was prepared from the compound of Example 62 using the procedures of Example 58. $^1$H NMR (300 MHz, DMSO-d$_6$): δ 9.33 (br s, 1H), 8.87 (s, 1H), 8.76 (s, 1H), 8.36 (s, 1H), 8.14 (s, 1H), 8.05 (s, 1H), 7.39 (m, 1H), 7.82-7.75 (m, 3H), 7.68-7.6 (m, 2H), 7.48 (m, 1H), 7.36 (t, 2H), 4.57 (t, 2H), 3.99-3.97 (m, 1H), 3.65-3.62 (m, 2H), 2.86 (d, 6H), 1.89-1.82 (m, 2H), 1.7-1.53 (m, 4H), 1.45-1.37 (m, 2H); LC-MS (ESI): Calculated mass: 551.66; Observed mass: 552.2 [M+H]⁺ (rt: 0.61 min).

Example 69

N-(4'-fluoro-5-(5-(6-methoxypyridin-3-yl)-1H-benzo[d]imidazol-1-yl)biphenyl-3-yl)acetamide The compound was prepared using the procedures of Example 53. $^1$H NMR (300 MHz, DMSO-d$_6$): δ 10.41 (s, 1H), 8.96 (s, 1H), 8.58 (d, 1H), 8.15-8.07 (m, 3H), 7.91-7.89 (m, 1H), 7.85-7.79 (m, 3H), 7.74-7.67 (m, 2H), 7.38 (t, 2H), 6.95 (d, 1H), 3.92 (s, 3H), 2.14 (s, 3H); LC-MS (ESI): Calculated mass: 452.48; Observed mass: 453.1 [M+H]⁺ (rt: 1.571 min).

Example 70

N-(5-(5-(1H-pyrazol-1-yl)-1H-benzo[d]imidazol-1-yl)-4'-fluorobiphenyl-3-yl)-acetamide To a solution of the compound of Example 53(e) (1.0 g, 2.36 mmol) in DMF (5 ml) were added pyrazole (1.0 mg, 14.87 mmol, 6.3 eq.), copper(I) oxide (1.0 g, 7.08 mmol, 3.0 eq.) and cesium carbonate (3.0 g, 9.204 mmol, 3.9 eq.) and the mixture was heated at 90° C. for 48 h. The mixture was quenched and extracted as in Example 1(d). The solvent was distilled off and the residue was purified by preparative HPLC to give the product in 62% yield (0.6 g). $^1$H NMR (300 MHz, DMSO-d$_6$): δ 10.39 (s, 1H), 8.8 (s, 1H), 8.6 (d, 1H), 8.24 (d, 1H), 8.02 (s, 1H), 7.93-7.9 (m, 2H), 7.82-7.56 (m, 4H), 7.65 (d, 1H), 7.37 (t, 2H), 6.56 (t, 1H), 2.13 (s, 3H); LC-MS (ESI): Calculated mass: 411.43; Observed mass: 412.3 [M+H]⁺ (rt: 1.43 min).

Example 71

N-(5-(5-(1H-pyrazol-1-yl)-1H-benzo[d]imidazol-1-yl)-4'-fluorobiphenyl-3-yl)-methanesulfonamide a) 5-(5-(1H-pyrazol-1-yl)-1H-benzo[d]imidazol-1-yl)-4'-fluorobiphenyl-3-amine To a solution of the compound of Example 70 (0.6 g, 1.46 mmol) in ethanol (40 ml) was added aqueous solution of NaOH (1.0 g, 25 mmol, 17.1 eq.) and the mixture was heated at 85° C. for 5 h. The mixture was quenched and extracted as in Example 1(d). The combined organic layer was washed with water, brine and dried over sodium sulphate. The solvent was distilled off to afford the product in 84% yield (0.45 g).

b) N-(5-(5-(1H-pyrazol-1-yl)-1H-benzo[d]imidazol-1-yl)-4'-fluorobiphenyl-3-yl)methanesulfonamide To a solution of the compound of Example 71(a) (150 mg, 0.406 mmol) in DCM was added pyridine (0.5 ml, 6.21 mmol, 15.3 eq.) followed by methanesulfonyl chloride (70 mg, 0.609 mmol, 1.5 eq.). The mixture was stirred for 1 h and quenched and extracted as in Example 2(b). The solvent was distilled off and the residue was purified by preparative HPLC to give the product in 17% yield (30 mg). $^1$H NMR (300 MHz, DMSO-$d_6$): δ 10.23 (s, 1H), 8.82 (s, 1H), 8.6 (d, 1H), 8.24 (d, 1H), 7.92 (dd, 1H), 7.85-7.8 (m, 3H), 7.76-7.71 (m, 2H), 7.54-7.53 (m, 2H), 7.38 (t, 2H), 6.56 (t, 1H), 3.19 (s, 3H); LC-MS (ESI): Calculated mass: 447.48; Observed mass: 449.1 [M+H]$^+$ (rt: 1.575 min).

Example 72

N-(5-(5-(1H-pyrazol-1-yl)-1H-benzo[d]imidazol-1-yl)-4'-fluorobiphenyl-3-yl)-ethanesulfonamide The compound was prepared from the compound of Example 70 using the procedures of Example 71. $^1$H NMR (300 MHz, DMSO-$d_6$): δ 10.3 (s, 1H), 8.81 (s, 1H), 8.6 (d, 1H), 8.24 (s, 1H), 7.93 (dd, 1H), 7.84-7.76 (m, 4H), 7.7-7.69 (m, 1H), 7.55-7.53 (m, 2H), 7.4-7.36 (m, 2H), 6.57-6.56 (m, 1H), 3.3 (quartet, 2H), 1.27 (t, 3H); LC-MS (ESI): Calculated mass: 461.51; Observed mass: 462.1 [M+H]$^+$ (rt: 1.563 min).

Example 73

N-(3-(5-(1-methyl-1H-pyrazol-4-yl)-1H-benzo[d]imidazol-1-yl)-5-(5-methyl-furan-2-yl)phenyl)acetamide a) N-[3-(5-Methyl-furan-2-yl)-5-nitro-phenyl]-acetamide

To a solution of N-(3-bromo-5-nitrophenyl)acetamide of Example 1(c) (5 g, 19.23 mmol) in 1,2-dimethoxyethane (200 ml) were added 4,4,5,5-tetramethyl-2-(5-methylfuran-2-yl)-1,3,2-dioxaborolane (5.9 g, 28.85 mmol), sodium carbonate (8.15 g, 76.92 mmol) and water (20 ml) and the mixture was degassed by $N_2$ bubbling 15 min. Pd(dppf)Cl$_2$ (3.2 g, 3.846 mmol) was added and the mixture was heated at 100° C. for 2 h. The mixture was brought to RT and quenched and extracted as in Example 1(d). The solvent was distilled off and the residue was purified by flash column chromatography (40% ethyl acetate in hexanes) to afford the product in 80% yield (4.0 g). $^1$H NMR (300 MHz, DMSO-$d_6$): δ 10.45 (s, 1H), 8.4 (s, 1H), 8.2 (d, 2H), 7.1 (s, 1H), 6.2 (s, 1H), 2.4 (s, 3H), 2.15 (s, 3H), Calculated mass: 260.25; Observed mass: 259.1 [M+H]$^+$ (rt: 1.578 min).

b) N-[3-Amino-5-(5-methyl-furan-2-yl)-phenyl]-acetamide

To a solution of the compound of Example 73(a) (4.0 g, 15.384 mmol) in methanol (50 ml) was added 10% palladium in carbon (500 mg) and the mixture was stirred at RT under hydrogen atmosphere (balloon pressure) for 6 h. The mixture was filtered over a pad of celite and washed with methanol. The solvent was evaporated to afford the compound in 95% yield (3.3 g). $^1$H NMR (300 MHz, DMSO-$d_6$): δ 9.6 (s, 1H), 7.0 (d, 2H), 6.45 (d, 2H), 6.2 (s, 1H), 5.2 (s, 2H), 2.4 (s, 3H), 2.15 (s, 3H), Calculated mass: 230.26; Observed mass: 231.2 [M+H]$^+$ (rt: 0.212 min).

c) N-[3-(4-Bromo-2-nitro-phenylamino)-5-(5-methyl-furan-2-yl)-phenyl]-acetamide To a solution of the compound of Example 73(b) (5 g, 22.73 mmol) in anhydrous DMF (25 ml), 4-bromo-1-fluoro-2-nitrobenzene (7.09 g, 27.3 mmol) and potassium fluoride (1.32 g, 22.73 mmol) were added. The mixture was stirred at 100° C. overnight. The mixture was brought to RT and DMF was removed under reduced pressure. The residue was purified by flash column chromatography (50% ethyl acetate in hexanes) to give the compound in 65% yield (6 g). $^1$H NMR (300 MHz, DMSO-$d_6$): δ 10.2 (s, 1H), 9.6 (s, 1H), 8.2 (s, 1H), 7.7 (s, 2H), 7.5 (m, 1H), 7.30 (s, 1H), 7.2 (s, 1H), 6.7 (d, 1H), 2.9 (s, 1H), 2.33 (s, 3H), 2.15 (s, 3H), Calculated mass: 430.25; Observed mass: 432 [M+H]$^+$ (rt: 1.85 min).

d) N-[3-(2-Amino-4-bromo-phenylamino)-5-(5-methyl-furan-2-yl)-phenyl]-acetamide To a solution of the compound of Example 73(c) (6.0 g, 13.945 mmol) in ethanol (100 ml) were added iron powder (500 mg) and 50% aqueous calcium chloride solution (10 ml). The mixture was stirred at 80° C. for 2 h and filtered through a celite pad. The celite pad was washed with ethyl acetate (200 ml). The combined organic layer was washed with water, brine and dried over sodium sulphate. The solvent was distilled off and the residue was purified by flash column chromatography (20% ethyl acetate in hexanes) to get the compound in 98% yield (5.5 g). $^1$H NMR (300 MHz, DMSO-$d_6$): δ 9.8 (s, 1H), 7.30 (d, 1H), 6.9 (m, 3H), 6.7 (m, 2H), 6.5 (d, 1H), 5.2 (s, 2H), 2.33 (s, 3H), 2.15 (s, 3H), Calculated mass: 400.27; Observed mass: 402 [M+H]$^+$ (rt: 1.695 min).

e) N-(3-(5-bromo-1H-benzo[d]imidazol-1-yl)-5-(5-methylfuran-2-yl)phenyl)-acetamide Formic acid (10 ml) was added to the compound of Example 73(d) (5 g, 12.49 mmol) at RT and then the mixture was heated at 100° C. for 2 h. Formic acid was removed and the residue was purified by flash column chromatography (3% methanol in chloroform) to afford the compound in 58% yield (3.0 g). $^1$H NMR (300 MHz, DMSO-$d_6$): δ 10.3 (s, 1H), 8.7 (s, 1H), 8.0 (s, 1H), 7.9 (s, 2H), 7.6 (m, 2H), 7.5 (m, 1H), 7.0 (s, 1H), 6.3 (d, 1H), 2.33 (s, 3H), 2.15 (s, 3H), Calculated mass: 410.26; Observed mass: 410.2 [M+H]$^+$ (rt: 1.616 min).

f) N-(3-(5-(1-methyl-1H-pyrazol-4-yl)-1H-benzo[d]imidazol-1-yl)-5-(5-methyl-furan-2-yl)phenyl)acetamide To a solution of the compound of Example 73(e) (100 mg, 0.244 mmmol) in 1,2-dimethoxyethane (10 ml), 1-methyl-4-(4,4,5,5-tetramethyl-1,3,2-dioxaborolan-2-yl)-1H-pyrazole (0.043 g, 0.341 mmol), sodium carbonate (0.0755 g, 0.731 mmol) and water (2.0 ml) were added and the mixture was degassed for 15 min by $N_2$ bubbling. $Pd(PPh_3)_4$ (0.0563 g, 0.0487 mmol) was added and the mixture was heated at 100° C. for 2 h. The mixture was brought to RT and then quenched and extracted as in Example 1(d). The solvent was distilled off and the residue was purified by preparative HPLC to afford the compound in 10% yield (10 mg). $^1$H NMR (300 MHz, DMSO-$d_6$): δ 10.2 (s, 1H), 8.6 (s, 1H), 8.4 (s, 1H), 7.8-8.1 (s, 4H), 7.6-7.7 (m, 4H), 7.0 (s, 1H), 6.3 (s, 1H), 3.9 (m, 1H), 2.4 (s, 3H), 2.15 (s, 4H), Calculated mass: 411.46; Observed mass: 412.1 [M+H]$^+$ (rt: 0.809 min).

Example 74

N-(3-(5-(1-methyl-1H-pyrazol-4-yl)-1H-benzo[d]imidazol-1-yl)-5-(5-methyl-furan-2-yl)phenyl)ethanesulfonamide a) 3-(5-(1-methyl-1H-pyrazol-4-yl)-1H-benzo[d]imidazol-1-yl)-5-(5-methyl-furan-2-yl)aniline A mixture of KOH (0.614 g, 10.94 mmol) and the compound of Example 73 (3.0 g, 7.29 mmol) in ethanol (5 ml) and water (2 ml) was heated at 60° C. for 2 h. The mixture was diluted with ethyl acetate (100 ml) and was washed with water (50 ml) and brine (25 ml). The organic phase was dried over sodium sulfate and concentrated under vacuum and the residue was purified by column chromatography to afford the product in 92% yield (2.5 g).

b) N-(3-(5-(1-methyl-1H-pyrazol-4-yl)-1H-benzo[d]imidazol-1-yl)-5-(5-methyl-furan-2-yl)phenyl)ethanesulfonamide To a solution of the compound of Example 74(a) (0.1 g, 0.27 mmol) in pyridine (1 ml) and DCM (2 ml) was added ethanesulfonyl chloride (0.1 ml) and the mixture was stirred at RT for 12 h. The solvent was removed and the crude was purified by preparative HPLC to afford the product in 24% yield (0.03 g). $^1$H NMR (300 MHz, CD$_3$OD): δ 9.2 (s, 1H), 8.1 (s, 1H), 8.0 (s, 1H), 7.95 (s, 1H), 7.6-7.7 (m, 4H), 7.5 (s, 1H), 6.8 (d, 1H), 6.2 (s, 1H), 4.0 (s, 3H), 3.3 (m, 2H), 2.4 (s, 3H), 1.4 (t, 3H). LC-MS (ESI): Calculated mass: 461.54; Observed mass: 462.1 [M+H]$^+$ (rt: 1.315 min).

Example 75

N-(3-(5-(1-methyl-1H-pyrazol-4-yl)-1H-benzo[d]imidazol-1-yl)-5-(5-methyl-furan-2-yl)phenyl)propane-2-sulfonamide The compound was prepared from the compound of Example 73 using the procedures of Example 74. $^1$H NMR (300 MHz, CD$_3$OD): δ; 8.5 (s, 1H), 8.0 (s, 1H), 7.95 (s, 1H), 7.9 (s, 1H), 7.6-7.7 (m, 5H), 7.5 (s, 1H), 6.8 (d, 1H), 6.2 (s, 1H), 4.0 (s, 3H), 3.5 (m, 1H), 2.4 (s, 3H), 1.5 (d, 6H). LC-MS (ESI): Calculated mass: 475.56; Observed mass: 475.9 [M+H]$^+$ (rt: 1.415 min).

Example 76

N-(3-(5-(1-methyl-1H-pyrazol-4-yl)-1H-benzo[d]imidazol-1-yl)-5-(5-methyl-furan-2-yl)phenyl)cyclopropanesulfonamide The compound was prepared from the compound of Example 73 using the procedures of Example 74 and cyclopropane sulfonyl chloride. $^1$H NMR (300 MHz, CD$_3$OD): δ 8.5 (s, 1H), 8.0 (s, 1H), 7.95 (s, 1H), 7.9 (s, 1H), 7.6-7.7 (m, 4H), 7.5 (s, 1H), 6.8 (d, 1H), 6.2 (s, 1H), 4.0 (s, 3H), 2.4 (s, 3H), 1.0-1.5 (m, 4H). LC-MS (ESI): Calculated mass: 473.55; Observed mass: 474.0 [M+H]$^+$ (rt: 1.382 min).

Example 77

N-(3-(5-(1-methyl-1H-pyrazol-4-yl)-1H-benzo[d]imidazol-1-yl)-5-(5-methyl-furan-2-yl)phenyl)benzenesulfonamide The compound was prepared from the compound of Example 73 using the procedures of Example 74. Yield 0.03 g, (25%), $^1$H NMR (300 MHz, CD$_3$OD): δ; 8.55 (s, 1H), 8.05 (s, 1H), 7.9 (m, 4H), 7.6-7.7 (m, 5H), 7.5 (s, 2H), 7.4 (d, 1H), 7.2 (t, 1H), 6.8 (d, 1H), 6.2 (s, 1H), 4.0 (s, 3H), 2.4 (s, 3H). LC-MS (ESI): Calculated mass: 509.58; Observed mass: 509.9 [M+H]$^+$ (rt: 1.482 min).

Example 78

1-(furan-2-ylmethyl)-3-(3-(5-(1-methyl-1H-pyrazol-4-yl)-1H-benzo[d]imidazol-1-yl)-5-(5-methylfuran-2-yl)phenyl)urea To a solution of the compound of Example 74(a) (0.1 g, 0.271 mmol) in DCM (10 ml), at 0° C., were added phosgene (0.04 g, 0.406 mmol) and furfuryl amine (0.029 g, 0.2977 mmol) sequentially. The mixture was heated at 60° C. for 2 h and the solvent was evaporated and the residue was purified by preparative HPLC to give the compound in 15% yield (20 mg). $^1$H NMR (300 MHz, CD$_3$OD): δ 9.6 (s, 1H), 8.2 (s, 1H), 8.0 (s, 1H), 7.95 (s, 2H), 7.6-7.7 (m, 5H), 7.7 (s, 1H), 7.6 (s, 1H), 6.4 (s, 1H), 6.3 (d, 1H), 6.2 (s, 1H), 4.5 (s, 2H), 4.0 (s, 3H), 2.4 (s, 3H), LC-MS (ESI): Calculated mass: 492.53; Observed mass: 493.1 [M+H]$^+$ (rt: 1.415 min).

Example 79

1-cyclopentyl-3-(3-(5-(1-methyl-1H-pyrazol-4-yl)-1H-benzo[d]imidazol-1-yl)-5-(5-methylfuran-2-yl)phenyl)urea The compound was prepared from the compound of Example 74(a) using the procedures of Example 78. $^1$H NMR (300 MHz, CD$_3$OD): δ 8.7 (s, 1H), 8.6 (s, 1H), 8.2 (s, 1H), 8.0 (s, 1H), 7.95 (s, 1H), 7.6-7.7 (m, 5H), 7.5 (s, 1H), 6.9 (d, 1H), 6.3 (s, 2H), 4.0 (s, 3H), 2.4 (s, 3H), 1.4-1.9 (m, 8H). LC-MS (ESI): Calculated mass: 480.56; Observed mass: 481.2 [M+H]$^+$ (rt: 1.517 min).

Example 80

N-(3-(5-(1-methyl-1H-pyrazol-4-yl)-1H-benzo[d]imidazol-1-yl)-5-(5-methyl-furan-2-yl)phenyl)morpholine-4-carboxamide The compound was prepared from the compound of Example 74(a) using the procedures of Example 78. $^1$H NMR (300 MHz, CD$_3$OD): δ 8.5 (s, 1H), 8.0 (s, 1H), 7.95 (s, 1H), 7.9 (s, 1H), 7.8 (s, 2H), 7.6-7.7 (m, 3H), 7.5 (s, 1H), 6.8 (d, 1H), 6.2 (s, 1H), 4.0 (s, 3H), 2.4 (s, 3H), 3.6 (t, 4H), 3.8 (t, 4H). LC-MS (ESI): Calculated mass: 482.53; Observed mass: 483.1 [M+H]$^+$ (rt: 0.814 min).

Example 81

N-(3-(5-(1-(2-hydroxyethyl)-1H-pyrazol-4-yl)-1H-benzo[d]imidazol-1-yl)-5-(5-methylfuran-2-yl)phenyl)acetamide The compound was prepared from the compound of Example 73(e) using the procedures of Example 73. $^1$H NMR (300 MHz, DMSO-d$_6$): δ 10.1 (s, 1H), 8.6 (s, 1H), 8.4 (s, 1H), 7.7-8.0 (m, 4H), 7.6 (m, 3H), 7.0 (d, 1H), 6.8 (d, 1H), 6.2 (d, 1H), 4.2 (t, 2H), 3.8 (t, 2H), 2.4 (s, 3H), 2.2 (s, 3H). LC-MS (ESI): Calculated mass: 441.48; Observed mass: 442.1[M+H]$^+$ (rt: 0.436 min).

Example 82

N-(3-(5-(1-(2-(dimethylamino)ethyl)-1H-pyrazol-4-yl)-1H-benzo[d]imidazol-1-yl)-5-(5-methylfuran-2-yl)phenyl)acetamide The compound was prepared from the compound of Example 73(e) using the procedures of Example 73. $^1$H NMR (300 MHz, CD$_3$OD): δ; 9.5 (s, 1H), 8.3 (s, 1H), 8.1 (m, 3H), 7.95 (m, 4H), 7.7 (m, 1H), 6.8 (d, 1H), 6.2 (s, 1H), 4.20 (m, 2H), 3.7 (m, 2H), 3.0 (s, 6H), 2.4 (s, 3H), 2.2 (s, 3H). LC-MS (ESI): Calculated mass: 468.55; Observed mass: 469.5 [M+H]$^+$ (rt: 0.179 min).

Example 83

N-(3-(5-methylfuran-2-yl)-5-(5-(1-(2-morpholinoethyl)-1H-pyrazol-4-yl)-1H-benzo[d]imidazol-1-yl)phenyl)acetamide The compound was prepared from the compound of Example 73(e) using the procedures of Example 73. $^1$H NMR (300 MHz, CD$_3$OD): δ; 9.5 (s, 1H), 8.3 (s, 1H), 8.1 (m, 3H), 7.95 (m, 3H), 7.7 (m, 1H), 6.8 (d, 1H), 6.2 (d, 1H), 4.70 (t, 2H), 4.0 (m, 3H), 3.7 (t, 2H), 3.50 (m, 3H), 2.4 (s, 4H), 2.2 (s, 4H). LC-MS (ESI): Calculated mass: 510; Observed mass: 511.2[M+H]$^+$ (rt: 0.277 min).

Example 84

N-(3-(5-(1H-pyrazol-1-yl)-1H-benzo[d]imidazol-1-yl)-5-(5-methylfuran-2-yl)-phenyl)acetamide To a solution of the compound of Example 73(e) (0.1 g, 0.243 mmol) in DMF (5 ml) were added pyrazole (0.022 g, 0.0317 mmol, 1.3 eq.), copper(I) oxide (0.01 g, 0.1 eq.) and cesium carbonate (0.158 g, 0.0487 mmol, 2.0 eq.) and the mixture was heated at 110° C. for 48 h. The mixture was quenched and extracted as in Example 1(d): The solvent was distilled off and the residue was purified by preparative HPLC to give the product in 68% yield (0.02 g). $^1$H NMR (300 MHz, DMSO-d$_6$): δ; 9.3 (s, 1H), 8.4 (s, 1H), 8.3 (s, 1H), 7.8-8.1 (m, 4H), 7.6-7.7 (m, 3H), 6.80 (m, 1H), 6.2 (d, 1H), 2.4 (s, 3H), 2.2 (s, 3H), LC-MS (ESI): Calculated mass: 397.43; Observed mass: 398.3 [M+H]$^+$ (rt: 1.382 min).

Example 85

N-(3-(5-(1H-imidazol-1-yl)-1H-benzo[d]imidazol-1-yl)-5-(5-methylfuran-2-yl)-phenyl)acetamide The compound was prepared from the compound of Example 73(e) using the procedures of Example 84. $^1$H NMR (300 MHz, DMSO-d$_6$): δ 9.5 (s, 1H), 9.0 (m, 1H), 8.2 (m, 2H), 8.0 (s, 2H), 7.8 (m, 4H), 7.6 (s, 1H), 6.80 (d, 1H), 6.2 (d, 1H), 2.4 (s, 3H), 2.2 (s, 3H), LC-MS (ESI): Calculated mass: 397.43; Observed mass: 398.3 [M+H]$^+$ (rt: 0.179 min).

Example 86

N-(3-(5-(4H-1,2,4-triazol-4-yl)-1H-benzo[d]imidazol-1-yl)-5-(5-methylfuran-2-yl)phenyl)acetamide The compound was prepared from the compound of Example 73(e) using the procedures of Example 84. $^1$H NMR (300 MHz, DMSO-d$_6$): δ; 10.4 (s, 1H), 9.3 (s, 1H), 8.8 (s, 1H), 8.4 (d, 2H), 7.8-8.1 (m, 4H), 7.6 (s, 1H), 6.80 (d, 1H), 6.2 (d, 1H), 2.4 (s, 3H), 2.2 (s, 3H), LC-MS (ESI): Calculated mass: 398.42; Observed mass: 399.2 [M+H]$^+$ (rt: 0.914 min).

Example 87

N-(3-(5-(1-methyl-1H-pyrazol-4-yl)-1H-benzo[d]imidazol-1-yl)-5-(1H-pyrrol-1-yl)phenyl)acetamide a) 1-(3,5-Dinitro-phenyl)-1H-pyrrole A solution of 3,5-dinitroaniline (10 g, 54.644 mmol) and 2,5-dimethoxytetrahydrofuran (18.05 g, 136.61 mmol, 2.5 eq.) in acetic acid (122 ml) was heated to 100° C. for 16 h. Completion of reaction was monitored by TLC. Then the mixture was brought to RT and poured into ice-cold water. The precipitate was filtered, washed with water (150 ml) and dried to give the product in 54% yield (8.2 g). LC-MS (ESI): Calculated mass: 233.18; Observed mass: 233.04 [M+H]$^+$ (rt: 1.667 min).

b) 3-Nitro-5-pyrrol-1-yl-phenylamine

To a solution of 1-(3,5-dinitro-phenyl)-1H-pyrrole (8.2 g, 35.19 mmol) and pyridine (10 ml) in ethanol (100 ml), at 80° C., was added a 20% aqueous solution of ammonium sulfide (38.4 ml, 140.76 mmol, 4.0 eq.) in water (10 ml). The mixture was stirred at the same temperature for 4 h. The mixture was quenched with ice water (200 ml) and the precipitated solid was filtered. The filtered solid was dried under vacuum to afford the product in 98% yield (7.0 g).

c) N-(3-Nitro-5-pyrrol-1-yl-phenyl)-acetamide

Acetic anhydride (7.0 ml) was added to 3-nitro-5-pyrrol-1-yl-phenylamine (7.0 g, 34.48 mmol). The mixture was stirred for 30 min at RT and subsequently quenched by the addition of crushed ice. The precipitate formed was filtered and was washed with cold water to obtain off-white solid. The solid was dried under high vacuum to give the product in 89% yield (7.52 g). LC-MS (ESI): Calculated mass: 245.23; Observed mass: 244.1 [M−H]$^+$ (rt: 0.24 min).

d) N-(3-Amino-5-pyrrol-1-yl-phenyl)-acetamide

To a solution of N-(3-nitro-5-pyrrol-1-yl-phenyl)acetamide (7.51 g, 30.61 mmol) in ethanol (100 ml), were added iron powder (4.273 g, 76.53 mmol, 2.5 eq.) and a solution of calcium chloride (8.49 g, 76.53 mmol, 2.5 eq.) in water (100 ml). The mixture was stirred at 80° C. for 2 h and then filtered through a pad of celite. The celite pad was washed with ethyl acetate (200 ml) and the combined organic layer was washed with water (100 ml) and brine (25 ml). The solvent was evaporated and the residue was purified by column chromatography (20% ethyl acetate in hexanes) to give the compound in 87% yield (5.7 g). $^1$H NMR (300 MHz, DMSO-d$_6$): δ 9.9 (s, 1H), 8.25 (s, 1H), 7.8 (d, 1H), 7.6 (s, 1H), 7.05 (d, 1H), 6.8 (s, 1H), 6.5 (m, 1H), 6.3 (m, 1H), 5.15 (s, 2H), 2.02 (s, 3H).

e) N-(3-(4-bromo-2-nitrophenylamino)-5-(1H-pyrrol-1-yl)phenyl)acetamide

To a solution of N-(3-amino-5-pyrrol-1-yl-phenyl)acetamide (5 g, 23.23 mmol) in anhydrous DMF (5 ml), 4-bromo-1-fluoro-2-nitrobenzene (5.11 g, 23.23 mmol) and potassium fluoride (1.35 g, 23.23 mmol) were added. The mixture was stirred at 110° C. for overnight. Then the mixture was brought to RT and DMF was removed under vacuum. Residue was subjected to flash column chromatography (50% ethyl acetate in hexanes) to get the compound in 63% yield (6.1 g).

f) N-(3-(2-amino-4-bromophenylamino)-5-(1H-pyrrol-1-yl)phenyl)acetamide

To a solution of the compound of Example 87(e) (6.0 g, 14.45 mmol) in ethanol (50 ml), iron powder (2.02 g, 36.12 mmol, 2.5 eq.) and calcium chloride (4.01 g, 36.12 mmol, 2.5 eq.) with 50 ml water were added. The mixture was stirred at 80° C. for 2 h and then filtered through a pad of celite. The celite pad was washed with ethyl acetate (100 ml) and the combined organic layer was washed with water (50 ml) and brine (25 ml). The solvent was evaporated and the residue was purified by column chromatography (20% ethyl acetate in hexanes) to give the compound in 86% yield (4.8 g). LC-MS (ESI): Calculated mass: 385.26; Observed mass: 385 [M+H]$^+$ (rt: 1.659 min).

g) N-(3-(5-bromo-1H-benzo[d]imidazol-1-yl)-5-(1H-pyrrol-1-yl)phenyl) acetamide

Formic acid (12 ml) was added to the compound of Example 87(f) (4 g, 10.38 mmol) at RT and the mixture was heated at 100° C. for 2 h. The formic acid was removed under reduced pressure and the residue was purified over flash column chromatography (3% methanol in chloroform) to afford the product in 76% yield (3.1 g). LC-MS (ESI): Calculated mass: 395.25; Observed mass: 396.8 [M+H]$^+$ (RT: 1.55 min).

h) N-(3-(5-(1-methyl-1H-pyrazol-4-yl)-1H-benzo[d]imidazol-1-yl)-5-(1H-pyrrol-1-yl)phenyl)acetamide To a solution of the compound of Example 87(g) (2.0 g, 5.06 mmol) in 1,2-methoxyethane (50 ml), 1-methyl-4-(4,4,5,5-tetramethyl-1,3,2-dioxaborolan-2-yl)-1H-pyrazole (1.58 g, 7.59 mmol, 1.5 eq.), sodium carbonate (1.34 g, 12.65 mmol, 2.5 eq.) and water (5.0 ml) were added and the mixture was degassed for 15 min (N$_2$ bubbling). Pd(PPh$_3$)$_4$ (2.92 g, 2.53 mmol, 0.5 eq.) was added and the mixture was heated at 100° C. for 2 h. The mixture was quenched and extracted as in Example 1(d). The solvent was distilled off and the residue was purified column chromatography afford the compound in 60% yield (1.2 g). $^1$H-NMR (300 MHz, CD$_3$OD): δ 8.53 (s, 1H), 8.0 (s, 1H), 7.9 (s, 1H), 7.82 (m, 2H), 7.79 (m, 1H), 7.7 (d, 1H), 7.6 (m, 1H), 7.48 (m, 1H), 7.29 (m, 2H), 6.31 (m, 2H), 3.95 (s, 3H), 2.15 (s, 3H); LC-MS (ESI): Calculated mass: 396.44; Observed mass: 396.8 [M+H]$^+$ (rt: 0.63 min).

Example 88

N-(3-(5-(1-methyl-1H-pyrazol-4-yl)-1H-benzo[d]imidazol-1-yl)-5-(1H-pyrrol-1-yl)phenyl)methanesulfonamide a) 3-(5-(1-methyl-1H-pyrazol-4-yl)-1H-benzo[d]imidazol-1-yl)-5-(1H-pyrrol-1-yl)aniline A mixture of 20% sodium hydroxide (5 ml) and the compound of Example 87 (1.15 g, 2.9 mmol) in 25 ml ethanol was heated at 100° C. for 2 h. The mixture was diluted with ethyl acetate (100 ml) and the organic layer was washed with water (50 ml) and brine (25 ml). The solvent was removed under reduced pressure and the crude was purified by column chromatography over silica gel to give the product in 68% yield (0.7 g).

b) N-(3-(5-(1-methyl-1H-pyrazol-4-yl)-1H-benzo[d]imidazol-1-yl)-5-(1H-pyrrol-1-yl)phenyl)methanesulfonamide To a solution of the compound of Example 88(a) (70 mg, 0.198 mmol) in DCM (1 ml) were added pyridine (0.5 ml) and methanesulfonyl chloride (27 mg, 0.237 mmol, 1.2 eq.) and the mixture was stirred at RT for 12 h. Pyridine was removed under reduced pressure and the crude was purified by preparative HPLC to give the product in 12% yield (10 mg). $^1$H-NMR (300 MHz, DMSO-d$_6$): δ: 10.2 (s, 1H), 8.7 (s, 1H), 8.21 (s, 1H), 7.99 (d, 2H), 7.7-7.61 (m, 3H), 7.45 (t, 2H), 7.38 (d, 2H), 6.33 (t, 2H), 3.88 (s, 3H), 3.2 (s, 3H); LC-MS (ESI): Calculated mass: 432.5; Observed mass: 433.1[M+H]$^+$ (rt: 0.88 min).

Example 89

N-(3-(5-(1-methyl-1H-pyrazol-4-yl)-1H-benzo[d]imidazol-1-yl)-5-(1H-pyrrol-1-yl)phenyl)cyclopropanesulfonamide The compound was prepared from the compound of Example 87 using the procedures of Example 88 and cyclopropane sulfonyl chloride. $^1$H-NMR (300 MHz, DMSO-d$_6$): δ 10.2 (s, 1H), 8.71 (s, 1H), 8.2 (s, 1H), 7.99 (m, 1H), 7.95 (s, 1H), 7.68-7.59 (m, 3H), 7.44-7.41 (m, 4H), 6.31 (m, 2H), 3.95 (s, 3H), 2.95 (m, 1H), 1.0 (m, 4H); LC-MS (ESI): Calculated mass: 458.54; Observed mass: 459.2 [M+H]$^+$ (rt: 1.29 min).

Example 90

N-(3-(5-(1-methyl-1H-pyrazol-4-yl)-1H-benzo[d]imidazol-1-yl)-5-(1H-pyrrol-1-yl)phenyl)benzenesulfonamide The compound was prepared from the compound of Example 87 using the procedures of Example 88. $^1$H-NMR (300 MHz, CD$_3$OD): δ 8.35 (s, 1H), 7.93 (s, 1H), 7.83-7.78 (m, 4H), 7.58-7.55 (m, 1H), 7.51-7.47 (m, 3H), 7.36 (t, 1H), 7.32 (d, 1H), 7.21 t, 1H), 7.14 (t, 1H), 7.12-7.11 (m, 2H), 6.22 (t, 2H), 3.9 (s, 3H); LC-MS (ESI): Calculated mass: 494.57; Observed mass: 495 [M+H]+ (rt: 1.71 min).

Example 91

1-(furan-2-ylmethyl)-3-(3-(5-(1-methyl-1H-pyrazol-4-yl)-1H-benzo[d]imidazol-1-yl)-5-(1H-pyrrol-1-yl)phenyl)urea To a solution of the compound of Example 88(a) (70 mg, 0.198 mmol) in DCM (1 ml) at 0° C. were added TEA (triethylamine) (0.055 ml, 0.396 mmol, 2.0 eq.) and 2-(isocyanatomethyl)furan (29 mg, 0.237 mmol, 1.2 eq.). The mixture was stirred at RT for 16 h. The solvent was removed under reduced pressure and the residue was purified by preparative HPLC to afford the compound in 40% yield (38 mg). $^1$H-NMR (300 MHz, CD$_3$OD): δ 9.0 (s, 1H), 8.07 (s, 1H), 7.97 (s, 1H), 7.92 (s, 1H), 7.81-7.74 (m, 3H), 7.63 (s, 1H), 7.44 (m, 2H), 7.3 (m, 2H), 6.36-6.31 (m, 4H), 4.41 (s, 2H), 3.96 (s, 3H); LC-MS (ESI): Calculated mass: 477.52; Observed mass: 478.1 [M+H]+ (rt: 1.393 min).

Example 92

1-cyclopentyl-3-(3-(5-(1-methyl-1H-pyrazol-4-yl)-1H-benzo[d]imidazol-1-yl)-5-(1H-pyrrol-1-yl)phenyl)urea The compound was prepared from the compound of Example 87 using the procedures of Example 91. $^1$H-NMR (300 MHz, CD$_3$OD): δ 9.52 (s, 1H), 8.16 (s, 1H), 8.03 (s, 1H), 7.98 (s, 1H), 7.88-7.84 (m, 3H), 7.65 (s, 1H), 7.47 (s, 1H), 7.3 (m, 2H), 6.35 (m, 2H), 4.1 (m, 1H), 3.95 (s, 3H), 2.05 (m, 2H), 1.8-1.6 (m, 4H), 1.51-1.48 (m, 2H); LC-MS (ESI): Calculated mass: 465.55; Observed mass: 466.1 [M+H]+ (rt: 1.45 min).

Example 93

N-(3-(5-(1-(2-(dimethylamino)ethyl)-1H-pyrazol-4-yl)-1H-benzo[d]imidazol-1-yl)-5-(1H-pyrrol-1-yl)phenyl)acetamide The compound was prepared from the compound of Example 87(g) using the procedures of Example 87. $^1$H-NMR (300 MHz, CD$_3$OD): δ 8.42 (s, 1H), 8.0 (s, 1H), 7.82-7.8 (m, 2H), 7.75 (s, 1H), 7.65 (s, 1H), 7.6 (d, 1H), 7.51 (d, 1H), 7.38 (s, 1H), 7.19 (m, 2H), 6.21 (m, 2H), 4.32 (t, 2H), 3.0 (t, 2H), 2.4 (s, 6H), 2.08 (s, 3H); LC-MS (ESI): Calculated mass: 453.23; Observed mass: 453.9 [M+H]+ (rt: 0.112 min).

Example 94

N-(3-(5-(1-(2-(dimethylamino)ethyl)-1H-pyrazol-4-yl)-1H-benzo[d]imidazol-1-yl)-5-(1H-pyrrol-1-yl)phenyl)benzenesulfonamide The compound was prepared from the compound of Example 93 using the procedures of Example 88. $^1$H-NMR (300 MHz, DMSO-d$_6$): δ 10.91 (s, 1H), 8.66 (s, 1H), 8.36 (s, 1H), 8.14 (s, 1H), 7.92 (s, 1H), 7.91-7.89 (m, 2H), 7.7-7.59 (m, 5H), 7.36-7.29 (m, 4H), 7.22 (m, 1H), 6.32 (t, 2H), (t, 2H), 3.64 (m, 2H), 2.86 (d, 6H); LC-MS (ESI): Calculated mass: 551.66; Observed mass: 552.2 [M+H]+ (rt: 0.54 min).

Example 95

N-(3-(5-(6-methoxypyridin-3-yl)-1H-benzo[d]imidazol-1-yl)-5-(1H-pyrrol-1-yl)-phenyl)acetamide The compound was prepared using the procedures of Example 87. $^1$H-NMR (300 MHz, CD$_3$OD): δ 9.0 (s, 1H), 8.37 (d, 1H), 7.96 (dd, 1H), 7.92 (s, 1H), 7.89-7.87 (m, 1H), 7.78 (d, 1H), 7.71 (t, 2H), 7.68-7.65 (m, 1H), 7.49 (t, 1H), 7.2 (t, 2H), 6.85 (d, 1H), 6.25 (t, 2H), 3.89 (s, 3H), 2.1 (s, 3H); LC-MS (ESI): Calculated mass: 423.47; Observed mass: 424.1[M+H]+ (rt: 1.518 min).

Example 96

N-(3-(5-(1H-pyrazol-1-yl)-1H-benzo[d]imidazol-1-yl)-5-(1H-pyrrol-1-yl)-phenyl)acetamide To a solution of the compound of Example 87(g) (2.0 g, 5.06 mmol) in DMF (50 ml) were added pyrazole (0.69 g, 10.12 mmol, 2.0 eq.), copper(I) oxide (0.145 g, 1.01 mmol, 0.2 eq.) and cesium carbonate (3.3 g, 10.12 mmol, 2.0 eq.) and the mixture was heated at 110° C. for 16 h. The mixture was quenched and extracted as in Example 1(d). The solvent was distilled off and the residue was purified by column chromatography to give the product in 78% yield (1.5 g). $^1$H-NMR (300 MHz, DMSO-d$_6$): δ 10.2 (s, 1H), 8.79 (s, 1H), 8.61 (d, 1H), 8.24 (d, 1H), 7.94-7.91 (m, 1H), 7.87-7.81 (m, 3H), 7.76 (d, 1H), 7.64-7.63 (m, 1H), 7.43-7.42 (m, 2H), 6.57 (t, 1H), 6.33 (m, 2H), 2.13 (s, 3H); LC-MS (ESI): Calculated mass: 382.42; Observed mass: 383.1 [M+H]+ (rt: 1.376 min).

Example 97

N-(3-(5-(1H-pyrazol-1-yl)-1H-benzo[d]imidazol-1-yl)-5-(1H-pyrrol-1-yl)-phenyl)ethanesulfonamide a) 3-(5-(1H-pyrazol-1-yl)-1H-benzo[d]imidazol-1-yl)-5-(1H-pyrrol-1-yl)aniline A mixture of 10% NaOH (5 ml) and the compound of Example 96 (1.45 g, 3.79 mmol) in 25 ml ethanol was heated at 100° C. for 2 h. The mixture was diluted with ethyl acetate (100 ml) and the organic layer was washed with water (50 ml) and brine (25 ml). The solvent was removed under reduced pressure and the residue was purified by column chromatography over silica gel to give the product in 85% yield (1.1 g).

b) N-(3-(5-(1H-pyrazol-1-yl)-1H-benzo[d]imidazol-1-yl)-5-(1H-pyrrol-1-yl)-phenyl)ethanesulfonamide To a solution of the compound of Example 97(a) (70 mg, 0.206 mmol) in DCM (2 ml) were added pyridine (0.033 ml, 0.411 mmol, 2.0 eq.) and ethanesulfonyl chloride (32 mg, 0.247 mmol, 1.2 eq.) and the mixture was stirred at RT for 12 h. Pyridine was removed under reduced pressure and the residue was purified by preparative HPLC to afford the product in 63% yield (56 mg). $^1$H-NMR (300 MHz, DMSO-d$_6$): δ 10.35 (s, 1H), 8.83 (s, 1H), 8.62 (d, 1H), 8.26 (d, 1H), 7.95 (dd, 1H), 7.82-7.78 (m, 2H), 7.69 (s, 1H), 7.46-7.42 (m, 4H), 6.58 (t, 1H), 6.35 (t, 2H), 3.34-3.32 (m, 2H), 1.28 (t, 3H); LC-MS (ESI): Calculated mass: 432.5; Observed mass: 433.2 [M+H]+ (rt: 1.43 min).

Example 98

N-(3-(5-(1H-pyrazol-1-yl)-1H-benzo[d]imidazol-1-yl)-5-(1H-pyrrol-1-yl)-phenyl)propane-2-sulfonamide The compound was prepared from the compound of Example 96 using the procedures of Example 87. $^1$H-NMR (300 MHz, DMSO-d$_6$): δ 10.3 (s, 1H), 8.81 (s, 1H), 8.6 (d, 1H), 8.25 (d, 1H), 7.95-7.92 (m, 1H), 7.79-7.76 (m, 2H), 7.66 (m, 1H), 7.43 (m, 4H), 6.57-6.56 (m, 1H), 6.34-6.33 (m, 2H), 3.53-3.5 (m, 1H), 1.31 (d, 6H); LC-MS (ESI): Calculated mass: 446.52: Observed mass: 447.2 [M+H]$^+$ (rt: 1.5 min).

Example 99

N-(3-(5-(1-methyl-1H-1,2,3-triazol-4-yl)-1H-benzo[d]imidazol-1-yl)-5-(1H-pyrrol-1-yl)phenyl)acetamide a) N-(3-(4-iodo-2-nitrophenylamino)-5-(1H-pyrrol-1-yl)phenyl)acetamide

A solution of N-(3-amino-5-pyrrol-1-yl-phenyl)acetamide of Example 87(d) (5.0 g, 18.72 mmol), 1-fluoro-4-iodo-2-nitrobenzene (4.02 g, 18.72 mmol, 1.0 eq.) and potassium fluoride (1.08 g, 18.72 mmol, 1.0 eq.) in DMF (30 ml) was heated at 130° C. for 5 h. The mixture was quenched and extracted as in Example 1(d). The solvent was distilled off and the residue was purified by column chromatography (60-120 silica gel, 50% ethyl acetate in hexane) to give the product in 49% yield (4.3 g).

b) N-(3-((2-amino-4-iodophenyl)amino)-5-(1H-pyrrol-1-yl)phenyl)acetamide

To a solution of the compound of Example 99(a) (0.5 g, 1.08 mmol) in THF (30 ml) were added a solution of ammonium chloride (0.289 g, 5.41 mmol, 5 eq.) in water (5 ml) and zinc (0.354 g, 5.41 mmol, 5 eq.). The mixture was stirred at RT for 0.5 h and filtered. The filtrate was diluted with water and extracted as in Example 1(d). The solvent was distilled off to afford the product in 75% yield (0.35 g). $^1$H NMR (300 MHz, DMSO-d$_6$): δ 9.88 (s, 1H), 7.38 (s, 1H), 7.19 (s, 1H), 7.09-7.06 (m, 3H), 6.84-6.8 (m, 3H), 6.51 (m, 1H), 6.22 (t, 2H), 5.04 (br s, 2H), 2.0 (s, 3H).

c) N-(3-(5-iodo-1H-benzo[d]imidazol-1-yl)-5-(1H-pyrrol-1-yl)phenyl) acetamide A mixture of the compound of Example 99(b) (0.35 g, 0.81 mmol) and formic acid (10 ml) was heated at 100° C. for 30 min. The formic acid was distilled off under reduced pressure and the residue was dissolved in ethyl acetate. The ethyl acetate layer was washed with water, brine and dried over sodium sulphate. The solvent was distilled off to afford the product in 84% yield (0.3 g). $^1$H NMR, 300 MHz: (DMSO-d$_6$): δ 10.4 (s, 1H), 8.7 (s, 1H), 8.18 (s, 1H), 7.82 (s, 2H), 7.67-7.54 (m, 3H), 7.4 (s, 2H), 6.32 (m, 2H), 2.05 (s, 3H).

d) N-(3-(1H-pyrrol-1-yl)-5-(5-((trimethylsilyl)ethynyl)-1H-benzo[d]imidazol-1-yl)phenyl)acetamide A solution of the compound of Example 99(c) (3.0 g, 7.4 mmol) in DMF-Et$_3$N (1:1; 60 ml) was degassed by N$_2$ bubbling for 15 min. Pd(PPh$_3$)$_4$ (1.2 g, 11.9 mmol, 0.1 eq.), copper(I) iodide (0.2 g, 11.9 mmol, 0.1 eq.) and ethynyltrimethylsilane (2.2 ml, 49.2 mmol, 2 eq.) were added sequentially and the mixture was stirred for 12 h at RT. The mixture was quenched and extracted as in Example 1(d). The solvent was distilled off and the residue was purified by column chromatography (60-120 silica gel, 60% ethyl acetate in hexane) to give the product in 71% yield (2.0 g). $^1$H NMR, 300 MHz: (DMSO-d$_6$): δ 10.4 (s, 1H), 8.85 (s, 1H), 7.9-7.8 (m, 2H), 7.75-7.5 (m, 6H), 7.45 (t, 2H), 2.05 (s, 3H), 0.2 (s, 9H); LC-MS (ESI): Calculated mass: 412.56; Observed mass: 413 [M+H]$^+$ (rt: 1.55 min).

e) N-(3-(5-ethynyl-1H-benzo[d]imidazol-1-yl)-5-(1H-pyrrol-1-yl)phenyl)acetamide To a solution of the compound of Example 99(d) (2.0 g, 4.85 mmol) in THF at 0° C. was added TBAF (1M in THF; 2.0 ml, 9.7 mmol, 2 eq.) and the mixture was stirred for 0.5 h. The mixture was filtered over a pad of silica and distilled to give the product in 96% yield (1.6 g). LC-MS (ESI): Calculated mass: 340.38; Observed mass: 341.1 [M+H]$^+$ (rt: 1.518 min).

f) N-(3-(5-(1-methyl-1H-1,2,3-triazol-4-yl)-1H-benzo[d]imidazol-1-yl)-5-(1H-pyrrol-1-yl)phenyl)acetamide A mixture of the compound of Example 99(e) (1.0 g, 29.4 mmol), sodium azide (0.19 g, 29.4 mmol, 1.0 eq.), methyl iodide (0.4 g, 29.4 mmol, 1.0 eq.), sodium ascorbate (0.6 g, 29.4 mmol, 1.0 eq.) and copper sulfate pentahydrate (0.36 g, 14.7 mmol, 0.5 eq.) in DMSO, DCM and water (1:1:1, 15:12:12 ml) was stirred for 12 h at RT. The mixture was quenched with water and the precipitate formed was filtered and dried to give the crude product which was purified by preparative HPLC to give the product in 15% yield (0.02 g). LC-MS (ESI): Calculated mass: 397.43; Observed mass: 398.1 [M+H]$^+$ (rt: 0.453 min).

Example 100

N-(3-(5-(1-methyl-1H-1,2,3-triazol-4-yl)-1H-benzo[d]imidazol-1-yl)-5-(1H-pyrrol-1-yl)phenyl)methanesulfonamide a) 3-(5-(1-methyl-1H-1,2,3-triazol-4-yl)-1H-benzo[d]imidazol-1-yl)-5-(1H-pyrrol-1-yl)aniline A mixture of 20% sodium hydroxide (5 ml) and the compound of Example 99 (1.0 g, 2.52 mmol) in 10 ml ethanol was heated at 100° C. for 3 h. The mixture was diluted with ethyl acetate (100 ml) and the organic layer was washed with water (50 ml) and brine (25 ml). The solvent was removed under reduced pressure and the residue was purified by column chromatography over silica gel to afford the product in 73% yield (0.65 g). LC-MS (ESI): Calculated mass: 355.4; Observed mass: 356.3 [M+H]$^+$ (rt: 0.49 min).

b) N-(3-(5-(1-methyl-1H-1,2,3-triazol-4-yl)-1H-benzo[d]imidazol-1-yl)-5-(1H-pyrrol-1-yl)phenyl) methanesulfonamide To a solution of the compound of Example 100(a) (100 mg, 0.281 mmol) in DCM (5 ml) were added pyridine (45 mg, 0.563 mmol, 2.0 eq.) and methanesulfonyl chloride (26 mg, 0.225 mmol, 0.8 eq.) and the mixture was stirred at RT for 12 h. Pyridine was removed under reduced pressure and the residue was purified by preparative HPLC to afford the product in 7% yield (8 mg). $^1$H NMR, 300 MHz: (DMSO-d$_6$): δ 10.33 (s, 1H), 9.01 (s, 1H), 8.64 (s, 1H), 8.27 (s, 1H), 7.97-7.94 (m, 1H), 7.83 (d, 1H), 7.71 (s, 1H), 7.46-7.42 (m, 4H), 6.35-6.34 (m, 2H), 4.12 (s, 3H), 3.21 (s, 3H); LC-MS (ESI): Calculated mass: 433.49; Observed mass: 434.3 [M+H]$^+$ (rt: 0.67 min).

Example 101

N-(3-(5-(1-methyl-1H-1,2,3-triazol-4-yl)-1H-benzo[d]imidazol-1-yl)-5-(1H-pyrrol-1-yl)phenyl)ethanesulfonamide The compound was prepared from the compound of Example 99 using the procedures of Example 100. $^1$H NMR, 300 MHz: (DMSO-d$_6$): δ 10.37 (s, 1H), 8.97 (s, 1H), 8.63 (s, 1H), 8.26 (s, 1H), 7.95-7.93 (m, 1H), 7.8 (d, 1H), 7.67 (m, 1H), 7.45-7.42 (m, 4H), 6.34 (t, 2H), 4.2 (s, 3H), 2.4 (m, 2H), 1.2 (d, 3H); LC-MS (ESI): Calculated mass: 447.51; Observed mass: 449.1 [M+H]$^+$ (rt: 0.97 min).

Example 102

N-(3-(5-(1-methyl-1H-1,2,3-triazol-4-yl)-1H-benzo[d]imidazol-1-yl)-5-(1H-pyrrol-1-yl)phenyl)cyclopropanesulfonamide The compound was prepared from the compound of Example 99 using the procedures of Example 100 and cyclopropane sulfonyl chloride. $^1$H NMR, 300 MHz: (DMSO-d$_6$): δ 10.3 (s, 1H), 8.8 (s, 1H), 8.61 (s, 1H), 8.25 (s, 1H), 7.91 (d, 1H), 7.78 (d, 1H), 7.69 (s, 1H), 7.46-7.43 (m, 4H), 6.34 (t, 2H), 4.12 (s, 3H), 2.94 (m, 1H), 1.04-1.02 (m, 4H); LC-MS (ESI): Calculated mass: 459.52; Observed mass: 460.1 [M+H]$^+$ (rt: 1.22 min).

Example 103

N-(3-(5-(1-methyl-1H-1,2,3-triazol-4-yl)-1H-benzo[d]imidazol-1-yl)-5-(1H-pyrrol-1-yl)phenyl)benzenesulfonamide The compound was prepared from the compound of Example 99 using the procedures of Example 100. $^1$H NMR, 300 MHz: (DMSO-d$_6$): δ 10.91 (s, 1H), 8.69 (s, 1H), 8.61 (s, 1H), 8.21 (s, 1H), 7.92-7.89 (m, 3H), 7.67-7.62 (m, 4H), 7.37-7.32 (m, 4H), 7.20 (s, 1H), 6.32 (d, 2H), 4.11 (s, 3H); LC-MS (ESI): Calculated mass: 495.56; Observed mass: 496.1 [M+H]$^+$ (rt: 1.42 min).

Example 104

1-(furan-2-ylmethyl)-3-(3-(5-(1-methyl-1H-1,2,3-triazol-4-yl)-1H-benzo[d]-imidazol-1-yl)-5-(1H-pyrrol-1-yl)phenyl)urea To a solution of the compound of Example 100(a) (100 mg, 0.281 mmol) in DCM (10 ml) at 0° C. was added 2-(isocyanatomethyl)furan (35 mg, 0.281 mmol, 1.0 eq.) and the mixture was stirred at RT for 16 h. The solvent was removed under reduced pressure and the residue was purified by preparative HPLC to give the compound in 13% yield (18 mg). $^1$H NMR, 300 MHz: (DMSO-d$_6$): δ 9.05 (s, 1H), 8.8 (s, 1H), 8.6 (s, 1H), 8.24 (s, 1H), 7.92-7.9 (m, 1H), 7.81 (d, 1H), 7.72-7.60 (m, 4H), 7.48-7.41 (m, 3H), 6.89 (t, 1H), 6.41 (m, 1H), 6.32-6.28 (m, 2H), 4.33 (d, 2H), 4.12 (s, 3H); LC-MS (ESI): Calculated mass: 478.51; Observed mass: 479.2 [M+H]$^+$ (rt: 1.39 min).

Example 105

N-(3-(5-(1-(2-morpholinoethyl)-1H-1,2,3-triazol-4-yl)-1H-benzo[d]imidazol-1-yl)-5-(1H-pyrrol-1-yl)phenyl)acetamide A mixture of the compound of Example 99(e) (100 mg, 0.294 mmol), 4-(2-azidoethyl)morpholine (55 mg, 0.353 mmol, 1.2 eq.), sodium ascorbate (58 mg, 0.294 mmol, 1.0 eq.) and copper sulfate pentahydrate (37 mg, 0.147 mmol, 0.5 eq.) in DMSO, DCM and water (1:1:1, 3 ml) was stirred for 12 h at RT. The mixture was quenched with water and the precipitate formed was filtered and dried to give the crude product which was purified by preparative HPLC to give the product in 7% yield (10 mg). $^1$H NMR, 300 MHz: (DMSO-d$_6$): δ 10.46 (s, 1H), 8.83 (s, 1H), 8.73 (s, 1H), 8.28 (s, 1H), 7.92 (m, 2H), 7.84-7.81 (m, 2H), 7.63 (s, 1H), 7.43-7.42 (m, 2H), 6.34 (m, 2H), 4.82 (t, 2H), 4.01 (m, 4H), 3.7 (m, 2H), 2.51-2.43 (m, 4H), 2.05 (s, 3H); LC-MS (ESI): Calculated mass: 496.56; Observed mass: 497 [M+H]$^+$ (rt: 0.08 min).

Example 106

N-(3-(5-(oxazol-5-yl)-1H-benzo[d]imidazol-1-yl)-5-(1H-pyrrol-1-yl)phenyl)-acetamide a) N-(3-(4-formyl-2-nitrophenylamino)-5-(1H-pyrrol-1-yl)phenyl)acetamide A solution of the compound of Example 87(d) (5.5 g, 25.7 mmol), 4-fluoro-3-nitrobenzaldehyde of Intermediate Example 4 (3.86 g, 25.7 mmol, 1.0 eq.) and potassium fluoride (1.49 g, 25.7 mmol, 1.0 eq.) in DMF (5 ml) was heated at 130° C. for 4 h. The mixture was quenched and extracted as in Example 1(d). The solvent was distilled off and the residue was purified by column chromatography (60-120 silica gel, 40% ethyl acetate in hexane) to give the product in 38% yield (3.58 g). $^1$H NMR (300 MHz, DMSO-d$_6$): δ 10.05 (s, 1H), 9.86 (s, 1H), 8.71 (s, 1H), 7.95 (d, 1H), 7.67 (m, 2H), 7.50 (s, 1H), 7.32-7.29 (m, 5H), 6.29 (s, 1H), 2.08 (s, 3H).

b) N-(3-(2-nitro-4-(oxazol-5-yl)phenylamino)-5-(1H-pyrrol-1-yl)phenyl)acetamide

To a solution of the compound of Example 106(a) (2.5 g, 6.88 mmol) in methanol (15 ml) was added potassium carbonate (1.04 g, 7.57 mmol, 1.1 eq.) and the mixture was stirred for 10 min at RT. Toluenesulfonylmethyl isocyanide (1.48 g, 7.57 mmol, 1.1 eq.) was added and the mixture was refluxed for 4 h. The solvent was distilled off and water was added to the crude. The mixture was extracted as in Example 1(d). The solvent was distilled off and the residue was purified by column chromatography (60-120 silica gel, 70% ethyl acetate in hexane) to give the product in 57% yield (1.58 g). $^1$H NMR (300 MHz, DMSO-d$_6$): δ 10.05 (d, 1H), 10.32 (d, 1H), 9.87 (s, 1H), 7.81 (s, 1H), 7.98-7.92 (m, 1H), 7.85-7.60 (m, 3H), 7.55 (s, 1H), 7.32-7.29 (m, 4H), 7.29 (s, 1H), 2.08 (s, 3H).

c) N-(3-(2-amino-4-(oxazol-5-yl)phenylamino)-5-(1H-pyrrol-1-yl)phenyl)acetamide

To a solution of the compound of Example 106(b) (1.58 g, 3.9 mmol) in methanol (30 ml) and ethylacetate (15 ml)

was added 10% Pd/C (300 mg, 0.2 eq.) and the reaction vessel was purged with nitrogen gas for 5 min. The mixture was then hydrogenated with $H_2$ balloon for 12 h. The mixture was filtered through a pad of celite and the filtrate was concentrated to afford the compound in 68% yield (1.0 g).

d) N-(3-(5-(oxazol-5-yl)-1H-benzo[d]imidazol-1-yl)-5-(1H-pyrrol-1-yl)phenyl)-acetamide A mixture of the compound of Example 106(c) (0.4 g, 1.07 mmol) and formic acid (4 ml) was heated at 100° C. for 30 min. The formic acid was distilled off and the residue was dissolved in ethyl acetate. The ethyl acetate layer was washed with water, brine and dried over sodium sulphate. The solvent was distilled off and the residue was purified by preparative HPLC to give the product in 12% yield (50 mg). $^1$H NMR (300 MHz, DMSO-$d_6$): δ 10.43 (s, 1H), 8.84 (s, 1H), 8.47 (s, 1H), 8.17 (s, 1H), 7.87-7.77 (m, 5H), 7.63 (s, 1H), 7.42 (t, 2H), 6.34 (t, 2H), 2.13 (s, 3H); LC-MS (ESI): Calculated mass: 383.40; Observed mass: 384.1 [M+H]$^+$ (rt: 1.108 min).

Example 107

N-(3-(5-(oxazol-5-yl)-1H-benzo[d]imidazol-1-yl)-5-(1H-pyrrol-1-yl)phenyl)-propane-2-sulfonamide a) 3-(5-(oxazol-5-yl)-1H-benzo[d]imidazol-1-yl)-5-(1H-pyrrol-1-yl)aniline

To a solution of the compound of Example 106 (800 mg, 2.1 mmol) in ethanol (15 ml) was added aqueous solution of NaOH (0.72 g, 18.06 mmol, 8.6 eq.) and the mixture was heated at 85° C. for 5 h. The mixture was quenched and extracted as in Example 1(d). The solvent was distilled off to afford the product in 70% yield (0.5 g).

b) N-(3-(5-(oxazol-5-yl)-1H-benzo[d]imidazol-1-yl)-5-(1H-pyrrol-1-yl)phenyl)-propane-2-sulfonamide To a solution of the compound of Example 107(a) (80 mg, 0.23 mmol) in DCM (2 ml) was added pyridine (37 mg, 0.47 mmol, 2.0 eq.) followed by propane-2-sulfonyl chloride (39 mg, 0.28 mmol, 1.2 eq.). The mixture was stirred for 1 h and quenched and extracted as in Example 2(b). The solvent was distilled off and the residue was purified by preparative HPLC to give the product in 14% yield (14 mg). $^1$H NMR (300 MHz, DMSO-$d_6$): δ 10.29 (s, 1H), 8.80 (s, 1H), 8.46 (s, 1H), 8.17 (s, 1H), 7.82-7.86 (m, 3H), 7.68 (s, 1H), 7.46-7.40 (m, 4H), 6.34 (t, 2H), 3.30 (m, 1H), 2.51-2.50 (m, 6H); LC-MS (ESI): Calculated mass: 447.51; Observed mass: 448.1 [M+H]$^+$ (rt: 2.001 min).

Example 108

N-(3-(5-(oxazol-5-yl)-1H-benzo[d]imidazol-1-yl)-5-(1H-pyrrol-1-yl)phenyl)-cyclopropanesulfonamide The compound was prepared from the compound of Example 106 using the procedures of Example 107 and cyclopropane sulfonyl chloride. $^1$H NMR (300 MHz, DMSO-$d_6$): δ 10.35 (s, 1H), 8.87 (s, 1H), 8.52 (s, 1H), 8.22 (s, 1H), 7.82 (d, 3H), 7.74-7.35 (m, 1H), 7.5-7.45 (m, 4H), 6.39 (t, 2H), 3.04-2.95 (m, 1H), 1.08-1.07 (m, 4H); LC-MS (ESI): Calculated mass: 445.49; Observed mass: 446.1 [M+H]$^+$ (rt: 1.43 min).

Example 109

N-(3-(5-(1-methyl-1H-pyrazol-4-yl)-1H-benzo[d]imidazol-1-yl)-5-(1H-pyrrol-1-yl)phenyl)ethanesulfonamide The compound was prepared from the compound of Example 87 using the procedures of Example 88. $^1$H NMR (300 MHz, DMSO-$d_6$): δ 10.3 (s, 1H), 8.67 (s, 1H), 8.2 (s, 1H), 8.0 (s, 1H), 7.95 (s, 1H), 7.67-7.61 (m, 3H), 7.43-7.39 (m, 4H), 6.38 (s, 2H), 3.88 (s, 3H), 3.32 (quartet, 2H), 1.27 (t, 3H); LC-MS (ESI): Calculated mass: 446.52; Observed mass: 447.1 [M+H]$^+$ (rt: 1.25 min).

Example 110

N-(3-(5-(1-methyl-1H-pyrazol-4-yl)-1H-benzo[d]imidazol-1-yl)-5-(1H-pyrrol-1-yl)phenyl)propane-2-sulfonamide The compound was prepared from the compound of Example 87 using the procedures of Example 88. $^1$H NMR (400 MHz, DMSO-$d_6$): δ 10.34 (s, 1H), 8.89 (s, 1H), 8.23 (s, 1H), 8.01 (s, 1H), 7.97 (s, 1H), 7.69-7.65 (m, 3H), 7.44-7.41 (m, 4H), 7.64 (d, 2H), 3.89 (s, 3H), 3.51-3.50 (m, 1H), 1.31 (d, 6H); LC-MS (ESI): Calculated mass: 460.55; Observed mass: 461.1 [M+H]$^+$ (rt: 1.377 min).

Example 111

N-(3-(5-(1-cyclopentyl-1H-pyrazol-4-yl)-1H-benzo[d]imidazol-1-yl)-5-(1H-pyrrol-1-yl)phenyl)acetamide The compound was prepared using the procedures of Example 87. $^1$H NMR (300 MHz DMSO-$d_6$): δ 10.45 (s, 1H), 8.96 (s, 1H), 8.34 (s, 1H), 8.04 (s, 1H), 7.98 (s, 1H), 7.91 (s, 1H), 7.83 (s, 1H), 7.72-7.68 (m, 2H), 7.64 (s, 1H), 7.42 (t, 2H), 6.34 (t, 2H), 4.68-4.57 (m, 1H), 2.14 (s, 3H), 2.08-1.93 (m, 4H), 1.87-1.73 (m, 2H), 1.72-1.60 (m, 2H); LC-MS (ESI): Calculated mass: 450.53; Observed mass: 451.2 [M+H]$^+$ (rt: 1.509 min).

Example 112

N-(3-(5-(1-(3-hydroxy-3-methylbutyl)-1H-1,2,3-triazol-4-yl)-1H-benzo[d]-imidazol-1-yl)-5-(1H-pyrrol-1-yl)phenyl)acetamide A mixture of the compound of Example 99(e) (0.3 g, 0.88 mmol), 4-azido-2-methylbutan-2-ol of Intermediate Example 6 (0.17 g, 1.06 mmol, 1.2 eq.), sodium-(L)-ascorbate (0.17 g, 0.88 mmol, 1.0 eq.) and copper sulfate pentahydrate (0.11 g, 0.44 mmol, 0.5 eq.) in DCM (2 ml), DMSO (2 ml) and water (2 ml) was stirred for 12 h at RT. The mixture was quenched with water and the precipitate was filtered and dried. The crude product was purified by preparative HPLC to give the product in 48% yield (0.2 g). $^1$H NMR (300 MHz, DMSO-$d_6$): δ 10.42 (s, 1H), 8.86 (s, 1H), 8.68 (s, 1H), 8.23 (s, 1H), 7.93-7.77 (m, 4H), 7.62 (s, 1H), 7.40 (t, 2H), 6.31 (t, 2H), 4.70 (t, 2H), 3.40 (br s, 1H), 2.48

(t, 2H), 2.11 (s, 3H), 1.16 (s, 6H); LC-MS (ESI): Calculated mass: 469.54; Observed mass: 470.2 [M+H]⁺ (rt: 0.666 min).

Example 113

N-(3-(5-(1-(3-hydroxy-3-methylbutyl)-1H-1,2,3-triazol-4-yl)-1H-benzo[d]-imidazol-1-yl)-5-(1H-pyrrol-1-yl)phenyl)ethanesulfonamide a) 4-(4-(1-(3-amino-5-(1H-pyrrol-1-yl)phenyl)-1H-benzo[d]imidazol-5-yl)-1H-1,2,3-triazol-1-yl)-2-methylbutan-2-ol To a solution of the compound of Example 112 (150 mg, 0.32 mmol) in ethanol (10 ml) was added aqueous solution of NaOH (160 mg, 4 mmol, 12.5 eq.) and the mixture was heated at 80° C. for 2 h. The mixture was quenched and extracted as in Example 1(d). The solvent was distilled off to afford the product in 58% yield (80 mg).

b) N-(3-(5-(1-(3-hydroxy-3-methylbutyl)-1H-1,2,3-triazol-4-yl)-1H-benzo[d]-imidazol-1-yl)-5-(1H-pyrrol-1-yl)phenyl)ethanesulfonamide To a solution of the compound of Example 113(a) (100 mg, 0.234 mmol) in DCM (5 ml) was added pyridine (36 mg, 0.47 mmol, 2 eq.) followed by ethanesulfonyl chloride (23 mg, 0.187 mmol, 0.8 eq.). The mixture was stirred for 2 h and quenched and extracted as in Example 2(b). The solvent was distilled off and the residue was purified by preparative HPLC to give the product in 10% yield (12 mg). ¹H NMR (300 MHz, DMSO-d₆): δ 10.35 (s, 1H), 8.88 (s, 1H), 8.70 (s, 1H), 8.25 (s, 1H), 7.93 (dd, 1H), 7.78 (d, 1H), 7.68 (m, 1H), 7.45-7.41 (m, 4H), 6.34 (t, 2H), 4.52-4.46 (m, 2H) 3.37-3.30 (m, 5H), 1.27 (t, 3H), 1.18 (s, 6H); LC-MS (ESI): Calculated mass: 519.62; Observed mass: 520.2 [M+H]⁺ (rt: 1.17 min).

Example 114

N-(3-(5-(1-methyl-1H-pyrazol-4-yl)-1H-benzo[d]imidazol-1-yl)-5-(1H-pyrazol-1-yl)phenyl)acetamide a) N-(3-nitro-5-(1H-pyrazol-1-yl)phenyl)acetamide To a solution of N-(3-bromo-5-nitrophenyl)acetamide of Example 1(c) (10 g, 38.6 mmol) in DMF (100 ml) were added pyrazole (5.26 g, 77.2 mmol, 2.0 eq.), copper(I) oxide (1.104 g, 7.72 mmol, 0.2 eq.) and cesium carbonate (25.15 g, 77.2 mmol, 2.0 eq.) and the mixture was heated at 120° C. for 16 h. The mixture was quenched and extracted as in Example 1(d). The solvent was distilled off and the residue was purified by column chromatography over silica gel (30% ethyl acetate in hexane) to afford the compound in 86% yield (8.2 g). ¹H NMR (300 MHz, DMSO-d₆): δ 10.62 (s, 1H), 8.7 (d, 1H), 8.5-8.48 (m, 2H), 8.32 (t, 1H), 7.84 (d, 1H), 6.62 (t, 1H), 2.08 (s, 3H); LC-MS (ESI): Calculated mass: 246.22; Observed mass: 247.1 [M+H]⁺ (rt: 0.6 min).

b) N-(3-amino-5-(1H-pyrazol-1-yl)phenyl)acetamide

To a solution of the compound of Example 114(a) (8.2 g, 33.3 mmol) in ethanol (70 ml) were added iron powder (3.72 g, 66.6 mmol, 2.0 eq.) and 50% aqueous calcium chloride solution (15 ml). The mixture was stirred at 100° C. for 4 h. The mixture was quenched and extracted as in Example 1(d). The solvent was distilled off and the residue was purified by column chromatography over silica gel to afford the compound in 99% yield (7.1 g). LC-MS (ESI): Calculated mass: 216.24; Observed mass: 217 [M+H]⁺ (rt: 0.12 min).

c) N-(3-((4-bromo-2-nitrophenyl)amino)-5-(1H-pyrazol-1-yl)phenyl)acetamide

A solution of the compound of Example 114(b) (6.97 g, 32.23 mmol), 4-bromo-1-fluoro-2-nitrobenzene (7.09 g, 32.23 mmol, 1.0 eq.) and potassium fluoride (1.87 g, 32.23 mmol, 1.0 eq.) in DMF was heated at 150° C. for 4 h. The mixture was quenched and extracted as in Example 2(b). The solvent was distilled off to give the crude residue which was purified by column chromatography over silica gel to give the compound in 75% yield (10 g). LC-MS (ESI): Calculated mass: 416.23; Observed mass: 417 [M+H]⁺ (rt: 1.65 min).

d) N-(3-((2-amino-4-bromophenyl)amino)-5-(1H-pyrazol-1-yl)phenyl)acetamide

To a solution of the compound of Example 114(c) (10 g, 24.03 mmol) in ethanol (70 ml) were added iron powder (2.68 g, 48.05 mmol, 2.0 eq.) and 50% aqueous calcium chloride solution (20 ml). The mixture was stirred at 100° C. for 4 h. The mixture was quenched and extracted as in Example 1(d). The solvent was distilled off and the residue was used without purification in the next step.

e) N-(3-(5-bromo-1H-benzo[d]imidazol-1-yl)-5-(1H-pyrazol-1-yl)phenyl)acetamide

A mixture of the compound of Example 114(d) (crude from previous step) and formic acid (20 ml) was heated at 100° C. for 30 min. The formic acid was distilled off and the crude was dissolved in ethyl acetate. The ethyl acetate layer was washed with water, brine and dried over sodium sulphate. The solvent was distilled off to afford the product in 84% yield (8.0 g). ¹H NMR (300 MHz, DMSO-d₆): δ 8.72 (s, 1H), 8.57 (d, 1H), 8.22 (m, 1H), 8.11 (s, 1H), 8.01 (d, 1H), 7.87-7.79 (m, 3H), 7.66 (d, 1H), 7.51 (dd, 1H), 6.58 (t, 1H), 2.1 (s, 3H); LC-MS (ESI): Calculated mass: 396.24; Observed mass: 397 [M+H]⁺ (rt: 1.38 min).

f) N-(3-(5-(1-methyl-1H-pyrazol-4-yl)-1H-benzo[d]imidazol-1-yl)-5-(1H-pyrazol-1-yl)phenyl)acetamide A solution of the compound of Example 114(e) (8.0 g, 20.19 mmol) in 1,2-dimethoxyethane (100 ml) was degassed by N₂ bubbling for 5 min. 1-Methyl-4-(4,4,5,5-tetramethyl-1,3,2-dioxaborolan-2-yl)-1H-pyrazole (6.3 g, 30.29 mmol, 1.5 eq.) was added and the mixture was degassed for another 5 min. Pd(PPh₃)₄ (4.67 g, 4.04 mmol, 0.2 eq.) and aqueous sodium carbonate (5.35 g, 50.5 mmol, 2.5 eq.) were added and the procedure of Example 1(d) was followed. The crude residue of the product was purified by column chromatography over silica gel to afford the compound in 62% yield (5.0 g). ¹H NMR (300 MHz, CD₃OD): δ 9.21 (s, 1H), 8.35 (d, 1H), 8.13-8.08 (m, 3H), 8.0 (s, 1H), 7.94 (s, 1H), 7.88-7.76 (m, 4H), 6.73-6.69 (m, 1H), 3.98 (s, 3H), 2.23 (s, 3H), LC-MS (ESI): Calculated mass: 397.43; Observed mass: 398.1 [M+H]⁺ (rt: 0.26 min).

Example 115

N-(3-(5-(1-methyl-1H-pyrazol-4-yl)-1H-benzo[d]imidazol-1-yl)-5-(1H-pyrazol-1-yl)phenyl)methanesulfonamide a) 3-(5-(1-methyl-1H-pyrazol-4-yl)-1H-benzo[d]imidazol-1-yl)-5-(1H-pyrazol-1-yl)aniline To a solution of the compound of Example 114 (4.0 g, 10.06 mmol) in ethanol (25 ml) was added 20% aqueous solution of NaOH (5 ml) and the reaction was heated at 100° C. for 2 h. The mixture was quenched and extracted as in Example 1(d). The solvent was distilled off to afford the product in 78% yield (2.8 g).

b) N-(3-(5-(1-methyl-1H-pyrazol-4-yl)-1H-benzo[d]imidazol-1-yl)-5-(1H-pyrazol-1-yl)phenyl)methanesulfonamide To a solution of the compound of Example 115(a) (50 mg, 0.14 mmol) in DCM was added pyridine (22 mg, 0.28 mmol, 2.0 eq.) followed by methanesulfonyl chloride (19 mg, 0.169 mmol, 1.2 eq.). The mixture was stirred for 1 h and quenched and extracted as in Example 2(b). The solvent was distilled off and the residue was purified by preparative HPLC to give the product in 20% yield (12 mg). $^1$H NMR (300 MHz, CD$_3$OD): δ 8.68 (s, 1H), 8.35 (d, 1H), 8.02 (s, 1H), 7.92 (s, 1H), 7.87 (s, 1H), 7.84-7.81 (m, 1H), 7.77-7.73 (m, 2H), 7.71 (s, 1H), 7.67-7.63 (m, 1H), 7.5-7.48 (m, 1H), 6.58-6.55 (m, 1H), 3.93 (s, 3H), 3.12 (s, 3H); LC-MS (ESI): Calculated mass: 433.49; Observed mass: 434.1 [M+H]$^+$ (rt: 0.35 min).

Example 116

N-(3-(5-(1-methyl-1H-pyrazol-4-yl)-1H-benzo[d]imidazol-1-yl)-5-(1H-pyrazol-1-yl)phenyl)propane-2-sulfonamide The compound was prepared from the compound of Example 114 using the procedures of Example 115. $^1$H NMR (300 MHz, CD$_3$OD): δ 8.65 (s, 1H), 8.37 (d, 1H), 8.05 (s, 1H), 7.96 (s, 1H), 7.91 (s, 1H), 7.81 (m, 3H), 7.76-7.74 (m, 1H), 7.69-7.67 (m, 1H), 7.55-7.54 (m, 1H), 6.61-6.6 (m, 1H), 3.95 (s, 3H), 3.54-3.49 (m, 1H), 1.43 (d, 6H); LC-MS (ESI): Calculated mass: 461.54; Observed mass: 462.1 [M+H]$^+$ (rt: 0.7 min).

Example 117

N-(3-(5-(1-methyl-1H-pyrazol-4-yl)-1H-benzo[d]imidazol-1-yl)-5-(1H-pyrazol-1-yl)phenyl)cyclopropanesulfonamide The compound was prepared from the compound of Example 114 using the procedures of Example 115 and cyclopropane sulfonyl chloride. $^1$H NMR (300 MHz, CD$_3$OD): δ 8.54 (s, 1H), 8.37 (d, 1H), 8.02 (s, 1H), 7.93 (d, 1H), 7.88 (s, 1H), 7.82-7.8 (m, 3H), 7.72 (d, 1H), 7.65-7.62 (m, 1H), 7.53-7.52 (m, 1H), 6.6-6.59 (m, 1H), 3.95 (s, 3H), 2.81-2.78 (m, 1H), 1.18-1.15 (m, 2H), 1.09-1.04 (m, 2H); LC-MS (ESI): Calculated mass: 459.52; Observed mass: 460.1 [M+H]$^+$ (rt: 0.58 min).

Example 118

N-(3-(5-(1-methyl-1H-pyrazol-4-yl)-1H-benzo[d]imidazol-1-yl)-5-(1H-pyrazol-1-yl)phenyl)benzenesulfonamide The compound was prepared from the compound of Example 114 using the procedures of Example 115. $^1$H NMR (300 MHz, CD$_3$OD): δ 9.2 (s, 1H), 8.29 (d, 1H), 8.12 (s, 1H), 8.0 (s, 1H), 7.96-7.93 (m, 3H), 7.83-7.75 (m, 4H), 7.69-7.65 (m, 1H), 7.61-7.54 (m, 3H), 7.45 (t, 1H), 6.58 (m, 1H), 3.98 (s, 3H); LC-MS (ESI): Calculated mass: 495.56; Observed mass: 496.2 [M+H]$^+$ (rt: 1.28 min).

Example 119

N-(3-(5-(1-methyl-1H-pyrazol-4-yl)-1H-benzo[d]imidazol-1-yl)-5-(1H-pyrazol-1-yl)phenyl)piperidine-1-sulfonamide The compound was prepared from the compound of Example 114 using the procedures of Example 115. $^1$H NMR (300 MHz, CD$_3$OD): δ 8.92 (s, 1H), 8.3 (d, 1H), 8.06 (s, 1H), 8.0 (s, 1H), 7.95 (s, 1H), 7.88 (s, 1H), 7.77-7.69 (m, 5H), 7.45 (m, 1H), 6.56 (m, 1H), 3.92 (s, 3H), 3.28-3.27 (m, 4H), 1.6-1.49 (m, 6H); LC-MS (ESI): Calculated mass: 502.59; Observed mass: 503.1 [M+H]$^+$ (rt: 0.1.33 min).

Example 120

1-(furan-2-ylmethyl)-3-(3-(5-(1-methyl-1H-pyrazol-4-yl)-1H-benzo[d]imidazol-1-yl)-5-(1H-pyrazol-1-yl)phenyl)urea To a solution of the compound of Example 115(a) (50 mg, 0.141 mmol) in DCM (1 ml) at 0° C. were added TEA (29 mg, 0.281 mmol, 2.0 eq.) and 2-(isocyanatomethyl)furan (21 mg, 0.169 mmol, 1.2 eq.) and the mixture was stirred at RT for 16 h. The solvent was removed under reduced pressure and the residue was purified by preparative HPLC to afford the compound in 15% yield (10 mg). $^1$H NMR (300 MHz, CD$_3$OD): δ 9.16 (s, 1H), 8.35 (d, 1H), 8.1 (s, 1H), 8.0 (s, 1H), 7.95-7.94 (m, 2H), 7.91 (m, 1H), 7.87 (d, 1H), 7.8-7.78 (m, 2H), 7.75-7.74 (m, 1H), 7.46 (d, 1H), 6.6-6.59 (m, 1H), 6.38-6.37 (m, 1H), 6.31-6.3 (m, 1H), 4.43 (s, 2H), 3.98 (s, 3H); LC-MS (ESI): Calculated mass: 478.51; Observed mass: 479.0 [M+H]$^+$ (rt: 0.72 min).

Example 121

1-(4-fluorophenyl)-3-(3-(5-(1-methyl-1H-pyrazol-4-yl)-1H-benzo[d]imidazol-1-yl)-5-(1H-pyrazol-1-yl)phenyl)urea The compound was prepared using the procedures of Example 120. $^1$H NMR (300 MHz, CD$_3$OD): δ 9.7 (s, 1H), 9.3 (s, 1H), 8.67 (s, 1H), 8.62 (d, 1H), 8.21 (s, 1H), 8.06 (s, 1H), 8.0 (s, 1H), 7.95 (s, 1H), 7.83-7.81 (m, 2H), 7.75-7.71 (m, 2H), 7.63-7.6 (m, 1H), 7.52-7.49 (m, 2H), 7.15 (t, 2H), 6.61-6.6 (m, 1H), 3.88 (s, 3H); LC-MS (ESI): Calculated mass: 492.51; Observed mass: 493.2 [M+H]$^+$ (rt: 1.37 min).

Example 122

N-(3-(5-(1H-pyrazol-1-yl)-1H-benzo[d]imidazol-1-yl)-5-(1H-pyrazol-1-yl)-phenyl)acetamide To a solution of the compound of Example 114(e) (200 mg, 0.505 mmol) in DMF (20 ml) were added pyrazole (41 mg, 0.606 mmol, 1.2 eq.), copper(I) oxide (0.7 mg, 0.0051 mmol, 0.01 eq.) and cesium carbonate (329 mg, 1.01 mmol, 2.0 eq.) and the mixture was heated at 110° C. for 12 h. The mixture was quenched and extracted as in Example 1(d). The solvent was distilled off and the residue was purified by preparative HPLC to give the product in 20% yield (37 mg). $^1$H NMR (300 MHz, CD$_3$OD): δ 8.9 (br s, 1H), 8.37-8.33 (m, 2H), 8.19 (s, 1H), 8.13-8.12 (m, 1H), 8.06-8.05 (m, 1H), 7.92 (m, 2H), 7.86-7.85 (m, 1H), 7.8-7.78 (m, 2H), 6.61-6.57 (m, 2H), 2.22 (s, 3H); LC-MS (ESI): Calculated mass: 383.41; Observed mass: 384.3 [M+H]$^+$ (rt: 0.52 min).

Example 123

1-(3-(5-(1H-pyrazol-1-yl)-1H-benzo[d]imidazol-1-yl)-5-(1H-pyrazol-1-yl)-phenyl)-3-(furan-2-ylmethyl)urea a) 3-(5-(1H-pyrazol-1-yl)-1H-benzo[d]imidazol-1-yl)-5-(1H-pyrazol-1-yl)aniline To a solution of the compound of Example 122 (230 mg, 0.6 mmol) in ethanol (20 ml) was added aqueous solution of sodium hydroxide (192 mg, 4.8 mmol, 8.0 eq.) and the mixture was heated at 90° C. for 3 h. The mixture was quenched and extracted as in Example 1(d). The solvent was distilled off to afford the product in 73% yield (150 mg).

b) 1-(3-(5-(1H-pyrazol-1-yl)-1H-benzo[d]imidazol-1-yl)-5-(1H-pyrazol-1-yl)phenyl)-3-(furan-2-ylmethyl)urea To a solution of the compound of Example 123(a) (50 mg, 0.146 mmol) in DCM was added TEA (45 mg, 0.439 mmol, 3.0 eq.) followed by 2-(isocyanatomethyl)-furan (23 mg, 0.19 mmol, 1.3 eq.). The mixture was stirred for 1 h and then quenched and extracted as of Example 1(d). The solvent was distilled off and the residue was purified by preparative HPLC to give the product in 8% yield (5 mg). $^1$H NMR (300 MHz, CD$_3$OD): δ 8.92 (br s, 1H), 8.34-8.31 (m, 2H), 8.16 (s, 1H), 7.92-7.89 (m, 4H), 7.77 (m, 2H), 7.71 (m, 1H), 7.44 (m, 1H), 6.57 (m, 2H), 6.36-6.35 (m, 1H), 6.29-6.28 (m, 1H), 4.41 (s, 2H); LC-MS (ESI): Calculated mass: 464.48; Observed mass: 465.2 [M+H]$^+$ (rt: 1.35 min).

Example 124

1-(3-(5-(1H-pyrazol-1-yl)-1H-benzo[d]imidazol-1-yl)-5-(1H-pyrazol-1-yl)-phenyl)-3-cyclopentylurea The compound was prepared from the compound of Example 122 using the procedures of Example 123. $^1$H NMR (300 MHz, CD$_3$OD): δ 9.21 (br s, 1H), 8.35-8.33 (m, 2H), 8.22 (s, 1H), 7.98 (s, 2H), 7.93-7.88 (m, 2H), 7.78-7.77 (m, 2H), 7.73-7.72 (m, 1H), 6.59-6.58 (m, 2H), 4.08 (m, 1H), 1.99-1.96 (m, 2H), 1.75-1.71 (m, 2H), 1.68-1.33 (m, 2H), 1.52-1.49 (m, 2H); LC-MS (ESI): Calculated mass: 452.51; Observed mass: 453.3 [M+H]$^+$ (rt 1.42 min).

Example 125

N-(3-(5-(1H-imidazol-1-yl)-1H-benzo[d]imidazol-1-yl)-5-(1H-pyrazol-1-yl)-phenyl)acetamide The compound was prepared from the compound of Example 114(e) using the procedures of Example 122. $^1$H NMR (300 MHz, CD$_3$OD): δ 9.43 (s, 1H), 8.77 (s, 1H), 8.35 (d, 2H), 8.16 (m, 1H), 8.12 (s, 1H), 8.09-8.08 (m, 1H), 8.03-8.02 (m, 1H), 8.0 (s, 1H), 7.98 (s, 1H), 7.83-7.82 (m, 1H), 7.79-7.72 (m, 3H), 6.59-6.58 (m, 1H), 2.21 (s, 3H); LC-MS (ESI): Calculated mass: 383.41; Observed mass: 384.1 [M+H]$^+$ (rt: 0.12 min).

Example 126

N-(3-(5-(1-methyl-1H-pyrazol-4-yl)-1H-benzo[d]imidazol-1-yl)-5-(1H-pyrazol-1-yl)phenyl)ethanesulfonamide The compound was prepared from the compound of Example 114 using the procedures of Example 115. $^1$H NMR (400 MHz, CD$_3$OD): δ 9.13 (s, 1H), 8.36 (d, 1H), 8.10 (s, 1H), 8.02 (s, 1H), 7.94 (s, 1H), 7.88-7.78 (m, 5H), 7.58 (s, 1H), 6.61-6.50 (m, 1H), 3.97 (s, 3H), 3.31 (quartet, 2H) 1.40 (t, 3H); LC-MS (ESI): Calculated mass: 447.51; Observed mass: 448.1 [M+H]$^+$ (rt: 0.49 min).

Example 127

N-(3-(5-(1-(cyclopropylmethyl)-1H-pyrazol-4-yl)-1H-benzo[d]imidazol-1-yl)-5-(1H-pyrazol-1-yl)phenyl)acetamide A solution of the compound of Example 114(e) (0.5 g, 1.26 mmol) in 1,2-dimethoxyethane (10 ml) was degassed by N$_2$ bubbling for 5 min. The compound of Intermediate Example 9 (0.47 g, 1.89 mmol, 1.5 eq.) was added and the mixture was degassed for another 5 min. Pd(dppf)Cl$_2$ (0.2 g, 0.25 mmol, 0.2 eq.) and aqueous sodium carbonate (0.27 g, 2.52 mmol, 2 eq.) were added and the procedure of Example 1(d) was followed. The crude residue of the product was purified by preparative HPLC to give the product in 11% yield (60 mg). $^1$H NMR (300 MHz, DMSO-d$_6$): δ 10.52 (s, 1H), 8.82-8.73 (m, 1H), 8.59 (d, 1H), 8.23-8.15 (m, 3H), 8.03-7.92 (m, 2H), 7.83-7.74 (m, 2H), 7.72-7.59 (m, 2H), 6.59 (s, 1H), 4.23 (d, 2H), 2.12 (s, 3H), 1.25-0.78 (m, 5H); LC-MS (ESI): Calculated mass: 437.50; Observed mass: 438.2 [M+H]$^+$ (rt: 0.812 min).

Example 128

N-(3-(5-(1-(piperidin-4-yl)-1H-pyrazol-4-yl)-1H-benzo[d]imidazol-1-yl)-5-(1H-pyrazol-1-yl)phenyl)acetamide a) tert-butyl 4-(4-(1-(3-acetamido-5-(1H-pyrazol-1-yl)phenyl)-1H-benzo[d]-imidazol-5-yl)-1H-pyrazol-1-yl)piperidine-1-carboxylate A solution of the compound of Example 114(e) (0.6 g, 1.51 mmol) in 1,2-dimethoxyethane (20 ml) was degassed by N$_2$ bubbling for 5 min. The compound of Intermediate Example 5 (0.85 g, 2.27 mmol, 1.5 eq.) was added and the mixture was degassed for another 5 min. Pd(dppf)Cl$_2$ (0.25 g, 0.302 mmol, 0.2 eq.) and aqueous sodium carbonate (0.5 g, 4.53 mmol, 3.0 eq.) were added and the procedure of Example 1(d) was followed. The crude residue of the product was purified by preparative HPLC to give the product in 35% yield (0.3 g).

b) N-(3-(5-(1-(piperidin-4-yl)-1H-pyrazol-4-yl)-1H-benzo[d]imidazol-1-yl)-5-(1H-pyrazol-1-yl)phenyl)acetamide To a solution of the compound of Example 128(a) (300 mg, 0.53 mmol) in DCM (4 ml) at 0° C. was added trifluoroacetic acid (0.6 ml) and the mixture was stirred at RT for 6 h. The solvent was distilled off and the residue was purified by preparative HPLC to give the product in 89% yield (220 mg). $^1$H NMR (300 MHz, DMSO-d$_6$): δ 10.50 (s, 1H), 8.84 (s, 1H), 8.73-8.63 (m, 1H), 8.61 (d, 1H), 8.52-8.38 (m, 1H), 8.35 (s, 1H), 8.20 (s, 1H), 8.07 (d, 1H), 8.01 (s, 1H), 7.87-7.83 (m, 2H), 7.73-7.65 (m, 2H), 6.62 (t, 1H), 4.36 (m, 1H), 3.50-3.35 (m, 2H), 3.17-3.10 (m, 2H), 2.32-2.21 (m, 4H), 2.14 (s, 3H); LC-MS (ESI): Calculated mass: 466.54; Observed mass: 467.2 [M+H]$^+$ (rt: 0.128 min).

Example 129

N-(3-(5-(1-(1-(methylsulfonyl)piperidin-4-yl)-1H-pyrazol-4-yl)-1H-benzo[d]-imidazol-1-yl)-5-(1H-pyrazol-1-yl)phenyl)acetamide To a solution of the compound of Example 128 (80 mg, 0.171 mmol) in DCM (10 ml) was added pyridine (27 mg, 0.34 mmol, 2 eq.) and methanesulfonyl chloride (19 mg, 0.171 mmol, 1 eq.). The mixture was stirred for 4 h and quenched and extracted as in Example 2(b). The solvent was distilled off and the residue was purified by preparative HPLC to give the product in 19% yield (18 mg). $^1$H NMR (300 MHz, DMSO-d$_6$): δ 10.52 (s, 1H), 10.06 (s, 1H), 8.58 (d, 1H), 8.43 (s, 1H), 8.24 (s, 1H), 8.06-8.00 (m, 3H), 7.89 (s, 1H), 7.83 (d, 1H), 7.78-7.74 (m, 2H), 6.62 (t, 1H), 4.36 (m, 1H), 3.01-2.94 (m, 6H), 2.30 (s, 3H), 2.13 (s, 3H), 2.10-2.01 (m, 2H); LC-MS (ESI): Calculated mass: 544.63; Observed mass: 545.2 [M+H]$^+$ (rt: 0.40 min).

Example 130

N-(3-(5-(oxazol-5-yl)-1H-benzo[d]imidazol-1-yl)-5-(1H-pyrazol-1-yl)phenyl)-acetamide a) N-(3-(4-formyl-2-nitrophenylamino)-5-(1H-pyrazol-1-yl)phenyl)acetamide A solution of the compound of Example 114(b) (0.35 g, 1.62 mmol), 4-fluoro-3-nitrobenzaldehyde (0.24 g, 1.62 mmol, 1.0 eq.) and potassium fluoride (94 mg, 1.62 mmol, 1.0 eq.) in DMF (2 ml) was heated at 130° C. for 4 h. The mixture was quenched and extracted as in Example 1(d). The solvent was distilled off and the residue was purified by column chromatography (60-120 silica gel, 40% ethyl acetate in hexane) to give the product in 51% yield (0.3 g). $^1$H NMR (300 MHz, DMSO-d$_6$): δ 10.29 (s, 1H), 10.03 (s, 1H), 9.87 (s, 1H), 8.71 (m, 1H), 8.43 (d, 1H), 8.05 (s, 1H), 7.92 (d, 1H), 7.76 (s, 1H), 7.60 (s, 1H), 7.54 (s, 1H), 7.27 (s, 1H), 6.55 (s, 1H), 2.10 (s, 3H).

b) N-(3-(2-nitro-4-(oxazol-4-yl)phenylamino)-5-(1H-pyrazol-1-yl)phenyl)-acetamide To a solution of the compound of Example 130(a) (0.3 g, 0.824 mmol) in methanol (8 ml) was added potassium carbonate (0.18 g, 0.904 mmol, 1.1 eq.) and the mixture was stirred for 10 min at RT. Toluenesulfonylmethyl isocyanide (0.124 g, 0.904 mmol, 1.1 eq.) was added and the mixture was refluxed for 4 h. The solvent was distilled off and water was added to the crude product. The mixture was extracted as in Example 1(d). The solvent was distilled off and the residue was purified by column chromatography (60-120 silica gel, 40% ethyl acetate in hexane) to give the product in 75% yield (0.25 g). $^1$H NMR (300 MHz, DMSO-d$_6$): δ 10.23 (s, 1H), 9.57 (s, 1H), 8.46-8.40 (m, 3H), 7.94-7.89 (m, 2H), 7.76-7.72 (m, 2H), 7.57 (s, 1H), 7.49 (s, 1H), 7.42 (d, 1H), 6.55 (t, 1H), 2.01 (s, 3H).

c) N-(3-(2-amino-4-(oxazol-4-yl)phenylamino)-5-(1H-pyrazol-1-yl)phenyl)-acetamide To a solution of the compound of Example 130(b) (0.25 g, 0.62 mmol) in methanol (15 ml) and ethyl acetate (7 ml) was added 10% Pd/C (30 mg) and the reaction vessel was purged with nitrogen gas for 5 min. The mixture was then hydrogenated with H$_2$ balloon for 4 h. The mixture was filtered through a pad of celite and the filtrate was concentrated to afford the compound in 86% yield (0.2 g).

d) N-(3-(5-(oxazol-5-yl)-1H-benzo[d]imidazol-1-yl)-5-(1H-pyrazol-1-yl)phenyl)-acetamide A mixture of the compound of Example 130(c) (0.2 g, 0.54 mmol) and formic acid (3 ml) was heated at 100° C. for 30 min. The formic acid was distilled off and the residue was dissolved in ethyl acetate. The ethyl acetate layer was washed with water, brine and dried over sodium sulphate. The solvent was distilled off and the residue was purified by preparative HPLC to give the product in 6% yield (12 mg). $^1$H NMR (300 MHz, DMSO-d$_6$): δ 10.47 (s, 1H), 8.80 (br s, 1H), 8.60 (d, 1H), 8.46 (s, 1H), 8.24 (s, 1H), 8.17 (s, 1H), 8.94 (s, 1H), 7.86-7.81 (m, 3H), 7.78-7.76 (m, 2H), 6.60 (t, 1H) 2.12 (s, 3H); LC-MS (ESI): Calculated mass: 384.39; Observed mass: 385.1 [M+H]$^+$ (rt: 0.39 min).

Example 131

N-(2',4'-difluoro-5-(6-(1-methyl-1H-pyrazol-4-yl)-3H-imidazo[4,5-b]pyridin-3-yl)biphenyl-3-yl)acetamide a) N-(5-(5-bromo-3-nitropyridin-2-ylamino)-2',4'-difluorobiphenyl-3-yl)acetamide A solution of the compound of Example 1(e) (1.07 g, 4.08 mmol), 5-bromo-2-chloro-3-nitropyridine (0.97 g, 4.08 mmol, 1.0 eq.) and potassium fluoride (0.24 g, 4.08 mmol, 1.0 eq.) in DMF (30 ml) was heated at 130° C. for 5 h. The mixture was quenched and extracted as in Example 1(d). The solvent was distilled off to afford the crude product (1.8 g).

b) N-(5-(3-amino-5-bromopyridin-2-ylamino)-2',4'-difluorobiphenyl-3-yl)acetamide To a solution of the compound of Example 131(a) (1.8 g, 3.8 mmol) in THF (30 ml) were added a solution of ammonium chloride (0.83 g, 15.5 mmol, 4 eq.) in water (15 ml) and zinc (1.02 g, 15.5 mmol, 10 eq.). The mixture was stirred at RT for 3 h and filtered. The mixture was quenched and extracted as in Example 1(d). The solvent was distilled off to afford the product in 97% yield (1.6 g).

c) N-(5-(6-bromo-3H-imidazo[4,5-b]pyridin-3-yl)-2',4'-difluorobiphenyl-3-yl)-acetamide A mixture of the compound of Example 131(b) (1.6 g, 3.7 mmol) and formic acid (15 ml) was heated at 90° C. for 1 h. Formic acid was then distilled off and the crude was dissolved in ethyl acetate. The ethyl acetate layer was washed with water, brine and dried over sodium sulphate. The solvent was distilled off to afford the product in 79% yield (1.3 g). ¹H NMR (300 MHz, DMSO-d₆): δ 10.43 (s, 1H), 9.0 (s, 1H), 8.55 (s, 1H), 8.24 (s, 1H), 7.89 (d, 1H), 7.75-7.65 (m, 2H), 7.48-7.41 (m, 2H), 7.27-7.26 (dt, 1H), 2.1 (s, 3H).

d) N-(2',4'-difluoro-5-(6-(1-methyl-1H-pyrazol-4-yl)-3H-imidazo[4,5-b]pyridin-3-yl)biphenyl-3-yl)acetamide A solution of the compound of Example 131(c) (75 mg, 0.17 mmol) in 1,2-dimethoxyethane (10 ml) was degassed by N₂ bubbling for 5 min. 1-Methyl-4-(4,4,5,5-tetramethyl-1,3,2-dioxaborolan-2-yl)-1H-pyrazole (42 mg, 0.203 mmol, 1.2 eq.) was added and the mixture was degassed for another 5 min. Pd(dppf)Cl₂ (28 mg, 0.033 mmol, 0.2 eq.) and aqueous sodium carbonate (54 mg, 0.507 mmol, 3.0 eq.) were added and the procedure of Example 1(d) was followed. The crude residue of the product was purified by preparative HPLC to give the product in 20% yield (15 mg). ¹H NMR (300 MHz, DMSO-d₆): δ 10.39 (s, 1H), 8.94 (s, 1H), 8.71 (d, 1H), 8.41 (d, 1H), 8.3 (s, 2H), 8.05 (s, 1H), 7.88 (s, 1H), 7.75-7.68 (m, 2H), 7.48-7.42 (dt, 1H), 7.29-7.25 (dt, 1H), 3.89 (s, 3H), 2.1 (s, 3H); LC-MS (ESI); Calculated mass: 444.15: Observed mass: 445.1 [M+H]⁺ (rt: 1.39 min).

Example 132

N-(2',4'-difluoro-5-(6-(1-methyl-1H-pyrazol-4-yl)-3H-imidazo[4,5-b]pyridin-3-yl)biphenyl-3-yl)methanesulfonamide a) 2',4'-difluoro-5-(6-(1-methyl-1H-pyrazol-4-yl)-3H-imidazo[4,5-b]pyridin-3-yl)biphenyl-3-amine To a solution of the compound of Example 131 (0.5 g, 1.1 mmol) in ethanol (10 ml) was added aqueous solution of NaOH (392 mg, 9.79 mmol, 8.9 eq.) and the mixture was heated at 85° C. for 2 h. The mixture was quenched and extracted as in Example 1(d). The solvent was distilled off to afford the product in 79% yield (0.35 g).

b) N-(2',4'-difluoro-5-(6-(1-methyl-1H-pyrazol-4-yl)-3H-imidazo[4,5-b]pyridin-3-yl)biphenyl-3-yl)methanesulfonamide To a solution of the compound of Example 132(a) (70 mg, 0.174 mmol) in DCM (5 ml) was added pyridine (28 mg, 0.348 mmol, 2.0 eq.) followed by methanesulfonyl chloride (22 mg, 0.192 mmol, 1.1 eq.). The reaction was stirred for 1 h and quenched and extracted as in Example 2(b). The solvent was distilled off and the residue was purified by preparative HPLC to give the product in 8% yield (7 mg). ¹H-NMR (300 MHz, CD₃OD): δ 8.8 (br s, 1H), 8.7 (s, 1H), 8.32-8.28 (m, 1H), 8.12 (s, 1H), 7.95 (s, 1H), 7.9-7.85 (m, 1H), 7.8-7.77 (s, 1H), 7.7-7.6 (m, 1H), 7.53-7.49 (m, 2H), 7.18-7.05 (m, 2H), 3.96 (s, 3H), 3.13 (s, 3H); LC-MS (ESI): Calculated mass: 480.12; Observed mass: 481.3 [M+H]⁺ (rt: 1.38 min).

Example 133

N-(2',4'-difluoro-5-(6-(1-methyl-1H-pyrazol-4-yl)-3H-imidazo[4,5-b]pyridin-3-yl)biphenyl-3-yl)ethanesulfonamide The compound was prepared from the compound of Example 131 using the procedures of Example 132. ¹H NMR (300 MHz, DMSO-d₆): δ 8.8 (s, 1H), 8.7 (d, 1H), 8.29 (d, 1H), 8.11 (s, 1H), 7.95 (s, 1H), 7.86 (t, 1H), 7.8-7.77 (m, 1H), 7.7-7.49 (m, 4H), 7.05-7.18 (m, 1H), 3.96 (s, 3H), 3.29 (quartet, 2H), 1.37 (t, 3H); LC-MS (ESI): Calculated mass: 494.13; Observed mass: 495.1 [M+H]⁺ (rt: 1.46 min).

Example 134

N-(2',4'-difluoro-5-(6-(1-methyl-1H-pyrazol-4-yl)-3H-imidazo[4,5-b]pyridin-3-yl)biphenyl-3-yl)benzenesulfonamide The compound was prepared from the compound of Example 131 using the procedures of Example 132. LC-MS (ESI): Calculated mass: 542.13; Observed mass: 543.1 [M+H]⁺ (rt: 1.64 min).

Example 135

N-(5-(6-(1-cyclopentyl-1H-pyrazol-4-yl)-3H-imidazo[4,5-b]pyridin-3-yl)-2',4'-difluorobiphenyl-3-yl)acetamide The compound was prepared from the compound of Example 131(c) using the procedures of Example 131(d). ¹H-NMR (300 MHz, DMSO-d₆): δ 10.43 (s, 1H), 8.92 (s, 1H), 8.73-8.74 (d, 1H), 8.44-8.40 (m, 1H), 8.30-8.25 (m, 1H), 8.05 (s, 1H), 7.25-7.9 (m, 6H), 3.59-3.50 (m, 1H), 2.11 (s, 3H), 2.02-1.93 (m, 2H), 1.88-1.83 (m, 4H), 1.71-1.66 (m, 2H); LC-MS (ESI): Calculated mass: 498.20; Observed mass: 499.2 [M+H]⁺ (rt: 1.63 min).

Example 136

N-(2',4'-difluoro-5-(6-(1-(piperidin-4-yl)-1H-pyrazol-4-yl)-3H-imidazo[4,5-b]-pyridin-3-yl)biphenyl-3-yl)acetamide a) tert-butyl 4-(4-(3-(5-acetamido-2',4'-difluorobiphenyl-3-yl)-3H-imidazo[4,5-b]pyridin-6-yl)-1H-pyrazol-1-yl)piperidine-1-carboxylate A solution of the compound of Example 131(c) (150 mg, 0.338 mmol) in 1,2-dimethoxyethane (20 ml) was degassed by N₂ bubbling for 5 min. tert-Butyl 4-(4-(4,4,5,5-tetramethyl-1,3,2-dioxaborolan-2-yl)-1H-pyrazol-1-yl)piperidine-1-carboxylate (153 mg, 0.406 mmol, 1.2 eq.) was added and the mixture was degassed for another 5 min. Pd(PPh₃)₄ (55 mg, 0.068 mmol, 0.2 eq.) and aqueous sodium carbonate (107 mg, 1.01 mmol, 3.0 eq.) were added and the procedure of Example 1(d) was followed. The crude residue of the product was obtained in 48% yield (100 mg).

b) N-(2',4'-difluoro-5-(6-(1-(piperidin-4-yl)-1H-pyrazol-4-yl)-3H-imidazo[4,5-b]pyridin-3-yl)biphenyl-3-yl)acetamide To a solution of the compound of Example 136(a) (100 mg, 0.16 mmol) in 1,4-dioxane (5 ml) at 0° C. was added HCl in dioxane and stirred at RT for 2 h. The solvent was distilled off and the residue was purified by preparative HPLC to give the product in 30% yield (25 mg). ¹H NMR (300 MHz, DMSO-d₆): δ 10.2 (s, 1H), 8.95-8.91 (m, 1H), 8.78-8.75 (m, 2H), 8.48-8.30 (m, 3H), 8.15-8.10 (m, 1H), 7.84-7.64 (m, 3H), 7.48-7.38 (m, 1H), 7.30-7.20 (m, 1H), 4.6-4.45 (m, 1H), 3.2-3.0 (m, 4H), 2.3-2.05 (m, 7H); LC-MS (ESI): Calculated mass: 513.21; Observed mass: 514.2 [M+H]$^+$ (rt: 0.21 min).

Example 137

N-(5-(6-(1H-pyrazol-1-yl)-3H-imidazo[4,5-b]pyridin-3-yl)-2',4'-difluorobiphenyl-3-yl)acetamide To a solution of the compound of Example 131(c) (1.5 g, 3.3 mmol) in DMF (20 ml) were added pyrazole (0.22 g, 3.3 mmol, 1 eq.), copper(I) oxide (0.243 g, 1.69 mmol, 0.5 eq.) and cesium carbonate (1.73 g, 5.3 mmol, 1.6 eq.) and then heated at 90° C. for 12 h. The mixture was quenched and extracted as in Example 1(d). The solvent was distilled off and the residue was purified by column chromatography (60-120 silica gel, 70% ethyl acetate in hexane) to give the product in 35% yield (0.5 g). $^1$H NMR (300 MHz, DMSO-d$_6$): δ 10.4 (s, 1H), 9.05-8.97 (m, 2H), 8.68-8.60 (m, 2H), 8.32-825 (br s, 1H), 7.92-7.8 (m, 2H), 7.75-7.65 (m, 2H), 7.48-7.38 (m, 1H), 7.30-7.20 (m, 1H), 6.63-6.60 (m, 1H), 2.1 (s, 3H); LC-MS (ESI): Calculated mass: 430.14; Observed mass: 431.1 [M+H]$^+$ (rt: 1.46 min).

Example 138

N-(2',5'-difluoro-5-(5-(1-methyl-1H-pyrazol-4-yl)-1H-benzo[d]imidazol-1-yl)biphenyl-3-yl)acetamide a) N-(2',5'-difluoro-5-nitrobiphenyl-3-yl)acetamide A solution of N-(3-bromo-5-nitrophenyl)acetamide of Example 1(c) (0.8 g, 3.07 mmol) in 1,2-dimethoxyethane (15 ml) was degassed by N$_2$ bubbling for 5 min. 2,5-Difluorophenylboronic acid (0.58 g, 3.69 mmol, 1.2 eq.) was added and the mixture was degassed for another 5 min. Pd(dppf)Cl$_2$ (0.5 g, 0.615 mmol, 0.2 eq.) and aqueous sodium carbonate (0.98 g, 9.23 mmol, 3.0 eq.) were added and the procedure of Example 1(d) was followed. The crude residue of the product was purified by column chromatography (60-120 silica gel, 25% ethyl acetate in hexane) to give the product in 67% yield (0.6 g). $^1$H NMR (300 MHz, DMSO-d$_6$): δ 10.56 (s, 1H), 8.65 (t, 1H), 8.14 (s, 1H), 8.06 (s, 1H), 7.56-7.52 (m, 1H), 7.47-7.37 (m, 2H), 2.12 (s, 3H).

b) N-(5-amino-2',5'-difluorobiphenyl-3-yl)acetamide

To a solution of the compound of Example 138(a) (0.6 g, 2.05 mmol) in methanol (10 ml) and ethyl acetate (3 ml) was added 10% Pd/C (100 mg) and the reaction vessel was purged with nitrogen gas for 5 min. The mixture was then hydrogenated with H$_2$ balloon for a period of 12 h. The mixture was filtered through a pad of celite and the filtrate was concentrated to afford the compound in 93% yield (0.5 g).

c) N-(5-(4-bromo-2-nitrophenylamino)-2',5'-difluorobiphenyl-3-yl)acetamide

A solution of Example 138(b) (0.5 g, 1.9 mmol), 4-bromo-1-fluoro-2-nitrobenzene (0.42 g, 1.9 mmol, 1.0 eq.) and potassium fluoride (0.11 g, 1.9 mmol, 1.0 eq.) in DMF (2 ml) was heated at 130° C. for 5 h. The mixture was quenched and extracted as in Example 1(d). The solvent was distilled off and the residue was purified by column chromatography (60-120 silica gel, 30% ethyl acetate in hexane) to give the product in 57% yield (0.5 g).

d) N-(5-(2-amino-4-bromophenylamino)-2',5'-difluorobiphenyl-3-yl)acetamide

To a solution of the compound of Example 138(c) (0.5 g, 1.08 mmol) in THF (10 ml) were added a solution of ammonium chloride (0.46 g, 8.67 mmol, 8 eq.) in water (2 ml) and zinc (0.57 g, 8.67 mmol, 8 eq.). The mixture was stirred at 45° C. for 2 h and filtered. The filtrate was diluted with water and extracted as in Example 1(d). The solvent was distilled off to afford the product in 86% yield (0.4 g).

e) N-(5-(5-bromo-1H-benzo[d]imidazol-1-yl)-2',5'-difluorobiphenyl-3-yl)acetamide A mixture of the compound of Example 138(d) (0.4 g, 0.93 mmol) and formic acid (4 ml) was heated at 100° C. for 30 min. The formic acid was distilled off and the residue was dissolved in ethyl acetate. The ethyl acetate layer was washed with water, brine and dried over sodium sulphate. The solvent was distilled off to afford the product in 85% yield (0.35 g). $^1$H NMR (300 MHz, DMSO-d$_6$): δ 10.42 (s, 1H), 8.75 (s, 1H), 8.04 (d, 2H), 7.86 (s, 1H), 7.69 (d, 1H), 7.64-7.56 (m, 3H), 7.54-7.38 (m, 1H), 7.37-7.31 (m, 1H), 2.12 (s, 3H).

f) N-(2',5'-difluoro-5-(5-(1-methyl-1H-pyrazol-4-yl)-1H-benzo[d]imidazol-1-yl)-biphenyl-3-yl)acetamide A solution of the compound of Example 138(e) (100 mg, 0.226 mmol) in 1,2-dimethoxyethane (10 ml) was degassed by N$_2$ bubbling for 5 min. 1-Methyl-4-(4,4,5,5-tetramethyl-1,3,2-dioxaborolan-2-yl)-1H-pyrazole (57 mg, 0.27 mmol, 1.2 eq.) was added and the mixture was degassed for another 5 min. Pd(dppf)Cl$_2$ (37 mg, 0.045 mmol, 0.2 eq.) and aqueous sodium carbonate (71 mg, 0.678 mmol, 3.0 eq.) were added and the procedure of Example 1(d) was followed. The crude residue of the product was purified by preparative HPLC to give the product in 20% yield (20 mg). $^1$H NMR (300 MHz, DMSO-d$_6$): δ 10.4 (s, 1H), 8.64 (s, 1H), 8.20 (s, 1H), 8.07 (s, 1H), 7.99 (s, 1H), 7.94 (s, 1H), 7.8-7.68 (m, 2H), 7.6-7.45 (m, 4H), 7.27 (t, 1H), 3.88 (s, 3H), 2.12 (s, 3H); LC-MS (ESI): Calculated mass: 443.45; Observed mass: 444.1 [M+H]$^+$ (rt: 1.147 min).

Example 139

N-(2',5'-difluoro-5-(5-(1-(2-morpholinoethyl)-1H-pyrazol-4-yl)-1H-benzo[d]-imidazol-1-yl)biphenyl-3-yl)acetamide A solution of the compound of Example 138(e) (5 g, 11.34 mmol) in 1,2-dimethoxyethane (100 ml) was degassed by N$_2$ bubbling for 5 min. 4-(2-(4-(4,4,5,5-Tetramethyl-1,3,2-dioxaborolan-2-yl)-1H-pyrazol-1-yl)ethyl)morpholine (4.2 g, 13.61 mmol, 1.2 eq.) was added and the mixture was degassed for another 5 min. Pd(PPh$_3$)$_4$ (1.3 g, 1.13 mmol, 0.1 eq.) and aqueous sodium carbonate (2.4 g, 22.67 mmol, 2.0 eq.) were added and the procedure of Example 1(d) was followed. The crude residue of the product was purified by preparative HPLC to give the product in 37% yield (2.3 g). $^1$H NMR (400 MHz, DMSO-d$_6$): δ 10.42 (s, 1H), 8.87 (s, 1H), 8.34 (s, 1H), 8.17 (s, 1H), 8.13 (s, 1H), 8.05 (s, 1H), 7.80-7.53 (m, 2H), 7.66-7.58 (m, 3H), 7.46-7.44 (m, 1H), 7.38-7.32 (m, 1H), 4.59 (t, 2H), 3.76-3.67 (m, 4H), 3.43-

3.39 (m, 2H), 2.54-2.44 (m, 4H), 2.07 (s, 3H); LC-MS (ESI): Calculated mass: 542.58; Observed mass: 543.3 [M+H]$^+$ (rt: 0.22 min).

Example 140

N-(2',5'-difluoro-5-(5-(1-(2-morpholinoethyl)-1H-pyrazol-4-yl)-1H-benzo[d]-imidazol-1-yl)biphenyl-3-yl)methanesulfonamide a) 2',5'-difluoro-5-(5-(1-(2-morpholinoethyl)-1H-pyrazol-4-yl)-1H-benzo[d]-imidazol-1-yl)biphenyl-3-amine To a solution of the compound of Example 139 (2.2 g, 4.0 mmol) in ethanol (100 ml) was added aqueous solution of NaOH (2.0 g, 50 mmol, 12.5 eq.) and the mixture was heated at 100° C. for 4 h. The mixture was quenched and extracted as in Example 1(d). The solvent was distilled off to afford the product in 90% yield (1.8 g).

b) N-(2',5'-difluoro-5-(5-(1-(2-morpholinoethyl)-1H-pyrazol-4-yl)-1H-benzo[d]-imidazol-1-yl)biphenyl-3-yl)methanesulfonamide To a solution of the compound of Example 140(a) (100 mg, 0.2 mmol) in DCM (2 ml) was added pyridine (32 mg, 0.4 mmol, 2.0 eq.) followed by methanesulfonyl chloride (30 mg, 0.26 mmol, 1.3 eq.). The mixture was stirred for 1 h and quenched and extracted as in Example 2(b). The solvent was distilled off and the residue was purified by preparative HPLC to give the product in 26% yield (30 mg). $^1$H NMR (400 MHz, CD$_3$OD): δ 9.34 (s, 1H), 8.25 (s, 1H), 8.06-8.05 (m, 2H), 7.86.7.80 (s, 2H), 7.74-7.73 (m, 1H), 7.68 (m, 1H), 7.60-7.59 (m, 1H), 7.44-7.39 (m, 1H), 7.33-7.27 (m, 1H), 7.24-7.19 (m, 1H), 4.69 (t, 2H), 3.94-3.88 (m, 4H), 3.76 (t, 2H), 3.54-3.40 (m, 4H), 3.19 (s, 3H); LC-MS (ESI): Calculated mass: 578.63; Observed mass: 579.3 [M+H]$^+$ (rt: 0.26 min).

Example 141

N-(2',5'-difluoro-5-(5-(1-(2-morpholinoethyl)-1H-pyrazol-4-yl)-1H-benzo[d]-imidazol-1-yl)biphenyl-3-yl)ethanesulfonamide The compound was prepared from the compound of Example 139 using the procedures of Example 140. $^1$H NMR (400 MHz, DMSO-d$_6$): δ 10.34 (s, 1H), 8.69 (s, 1H), 8.27 (s, 1H), 8.01 (s, 1H), 7.98 (s, 1H), 7.72-7.61 (m, 5H), 7.51-7.44 (m, 2H), 7.39-7.35 (m, 1H), 4.27 (t, 2H), 3.58 (t, 4H), 3.32-3.28 (m, 2H), 2.77 (t, 2H), 2.45 (m, 4H), 1.22 (t, 3H); LC-MS (ESI): Calculated mass: 592.66; Observed mass: 593.2 [M+H]$^+$ (rt: 0.332 min).

Example 142

N-(2',5'-difluoro-5-(5-(1-(2-morpholinoethyl)-1H-pyrazol-4-yl)-1H-benzo[d]-imidazol-1-yl)biphenyl-3-yl)propane-2-sulfonamide The compound was prepared from the compound of Example 139 using the procedures of Example 140. $^1$H NMR (400 MHz, DMSO-d$_6$): δ 10.35 (s, 1H), 8.79 (s, 1H), 8.37 (s, 1H), 8.15 (s, 1H), 8.07 (s, 1H), 7.74-7.62 (m, 5H), 7.54 (s, 1H), 7.51-7.45 (m, 1H), 7.41-7.35 (m, 1H), 4.61 (t, 2H), 3.70-3.63 (m, 6H), 3.52-3.42 (m, 3H), 3.40-3.28 (m, 2H), 1.43 (d, 6H); LC-MS (ESI): Calculated mass: 606.69; Observed mass: 607.4 [M+H]$^+$ (rt: 0.55 min).

Example 143

N-(2',5'-difluoro-5-(5-(1-(2-morpholinoethyl)-1H-pyrazol-4-yl)-1H-benzo[d]-imidazol-1-yl)biphenyl-3-yl)cyclopropanesulfonamide The compound was prepared from the compound of Example 139 using the procedures of Example 140 and cyclopropane sulfonyl chloride. $^1$H NMR (400 MHz, DMSO-d$_6$): δ 10.31 (s, 1H), 8.76 (s, 1H), 8.36 (s, 1H), 8.14 (s, 1H), 8.07 (s, 1H), 7.73 (d, 1H), 7.67-7.63 (m, 4H), 7.55 (s, 1H), 7.50-7.45 (m, 2H), 4.60 (t, 2H), 3.99-3.79 (m, 2H), 3.69-3.63 (m, 6H), 3.20-3.17 (m, 2H), 2.91-2.88 (m, 1H), 1.1-1.0 (d, 4H); LC-MS (ESI): Calculated mass: 604.67; Observed mass: 605.4 [M+H]$^+$ (rt: 0.48 min).

Example 144

N-(5-(5-(1-(2-(dimethylamino)ethyl)-1H-pyrazol-4-yl)-1H-benzo[d]imidazol-1-yl)-2',5'-difluorobiphenyl-3-yl)acetamide The compound was prepared from the compound of Example 138(e) using the procedures of Example 139. $^1$H NMR (400 MHz, DMSO-d$_6$): δ 10.42 (s, 1H), 8.74 (s, 1H), 8.34 (s, 1H), 8.16 (s, 1H), 8.12 (s, 1H), 8.04 (s, 1H), 7.79-7.73 (m, 2H), 7.64-7.57 (m, 3H), 7.45-7.42 (m, 1H), 7.36-7.34 (m, 1H), 4.56 (t, 2H), 3.62 (t, 2H), 3.84 (s, 6H), 2.12 (s, 3H); LC-MS (ESI): Calculated mass: 500.54; Observed mass: 501.2 [M+H]$^+$ (rt: 0.22 min).

Example 145

N-(5-(5-(1H-pyrazol-1-yl)-1H-benzo[d]imidazol-1-yl)-2',5'-difluorobiphenyl-3-yl)acetamide To a solution of the compound of Example 138(e) (2.5 g, 5.67 mmol, 1 eq.) in DMF (10 ml) were added pyrazole (0.77 g, 11.3 mmol, 2 eq.), copper(I) oxide (1.62 g, 11.3 mmol, 2.0 eq.) and cesium carbonate (3.67 g, 11.3 mmol, 2.0 eq.) and the mixture was heated at 90° C. for 48 h The mixture was quenched and extracted as in Example 1(d). The solvent was distilled off and the residue was purified by preparative HPLC to give the product in 79% yield (1.92 g). $^1$H NMR (400 MHz, CD$_3$OD): δ 10.43 (s, 1H), 8.84 (s, 1H), 8.60 (d, 1H), 8.24 (s, 1H), 8.12 (s, 1H), 7.97-7.82 (m, 3H), 7.76 (s, 1H), 7.63-7.60 (m, 2H), 7.49-7.32 (m, 1H), 6.56 (s, 1H), 2.10 (s, 3H); LC-MS (ESI): Calculated mass: 429.42; Observed mass: 430.2 [M+H]$^+$ (rt: 1.45 min).

Example 146

N-(5-(5-(1H-pyrrol-1-yl)-1H-benzo[d]imidazol-1-yl)-2',5'-difluorobiphenyl-3-yl)acetamide To a solution of the compound of Example 138(e) (250 mg, 0.57 mmol, 1 eq.) in DMF (1 ml) were added pyrazole (77 mg, 1.13 mmol, 2 eq.), copper(I) oxide (162 mg, 1.13 mmol, 2.0 eq.) and cesium carbonate (367 mg, 1.13 mmol, 2.0 eq.) and the mixture was heated at 90° C. for 48 h. The mixture was quenched and extracted as in Example 1(d). The solvent was distilled off and the residue was purified by preparative HPLC to give the product in 45% yield (110 mg). $^1$H NMR (400 MHz, DMSO-d$_6$): δ 10.45 (s, 1H), 8.81

(s, 1H), 8.15 (s, 1H), 8.00 (d, 1H), 7.86-7.80 (m, 2H), 7.66-7.62 (m, 3H), 7.46-7.44 (m, 4H), 6.29 (t, 2H), 2.13 (s, 3H); LC-MS (ESI): Calculated mass: 428.43; Observed mass: 429.1 [M+H]$^+$ (rt: 1.647 min).

Example 147

N-(3-(benzofuran-2-yl)-5-(5-(1-methyl-1H-pyrazol-4-yl)-1H-benzo[d]imidazol-1-yl)phenyl)acetamide a) N-(3-(benzofuran-2-yl)-5-nitrophenyl)acetamide A solution of N-(3-bromo-5-nitrophenyl)acetamide of Example 1(c) (2 g, 7.7 mmol) in 1,2-dimethoxyethane (25 ml) was degassed by N$_2$ bubbling for 5 min. 2-(Benzofuran-2-yl)-4,4,5,5-tetramethyl-1,3,2-dioxaborolane (2.45 g, 10 mmol, 1.3 eq.) was added and the mixture was degassed for another 5 min. Pd(dppf)Cl$_2$ (0.63 g, 0.77 mmol, 0.1 eq.) and aqueous sodium carbonate (2.45 g, 23.1 mmol, 3.0 eq.) were added and the procedure of Example 1(d) was followed. The crude residue of the product was directly used for the next step.

b) N-(3-amino-5-(benzofuran-2-yl)phenyl)acetamide

To a solution of the compound of Example 147(a) (1.8 g, 6.08 mmol) in ethanol (30 ml) were added calcium chloride (1.35 g, 12.16 mmol, 2 eq.) and iron powder (0.7 g, 12.16 mmol, 2 eq.) and the mixture was heated at 100° C. for 2 h and filtered. The filtrate was diluted with water and extracted as in Example 1(d). The solvent was distilled off and the residue was purified by column chromatography (100-200 neutral alumina, 4% methanol in chloroform) to give the product in 90% yield (1.45 g).

c) N-(3-(benzofuran-2-yl)-5-(4-bromo-2-nitrophenylamino)phenyl)acetamide

A solution of the compound of Example 147(b) (1.45 g, 5.45 mmol), 4-bromo-1-fluoro-2-nitrobenzene (1.2 g, 5.45 mmol, 1.0 eq.) and potassium fluoride (0.32 g, 5.45 mmol, 1.0 eq.) in DMF (5 ml) was heated at 100° C. for 12 h. The mixture was quenched and extracted as in Example 1(d). The solvent was distilled off and the residue was purified by column chromatography (60-120 silica gel, 40% ethyl acetate in hexane) to give the product in 59% yield (1.5 g).

d) N-(3-(2-amino-4-bromophenylamino)-5-(benzofuran-2-yl)phenyl)acetamide

To a solution of the compound of Example 147(c) (1.45 g, 3.12 mmol) in ethanol (35 ml) were added calcium chloride (0.69 g, 6.24 mmol, 2 eq.) and iron powder (0.36 g, 6.24 mmol, 2 eq.) and the mixture was heated at 100° C. for 2 h and filtered. The filtrate was diluted with water and extracted as in Example 1(d). The solvent was distilled off and the residue was directly used for the next step.

e) N-(3-(benzofuran-2-yl)-5-(5-bromo-1H-benzo[d]imidazol-1-yl)phenyl)acetamide

A mixture of the compound of Example 147(d) (1.36 g, 3.2 mmol) and formic acid (2 ml) was heated at 100° C. for 30 min. The formic acid was distilled off and the residue was dissolved in ethyl acetate. The ethyl acetate layer was washed with water, brine and dried over sodium sulphate. The solvent was distilled off to afford the product in 61% yield (0.85 g).

f) N-(3-(benzofuran-2-yl)-5-(5-(1-methyl-1H-pyrazol-4-yl)-1H-benzo[d]-imidazol-1-yl)phenyl)acetamide A solution of the compound of Example 147(e) (0.8 g, 1.8 mmol) in 1,2-dimethoxyethane (20 ml) was degassed by N$_2$ bubbling for 5 min. 1-Methyl-4-(4,4,5,5-tetramethyl-1,3,2-dioxaborolan-2-yl)-1H-pyrazole (0.56 g, 2.7 mmol, 1.5 eq.) was added and the mixture was degassed for another 5 min. Pd(PPh$_3$)$_4$ (0.207 g, 0.18 mmol, 0.1 eq.) and aqueous sodium carbonate (3.8 g, 3.6 mmol, 2.0 eq.) were added and the procedure of Example 1(d) was followed. The crude residue of the product was purified by preparative HPLC to give the pure product in 75% yield (0.6 g). $^1$H NMR (300 MHz, DMSO-d$_6$): δ 10.46 (s, 1H), 8.78 (s, 1H), 8.21 (m, 2H), 8.06 (s, 1H), 8.01 (s, 1H), 7.96 (s, 2H), 7.74-7.64 (m, 3H), 7.63-7.59 (m, 2H), 7.34-7.31 (m, 2H), 3.89 (s, 3H), 2.15 (s, 3H); LC-MS (ESI): Calculated mass: 447.49; Observed mass: 448.1 [M+H]$^+$ (rt: 1.397 min).

Example 148

N-(5-(5-(1-methyl-1H-pyrazol-4-yl)-1H-benzo[d]imidazol-1-yl)biphenyl-3-yl)-acetamide a) N-(5-nitrobiphenyl-3-yl)acetamide A solution of N-(3-bromo-5-nitrophenyl)acetamide of Example 1(c) (1 g, 3.87 mmol) in 1,2-dimethoxyethane (20 ml) was degassed by N$_2$ bubbling for 5 min. Phenyl-boronic acid (0.61 g, 5.04 mmol, 1.3 eq.) was added and the mixture was degassed for another 5 min. Pd(dppf)Cl$_2$ (0.63 g, 0.77 mmol, 0.2 eq.) and aqueous sodium carbonate (1.23 g, 11.6 mmol, 3.0 eq.) were added and the procedure of Example 1(d) was followed. The crude residue of the product was purified by column chromatography (60-120 silica gel, 50% ethyl acetate in hexane) to give the product in 61% yield (0.6 g).

b) N-(5-aminobiphenyl-3-yl)acetamide

To a solution of N-(5-nitrobiphenyl-3-yl)acetamide (1.2 g, 4.68 mmol) in THF (10 ml) were added a solution of ammonium chloride (2 g, 37.4 mmol, 8 eq.) in water (2 ml) and zinc (2.36 g, 37.4 mmol, 8 eq.). The mixture was stirred at 45° C. for 2 h and filtered. The filtrate was diluted with water and extracted as in Example 1(d). The solvent was distilled off to afford the product in 94% yield (1 g).

c) N-(5-(4-bromo-2-nitrophenylamino)biphenyl-3-yl)acetamide

A solution of N-(5-aminobiphenyl-3-yl)acetamide (1 g, 4.54 mmol), 4-bromo-1-fluoro-2-nitrobenzene (1.03 g, 4.54 mmol, 1.0 eq.) and potassium fluoride (0.26 g, 4.54 mmol, 1.0 eq.) in DMF (5 ml) was heated at 100° C. for 12 h. The mixture was quenched and extracted as in Example 1(d). The solvent was distilled off and the residue was purified by column chromatography (60-120 silica gel, 50% ethyl acetate in hexane) to give the product in 52% yield (1 g).

d) N-(5-(2-amino-4-bromophenylamino)biphenyl-3-yl)acetamide

To a solution of the compound of Example 148(c) (1.0 g, 2.35 mmol) in THF (10 ml) were added a solution of ammonium chloride (1.18 g, 18.8 mmol, 8 eq.) in water (2 ml) and zinc (1 g, 18.8 mmol, 8 eq.). The mixture was stirred at 45° C. for 2 h and filtered. The filtrate was diluted with water and extracted as in Example 1(d). The solvent was distilled off to afford the product in 43% yield (0.4 g).

e) N-(5-(5-bromo-1H-benzo[d]imidazol-1-yl)biphenyl-3-yl)acetamide

A mixture of the compound of Example 148(d) (0.4 g, 1.01 mmol) and formic acid (10 ml) was heated at 100° C. for 2 h. The formic acid was distilled off and the crude was dissolved in ethyl acetate. The ethyl acetate layer was washed with water, brine and dried over sodium sulphate. The solvent was distilled off and the residue was purified by column chromatography (60-120 silica gel, 50% ethyl acetate in hexane) to give the product in 85% yield (0.35 g).

f) N-(5-(5-(1-methyl-1H-pyrazol-4-yl)-1H-benzo[d]imidazol-1-yl)biphenyl-3-yl)-acetamide A solution of the compound of Example 148(e) (400 mg, 0.99 mmol) in 1,2-dimethoxyethane (10 ml) was degassed by $N_2$ bubbling for 5 min. 1-Methyl-4-(4,4,5,5-tetramethyl-1,3,2-dioxaborolan-2-yl)-1H-pyrazole (220 mg, 1.05 mmol, 1.2 eq.) was added and the mixture was degassed for another 5 min. Pd(PPh$_3$)$_4$ (230 mg, 0.197 mmol, 0.2 eq.) and aqueous sodium carbonate (320 mg, 3.01 mmol, 3.0 eq.) were added and the procedure of Example 1(d) was followed. The crude residue of the product was purified by preparative HPLC to give the product in 12% yield (50 mg). $^1$H NMR (300 MHz, DMSO-d$_6$): δ 10.36 (s, 1H), 8.68 (s, 1H), 8.18 (s, 1H), 8.02-7.97 (m, 2H), 7.93-7.88 (m, 2H), 7.75-7.67 (s, 3H), 7.61-7.49 (m, 4H), 7.43 (t, 1H), 3.87 (s, 3H), 2.12 (s, 3H); LC-MS (ESI): Calculated mass: 407.47; Observed mass: 408.1 [M+H]$^+$ (rt: 1.67 min).

Example 149

N-(4'-methoxy-5-(5-(1-methyl-1H-pyrazol-4-yl)-1H-benzo[d]imidazol-1-yl)biphenyl-3-yl)acetamide a) N-(4'-methoxy-5-nitrobiphenyl-3-yl)acetamide A solution of N-(3-bromo-5-nitrophenyl)acetamide of Example 1(c) (1 g, 3.8 mmol) in 1,2-dimethoxyethane (20 ml) was degassed by $N_2$ bubbling for 5 min. 4-Methoxyphenylboronic acid (0.69 g, 4.4 mmol, 1.1 eq.) was added and the mixture was degassed for another 5 min. Pd(dppf)Cl$_2$ (0.31 g, 0.38 mmol, 0.1 eq.) and aqueous sodium carbonate (1 g, 9.5 mmol, 2.5 eq.) were added and the procedure of Example 1(d) was followed. The crude residue of the product was purified by column chromatography (60-120 silica gel, 40% ethyl acetate in hexane) to give the product in 73% yield (0.8 g).

b) N-(5-amino-4'-methoxybiphenyl-3-yl)acetamide

To a solution of N-(4'-methoxy-5-nitrobiphenyl-3-yl)acetamide (4 g, 13.98 mmol) in ethanol (50 ml) were added calcium chloride (3.1 g, 27.96 mmol, 2 eq.) and iron powder (1.45 g, 27.96 mmol, 2 eq.) and the mixture was heated at 100° C. for 2 h and filtered. The filtrate was diluted with water and extracted as in Example 1(d). The solvent was distilled off to afford the product in 87% yield (3.1 g).

c) N-(5-(4-bromo-2-nitrophenylamino)-4'-methoxybiphenyl-3-yl)acetamide

The compound was prepared from the compound of Example 149(b) (3.1 g, 12.11 mmol) using the procedure of Example 148(c) to give the title product in 52% yield (2.9 g).

d) N-(5-(2-amino-4-bromophenylamino)-4'-methoxybiphenyl-3-yl)acetamide

To a solution of the compound of Example 149(c) (2.9 g, 6.37 mmol) in ethanol (30 ml) were added calcium chloride (1.4 g, 12.74 mmol, 2 eq.) and iron powder (0.66 g, 12.74 mmol, 2 eq.) and the mixture was heated at 100° C. for 2 h and filtered. The filtrate was diluted with water and extracted as described in Example 1(d). The solvent was distilled off to afford the crude residue which was directly used for the next step.

e) N-(5-(5-bromo-1H-benzo[d]imidazol-1-yl)-4'-methoxybiphenyl-3-yl)acetamide

The compound was prepared from the compound of Example 149(d) (2.7 g, 6.37 mmol) using the procedure of Example 148(e) to give the product in 79% yield (2.2 g).

f) N-(4'-methoxy-5-(5-(1-methyl-1H-pyrazol-4-yl)-1H-benzo[d]imidazol-1-yl)biphenyl-3-yl)acetamide The compound was prepared from the compound of Example 149(e) using the procedure of Example 148(f) to give the product in 67% yield (0.54 g). $^1$H NMR (300 MHz, DMSO-d$_6$): δ 8.48 (s, 1H), 7.96-7.84 (m, 4H), 7.74-7.45 (m, 7H), 7.01 (d, 2H), 3.93 (s, 3H), 3.83 (s, 3H), 2.19 (s, 3H); LC-MS (ESI): Calculated mass: 437.49; Observed mass: 437.9 [M+H]$^+$ (rt: 0.89 min).

Example 150

N-(3',4'-difluoro-5-(5-(1-methyl-1H-pyrazol-4-yl)-1H-benzo[d]imidazol-1-yl)biphenyl-3-yl)acetamide a) N-(3',4'-difluoro-5-nitrobiphenyl-3-yl)acetamide A solution of N-(3-bromo-5-nitrophenyl)acetamide of Example 1(c) (0.7 g, 2.69 mmol) in 1,2-dimethoxyethane (15 ml) was degassed by $N_2$ bubbling for 5 min. 3,4-Difluorophenylboronic acid (0.5 g, 3.23 mmol, 1.2 eq.) was added and the mixture was degassed for another 5 min. Pd(dppf)Cl$_2$ (0.44 g, 0.54 mmol, 0.2 eq.) and aqueous sodium carbonate (0.86 g, 8.07 mmol, 3.0 eq.) were added and the procedure of Example 1(d) was followed. The crude residue of the product was purified by column chromatography (60-120 silica gel, 25% ethyl acetate in hexane) to give the product in 76% yield (0.6 g).

b) N-(5-amino-3',4'-difluorobiphenyl-3-yl)acetamide

To a solution of the compound of Example 150(a) (0.6 g, 2.05 mmol) in methanol (10 ml) and ethyl acetate (2 ml) was added 10% Pd/C (100 mg) and the reaction vessel was purged with nitrogen gas for 5 min. The mixture was then hydrogenated with $H_2$ balloon for 12 h. The mixture was filtered through a pad of celite and the filtrate was concentrated under reduced pressure to afford the compound in 93% yield (0.5 g).

c) N-(5-(4-bromo-2-nitrophenylamino)-3',4'-difluorobiphenyl-3-yl)acetamide

The compound was prepared from the compound of Example 150(b) (3.1 g, 12.11 mmol) using the procedure of Example 148(c) to give the product in 57% yield (0.5 g). $^1$H NMR (300 MHz, DMSO-$d_6$): δ 10.16 (s, 1H), 9.43 (s, 1H), 8.23 (d, 1H), 7.69-7.58 (m, 3H), 7.41-7.38 (m, 2H), 7.29-7.26 (m, 2H), 7.19 (s, 1H), 2.04 (s, 3H).

d) N-(5-(2-amino-4-bromophenylamino)-3',4'-difluorobiphenyl-3-yl)acetamide

The compound was prepared from the compound of Example 150(c) (0.5 g, 1.08 mmol) using the procedure of Example 148(d) to give the product in 86% yield (0.4 g).

e) N-(5-(5-bromo-1H-benzo[d]imidazol-1-yl)-3',4'-difluorobiphenyl-3-yl)acetamide The compound was prepared from the compound of Example 150(d) (0.4 g, 0.93 mmol) using the procedure of Example 148(e) to give the product in 97% yield (0.4 g).

1) N-(3',4'-difluoro-5-(5-(1-methyl-1H-pyrazol-4-yl)-1H-benzo[d]imidazol-1-yl)-biphenyl-3-yl)acetamide The compound was prepared from the compound of Example 150(e) (0.1 g, 0.226 mmol) using the procedure of Example 148(f) to give the product in 30% yield (30 mg). $^1$H NMR (300 MHz, DMSO-$d_6$): δ 10.43 (s, 1H), 9.03 (s, 1H), 8.24 (s, 1H), 8.09 (s, 1H), 8.01 (s, 1H), 7.97 (s, 1H), 7.90-7.85 (s, 2H), 7.76-7.74 (m, 1H), 7.71 (s, 1H), 7.68-7.66 (m, 1H), 7.61-7.59 (m, 2H), 3.88 (s, 3H), 2.13 (s, 3H); LC-MS (ESI): Calculated mass: 443.45; Observed mass: 444.1 [M+H]$^+$ (rt: 1.3 min).

Example 151

N-(2',6'-difluoro-5-(5-(1-methyl-1H-pyrazol-4-yl)-1H-benzo[d]imidazol-1-yl)-biphenyl-3-yl)acetamide a) N-(2',6'-difluoro-5-nitrobiphenyl-3-yl)acetamide

A solution of N-(3-bromo-5-nitrophenyl)acetamide of Example 1(c) (20 g, 77 mmol) in 1,2-dimethoxyethane (250 ml) was degassed by N$_2$ bubbling for 5 min. 2,6-Difluorophenylboronic acid (14.6 g, 92.4 mmol, 1.2 eq.) was added and the mixture was degassed for another 5 min. Pd(dppf)Cl$_2$ (6.28 g, 7.7 mmol, 0.1 eq.) and aqueous sodium carbonate (24.49 g, 231 mmol, 3.0 eq.) were added and the procedure of Example 1(d) was followed. The crude residue of the product was purified by column chromatography (60-120 silica gel, 30% ethyl acetate in hexane) to give the product in 94% yield (21.2 g). LC-MS (ESI): Calculated mass: 292.24; Observed mass: 293.1 [M+H]$^+$ (rt: 1.49 min).

b) N-(5-amino-2',6'-difluorobiphenyl-3-yl)acetamide

The compound was prepared from the compound of Example 151(a) (21 g, 72 mmol) using the procedure of Example 148(b) to give the product in 95% yield (18 g).

c) N-(5-(4-bromo-2-nitrophenylamino)-2',6'-difluorobiphenyl-3-yl)acetamide

The compound was prepared from the compound of Example 151(b) (8 g, 30.5 mmol) using the procedure of Example 148(c) to give the product in 96% yield (13.5 g).

d) N-(5-(2-amino-4-bromophenylamino)-2',6'-difluorobiphenyl-3-yl)acetamide

The compound was prepared from the compound of Example 151(c) (13.5 g, 29.22 mmol) using the procedure of Example 148(d) to give the product in 95% yield (12 g).

e) N-(5-(5-bromo-1H-benzo[d]imidazol-1-yl)-2',6'-difluorobiphenyl-3-yl)-acetamide The compound was prepared from the compound of Example 151(d) (12 g, 27.84 mmol) using the procedure of Example 148(e) to give the product in 96% yield (11.8 g).

f) N-(2',6'-difluoro-5-(5-(1-methyl-1H-pyrazol-4-yl)-1H-benzo[d]imidazol-1-yl)-biphenyl-3-yl)acetamide The compound was prepared from the compound of Example 151(e) (2.5 g, 5.67 mmol) using the procedure of Example 148(f) to give the product in 84% yield (2.1 g). $^1$H NMR (400 MHz, DMSO-$d_6$): δ 10.39 (s, 1H), 8.56 (s, 1H), 8.18 (s, 1H), 8.05 (s, 1H), 7.97 (s, 1H), 7.92 (s, 1H), 7.71-7.47 (m, 5H), 7.27 (t, 2H), 3.85 (s, 3H), 2.09 (s, 3H); LC-MS (ESI): Calculated mass: 443.45; Observed mass: 444.0 [M+H]$^+$ (rt: 1.34 min).

Example 152

N-(5-(5-(1H-pyrazol-1-yl)-1H-benzo[d]imidazol-1-yl)-2',6'-difluorobiphenyl-3-yl)acetamide To a solution of the compound of Example 151(e) (2.5 g, 5.67 mmol) in DMF (20 ml) were added pyrazole (0.96 g, 14.18 mmol, 2.5 eq.), copper(I) oxide (0.81 g, 5.67 mmol, 1 eq.) and cesium carbonate (4.6 g, 14.18 mmol, 2.5 eq.) and the mixture was heated at 90° C. for 48 h. The mixture was quenched and extracted as in Example 1(d). The solvent was distilled off and the residue was purified by preparative HPLC to give the product in 91% yield (2.2 g). $^1$H NMR (300 MHz, DMSO-$d_6$): δ 10.43 (s, 1H), 8.67 (s, 1H), 8.57 (d, 1H), 8.20 (d, 1H), 8.06 (s, 1H), 7.92-7.88 (m, 1H), 7.77-7.74 (m, 3H), 7.53-7.49 (m, 2H), 7.30-7.25 (m, 2H), 6.54 (t, 1H), 2.1 (s, 3H); LC-MS (ESI): Calculated mass: 429.42; Observed mass: 430.1 [M+H]$^+$ (rt: 1.50 min).

Example 153

N-(3-(1-methyl-1H-pyrazol-4-yl)-5-(5-(1-methyl-1H-pyrazol-4-yl)-1H-benzo[d]-imidazol-1-yl)phenyl)acetamide a) N-(3-(1-methyl-1H-pyrazol-4-yl)-5-nitrophenyl)acetamide

A solution of N-(3-bromo-5-nitrophenyl)acetamide (0.5 g, 1.9 mmol) in 1,2-dimethoxyethane (20 ml) was degassed by N$_2$ bubbling for 5 min. 1-Methyl-4-(4,4,5,5-tetramethyl-1,3,2-dioxaborolan-2-yl)-1H-pyrazole (0.513 g, 2.47 mmol, 1.3 eq.) was added and the mixture was degassed for another 5 min. Pd(dppf)Cl$_2$ (0.155 g, 0.19 mmol, 0.1 eq.) and aqueous sodium carbonate (0.5 g, 4.75 mmol, 2.5 eq.) were added and the procedure of Example 1(d) was followed. The crude residue of the product was purified by column chromatography (60-120 silica gel, 30% ethyl acetate in hexane) to give the product in 81% yield (0.4 g).

b) N-(3-amino-5-(1-methyl-1H-pyrazol-4-yl)phenyl) acetamide

To a solution of the compound of Example 153(a) (0.4 g, 1.54 mmol) in ethanol (25 ml) were added calcium chloride (0.34 g, 3.08 mmol, 2 eq.) and iron powder (0.16 g, 3.08 mmol, 2 eq.) and the mixture was heated at 100° C. for 2 h and filtered. The filtrate was diluted with water and extracted as in Example 1(d). The solvent was distilled off to afford the product in 85% yield (0.3 g). LC-MS (ESI): Calculated mass: 230.27; Observed mass: 231.1 [M+H]$^+$ (rt: 0.225 min).

c) N-(3-(4-bromo-2-nitrophenylamino)-5-(1-methyl-1H-pyrazol-4-yl)phenyl)-acetamide A solution of the compound of Example 153(b) (0.3 g, 1.3 mmol), 4-bromo-1-fluoro-2-nitrobenzene (0.29 g, 1.3 mmol, 1.0 eq.) and potassium fluoride (0.075 g, 1.3 mmol, 1.0 eq.) in DMF (5 ml) was heated at 100° C. for 12 h. The mixture was quenched and extracted as in Example 1(d). The solvent was distilled off and the residue was directly used for the next step.

d) N-(3-(2-amino-4-bromophenylamino)-5-(1-methyl-1H-pyrazol-4-yl)phenyl)-acetamide To a solution of the compound of Example 153(c) (0.6 g, 1.3 mmol) in ethanol (20 ml) were added calcium chloride (0.29 g, 2.6 mmol, 2 eq.) and iron powder (0.14 g, 2.6 mmol, 2 eq.) and the mixture was heated at 100° C. for 2 h and filtered. The filtrate was diluted with water and extracted as in Example 1(d). The solvent was distilled off and the residue was directly used for the next step.

e) N-(3-(5-bromo-1H-benzo[d]imidazol-1-yl)-5-(1-methyl-1H-pyrazol-4-yl)-phenyl)acetamide A mixture of the compound of Example 153(d) (0.52 g, 1.3 mmol) and formic acid (2 ml) was heated at 100° C. for 30 min. The formic acid was distilled off and the residue was dissolved in ethyl acetate. The ethyl acetate layer was washed with water, brine and dried over sodium sulphate. The solvent was distilled off to afford the product in 54% yield (0.28 g). LC-MS (ESI): Calculated mass: 410.27; Observed mass: 411.0 [M+H]$^+$ (rt: 0.84 min).

f) N-(3-(1-methyl-1H-pyrazol-4-yl)-5-(5-(1-methyl-1H-pyrazol-4-yl)-1H-benzo[d]imidazol-1-yl)phenyl) acetamide A solution of the compound of Example 153(e) (0.15 g, 0.365 mmol) in 1,2-dimethoxyethane (10 ml) was degassed by N$_2$ bubbling for 5 min. 1-Methyl-4-(4,4,5,5-tetramethyl-1,3,2-dioxaborolan-2-yl)-1H-pyrazole (0.091 g, 0.439 mmol, 1.2 eq.) was added and the mixture was degassed for another 5 min. Pd(PPh$_3$)$_4$ (0.043 g, 0.037 mmol, 0.1 eq.) and aqueous sodium carbonate (0.077 g, 0.73 mmol, 2.0 eq.) were added and the procedure of Example 1(d) was followed. The crude residue of the product was purified by preparative HPLC to give the product in 12% yield (18 mg).

$^1$H NMR (300 MHz, CD$_3$OD): δ 9.39 (s, 1H), 8.10-7.91 (m, 6H), 7.80-7.77 (m, 3H), 7.63 (s, 1H), 3.96 (s, 6H), 2.20 (s, 3H); LC-MS (ESI): Calculated mass: 443.45; Observed mass: 411.46 [M+H]$^+$ (rt: 0.28 min).

Example 154

N-(3-(5-(1-methyl-1H-pyrazol-4-yl)-1H-benzo[d] imidazol-1-yl)-5-(2-oxopyridin-1(2H)-yl)phenyl) acetamide a) N-(3-nitro-5-(2-oxopyridin-1(2H)-yl)phenyl)acetamide To a solution of N-(3-bromo-5-nitrophenyl)acetamide (1 g, 3.85 mmol), pyridin-2-ol (0.4 g, 4.24 mmol, 1.1 eq.), potassium carbonate (1 g, 1.3 mmol, 1.0 eq.) and copper(I) iodide (10 mg) in toluene (20 ml) was added trans cyclohexyl diamine (5 mg, 0.039 mmol, 0.01 eq.) and the mixture was heated at 100° C. for 16 h. The mixture was quenched and extracted as in Example 1(d). The solvent was distilled off and the residue was purified by column chromatography (60-120 silica gel, 50% ethyl acetate in hexane) to give the product in 95% yield (1 g).

b) N-(3-amino-5-(2-oxopyridin-1(2H)-yl)phenyl) acetamide

To a solution of the compound of Example 154(a) (1.2 g, 4.4 mmol) in ethanol (20 ml) and water (2 ml) were added calcium chloride (0.98 g, 8.8 mmol, 2 eq.) and iron powder (0.46 g, 8.8 mmol, 2 eq.) and the mixture was heated at 100° C. for 4 h and filtered. The filtrate was diluted with water and extracted as in Example 1(d). The solvent was distilled off to afford the product in 89% yield (0.95 g). LC-MS (ESI): Calculated mass: 243.26; Observed mass: 244.1 [M+H]$^+$ (rt: 0.19 min)

c) N-(3-(4-bromo-2-nitrophenylamino)-5-(2-oxopyridin-1(2H)-yl)phenyl)-acetamide

A solution of the compound of Example 154(b) (0.95 g, 3.9 mmol), 4-bromo-1-fluoro-2-nitrobenzene (0.86 g, 3.9 mmol, 1.0 eq.) and potassium fluoride (0.23 g, 3.9 mmol, 1.0 eq.) in DMF (1 ml) was heated at 150° C. for 2 h. The mixture was quenched and extracted as in Example 1(d). The solvent was distilled off and the residue was purified by column chromatography (100-200 silica gel, 1% methanol in DCM) to give the product in 69% yield (1.2 g).

d) N-(3-(2-amino-4-bromophenylamino)-5-(2-oxopyridin-1(2H)-yl)phenyl)acetamide

To a solution of the compound of Example 154(c) (1.2 g, 2.7 mmol) in ethanol (20 ml) were added calcium chloride (0.6 g, 5.4 mmol, 2 eq.) and iron powder (0.28 g, 5.4 mmol, 2 eq.) and the mixture was heated at 100° C. for 4 h and filtered. The mixture was quenched and extracted as in Example 1(d). The solvent was distilled off and the crude residue was directly used for the next step.

e) N-(3-(5-bromo-1H-benzo[d]imidazol-1-yl)-5-(2-oxopyridin-1(2H)-yl)phenyl)-acetamide A mixture of the compound of Example 154(d) (1.12 g, 2.7 mmol) and formic acid (1 ml) was heated at 100° C. for 2 h. The formic acid was distilled off and the residue was dissolved in ethyl acetate. The ethyl acetate layer was washed with water, brine and dried over sodium sulphate. The solvent was distilled off to afford the product in 61% yield (0.7 g). LC-MS (ESI): Calculated mass: 423.26; Observed mass: 424.9 [M+H]$^+$ (rt: 1.065 min).

f) N-(3-(5-(1-methyl-1H-pyrazol-4-yl)-1H-benzo[d]imidazol-1-yl)-5-(2-oxopyridin-1(2H)-yl)phenyl)acetamide A solution of the compound of Example 154(e) (0.7 g, 1.65 mmol) in 1,2-dimethoxyethane (10 ml) was degassed by N$_2$ bubbling for 5 min. 1-Methyl-4-(4,4,5,5-tetramethyl-1,3,2-dioxaborolan-2-yl)-1H-pyrazole (0.41 g, 1.98 mmol, 1.2 eq.) was added and the mixture was degassed for another 5 min. Pd(PPh$_3$)$_4$ (0.19 g, 0.165 mmol, 0.1 eq.) and aqueous sodium carbonate (0.35 g, 3.3 mmol, 2.0 eq.) were added and the procedure of Example 1(d) was followed. The crude residue of the product was purified by preparative HPLC to give the product in 64% yield (0.45 g). $^1$H NMR (300 MHz, CD$_3$OD-d$_6$): δ 9.35 (s, 1H), 8.29-8.28 (m, 1H), 8.11 (s, 1H), 8.00 (s, 1H), 7.94 (d, 1H), 7.86-7.83 (m, 2H), 7.77-7.73 (m, 2H), 7.67-7.63 (m, 1H), 7.59 (t, 1H), 6.70-6.67 (m, 1H), 6.55 (dt, 1H), 3.96 (s, 3H), 2.20 (s, 3H); LC-MS (ESI): Calculated mass: 424.45; Observed mass: 425.2 [M+H]$^+$ (rt: 0.23 min).

Example 155

N-(3-(5-(1-methyl-1H-pyrazol-4-yl)-1H-benzo[d]imidazol-1-yl)-5-(1H-1,2,4-triazol-1-yl)phenyl)acetamide a) N-(3-nitro-5-(1H-1,2,4-triazol-1-yl)phenyl)acetamide

To a solution of N-(3-bromo-5-nitrophenyl)acetamide (5 g, 19.3 mmol) in DMF (50 ml) were added 1,2,4-triazole (3.3 g, 48.25 mmol, 2.5 eq.), copper(I) oxide (0.56 g, 3.86 mmol, 0.2 eq.) and cesium carbonate (12.5 g, 38.6 mmol, 2 eq.) and the mixture was heated at 90° C. for 48 h. The mixture was quenched and extracted as in Example 1(d). The solvent was distilled off and the residue was purified by column chromatography (60-120 silica gel, 30% ethyl acetate in hexane) to give the product in 86% yield (4.1 g). LC-MS (ESI): Calculated mass: 247.21; Observed mass: 248.0 [M+H]$^+$ (rt: 0.257 min).

b) N-(3-amino-5-(1H-1,2,4-triazol-1-yl)phenyl)acetamide

To a solution of the compound of Example 155(a) (4.1 g, 16.6 mmol) in THF (50 ml) and methanol (10 ml) were added ammonium chloride (0.88 g, 16.6 mmol) and zinc (1.08 g, 16.6 mmol). The mixture was stirred at RT overnight and filtered. The filtrate was diluted with water and extracted as in Example 1(d). The solvent was distilled off and the residue was purified by column chromatography (60-120 silica gel, 3% methanol in DCM) to give the product in 94% yield (3.4 g).

c) N-(3-(4-bromo-2-nitrophenylamino)-5-(1H-1,2,4-triazol-1-yl)phenyl)acetamide A solution of the compound of Example 155(b) (3.43 g, 15.67 mmol), 4-bromo-1-fluoro-2-nitrobenzene (3.4 g, 15.67 mmol, 1.0 eq.) and potassium fluoride (0.91 g, 15.67 mmol, 1.5 eq.) in DMF (5 ml) was heated at 80° C. for 7 h. The mixture was quenched and extracted as in Example 1(d). The solvent was distilled off and the residue was purified by column chromatography (60-120 silica gel, 4% methanol in DCM) to give the product in 80% yield (5.2 g).

d) N-(3-(2-amino-4-bromophenylamino)-5-(1H-1,2,4-triazol-1-yl)phenyl)acetamide To a solution of the compound of Example 155(c) N-(3-(4-bromo-2-nitro-phenylamino)-5-(1H-1,2,4-triazol-1-yl)phenyl)acetamide (5.2 g, 12.5 mmol) in ethanol (100 ml) were added calcium chloride (2.78 g, 25 mmol, 2 eq.) and iron powder (1.3 g, 25 mmol, 2 eq.) and the mixture was heated at 100° C. for 4 h and filtered. The filtrate was diluted with water and extracted as in Example 1(d). The solvent was distilled off and the crude residue was directly used for the next step.

e) N-(3-(5-bromo-1H-benzo[d]imidazol-1-yl)-5-(1H-1,2,4-triazol-1-yl)phenyl)-acetamide A mixture of the compound of Example 155(d) (4.84 g, 12.5 mmol) and formic acid (10 ml) was heated at 80° C. for 2 h. The formic acid was distilled off and the residue was dissolved in ethyl acetate. The ethyl acetate layer was washed with water, brine and dried over sodium sulphate. The solvent was distilled off to afford the product in 85% yield (4.2 g).

N-(3-(5-(1-methyl-1H-pyrazol-4-yl)-1H-benzo[d]imidazol-1-yl)-5-(1H-1,2,4-triazol-1-yl)phenyl)acetamide A solution of the compound of Example 155(e) (100 mg, 0.25 mmol) in 1,2-dimethoxyethane (10 ml) was degassed by N$_2$ bubbling for 5 min. 1-Methyl-4-(4,4,5,5-tetramethyl-1,3,2-dioxaborolan-2-yl)-1H-pyrazole (62 mg, 0.3 mmol, 1.2 eq.) was added and the mixture was degassed for another 5 min. Pd(PPh$_3$)$_4$ (35 mg, 0.03 mmol, 0.12 eq.) and aqueous sodium carbonate (0.53 g, 0.5 mmol, 2.0 eq.) were added and the procedure of Example 1(d) was followed. The crude residue of the product was purified by preparative HPLC to give the product in 50% yield (50 mg). $^1$H NMR (400 MHz, DMSO-d$_6$): δ 10.50 (s, 1H), 9.36 (s, 1H), 8.77 (s, 1H), 8.28 (s, 1H), 8.19-8.18 (m, 2H), 8.00-7.93 (m, 4H), 7.72 (d, 1H), 7.60 (dd, 1H), 3.86 (s, 3H), 2.11 (s, 3H); LC-MS (ESI): Calculated mass: 398.42; Observed mass: 399.4 [M+H]$^+$ (rt: 0.13 min).

Example 156

N-(3-(5-(1-methyl-1H-pyrazol-4-yl)-1H-benzo[d]imidazol-1-yl)-5-(thiazol-2-yl)phenyl)acetamide a) N-(3-nitro-5-(4,4,5,5-tetramethyl-1,3,2-dioxaborolan-2-yl)phenyl)acetamide A solution of N-(3-bromo-5-nitrophenyl)acetamide (2.1 g, 8.1 mmol) in 1,2-dimethoxyethane (25 ml) was degassed by N$_2$ bubbling for 5 min. Bis(pinacolato)diboron (3.09 g, 12.15 mmol, 1.3 eq.) was added and the mixture was degassed for another 5 min. Pd(dppf)Cl$_2$ (0.066 g, 0.081 mmol, 0.1 eq.) and potassium acetate (2.38 g, 24.3 mmol, 3 eq.) were added and the procedure of Example 1(d) was followed. The crude residue of the product was purified by column chromatography (60-120 silica gel, 30% ethyl acetate in hexane) to give the product in 60% yield (1.5 g).

b) N-(3-nitro-5-(thiazol-2-yl)phenyl)acetamide

A solution of the compound of Example 156(a) (2.8 g, 9.14 mmol) in 1,2-dimethoxyethane (10 ml) was degassed by $N_2$ bubbling for 5 min. 2-Bromothiazole (1 g, 9.14 mmol, 1 eq.) was added and the mixture was degassed for another 5 min. Pd(dppf)$Cl_2$ (0.74 g, 0.91 mmol, 0.1 eq.) and aqueous sodium carbonate (1.9 g, 18.2 mmol, 2 eq.) were added and the procedure of Example 1(d) was followed. The crude residue of the product was purified by column chromatography (60-120 silica gel, 40% ethyl acetate in hexane) to give the product in 33% yield (0.8 g). $^1$H NMR (300 MHz, DMSO-$d_6$): δ 10.64 (s, 1H), 8.65 (t, 1H), 8.55 (t, 1H), 8.34 (t, 1H), 8.04 (d, 1H), 7.94 (d, 1H), 2.13 (s, 3H).

c) N-(3-amino-5-(thiazol-2-yl)phenyl)acetamide

To a solution of the compound of Example 156(b) (0.8 g, 3.03 mmol) in methanol (25 ml) and ethyl acetate (10 ml) was added 10% Pd/C (300 mg, 0.1 eq.) and the reaction vessel was purged with nitrogen gas for 5 min. The mixture was then hydrogenated with $H_2$ balloon for 12 h. The mixture was filtered through a pad of celite and the filtrate was concentrated to afford the compound in 71% yield (0.5 g). $^1$H NMR (300 MHz, DMSO-$d_6$): δ 9.83 (s, 1H), 7.86-7.85 (m, 1H), 7.71-7.70 (m, 1H), 7.35 (s, 1H), 7.04 (s, 1H), 6.88 (s, 1H), 5.45 (br s, 2H), 2.03 (s, 3H).

d) N-(3-(4-bromo-2-nitrophenylamino)-5-(thiazol-2-yl)phenyl)acetamide

A solution of the compound of Example 156(c) (0.5 g, 2.14 mmol), 4-bromo-1-fluoro-2-nitrobenzene (0.47 g, 2.14 mmol, 1.0 eq.) and potassium fluoride (0.19 g, 3.21 mmol, 1.5 eq.) in DMF was heated at 80° C. for 7 h. The mixture was quenched and extracted as in Example 1(d). The solvent was distilled off and the residue was purified by column chromatography (60-120 silica gel, 40% ethyl acetate in hexane) to give the product in 24% yield (0.22 g).

e) N-(3-(2-amino-4-bromophenylamino)-5-(thiazol-2-yl)phenyl)acetamide

To a solution of the compound of Example 156(d) (0.22 g, 0.507 mmol) in THF (15 ml) were added a solution of ammonium chloride (0.11 g, 2.02 mmol, 4 eq.) in water (5 ml) and zinc (0.13 g, 2.02 mmol, 4 eq.). The mixture was stirred at RT overnight and filtered. The filtrate was diluted with water and extracted as in Example 1(d). The solvent was distilled off to afford the product in 83% yield (0.17 g).

f) N-(3-(5-bromo-1H-benzo[d]imidazol-1-yl)-5-(thiazol-2-yl)phenyl)acetamide

A mixture of the compound of Example 156(e) (0.17 g, 0.42 mmol) and formic acid (3 ml) was heated at 80° C. for 2 h. The formic acid was distilled off and the crude was dissolved in ethyl acetate. The ethyl acetate layer was washed with water, brine and dried over sodium sulphate. The solvent was distilled off to afford the product in 86% yield (0.15 g). $^1$H NMR (300 MHz, DMSO-$d_6$): δ 10.52 (s, 1H), 8.77 (s, 1H), 8.32 (s, 1H), 8.07-8.00 (m, 3H), 7.90-7.87 (m, 2H), 7.66-7.63 (m, 1H), 7.55 (s, 1H), 2.13 (s, 3H).

g) N-(3-(5-(1-methyl-1H-pyrazol-4-yl)-1H-benzo[d]imidazol-1-yl)-5-(thiazol-2-yl)phenyl)acetamide A solution of the compound of Example 156(f) (0.2 g, 0.48 mmol) in 1,2-dimethoxyethane (15 ml) was degassed by $N_2$ bubbling for 5 min. 1-Methyl-4-(4,4,5,5-tetramethyl-1,3,2-dioxaborolan-2-yl)-1H-pyrazole (0.15 g, 0.73 mmol, 1.5 eq.) was added and the mixture was degassed for another 5 min. Pd(PPh$_3$)$_4$ (0.11 g, 0.096 mmol, 0.2 eq.) and aqueous sodium carbonate (0.1 g, 0.96 mmol, 2.0 eq.) were added and the procedure of Example 1(d) was followed. The crude residue of the product was purified by preparative HPLC to give the product in 1.5% yield (3 mg). $^1$H NMR (300 MHz, CD$_3$OD): δ 8.20-8.11 (m, 2H), 8.05-7.82 (m, 5H), 7.68-7.61 (m, 3H), 7.55-7.45 (m, 1H), 3.88 (s, 3H), 2.12 (s, 3H); LC-MS (ESI): Calculated mass: 414.48; Observed mass: 415.0 [M+H]$^+$ (rt: 0.31 min).

Example 157

N-(3-(1H-indol-3-yl)-5-(5-(1-methyl-1H-pyrazol-4-yl)-1H-benzo[d]imidazol-1-yl)phenyl)acetamide a) N-(3-nitro-5-(1-(phenylsulfonyl)-1H-indol-3-yl)phenyl)acetamide A solution of N-(3-bromo-5-nitrophenyl)acetamide (0.38 g, 1.48 mmol) in 1,2-dimethoxyethane (15 ml) was degassed by $N_2$ bubbling for 5 min. 1-(Phenylsulfonyl)-3-(4,4,5,5-tetramethyl-1,3,2-dioxaborolan-2-yl)-1H-indole (0.68 g, 1.77 mmol, 1.2 eq.) was added and the mixture was degassed for another 5 min. Pd(dppf)$Cl_2$ (0.12 g, 0.148 mmol, 0.1 eq.) and aqueous sodium carbonate (0.47 g, 4.45 mmol, 3.0 eq.) were added and the procedure of Example 1(d) was followed. The crude residue of the product was purified by column chromatography (60-120 silica gel, 30% ethyl acetate in hexane) to give the product in 77% yield (0.5 g).

b) N-(3-amino-5-(1-(phenylsulfonyl)-1H-indol-3-yl)phenyl)acetamide

To a solution of the compound of Example 157(a) (1 g, 2.29 mmol) in methanol (10 ml) was added 10% Pd/C (100 mg, 0.1 eq.) and the reaction vessel was purged with nitrogen gas for 5 min. The mixture was then hydrogenated with $H_2$ balloon for 12 h. The mixture was filtered through a pad of celite and the filtrate was concentrated to afford the compound in 89% yield (0.83 g).

c) N-(3-(4-bromo-2-nitrophenylamino)-5-(1-(phenylsulfonyl)-1H-indol-3-yl)-phenyl)acetamide A solution of the compound of Example 157(b) (0.83 g, 2.04 mmol), 4-bromo-1-fluoro-2-nitrobenzene (0.45 g, 2.04 mmol, 1.0 eq.) and potassium fluoride (0.12 g, 2.04 mmol, 1.0 eq.) in DMF (10 ml) was heated at 130° C. for 5 h. The mixture was quenched and extracted as in Example 1(d). The solvent was distilled off and the residue was purified by column chromatography (60-120 silica gel, 30% ethyl acetate in hexane) to give the product in 48% yield (0.6 g).

d) N-(3-(2-amino-4-bromophenylamino)-5-(1-(phenylsulfonyl)-1H-indol-3-yl)-phenyl)acetamide To a solution of the compound of Example 157(c) (0.61 g, 1 mmol) in THF (10 ml) and methanol (10 ml) were added a solution of ammonium chloride (0.53 g, 10 mmol, 10 eq.)

in water (5 ml) and zinc (0.63 g, 10 mmol, 10 eq.). The mixture was stirred at RT for 6 h and filtered. The filtrate was diluted with water and extracted as in Example 1(d). The solvent was distilled off to give the product in 70% yield (0.4 g).

e) N-(3-(5-bromo-1H-benzo[d]imidazol-1-yl)-5-(1-(phenylsulfonyl)-1H-indol-3-yl)phenyl)acetamide A mixture of the compound of Example 157(d) (0.4 g, 0.7 mmol) and formic acid (10 ml) was heated at 100° C. for 30 min. The formic acid was distilled off and the crude was dissolved in ethyl acetate. The ethyl acetate layer was washed with water, brine and dried over sodium sulphate. The solvent was distilled off to afford the product in 73% yield (0.3 g).

f) N-(3-(5-(1-methyl-1H-pyrazol-4-yl)-1H-benzo[d]imidazol-1-yl)-5-(1-(phenylsulfonyl)-1H-indol-3-yl)phenyl)acetamide A solution of the compound of Example 157(e) (0.3 g, 0.5 mmol) in 1,2-dimethoxyethane (15 ml) was degassed by $N_2$ bubbling for 5 min. 1-Methyl-4-(4,4,5,5-tetramethyl-1,3,2-dioxaborolan-2-yl)-1H-pyrazole (0.13 g, 0.62 mmol, 1.2 eq.) was added and the mixture was degassed for another 5 min. Pd(PPh$_3$)$_4$ (0.057 g, 0.05 mmol, 0.1 eq.) and aqueous sodium carbonate (0.16 g, 1.54 mmol, 3.0 eq.) were added and the procedure of Example 1(d) was followed. The crude residue of the product was purified by column chromatography (60-120 silica gel, 50% ethyl acetate in hexane) to give the product in 100% yield (0.29 g). LC-MS (ESI): Calculated mass: 586.66; Observed mass: 587.2 [M+H]$^+$ (rt: 1.53 min).

g) N-(3-(1H-indol-3-yl)-5-(5-(1-methyl-1H-pyrazol-4-yl)-1H-benzo[d]imidazol-1-yl)phenyl)acetamide To a solution of Example 157(f) (0.3 g, 0.5 mmol, 1 eq.) in THF (10 ml) and methanol (10 ml) was added cesium carbonate (0.33 g, 1 mmol, 2 eq.) and the mixture was stirred at RT for 12 h. The mixture was quenched and extracted as in Example 1(d). The solvent was distilled off to afford the product in 7% yield (15 mg). $^1$H NMR (400 MHz, DMSO-d$_6$): δ 11.52 (s, 1H), 10.33 (s, 1H), 8.65 (s, 1H), 8.19 (s, 1H), 8.04-7.89 (m, 4H), 7.68 (d, 1H), 7.60-7.58 (m, 2H), 7.49-7.47 (m, 3H), 7.21-7.13 (m, 2H), 3.88 (s, 3H), 2.13 (s, 3H); LC-MS (ESI): Calculated mass: 446.50; Observed mass: 447.1 [M+H]$^+$ (rt: 0.55 min).

Example 158

N-(3-(6-methoxypyridin-3-yl)-5-(5-(1-methyl-1H-pyrazol-4-yl)-1H-benzo[d]-imidazol-1-yl)phenyl)acetamide a) N-(3-(6-methoxypyridin-3-yl)-5-nitrophenyl)acetamide A solution of N-(3-bromo-5-nitrophenyl)acetamide (1 g, 3.86 mmol) in 1,2-dimethoxyethane (20 ml) was degassed by $N_2$ bubbling for 5 min. (6-Methoxypyridin-3-yl)boronic acid (0.77 g, 5.0 mmol, 1.3 eq.) was added and the mixture was degassed for 5 min. Pd(dppf)Cl$_2$ (0.630 g, 0.77 mmol, 0.2 eq.) and aqueous sodium carbonate (1.23 g, 11.58 mmol, 3.0 eq.) were added and the procedure of Example 1(d) was followed. The crude residue of the product was purified by column chromatography (60-120 silica gel, 40% ethyl acetate in hexane) to give the product in 81% yield (0.9 g).

b) N-(3-amino-5-(6-methoxypyridin-3-yl)phenyl)acetamide

To a solution of the compound of Example 158(a) (0.9 g, 3.13 mmol) in methanol (50 ml) was added 10% Pd/C (250 mg) and the reaction vessel was purged with nitrogen gas for 5 min. The mixture was then hydrogenated with $H_2$ balloon for a period of 4 h. The mixture was filtered through a pad of celite and the filtrate was concentrated to afford the compound in 99% yield (0.8 g).

c) N-(3-((4-bromo-2-nitrophenyl)amino)-5-(6-methoxypyridin-3-yl)phenyl)acetamide A solution of the compound of Example 158(b) (0.8 g, 3.11 mmol), 4-bromo-1-fluoro-2-nitrobenzene (0.68 g, 3.11 mmol, 1.0 eq.) and potassium fluoride (0.18 g, 3.111 mmol, 1.0 eq.) in DMF (5 ml) was heated at 90° C. for 20 h. The mixture was quenched and extracted as in Example 1(d). The solvent was distilled off and the residue was purified by column chromatography (60-120 silica gel, 40% ethyl acetate in hexane) to give the product in 42% yield (0.6 g). LC-MS (ESI): Calculated mass: 457.28; Observed mass: 458.9 [M+H]$^+$ (rt: 1.71 min).

d) N-(3-((2-amino-4-bromophenyl)amino)-5-(6-methoxypyridin-3-yl)phenyl)-acetamide To a solution of the compound of Example 158(c) (0.3 g, 0.66 mmol) in ethanol (20 ml) and water (5 ml) were added calcium chloride (0.73 g, 6.6 mmol, 10 eq.) and iron powder (0.36 g, 6.6 mmol, 10 eq.) and the mixture was heated at 90° C. for 6 h and filtered. The filtrate was diluted with water and extracted as in Example 1(d). The solvent was distilled off and the crude residue was directly used for the next step.

e) N-(3-(5-bromo-1H-benzo[d]imidazol-1-yl)-5-(6-methoxypyridin-3-yl)phenyl)-acetamide A mixture of the compound of Example 158(d) (0.26 g, 0.61 mmol) and formic acid (5 ml) was heated at 100° C. for 2 h. The formic acid was distilled off and the crude was dissolved in ethyl acetate. The ethyl acetate layer was washed with water, brine and dried over sodium sulphate. The solvent was distilled off and the residue was purified by column chromatography (60-120 silica gel, 10% methanol in chloroform) to give the product in 86% yield (0.23 g). LC-MS (ESI): Calculated mass: 437.29; Observed mass: 438.0 [M+H]$^+$ (rt: 1.52 min).

f) N-(3-(6-methoxypyridin-3-yl)-5-(5-(1-methyl-1H-pyrazol-4-yl)-1H-benzo[d]-imidazol-1-yl)phenyl)acetamide A solution of the compound of Example 158(e) (0.22 g, 0.5 mmol) in 1,2-dimethoxyethane (20 ml) was degassed by $N_2$ bubbling for 5 min. 1-Methyl-4-(4,4,5,5-tetramethyl-1,3,2-dioxaborolan-2-yl)-1H-pyrazole (0.11 g, 0.55 mmol, 1.1 eq.) was added and the mixture was degassed for another 5 min. Pd(PPh$_3$)$_4$ (0.116 g, 0.1 mmol, 0.2 eq.) and aqueous sodium carbonate (0.16 g, 1.5 mmol, 3.0 eq.) were added and the procedure of Example 1(d) was followed. The crude residue of the product was purified by preparative HPLC to give the product in 18% yield (40 mg). $^1$H NMR (300 MHz, DMSO-d$_6$): δ 10.4 (s, 1H), 8.82 (s, 1H), 8.55 (s, 1H), 8.23 (s, 1H), 8.1-8.04 (m, 2H), 7.98-7.91 (m, 2H), 7.85 (s, 1H), 7.74-7.65 (m, 3H), 6.97 (d, 1H), 3.92 (s, 3H), 3.88 (s, 3H), 2.12 (s, 3H); LC-MS (ESI): Calculated mass: 438.48; Observed mass: 439.1 [M+H]$^+$ (rt: 0.4 min).

Example 159

N-(5-(5-(1H-pyrazol-1-yl)-1H-benzo[d]imidazol-1-yl)-2',4'-difluoro-[1,1'-biphenyl]-3-yl)propionamide To a solution of the compound of Example 29(a) (0.5 g, 1.3 mmol) in DMF (10 ml) was added HATU (0.98 g, 2.6 mmol, 2.0 eq.) followed by DIPEA (0.5 g, 3.9 mmol, 3 eq.) and propionic acid (0.19 g, 2.6 mmol, 2.0 eq.). The mixture was stirred for 4 h and then quenched and extracted as in Example 1(d). The solvent was distilled off and the residue was purified by preparative HPLC to give the product in 9% yield (50 mg). $^1$H NMR (300 MHz, DMSO-d$_6$): δ 10.12 (s, 1H), 8.9-8.8 (s, 1H), 8.6 (d, 1H), 8.2 (s, 1H), 8.12 (s, 1H), 7.95 (d, 1H), 7.89-7.82 (m, 2H), 7.8-7.7 (m, 2H), 7.55 (s, 1H), 7.45-7.40 (m, 1H), 7.3-7.22 (m, 1H), 6.6-6.52 (s, 1H), 2.4 (quartet, 2H), 1.15 (t, 3H); LC-MS (ESI): Calculated mass: 443.45; Observed mass: 444.1 [M+H]$^+$ (rt: 1.58 min).

Example 160

N-(5-(5-(1H-pyrazol-1-yl)-1H-benzo[d]imidazol-1-yl)-2',4'-difluoro-[1,1'-biphenyl]-3-yl)isobutyramide The compound was prepared from the compound of Example 29(a) using the procedures of Example 159. $^1$H NMR (300 MHz, DMSO-d$_6$): δ 10.28 (s, 1H), 8.8 (s, 1H), 8.58 (d, 1H), 8.22 (d, 1H), 8.11 (s, 1H), 7.95 (d, 1H), 7.92 (d, 1H), 7.87 (d, 1H), 7.82 (s, 1H), 7.78 (s, 1H), 7.53 (s, 1H), 7.45 (d, 1H), 7.25 (s, 1H), 6.55-6.54 (m, 1H), 2.67-2.58 (m, 1H), 1.12 (d, 6H); LC-MS (ESI): Calculated mass: 457.47; Observed mass: 458.1 [M+H]$^+$ (rt: 1.6 min).

Example 161

N-(5-(5-(1H-pyrazol-1-yl)-1H-benzo[d]imidazol-1-yl)-2',4'-difluoro-[1,1'-biphenyl]-3-yl)cyclopropanecarboxamide The compound was prepared from the compound of Example 29(a) using the procedures of Example 159. $^1$H NMR (300 MHz, DMSO-d$_6$): δ 10.63 (s, 1H), 8.72 (s, 1H), 8.57 (d, 1H), 8.21 (d, 1H), 8.08 (s, 1H), 7.93-7.74 (m, 5H), 7.52 (s, 1H), 7.46-7.39 (m, 1H), 7.29-7.23 (m, 1H), 6.55 (s, 1H), 1.85-1.79 (m, 1H), 0.87 (d, 4H); LC-MS (ESI): Calculated mass: 455.46; Observed mass: 456.1 [M+H]$^+$ (rt: 1.58 min).

Example 162

N-(5-(5-(1H-pyrazol-1-yl)-1H-benzo[d]imidazol-1-yl)-2',4'-difluoro-[1,1'-biphenyl]-3-yl)pivalamide The compound was prepared from the compound of Example 29(a) using the procedures of Example 159. $^1$H NMR (400 MHz, DMSO-d$_6$): δ 9.65 (s, 1H), 8.74 (s, 1H), 8.0 (d, 1H), 8.23 (d, 1H), 8.17 (s, 1H), 8.01 (s, 1H), 7.95-7.92 (m, 1H), 7.84-7.81 (m, 1H), 7.78-7.72 (m, 2H), 7.54 (s, 1H), 7.48-7.42 (m, 1H), 7.29-7.25 (m, 1H), 6.57- 6.56 (m, 1H), 1.27 (s, 9H); LC-MS (ESI): Calculated mass: 471.5; Observed mass: 472.2 [M+H]$^+$ (rt: 1.68 min).

Example 163

N-(5-(5-(1H-pyrazol-1-yl)-1H-benzo[d]imidazol-1-yl)-2',4'-difluoro-[1,1'-biphenyl]-3-yl)-2-morpholinoacetamide To a solution of the compound of Example 29(a) (0.1 g, 0.26 mmol) in DMF (3 ml) was added EDC (74 mg, 0.39 mmol, 1.5 eq.), HOBt (70 mg, 0.52 mmol, 2 eq.) followed by DIPEA (0.1 g, 0.77 mmol, 3 eq.) and 2-morpholinoacetic acid (Intermediate Example 10) (56 mg, 0.39 mmol, 1.5 eq.). The mixture was stirred for 12 h and then quenched and extracted as in Example 1(d). The solvent was distilled off and the crude residue was purified by preparative HPLC to give the product in 27% yield (36 mg). $^1$H NMR (400 MHz, D$_2$O): δ 8.74 (s, 1H), 8.60 (d, 1H), 8.24 (d, 1H), 8.14 (s, 1H), 7.96-7.91 (m, 2H), 7.84-7.76 (m, 3H), 7.57 (s, 1H), 7.49-7.40 (m, 1H), 7.35-7.22 (m, 1H), 6.56 (m, 1H), 3.66 (t, 4H), 3.61-3.59 (m, 4H), 3.21 (s, 2H); LC-MS (ESI): Calculated mass: 514.53; Observed mass: 515.1 [M+H]$^+$ (rt: 0.53 min).

Example 164

N-(2',4'-difluoro-5-(5-(1-(1-methylpiperidin-4-yl)-1H-1,2,3-triazol-4-yl)-1H-benzo[d]imidazol-1-yl)-[1,1'-biphenyl]-3-yl)acetamide A mixture of the compound of Example 17(e) (0.7 g, 1.8 mmol), 4-azido-1-methylpiperidine (0.3 g, 2.17 mmol, 1.2 eq.), sodium ascorbate (0.35 g, 1.8 mmol, 1.0 eq.) and copper sulfate pentahydrate (0.22 g, 0.9 mmol, 0.5 eq.) in DMSO, DCM and water (1:1:1, 3 ml) was stirred for 12 h at RT. The mixture was quenched with water and the precipitate formed was filtered and dried to give the crude product which was recrystallized from diethyl ether to give the product in 71% yield (0.67 g). $^1$H NMR (300 MHz, DMSO-d$_6$): δ 10.41 (s, 1H), 8.75 (s, 2H), 8.28 (d, 1H), 8.11 (s, 1H), 7.95-7.92 (m, 1H), 7.81-7.74 (m, 2H), 7.53 (s, 1H), 7.45 (m, 1H), 7.27 (m, 1H), 3.66-3.62 (m, 1H), 3.26-3.22 (m, 4H), 2.87 (s, 3H), 2.27-2.22 (m, 4H), 2.12 (m, 3H); LC-MS (ESI): Calculated mass: 527.57; Observed mass: 528.2 [M+H]$^+$ (rt: 0.19 min).

Example 165

N-(2',4'-difluoro-5-(5-(1-(1-methylpiperidin-4-yl)-1H-1,2,3-triazol-4-yl)-1H-benzo[d]imidazol-1-yl)-[1,1'-biphenyl]-3-yl)ethanesulfonamide a) 2',4'-difluoro-5-(5-(1-(1-methylpiperidin-4-yl)-1H-1,2,3-triazol-4-yl)-1H-benzo[d]imidazol-1-yl)-[1,1'-biphenyl]-3-amine A solution of the compound of Example 164 (0.48 g, 0.91 mmol) in 6 N HCl (10 ml) was heated at 70° C. for 3 h. The mixture was quenched with NaHCO$_3$ solution and extracted as in Example 1(d). The solvent was distilled off to afford the product in 27% yield (0.12 g).

b) N-(2',4'-difluoro-5-(5-(1-(1-methylpiperidin-4-yl)-1H-1,2,3-triazol-4-yl)-1H-benzo[d]imidazol-1-yl)-[1,1'-biphenyl]-3-yl)ethanesulfonamide To a solution of the compound of Example 165(a) (60 mg, 0.123 mmol) in DCM (2 ml) was added pyridine (19 mg, 0.246 mmol, 2.0 eq.) followed by ethanesulfonyl chloride (19 mg, 0.148 mmol, 1.2 eq.). The reaction was monitored by LCMS. After completion of the reaction the solvent was removed under reduced pressure and the crude product was purified by flash chromatography (using 2% methanol in chloroform) to give the product in 13% yield (9 mg). LC-MS (ESI): Calculated mass: 577.65; Observed mass: 578.2 [M+H]$^+$ (rt: 0.42 min).

Example 166

N-(2',4'-difluoro-5-(5-(1-(1-methylpiperidin-4-yl)-1H-1,2,3-triazol-4-yl)-1H-benzo[d]imidazol-1-yl)-[1,1'-biphenyl]-3-yl)cyclopropanesulfonamide The compound was prepared from the compound of Example 164 using the procedures of Example 165 and cyclopropane sulfonyl chloride. LC-MS (ESI): Calculated mass: 553.61; Observed mass: 554.2 [M+H]$^+$ (rt: 0.57 min).

Example 167

N-(2',4'-difluoro-5-(5-(1-isopropyl-1H-pyrazol-4-yl)-1H-benzo[d]imidazol-1-yl)-[1,1'-biphenyl]-3-yl)acetamide The compound was prepared from compound of Intermediate Example 12 using the procedure of Example 8. $^1$H NMR (300 MHz, DMSO-d$_6$): δ 10.43 (s, 1H), 9.12 (s, 1H), 8.34 (s, 1H), 8.12 (s, 1H), 8.02-7.97 (m, 2H), 7.81 (s, 1H), 7.75-7.67 (m, 3H), 7.55 (s, 1H), 7.47-7.41 (m, 1H), 7.29-7.22 (m, 1H), 4.52-4.45 (m, 1H), 2.10 (s, 3H), 1.45 (d, 6H); LC-MS (ESI): Calculated mass: 471.5; Observed mass: 471.6 [M+H]$^+$ (rt: 1.4 min).

Example 168

N-(2',4'-difluoro-5-(5-(1-methyl-1H-pyrazol-3-yl)-1H-benzo[d]imidazol-1-yl)-[1,1'-biphenyl]-3-yl)acetamide a) N-(5-((4-acetyl-2-nitrophenyl)amino)-2',4'-difluoro-[1,1'-biphenyl]-3-yl)acetamide A solution of the compound of Example 1(e) (0.6 g, 2.28 mmol), 1-(4-fluoro-3-nitrophenyl)ethanone (0.4 g, 2.28 mmol, 1.0 eq.) and potassium fluoride (0.26 g, 4.56 mmol, 2.0 eq.) in DMF was heated at 80° C. for 7 h. The mixture was quenched and extracted as in Example 1(d). The solvent was distilled off and the residue was purified by column chromatography (60-120 silica gel, 1% methanol in chloroform) to give the product in 68% yield (0.66 g). $^1$H NMR (300 MHz, DMSO-d$_6$): δ 10.18 (s, 1H), 9.83 (s, 1H), 8.63 (d, 1H), 8.01 (m, 1H), 7.71 (s, 1H), 7.59 (m, 2H), 7.35 (m, 1H), 7.27-7.16 (m, 3H), 2.52 (s, 3H), 2.05 (s, 3H).

b) (E)-N-(5-((4-(3-(dimethylamino)acryloyl)-2-nitrophenyl)amino)-2',4'-difluoro-[1,1'-biphenyl]-3-yl)acetamide To a solution of the compound of Example 168(a) (0.66 g, 1.55 mmol) in DMF (4 ml) and ethanol (4 ml) was added DMF dimethylacetal (7 ml) and stirred at 110° C. for 12 h. The mixture was extracted as in Example 1(d). The solvent was distilled off to give the product in 89% yield (0.66 g) which was directly used for the next step.

c) N-(2',4'-difluoro-5-((4-(1-methyl-1H-pyrazol-3-yl)-2-nitrophenyl)amino)-[1,1'-biphenyl]-3-yl)acetamide To a solution of the compound of Example 168(b) (0.66 g, 1.37 mmol) in ethanol (15 ml) was added methyl hydrazine (7 ml) and stirred at RT overnight. The mixture was quenched with chilled water and the solid formed was filtered, washed with water and used for the next step. $^1$H NMR (300 MHz, DMSO-d$_6$): δ 10.12 (s, 1H), 9.52 (s, 1H), 8.19 (d, 1H), 7.73-7.60 (m, 2H), 7.59-7.54 (m, 2H), 7.46-7.35 (m, 3H), 7.30-7.14 (m, 2H), 6.44 (d, 1H), 3.85 (s, 3H), 2.05 (s, 3H).

d) N-(5-((2-amino-4-(1-methyl-1H-pyrazol-3-yl)phenyl)amino)-2',4'-difluoro-[1,1'-biphenyl]-3-yl)acetamide To a solution of the compound of Example 168(c) (0.5 g, 1.07 mmol) in THF (20 ml) were added a solution of ammonium chloride (0.23 g, 4.28 mmol, 4 eq.) in water (10 ml) and zinc (0.28 g, 4.28 mmol, 4 eq.). The mixture was stirred at RT for 4 h and filtered. The filtrate was diluted with water and extracted as in Example 1(d). The solvent was distilled off to afford the product in 65% yield (0.3 g). LC-MS (ESI): Calculated mass: 433.45; Observed mass: 434.1 [M+H]$^+$ (rt: 0.49 min).

e) N-(2',4'-difluoro-5-(5-(1-methyl-1H-pyrazol-3-yl)-1H-benzo[d]imidazol-1-yl)-[1,1'-biphenyl]-3-yl)acetamide A mixture of the compound of Example 168(d) (0.3 g, 0.69 mmol) and formic acid (3 ml) was heated at 100° C. for 2 h. The formic acid was distilled off and the crude was extracted with in ethyl acetate. The solvent was distilled off and the residue was purified by preparative HPLC to give the product in 9% yield (28 mg). $^1$H NMR (300 MHz, DMSO-d$_6$): δ 10.42 (s, 1H), 8.81 (s, 1H), 8.10 (s, 1H), 7.96 (s, 1H), 7.83-7.72 (m, 3H), 7.54-7.42 (m, 4H), 7.30-7.25 (m, 1H), 6.45 (d, 1H), 3.9 (s, 3H), 2.13 (s, 3H); LC-MS (ESI): Calculated mass: 443.45; Observed mass: 443.7 [M+H]$^+$ (RT: 1.37 min).

Example 169

N-(5-(5-(4,5-dihydro-1H-imidazol-2-yl)-1H-benzo[d]imidazol-1-yl)-2',4'-difluoro-[1,1'-biphenyl]-3-yl)acetamide a) N-(5-((4-(4,5-dihydro-1H-imidazol-2-yl)-2-nitrophenyl)amino)-2',4'-difluoro-[1,1'-biphenyl]-3-yl)acetamide To a solution of the compound of Example 22(a) (200 mg, 0.49 mmol) in DCM (10 ml) at 0° C. was added ethylene diamine (0.036 ml, 0.54 mmol, 1.1 eq.) followed by N-bromosuccinimide (95 mg, 0.54 mmol, 1.1 eq.). The mixture was stirred for 12 h, quenched with water and extracted as in Example 2(b). The solvent was distilled off and the residue was purified column chromatography (60-120 silica gel, 20% methanol in chloroform) to give the product in 50% yield (0.11 g). LC-MS (ESI): Calculated mass: 451.43; Observed mass: 452.1 [M+H]$^+$ (rt: 0.63 min).

b) N-(5-((2-amino-4-(4,5-dihydro-1H-imidazol-2-yl)phenyl)amino)-2',4'-difluoro-[1,1'-biphenyl]-3-yl)acetamide To a solution of the compound of Example 169(a) (0.11 g, 0.23 mmol) in THF (10 ml) were added a solution of ammonium chloride (50 mg, 0.93 mmol, 4 eq.) in water (10 ml) and zinc (60 mg, 0.93 mmol, 4 eq.). The mixture was stirred at RT for 4 h and filtered. The filtrate was diluted with water and extracted as in Example 1(d). The solvent was distilled off to afford the product in 88% yield (85 mg). LC-MS (ESI): Calculated mass: 421.44; Observed mass: 422.2 [M+H]$^+$ (rt: 0.49 min).

c) N-(5-(5-(4,5-dihydro-1H-imidazol-2-yl)-1H-benzo[d]imidazol-1-yl)-2',4'-difluoro-[1,1'-biphenyl]-3-yl)acetamide A mixture of the compound of Example 169(b) (80 mg, 0.19 mmol) and formic acid (3 ml) was heated at 100° C. for 4 h. The formic acid was distilled off and the crude was extracted with in ethyl acetate. The solvent was distilled off and the residue was purified by preparative HPLC to give the product in 12% yield (10 mg). $^1$H NMR (400 MHz, D$_2$O): δ 8.75 (s, 1H), 8.33 (s, 1H), 7.96 (s, 1H), 7.84-7.79 (m, 2H), 7.74 (s, 1H), 7.66-7.6 (m, 1H), 7.47 (s, 1H), 7.29-7.23 (m, 1H), 7.19-7.14 (m, 1H), 3.99 (m, 4H), 2.06 (s, 3H); LC-MS (ESI): Calculated mass: 431.44; Observed mass: 432.1 [M+H]$^+$ (rt: 0.36 min).

Example 170

N-(4'-fluoro-5-(5-(6-fluoropyridin-3-yl)-1H-benzo[d]imidazol-1-yl)-[1,1'-biphenyl]-3-yl)acetamide The compound was synthesized using the procedures of Example 53. LC-MS (ESI): Calculated mass: 440.44; Observed mass: 441.1 [M+H]$^+$ (rt: 1.57 min).

Example 171

N-(3-(5-(1-Ethyl-1H-pyrazol-4-yl)-1H-benzo[d]imidazol-1-yl)-5-(1H-pyrrol-1-yl)phenyl)acetamide To a solution of the compound of Example 87(g) (1.5 g, 3.8 mmol) in 1,2-dimethoxyethane (40 ml), the compound of Intermediate Example 13 (1.68 g, 7.59 mmol, 2 eq.), sodium carbonate (1 g, 9.5 mmol, 2.5 eq.) and water (4 ml) were added and the mixture was degassed for 15 min (N$_2$ bubbling). Pd(PPh$_3$)$_4$ (0.9 g, 0.76 mmol, 0.2 eq.) was added and the mixture was heated at 100° C. for 2 h. The mixture was quenched and extracted as in Example 1(d). The solvent was distilled off and the residue was purified column chromatography afford the compound in 74% yield (1.15 g). $^1$H NMR (300 MHz, DMSO-d$_6$): δ 8.86 (m, 1H), 8.26 (m, 1H), 7.99-7.94 (m, 2H), 7.87-7.80 (m, 2H), 7.72-7.60 (m, 3H), 7.39 (s, 2H), 6.31 (s, 2H), 4.15 (quartet, 2H), 2.10 (s, 3H), 1.40 (t, 3H); LC-MS (ESI): Calculated mass: 410.47; Observed mass: 411.2 [M+H]$^+$ (rt: 1.11 min).

Example 172

N-(3-(5-(1-Ethyl-1H-pyrazol-4-yl)-1H-benzo[d]imidazol-1-yl)-5-(1H-pyrrol-1-yl)phenyl)ethanesulfonamide a) 3-(5-(1-Ethyl-1H-pyrazol-4-yl)-1H-benzo[d]imidazol-1-yl)-5-(1H-pyrrol-1-yl)aniline A mixture of 20% NaOH (5 ml) and the compound of Example 171 (0.9 g, 2.12 mmol) in 25 ml of ethanol was heated at 90° C. for 2 h. The mixture was diluted with ethyl acetate (100 ml) and the organic layer was washed with water (50 ml) and brine (25 ml). The solvent was distilled off and the residue was purified by column chromatography over silica gel to afford the compound in 78% yield (0.7 g).

b) N-(3-(5-(1-Ethyl-1H-pyrazol-4-yl)-1H-benzo[d]imidazol-1-yl)-5-(1H-pyrrol-1-yl)phenyl)ethanesulfonamide To a solution of the compound of Example 172(a) (75 mg, 0.2 mmol) in DCM (1 ml) were added pyridine (0.5 ml) and ethanesulfonyl chloride (52 mg, 0.4 mmol, 2 eq.) and the mixture was stirred at RT for 2 h. Pyridine was distilled off and the residue was purified by preparative HPLC to afford the compound in 25% yield (23 mg). $^1$H NMR (300 MHz, DMSO-d$_6$): δ 10.31 (s, 1H), 8.74 (s, 1H), 8.26 (s, 1H), 7.98 (d, 2H), 7.69-7.61 (m, 3H), 7.42-7.38 (m, 4H), 6.33 (s, 2H), 4.15 (quartet, 2H), 3.16 (quartet, 2H), 1.43 (t, 3H), 1.25 (t, 3H); LC-MS (ESI): Calculated mass: 460.55; Observed mass: 461.18 [M+H]$^+$ (rt: 1.38 min).

Example 173

N-(3-(5-(1-Isopropyl-1H-pyrazol-4-yl)-1H-benzo[d]imidazol-1-yl)-5-(1H-pyrrol-1-yl)phenyl)acetamide The compound was prepared from the compound of Intermediate Example 12 using the procedure of Example 171. $^1$H NMR (300 MHz, DMSO-d$_6$): δ 10.40 (s, 1H), 8.67 (s, 1H), 8.29 (s, 1H), 8.01 (s, 1H), 7.94 (s, 1H), 7.86-7.81 (m, 2H), 7.70-7.59 (m, 3H), 7.41 (s, 2H), 6.32 (s, 2H), 4.53-4.49 (m, 1H), 2.12 (s, 3H), 1.46 (d, 6H); LC-MS (ESI): Calculated mass: 424.5; Observed mass: 425.2 [M+H]$^+$ (rt: 1.34 min).

Example 174

N-(3-(5-(1-Isopropyl-1H-pyrazol-4-yl)-1H-benzo[d]imidazol-1-yl)-5-(1H-pyrrol-1-yl)phenyl)methanesulfonamide a) 3-(5-(1-Isopropyl-1H-pyrazol-4-yl)-1H-benzo[d]imidazol-1-yl)-5-(1H-pyrrol-1-yl)aniline A mixture of 20% NaOH (5 ml) and the compound of Example 173 (1 g, 2.43 mmol) in 25 ml ethanol was heated at 90° C. for 2 h. The mixture was diluted with ethyl acetate (100 ml) and the organic layer was washed with water (50 ml) and brine (25 ml). The solvent was distilled off and the crude was purified by column chromatography over silica gel to afford the compound in 93% yield (0.75 g).

b) N-(3-(5-(1-Isopropyl-1H-pyrazol-4-yl)-1H-benzo[d]imidazol-1-yl)-5-(1H-pyrrol-1-yl)phenyl)methanesulfonamide To a solution of the compound of Example 174(a) (100 mg, 0.26 mmol) in DCM (1 ml) were added pyridine (0.5 ml) and ethanesulfonyl chloride (60 mg, 0.52 mmol, 2 eq.) and the mixture was stirred at RT for 12 h. Pyridine was distilled off and the residue was purified by preparative HPLC to afford the compound in 8% yield (10 mg). $^1$H NMR (300 MHz, CD$_3$OD): δ 9.20 (s, 1H), 8.18 (s, 1H), 8.01 (s, 1H), 7.94 (s, 1H), 7.80 (s, 2H), 7.62 (s, 1H), 7.49 (m, 2H), 7.31 (m, 2H), 6.35 (m, 2H), 4.65-4.51 (m, 1H), 3.14 (s, 3H), 1.55 (d, 6H); LC-MS (ESI): Calculated mass: 461.0; Observed mass: 460.55 [M+H]$^+$ (rt: 1.44 min).

Example 175

N-(3-(5-(1-isopropyl-1H-pyrazol-4-yl)-1H-benzo[d]imidazol-1-yl)-5-(1H-pyrrol-1-yl)phenyl)ethanesulfonamide The compound was prepared from the compound of Example 173 using the procedure of Example 174. $^1$H NMR (300 MHz, CD$_3$OD): δ 9.05 (s, 1H), 8.16 (s, 1H), 7.99-7.93 (m, 2H), 7.77 (s, 2H), 7.58 (s, 1H), 7.47 (m, 2H), 7.30 (m, 2H), 6.35 (m, 2H), 4.60-4.51 (m, 1H), 3.30 (quartet, 2H), 1.56-1.54 (d, 6H), 1.38 (t, 3H); LC-MS (ESI): Calculated mass: 474.58; Observed mass: 475.1 [M+H]$^+$ (rt: 1.50 min).

Example 176

N-(2',4'-difluoro-5-(6-(1-methyl-1H-pyrazol-4-yl)-3H-imidazo[4,5-b]pyridin-3-yl)-[1,1'-biphenyl]-3-yl)propionamide To a solution of propionic acid (20 mg, 0.274 mmol) in DMF (2 ml) was added HATU (155 mg, 0.41 mmol, 1.5 eq.) and the mixture was stirred at RT for 0.5 h. The compound of Example 132(a) (110 mg, 0.274 mmol) and DIPEA (0.15 ml, 0.821 mmol, 3 eq.) were added and the mixture was stirred for 12 h, quenched with water and extracted with DCM (3×50 ml). The combined organic layer was washed with water to obtain precipitate which was filtered. The crude product was purified by preparative HPLC to give the product (14 mg). $^1$H NMR (400 MHz, DMSO-d$_6$): δ 10.23 (s, 1H), 8.92 (s, 1H), 8.72 (d, 1H), 8.41 (d, 1H), 8.33-8.31 (m, 2H), 8.04 (d, 1H), 7.89 (d, 1H), 7.75-7.69 (m, 2H), 7.48-7.42 (m, 1H), 7.29-7.25 (m, 1H), 3.90 (s, 3H), 2.40 (quartet, 2H), 1.11 (t, 3H); LC-MS (ESI): Calculated mass: 458.46; Observed mass: 459.1 [M+H]$^+$ (rt: 1.44 min).

Example 177

N-(2',4'-difluoro-5-(6-(1-methyl-1H-pyrazol-4-yl)-3H-imidazo[4,5-b]pyridin-3-yl)-[1,1'-biphenyl]-3-yl)cyclopropanecarboxamide The compound was prepared using the procedure of Example 176. $^1$H NMR (400 MHz, DMSO-d$_6$): δ 10.62 (s, 1H), 8.94 (s, 1H), 8.72 (d, 1H), 8.41 (d, 1H), 8.31 (d, 2H), 8.04 (s, 1H), 7.88 (br s, 1H), 7.72-7.68 (m, 2H), 7.47-7.41 (m, 1H), 7.29-7.25 (m. 1H), 3.89 (s, 3H), 1.85 (m, 1H), 0.84 (d, 4H); LC-MS (ESI): Calculated mass: 470.4; Observed mass: 471.1 [M+H]$^+$ (rt: 1.52 min).

Example 178

N-(2',4'-difluoro-5-(6-(6-fluoropyridin-3-yl)-3H-imidazo[4,5-b]pyridin-3-yl)-[1,1'-biphenyl]-3-yl)acetamide A solution of the compound of Example 131(c) (330 mg, 0.75 mmol) in 1,2-dimethoxyethane (10 ml) was degassed by N$_2$ bubbling for 5 min. (6-Fluoropyridin-3-yl)boronic acid (130 mg, 0.9 mmol, 1.2 eq.) was added and the mixture was degassed for another 5 min. Pd(dppf)Cl$_2$ (120 mg, 0.15 mmol, 0.2 eq.) and aqueous sodium carbonate (290 mg, 2.7 mmol, 3.0 eq.) were added and the procedure of Example 1(d) was followed. The crude residue of the product was purified by preparative HPLC to give the product. $^1$H NMR (400 MHz, DMSO-d$_6$): δ 10.40 (s, 1H), 9.03 (s, 1H), 8.79 (d, 1H), 8.68 (s, 1H), 8.60 (s, 1H), 8.43 (dt, 1H), 8.30 (s, 1H), 7.87 (s, 1H), 7.70 (s, 2H), 7.47-7.26 (m, 3H), 2.07 (s, 3H); LC-MS (ESI): Calculated mass: 459.4; Observed mass: 460.1 [M+H]$^+$ (rt: 1.53 min).

Example 179

N-(5-(6-(1H-pyrazol-1-yl)-3H-imidazo[4,5-b]pyridin-3-yl)-2'-fluoro-4'-methoxy-[1,1'-biphenyl]-3-yl)acetamide The compound was prepared using the procedures of Example 148 starting from N-(3-bromo-5-nitrophenyl)acetamide (0.8 g, 3.089 mmol) and 2-Fluoro-4-methoxy-phenyl)boronic acid (0.63 g, 3.71 mmol, 1.2 eq.). $^1$H NMR (400 MHz, DMSO-d$_6$): δ 10.39 (s, 1H), 9.05 (s, 1H), 9.02 (d, 1H), 8.67 (d, 2H), 8.26 (s, 1H), 7.89 (s, 1H), 7.84 (d, 1H), 7.68 (s, 1H), 7.59 (t, 1H), 7.04-6.95 (m, 2H), 6.64 (t, 1H), 3.85 (s, 3H), 2.13 (s, 3H); LC-MS (ESI): Calculated mass: 442.45; Observed mass: 443.1 [M+H]$^+$ (rt: 1.42 min).

Example 180

N-(2'-fluoro-4'-methoxy-5-(6-(1-methyl-1H-pyrazol-4-yl)-3H-imidazo[4,5-b]pyridin-3-yl)-[1,1'-biphenyl]-3-yl)acetamide A solution of the compound of Example 179(e) (250 mg, 0.549 mmol) in 1,2-dimethoxyethane (10 ml) was degassed by N$_2$ bubbling for 5 min. 1-Methyl-4-(4,4,5,5-tetramethyl-1,3,2-dioxaborolan-2-yl)-1H-pyrazole (137 mg, 0.66 mmol, 1.2 eq.) was added and the mixture was degassed for another 5 min. Pd(PPh$_3$)$_4$ (63 mg, 0.0549 mmol, 0.1 eq.) and aqueous sodium carbonate (117 mg, 1.1 mmol, 2.0 eq.) were added and the procedure of Example 1(d) was followed. The crude residue of the product was purified by preparative HPLC to give the product in 90% yield (225 mg). $^1$H NMR (400 MHz, DMSO-d$_6$): δ 10.39 (s, 1H), 8.92 (s, 1H), 8.71 (d, 1H), 8.41 (d, 1H), 8.30 (s, 1H), 8.25 (t, 1H), 8.04 (s, 1H), 7.84 (d, 1H), 7.67 (s, 1H), 7.58 (t, 1H), 7.03-6.93 (m, 2H), 3.90 (s, 3H), 3.84 (s, 3H), 2.11 (s, 3H); LC-MS (ESI): Calculated mass: 456.47; Observed mass: 456.6 [M+H]$^+$ (rt: 1.07 min).

Example 181

N-(2',4'-difluoro-5-(6-(1-(1-methylpiperidin-4-yl)-1H-1,2,3-triazol-4-yl)-3H-imidazo[4,5-b]pyridin-3-yl)-[1,1'-biphenyl]-3-yl)acetamide a) N-(2',4'-difluoro-5-((5-iodo-3-nitropyridin-2-yl)amino)-[1,1'-biphenyl]-3-yl)-acetamide A solution of the compound of Example 1(e) (2.58 g, 9.85 mmol), 2-chloro-5-iodo-3-nitropyridine of Intermediate Example 14 (2.8 g, 9.85 mmol, 1.0 eq.) and potassium fluoride (0.57 g, 9.85 mmol, 1.0 eq.) in DMF (30 ml) was heated at 130° C. for 5 h. The mixture was quenched and extracted as in Example 1(d). The solvent was distilled off and the residue was purified by column chromatography (60-120 silica gel, 30% ethyl acetate in hexane) to give the product in 40% yield (2.0 g). $^1$H NMR (300 MHz, DMSO-d$_6$): δ 10.10 (s, 1H), 9.95 (s, 1H), 8.74 (d, 1H), 8.66 (d, 1H), 7.88 (s, 1H), 7.60-7.52 (m, 2H), 7.42-7.34 (m, 2H), 7.24-

7.21 (m, 1H), 2.07 (s, 3H), LC-MS (ESI): Calculated mass: 510.2; Observed mass: 510.9 [M+H]+ (rt: 1.75 min).

b) N-(5-((3-amino-5-iodopyridin-2-yl)amino)-2',4'-difluoro-[1,1'-biphenyl]-3-yl)acetamide To a solution of the compound of Example 181(a) (0.5 g, 0.98 mmol) in THF (30 ml) were added a solution of ammonium chloride (0.2 g, 3.92 mmol, 4 eq.) in water (15 ml) and zinc (0.25 g, 3.92 mmol, 4 eq.). The mixture was stirred at RT for 3 h and filtered. The filtrate was diluted with water and extracted as in Example 1(d). The solvent was distilled off to give the product in 64% yield (0.3 g). $^1$H NMR (400 MHz, DMSO-d$_6$): δ 9.96 (s, 1H), 7.99 (s, 1H), 7.90 (s, 1H), 7.61 (d, 1H), 7.50 (quartet, 1H) 7.43 (s, 1H), 7.39-7.33 (m, 1H), 7.28 (s, 1H), 7.22-7.18 (m, 2H), 5.39 (s, 2H), 2.05 (s, 3H); LC-MS (ESI): Calculated mass: 480.2; Observed mass: 481.1 [M+H]+ (rt: 1.53 min).

c) N-(2',4'-difluoro-5-(6-iodo-3H-imidazo[4,5-b]pyridin-3-yl)-[1,1'-biphenyl]-3-yl)acetamide A mixture of the compound of Example 181(b) (3.12 g, 1.5 g) and formic acid (15 ml) was heated at 90° C. for 1 h. Formic acid was then distilled off and the residue was dissolved in ethyl acetate. The ethyl acetate layer was washed with water, brine and dried over sodium sulphate. The solvent was distilled off to afford the product in 92% yield (1.4 g). $^1$H NMR (300 MHz, DMSO-d$_6$): δ 10.38 (s, 1H), 8.93 (s, 1H), 8.63 (s, 2H), 8.21 (s, 1H), 7.89 (s, 1H), 7.74-7.64 (m, 2H), 7.42 (t, 1H), 7.26 (t, 1H), 2.11 (s, 3H); LC-MS (ESI): Calculated mass: 490.2; Observed mass: 491.1 [M+H]+ (rt: 1.60 min).

d) N-(2',4'-difluoro-5-(6-((trimethylsilyl)ethynyl)-3H-imidazo[4,5-b]pyridin-3-yl)-[1,1'-biphenyl]-3-yl)acetamide A solution of the compound of Example 181(c) (1.6 g, 3.265 mmol) in DMF-Et$_3$N (1:1; 60 ml) was degassed by N$_2$ bubbling for 15 min. Pd(PPh$_3$)$_4$ (0.18 g, 0.163 mmol, 0.05 eq.), copper(I) iodide (62 mg, 0.326 mmol, 0.1 eq.) and ethynyltrimethylsilane (0.38 g, 3.91 mmol, 1.2 eq.) were added sequentially and the mixture was stirred for 12 h at RT. The mixture was quenched and extracted as in Example 1(d). The solvent was distilled off and the residue was purified by column chromatography (60-120 silica gel, 40% ethyl acetate in hexane) to give the product in 73% yield (1.1 g). $^1$H NMR (300 MHz, DMSO-d$_6$): δ 10.41 (s, 1H), 9.02 (s, 1H), 8.52 (d, 1H), 8.33 (d, 1H), 8.21 (s, 1H), 7.91 (s, 1H), 7.73-7.64 (m, 2H), 7.43 (m, 1H), 7.26 (m, 1H), 2.11 (s, 3H), 0.27 (s, 9H); LC-MS (ESI): Calculated mass: 460.55; Observed mass: 461.2 [M+H]+ (rt: 1.83 min).

e) N-(5-(6-ethynyl-3H-imidazo[4,5-b]pyridin-3-yl)-2',4'-difluoro-[1,1'-biphenyl]-3-yl)acetamide To a solution of the compound of Example 181(d) (1.1 g, 2.4 mmol) in THF at 0° C. was added TBAF (1 M in THF; 0.6 ml, 2.4 mmol, 1.0 eq.) and the mixture was stirred for 0.5 h. The mixture was filtered over a pad of silica and distilled to give crude residue which was purified by column chromatography (60-120 silica gel, 5% methanol in chloroform) to give the product in 86% yield (0.8 g). $^1$H NMR (300 MHz, DMSO-d$_6$): δ 10.39 (s, 1H), 9.03 (s, 1H), 8.56 (d, 1H), 8.38 (d, 1H), 8.23 (s, 1H), 7.91 (s, 1H), 7.75-7.66 (m, 2H), 7.48-7.41 (m, 1H), 7.30-7.24 (m, 1H), 4.39 (s, 1H), 2.07 (s, 3H); LC-MS (ESI): Calculated mass: 388.3; Observed mass: 389.2 [M+H]+ (rt: 1.49 min).

f) N-(2',4'-difluoro-5-(6-(1-(1-methylpiperidin-4-yl)-1H-1,2,3-triazol-4-yl)-3H-imidazo[4,5-b]pyridin-3-yl)-[1,1'-biphenyl]-3-yl)acetamide A mixture of the compound of Example 181(e) (0.5 g, 1.28 mmol), 4-azido-1-methylpiperidine of Intermediate Example 11 (0.21 g, 1.54 mmol, 1.2 eq.), sodium ascorbate (0.25 g, 1.28 mmol, 1.0 eq.) and copper sulfate pentahydrate (0.16 g, 0.6 mmol, 0.5 eq.) in DMSO, DCM and water (2:5:2, 9 ml) was stirred for 12 h at RT. The mixture was quenched with water and the precipitate formed was filtered and dried to give the crude product which was purified by preparative HPLC to give the product in 74% yield (0.5 g). $^1$H NMR (300 MHz, CDCl$_3$): δ 8.94 (d, 1H), 8.56 (d, 1H), 8.43 (s, 1H), 8.15 (s, 1H), 7.90 (s, 1H), 7.72 (s, 1H), 7.65 (s, 2H), 7.53-7.45 (m, 1H), 7.05-7.49 (m, 1H), 4.68-4.59 (m, 1H), 3.18-3.13 (m, 4H), 2.62 (s, 3H), 2.44-2.39 (m, 4H), 2.24 (s, 3H); LC-MS (ESI): Calculated mass: 558.50; Observed mass: 529.2 [M+H]+ (rt: 0.39 min).

Example 182

N-(2',4'-difluoro-5-(6-(1-(1-methylpiperidin-4-yl)-1H-1,2,3-triazol-4-yl)-3H-imidazo[4,5-b]pyridin-3-yl)-[1,1'-biphenyl]-3-yl)ethanesulfonamide a) 2',4'-difluoro-5-(6-(1-(1-methylpiperidin-4-yl)-1H-1,2,3-triazol-4-yl)-3H-imidazo[4,5-b]pyridin-3-yl)-[1,1'-biphenyl]-3-amine The compound of Example 181 (0.4 g, 0.757 mmol) was added to aqueous 6 N HCl (10 ml) at 0° C. and the mixture was stirred at 70° C. for 3 h. The mixture was quenched with saturated aqueous sodium bicarbonate solution and extracted with ethyl acetate (3×50 ml). The combined organic layer was washed with water, brine and dried over sodium sulphate and the residue was purified by column chromatography (60-120 silica gel, 10% methanol in DCM) to give the product in 30% yield (0.11 g). LC-MS (ESI): Calculated mass: 486.52; Observed mass: 487.3 [M+H]+ (rt: 0.22 min).

b) N-(2',4'-difluoro-5-(6-(1-(1-methylpiperidin-4-yl)-1H-1,2,3-triazol-4-yl)-3H-imidazo[4,5-b]pyridin-3-yl)-[1,1'-biphenyl]-3-yl)ethanesulfonamide To a solution of the compound of Example 182(a) (55 mg, 0.113 mmol) in DCM was added pyridine (17 mg, 0.226 mmol, 2.0 eq.) followed by ethanesulfonyl chloride (17 mg, 0.135 mmol, 1.2 eq.). The reaction was monitored by LCMS. After completion of the reaction the solvent was distilled off and the crude product was purified by preparative HPLC to give the product in 46% yield (30 mg). $^1$H NMR (300 MHz, DMSO-d$_6$): δ10.31 (s, 1H), 9.01 (s, 1H), 8.97 (d, 1H), 8.84 (s, 1H), 8.62 (s, 1H), 7.93 (s, 1H), 7.75-7.71 (m, 2H), 7.48-7.419 (m, 2H), 7.27 (m, 1H), 3.45 (m, 1H), 2.79 (s, 3H), 2.41-2.34 (m, 4H), 2.28-2.24 (quartet, 2H), 1.27-1.22 (m, 4H), 1.03 (t, 3H); LC-MS (ESI): Calculated mass: 578.64; Observed mass: 578.9 [M+H]+ (RT: 0.11 min).

Example 183

N-(2',4'-difluoro-5-(6-(1-(1-methylpiperidin-4-yl)-1H-1,2,3-triazol-4-yl)-3H-imidazo[4,5-b]pyridin-3-yl)-[1,1'-biphenyl]-3-yl)cyclopropanecarboxamide To a solution of cyclopropanecarboxylic acid (14 mg, 0.169 mmol, 1.5 eq.) in DMF (2 ml) was added HATU (90 mg, 0.226 mmol, 2.0 eq.) and the mixture was stirred at RT for 0.5 h. The compound of Example 182(a) (55 mg, 0.113 mmol) and DIPEA (45 mg, 0.339 mmol, 3 eq.) were added and the mixture was stirred for 12 h, quenched with water and extracted with DCM (3×50 ml). The combined organic layer was washed with water to obtain precipitate which was filtered. The crude product was purified by preparative HPLC to give the product in 13% yield (12 mg). $^1$H NMR (300 MHz, DMSO-$d_6$): δ 10.68 (s, 1H), 8.98 (s, 2H), 8.83 (s, 1H), 8.62 (s, 1H), 8.33 (s, 1H), 8.88 (s, 1H), 7.71-7.66 (m, 2H), 7.46-7.39 (m, 1H), 7.28-7.23 (m, 1H), 4.83 (m, 1H), 3.62-3.52 (m, 4H), 2.81 (s, 3H), 2.30-2.26 (m, 4H), 1.85 (m, 1H), 0.83 (d, 4H); LC-MS (ESI): Calculated mass: 554.59; Observed mass: 554.9 [M+H]$^+$ (rt: 0.183 min).

Example 184

N-(5-(5-(1H-pyrazol-1-yl)-1H-benzo[d]imidazol-1-yl)-2',6'-difluoro-[1,1'-biphenyl]-3-yl)methanesulfonamide a) 5-(5-(1H-pyrazol-1-yl)-1H-benzo[d]imidazol-1-yl)-2',6'-difluoro-[1,1'-biphenyl]-3-amine To a solution of the compound of Example 152 (2.1 g, 4.895 mmol) in ethanol (50 ml) was added 10% aqueous solution of NaOH (10 ml) and the mixture was heated at 100° C. for 2 h. The mixture was quenched and extracted as in Example 1(d). The solvent was distilled off to afford the product in 89% yield (1.6 g).

b) N-(5-(5-(1H-pyrazol-1-yl)-1H-benzo[d]imidazol-1-yl)-2',6'-difluoro-[1,1'-biphenyl]-3-yl)methanesulfonamide To a solution of the compound of Example 184(a) (50 mg, 0.129 mmol) in DCM was added pyridine (20 mg, 0.258 mmol, 2.0 eq.) followed by methanesulfonyl chloride (18 mg, 0.155 mmol, 1.2 eq.). The reaction was monitored by LCMS. After completion of the reaction the solvent was distilled off and the crude product was purified by preparative HPLC to give the product in 50% yield (30 mg). $^1$H NMR (400 MHz, DMSO-$d_6$): δ 10.32 (s, 1H), 8.76 (s, 1H), 8.61 (d, 1H), 8.24 (d, 1H), 7.93 (dd, 1H), 7.79 (s, 1H), 7.76 (d, 1H), 7.61-7.57 (m, 4H), 7.37 (s, 1H), 7.31 (t, 2H), 3.19 (s, 3H); LC-MS (ESI): Calculated mass: 465.48; Observed mass: 466.1 [M+H]$^+$ (rt: 1.47 min).

Example 185

N-(5-(5-(1H-pyrazol-1-yl)-1H-benzo[d]imidazol-1-yl)-2',6'-difluoro-[1,1'-biphenyl]-3-yl)ethanesulfonamide The compound was prepared from the compound of Example 152 using the procedure of Example 184. $^1$H NMR (400 MHz, DMSO-$d_6$): δ 10.35 (s, 1H), 8.72 (s, 1H), 8.60 (d, 1H), 8.24 (d, 1H), 7.93 (dd, 1H), 7.76 (t, 2H), 7.61-7.54 (m, 3H), 7.39 (s, 1H), 7.31 (t, 2H), 6.56 (t, 1H), 2.40 (quartet, 2H), 1.26 (t, 3H); LC-MS (ESI): Calculated mass: 479.5; Observed mass: 480.0 [M+H]$^+$ (rt: 1.51 min).

Example 186

N-(2',6'-difluoro-5-(5-(1-methyl-1H-pyrazol-4-yl)-1H-benzo[d]imidazol-1-yl)-[1,1'-biphenyl]-3-yl)methanesulfonamide a) 2',6'-difluoro-5-(5-(1-methyl-1H-pyrazol-4-yl)-1H-benzo[d]imidazol-1-yl)-[1,1'-biphenyl]-3-amine To a solution of the compound of Example 151 (2.0 g, 4.514 mmol) in ethanol (50 ml) was added 10% aqueous solution of NaOH (2.5 ml) and the mixture was heated at 100° C. for 2 h. The mixture was quenched and extracted as in Example 1(d). The solvent was distilled off to afford the product in 99% yield (1.8 g).

b) N-(2',6'-difluoro-5-(5-(1-methyl-1H-pyrazol-4-yl)-1H-benzo[d]imidazol-1-yl)-[1,1'-biphenyl]-3-yl)methanesulfonamide To a solution of the compound of Example 186(a) (50 mg, 0.124 mmol) in DCM was added pyridine (20 mg, 0.258 mmol, 2.0 eq.) followed by methanesulfonyl chloride (29 mg, 0.155 mmol, 2.0 eq.). The reaction was monitored by LCMS. After completion of the reaction the solvent was distilled off and the crude product was purified by preparative HPLC to give the product in 42% yield (25 mg). $^1$H NMR (300 MHz, DMSO-$d_6$): δ 10.34 (s, 1H), 8.76 (s, 1H), 8.22 (s, 1H), 7.97 (d, 2H), 7.66-7.57 (m, 5H), 7.36-7.30 (m, 3H), 3.88 (s, 3H), 3.19 (s, 3H); LC-MS (ESI): Calculated mass: 479.50; Observed mass: 480.2 [M+H]$^+$ (rt: 1.27 min).

Example 187

N-(2',6'-difluoro-5-(5-(1-methyl-1H-pyrazol-4-yl)-1H-benzo[d]imidazol-1-yl)-[1,1'-biphenyl]-3-yl)ethanesulfonamide The compound was prepared from the compound of Example 151 using the procedure of Example 186. $^1$H NMR (400 MHz, DMSO-$d_6$): δ 10.37 (s, 1H), 8.80 (s, 1H), 8.23 (s, 1H), 7.98 (d, 2H), 7.67 (s, 2H), 7.61 (s, 1H), 7.56 (s, 2H), 7.38 (s, 1H), 7.30 (t, 2H), 3.88 (s, 3H), 3.30 (quartet, 2H), 1.26 (t, 3H); LC-MS (ESI): Calculated mass: 493.3; Observed mass: 494.1 [M+H]$^+$ (rt: 1.38 min).

Example 188

N-(4'-fluoro-2'-methoxy-5-(5-(1-methyl-1H-pyrazol-4-yl)-1H-benzo[d]imidazol-1-yl)-[1,1'-biphenyl]-3-yl)acetamide The compound was prepared using the procedures of Example 148 starting from N-(3-bromo-5-nitrophenyl)acetamide (0.8 g, 3.089 mmol) and 4-Fluoro-2-methoxy-phenyl) boronic acid (0.63 g, 3.71 mmol, 1.2 eq.). $^1$H NMR (400 MHz, DMSO-$d_6$): δ 10.35 (s, 1H), 8.93 (s, 1H), 8.24 (s, 1H), 8.07 (s, 1H), 7.98 (d, 2H), 7.71-7.69 (m, 3H), 7.47-7.44 (m, 2H), 7.08 (dd, 1H), 6.93 (dt, 1H), 3.88 (s, 3H), 3.17 (s, 3H), 2.08 (s, 3H); LC-MS (ESI): Calculated mass: 455.48; Observed mass: 456.1 [M+H]+ (rt: 1.13 min).

Example 189

N-(5-(5-(1H-pyrazol-1-yl)-1H-benzo[d]imidazol-1-yl)-2'-fluoro-4'-methoxy-[1,1'-biphenyl]-3-yl)acetamide a) N-(2'-fluoro-4'-methoxy-5-nitro-[1,1'-biphenyl]-3-yl)acetamide The compound was prepared from the compound of Example 1(c) (0.8 g, 3.089 mmol) and (2-Fluoro-4-methoxyphenyl)boronic acid (0.63 g, 3.71 mmol, 1.2 eq.) using the procedure of Example 148(a) to give the product in 97% yield (0.91 g). $^1$H NMR (300 MHz, DMSO-$d_6$): δ 10.52 (s, 1H), 8.59 (s, 1H), 8.07 (s, 1H), 7.97 (s, 1H), 7.55 (t, 1H), 7.05-6.93 (m, 2H), 3.84 (s, 3H), 2.11 (s, 3H).

b) N-(5-amino-2'-fluoro-4'-methoxy-[1,1'-biphenyl]-3-yl)acetamide

The compound was prepared from the compound of Example 189(a) (0.9 g, 2.96 mmol) using the procedure of Example 148(b) to give the product in 97% yield (790 mg). $^1$H NMR (300 MHz, DMSO-$d_6$): δ 9.74 (s, 1H), 7.28 (t, 1H), 6.91-6.78 (m, 4H), 6.34 (s, 1H), 5.15 (br s, 2H), 3.77 (s, 3H), 1.98 (s, 3H); LC-MS (ESI): Calculated mass: 274.3; Observed mass: 275.2 [M+H]+ (rt: 0.35 min).

c) N-(5-((4-bromo-2-nitrophenyl)amino)-2'-fluoro-4'-methoxy-[1,1'-biphenyl]-3-yl)acetamide The compound was prepared from the compound of Example 189(b) (3 g, 10.95 mmol) using the procedure of Example 148(c) to give the crude product in 93% yield (4.82 g). $^1$H NMR (300 MHz, DMSO-$d_6$): δ 10.13 (s, 1H), 9.43 (s, 1H), 8.23 (d, 1H), 7.68-7.64 (m, 2H), 7.53 (s, 1H), 7.44 (t, 1H), 7.24 (d, 1H), 7.11 (s, 1H), 6.98-6.88 (m, 2H), 3.81 (s, 3H), 2.06 (s, 3H); LC-MS (ESI): Calculated mass: 474.3; Observed mass: 476.01 [M+H]+ (rt: 1.85 min).

d) N-(5-((2-amino-4-bromophenyl)amino)-2'-fluoro-4'-methoxy-[1,1'-biphenyl]-3-yl)acetamide The compound was prepared from the compound of Example 189(c) (4.8 g, 10.13 mmol) using the procedure of Example 148(d) to give the product in 93% yield (4.12 g). $^1$H NMR (300 MHz, DMSO-$d_6$): δ 10.80 (s, 1H), 7.30 (t, 2H), 7.11 (d, 1H), 6.98-6.82 (m, 5H), 6.63 (dd, 1H), 6.52 (s, 1H), 5.09 (br s, 2H), 3.77 (s, 3H), 1.98 (s, 3H); LC-MS (ESI): Calculated mass: 444.30; Observed mass: 441.0 [M+H]+ (rt: 1.66 min).

e) N-(5-(5-bromo-1H-benzo[d]imidazol-1-yl)-2'-fluoro-4'-methoxy-[1,1'-biphenyl]-3-yl)acetamide The compound was prepared from the compound of Example 189(d) (4 g, 9 mmol) using the procedure of Example 148(e) to give the product in 95% yield (3.8 g). $^1$H NMR (300 MHz, DMSO-$d_6$): δ 10.38 (s, 1H), 8.69 (s, 1H), 7.99 (t, 2H), 7.77 (d, 1H), 7.65-7.44 (m, 4H), 7.01-6.89 (m, 2H), 3.81 (s, 3H), 2.09 (s, 3H); LC-MS (ESI): Calculated mass: 454.3.30; Observed mass: 456.0 [M+H]+ (rt: 1.68 min).

f) N-(5-(5-(1H-pyrazol-1-yl)-1H-benzo[d]imidazol-1-yl)-2'-fluoro-4'-methoxy-[1,1'-biphenyl]-3-yl)acetamide The compound was prepared from the compound of Example 189(e) (0.8 g, 1.76 mmol) using the procedure of Example 148(f) to give the product in 71% yield (0.55 g). $^1$H NMR (400 MHz, DMSO-$d_6$): δ 10.34 (s, 1H), 8.84 (s, 1H), 8.61 (d, 1H), 8.24 (d, 1H), 8.06 (s, 1H), 7.95-7.93 (m, 1H), 7.82-7.77 (m, 3H), 7.61 (t, 1H), 7.51 (s, 1H), 7.04-6.94 (m, 2H), 6.57 (t, 1H), 3.84 (s, 3H), 2.12 (s, 3H); LC-MS (ESI): Calculated mass: 441.4; Observed mass: 442.1 [M+H]+ (rt: 1.44 min).

Example 190

N-(2'-fluoro-4'-methoxy-5-(5-(1-methyl-1H-pyrazol-4-yl)-1H-benzo[d]imidazol-1-yl)-[1,1'-biphenyl]-3-yl)acetamide A solution of the compound of Example 189(e) (0.25 g, 0.55 mmol) in 1,2-dimethoxyethane (10 ml) was degassed by $N_2$ bubbling for 5 min. 1-Methyl-4-(4,4,5,5-tetramethyl-1,3,2-dioxaborolan-2-yl)-1H-pyrazole (0.14 g, 0.66 mmol, 1.2 eq.) was added and the mixture was degassed for another 5 min. Pd(PPh$_3$)$_4$ (63 mg, 0.055 mmol, 0.1 eq.) and aqueous sodium carbonate (0.12 g, 1.1 mmol, 2.0 eq.) were added and the procedure of Example 1(d) was followed. The crude residue of the product was purified by preparative HPLC to give the product in 90% yield (0.23 g). $^1$H NMR (400 MHz, DMSO-$d_6$): δ 10.42 (s, 1H), 9.08 (s, 1H), 8.26 (s, 1H), 8.11 (s, 1H), 8.02 (s, 1H), 7.99 (s, 1H), 7.80 (s, 1H), 7.75-7.68 (m, 2H), 7.58 (t, 1H), 7.53 (s, 1H), 7.04-6.94 (m, 2H), 3.89 (s, 3H), 3.84 (s, 3H), 2.12 (s, 3H); LC-MS (ESI): Calculated mass: 445.4; Observed mass: 455.7 [M+H]+ (rt: 0.75 min).

Example 191

N-(2'-fluoro-4'-methoxy-5-(5-(1-methyl-1H-pyrazol-4-yl)-1H-benzo[d]imidazol-1-yl)-[1,1'-biphenyl]-3-yl)cyclopropanesulfonamide a) 5-(5-bromo-1H-benzo[d]imidazol-1-yl)-2'-fluoro-4'-methoxy-[1,1'-biphenyl]-3-amine To a solution of the compound of Example 189(e) (2.5 g, 5.5 mmol) in ethanol (50 ml) was added aqueous solution of NaOH (2 g, 50 mmol, 9 eq.) and the mixture was heated at 90° C. for 2 h. The mixture was quenched and extracted as in Example 1(d). The solvent was then distilled off to afford the compound in 92% yield (2.1 g).

b) N-(5-(5-bromo-1H-benzo[d]imidazol-1-yl)-2'-fluoro-4'-methoxy-[1,1'-biphenyl]-3-yl)cyclopropanesulfonamide To a solution of the compound of Example 191(a) (0.8 g, 1.94 mmol) in DCM was added pyridine (0.8 ml, 10.12 mmol) followed by cyclopropane sulfonyl chloride (0.326 g, 2.33 mmol, 1.2 eq.). The mixture was stirred for 16 h and quenched and extracted as in Example 2(b). The solvent was distilled off to afford the crude residue which was purified by column chromatography (60-120 silica gel, 4% methanol in DCM) to afford the product in 80% yield (0.8 g).

c) N-(2'-fluoro-4'-methoxy-5-(5-(1-methyl-1H-pyrazol-4-yl)-1H-benzo[d]-imidazol-1-yl)-[1,1'-biphenyl]-3-yl)cyclopropanesulfonamide The compound was prepared from the compound of Example 191(b) (150 mg, 0.295 mmol) using the procedure of Example 148(f) to give the product in 41% yield (45 mg). H-NMR (400 MHz, DMSO-D6) δ=8.94 (bs, 1H), 8.25 (s, 1H), 8.02 (s, 1H), 7.98 (s, 1H), 7.72-7.66 (m, 2H), 7.64-7.560 (m, 3H), 7.51 (s, 1H), 7.03 (d, 1H), 6.95 (dd, 1H), 3.89 (s, 3H), 3.84 (s, 3H), 2.87 (m, 1H), 1.02 (d, 4H); LC-MS (ESI); Calculated mass: 517.57: Observed mass: 518.1 $[M+H]^+$ (rt: 1.39 min).

Example 192

Cyclopropanesulfonic acid {2'-fluoro-4'-methoxy-5-[5-(1H-pyrazol-4-yl)-benzoimidazol-1-yl]-biphenyl-3-yl}-amide The compound was prepared from the compound of Example 189(e) using procedure of Example 2 and cyclopropane sulfonyl chloride and the procedure of Example 148(f). $^1$H-NMR (400 MHz, DMSO-D6) δ=10.22 (s, 1H), 8.83 (s, 1H), 8.17 (s, 2H), 8.07 (s, 1H), 7.70 (s, 2H), 7.64-7.60 (t, 1H), 7.56 (s, 2H), 7.50 (s, 1H), 7.03 (d, 1H), 6.96 (d, 1H), 3.85 (s, 3H), 2.90-2.80 (m, 1H), 1.10 (t, 3H), 1.02 (d, 4H); LC-MS (ESI): Calculated mass: 503.55; Observed mass: 503.9 $[M+H]^+$ (rt: 1.24 min).

Example 193

N-(2',4'-difluoro-5-(5-(1-methyl-1H-pyrazol-3-yl)-1H-benzo[d]imidazol-1-yl)-[1,1'-biphenyl]-3-yl)methanesulfonamide a) 2',4'-difluoro-5-(5-(1-methyl-1H-pyrazol-3-yl)-1H-benzo[d]imidazol-1-yl)-[1,1'-biphenyl]-3-amine The compound was prepared from the compound of Example 168(e) (0.6 g, 1.35 mmol) using the procedure of Example 186(a) to give the product in 70% yield (0.38 g). LC-MS (ESI): Calculated mass: 401.41; Observed mass: 402.1 $[M+H]^+$ (rt: 1.198 min).

b) N-(2',4'-difluoro-5-(5-(1-methyl-1H-pyrazol-3-yl)-1H-benzo[d]imidazol-1-yl)-[1,1'-biphenyl]-3-yl)methanesulfonamide The compound was prepared from the compound of Example 193(a) (85 mg, 0.211 mmol) using the procedure of Example 186(b) to give the product in 35% yield (34 mg). $^1$H NMR (400 MHz, DMSO-d$_6$): δ 8.73 (s, 1H), 7.94 (s, 1H), 7.79-7.69 (m, 2H), 7.51-7.49 (m, 1H), 7.42 (m, 2H), 7.34 (s, 1H), 7.31 (s, 1H), 7.25 (m, 1H), 6.44 (s, 1H), 3.89 (s, 3H), 3.00 (s, 3H); LC-MS (ESI): Calculated mass: 479.5; Observed mass: 480.1 $[M+H]^+$ (rt: 1.34 min).

Example 194

N-(5-(5-(1H-1,2,4-triazol-1-yl)-1H-benzo[d]imidazol-1-yl)-2',4'-difluoro-[1,1'-biphenyl]-3-yl)acetamide a) N-(2',4'-difluoro-5-((2-nitro-4-(1H-1,2,4-triazol-1-yl)phenyl)amino)-[1,1'-biphenyl]-3-yl)acetamide To a solution of the compound of Example 17(c) (0.67 g, 1.31 mmol) in DMF (2 ml) were added 1,2,4-triazole (0.136 g, 1.95 mmol, 1.5 eq.), copper(I) oxide (0.188 g, 1.31 mmol, 1 eq.) and cesium carbonate (0.85 g, 2.62 mmol, 2 eq.) and then the mixture was heated at 90° C. for 12 h. The mixture was quenched and extracted as in Example 1(d). The solvent was distilled off to afford the crude residue which was purified by column chromatography (60-120 silica gel, 70% ethyl acetate in hexane) to give the product in 68% yield (0.4 g).

b) N-(5-((2-amino-4-(1H-1,2,4-triazol-1-yl)phenyl)amino)-2',4'-difluoro-[1,1'-biphenyl]-3-yl)acetamide To a solution of the compound of Example 194(a) (0.4 g, 0.88 mmol) in acetic acid (10 ml) at 80° C. was added iron powder (0.12 g, 2.2 mmol, 2.5 eq) slowly portionwise over a period of 10 min (caution: highly exothermic reaction). After completion of the addition, the mixture was heated at 80° C. for 1 h and quenched by the addition of crushed ice. The precipitate formed was filtered and washed with cold water to obtain a solid which was dried under high vacuum to give the product in 67.5% yield (0.25 g).

c) N-(5-(5-(1H-1,2,4-triazol-1-yl)-1H-benzo[d]imidazol-1-yl)-2',4'-difluoro-[1,1'-biphenyl]-3-yl)acetamide A mixture of the compound of Example 194(b) (0.250 g, 0.595 mmol) and formic acid (3 ml) was heated at 80° C. for 1 h. The formic acid was distilled off and the crude was dissolved in ethyl acetate. The crude material was purified by preparative HPLC to afford the product in 29% yield (75 mg). $^1$H NMR (300 MHz, DMSO-d$_6$): δ 10.41 (s, 1H), 9.36 (s, 1H), 8.81 (s, 1H), 8.3 (s, 1H), 8.26 (s, 1H), 8.08 (m, 1H), 7.88-7.87 (m, 3H), 7.8-7.7 (m, 3H), 7.55 (s, 1H), 7.5-7.4 (m, 1H), 7.32-7.24 (m, 1H), 2.12 (s, 3H); LC-MS (ESI): Calculated mass: 430.41; Observed mass: 430.8 $[M+H]^+$ (rt: 1.17 min).

Example 195

N-(5-(5-(1H-1,2,4-triazol-1-yl)-1H-benzo[d]imidazol-1-yl)-2',4'-difluoro-[1,1'-biphenyl]-3-yl)ethanesulfonamide a) 5-(5-(1H-1,2,4-triazol-1-yl)-1H-benzo[d]imidazol-1-yl)-2',4'-difluoro-[1,1'-biphenyl]-3-amine To a solution of the compound of Example 194(c) (0.26 g, 0.6 mmol) in ethanol (5 ml) was added 1:1 HCl solution (3 ml) and the mixture was heated at 80° C. for 1 h. The mixture was neutralised with sodium bicarbonate solution and extracted as in Example 2(b). The solvent was distilled off to afford the product in 56% yield (0.13 g). LC-MS (ESI): Calculated mass: 388.37; Observed mass: 388.8 $[M+H]^+$ (rt: 0.5 min).

b) N-(5-(5-(1H-1,2,4-triazol-1-yl)-1H-benzo[d]imidazol-1-yl)-2',4'-difluoro-[1,1'-biphenyl]-3-yl)ethanesulfonamide The compound was prepared from the compound of Example 195(a) (65 mg, 0.167 mmol) using the procedure of Example 186(b) and ethanesulfonyl chloride (32 mg, 0.15 mmol, 1.5 eq.) to give the product in 15% yield (12 mg). $^1$H NMR (300 MHz, DMSO-d$_6$): δ 10.50 (br s, 1H), 9.15 (m, 1H), 8.85 (s, 1H), 8.30-8.25 (m, 2H), 7.83-7.76 (m, 3H), 7.60-7.48 (m, 4H), 7.22 (m, 1H), 3.32 (q, 2H), 1.27-1.24 (t, 3H); LC-MS (ESI): Calculated mass: 480.49; Observed mass: 480.8 [M+H]⁺ (rt: 1.41 min).

Example 196

N-(5-(5-(1H-1,2,4-triazol-1-yl)-1H-benzo[d]imidazol-1-yl)-2',4'-difluoro-[1,1'-biphenyl]-3-yl)methanesulfonamide The compound was prepared from the compound of Example 195(a) using the procedures of Example 195. $^1$H NMR (300 MHz, DMSO-d$_6$): δ 10.30 (br s, 1H), 9.35 (m, 1H), 8.82 (s, 1H), 8.29-8.25 (m, 2H), 7.87-7.76 (m, 3H), 7.61-7.46 (m, 4H), 7.27 (m, 1H), 3.18 (s, 3H); LC-MS (ESI): Calculated mass: 466.46; Observed mass: 467.8 [M+H]⁺ (rt: 0.71 min).

Example 197

N-(5-(5-(1H-1,2,4-triazol-1-yl)-1H-benzo[d]imidazol-1-yl)-2',4'-difluoro-[1,1'-biphenyl]-3-yl)cyclopropanesulfonamide The compound was prepared from the compound of Example 195(a) using the procedures of Example 195 and cyclopropane sulfonyl chloride. $^1$H NMR (300 MHz, DMSO-d$_6$): δ 10.40 (br s, 1H), 9.45 (m, 1H), 8.80 (s, 1H), 8.35-8.25 (m, 2H), 7.88-7.76 (m, 3H), 7.65-7.48 (m, 4H), 7.21 (m, 1H), 2.96-2.9 (m, 1H), 1.04-1.0 (m, 4H); LC-MS (ESI): Calculated mass: 492.5; Observed mass: 493.1 [M+H]⁺ (rt: 1.43 min).

Example 198

N-(5-(5-(1H-1,2,4-triazol-1-yl)-1H-benzo[d]imidazol-1-yl)-2',4'-difluoro-[1,1'-biphenyl]-3-yl)propionamide To a solution of the compound of Example 195(a) (50 mg, 0.128 mmol) in DMF (2 ml) was added propionic acid (14 mg, 0.192 mmol, 1.5 eq.). HATU (73 mg, 0.192 mmol, 1.5 eq.) was added and the mixture was stirred at RT for 6 h. The mixture was quenched with chilled water and the precipitate was collected to afford the product in 26% yield (15 mg). $^1$H NMR (400 MHz, CD$_3$OD): δ 9.17 (s, 1H), 8.67 (s, 1H), 8.24-8.22 (m, 2H), 8.17 (m, 1H), 7.89 (s, 2H), 7.7-7.64 (m, 1H), 7.55 (m, 1H), 7.17-7.11 (m, 2H), 2.52-2.46 (q, 2H), 1.27-1.23 (t, 3H); LC-MS (ESI): Calculated mass: 444.44; Observed mass: 445.2 [M+H]⁺ (rt: 1.35 min).

Example 199

N-(5-(5-(1H-1,2,3-triazol-1-yl)-1H-benzo[d]imidazol-1-yl)-2',4'-difluoro-[1,1'-biphenyl]-3-yl)acetamide The compound was prepared from the compound of Example 17(c) using the procedures of Example 194 and 1,2,3-triazole. $^1$H NMR, 300 MHz: (DMSO-d$_6$): δ 10.37 (s, 1H), 8.24 (m, 3H), 8.11-8.08 (m, 3H), 7.98-7.9 (m, 1H), 7.85 (s, 1H), 7.8-7.7 (m, 1H), 7.55 (m, 1H), 7.5-7.42 (m, 1H), 7.32-7.24 (m, 1H), 2.1 (s, 3H); LC-MS (ESI): Calculated mass: 430.41; Observed mass: 431.1 [M+H]⁺ (rt: 1.53 min).

Example 200

N-(5-(5-(1-(cyclopropylsulfonyl)-1H-pyrazol-4-yl)-1H-benzo[d]imidazol-1-yl)-2',4'-difluoro-[1,1'-biphenyl]-3-yl)ethanesulfonamide a) 5-(5-bromo-1H-benzo[d]imidazol-1-yl)-2',4'-difluoro-[1,1'-biphenyl]-3-amine To a solution of the compound of Example 1(h) (20 g, 45.2 mmol) in ethanol (250 ml) was added aqueous solution of NaOH (5 g, 125 mmol, 2.75 eq.) and the mixture was heated at 85° C. for 5 h. The mixture was quenched and extracted as in Example 1(d). The solvent was distilled off to afford the product in 99% yield (18 g).

b) N-(5-(5-bromo-1H-benzo[d]imidazol-1-yl)-2',4'-difluoro-[1,1'-biphenyl]-3-yl)ethanesulfonamide The compound was prepared from the compound of Example 200(a) (3.0 g, 7.5 mmol) using the procedure of Example 186(b) and ethanesulfonyl chloride (4 g, 30.7 mmol, 4 eq.) to give the product in 95% yield (3.5 g).

c) N-(5-(5-(1H-pyrazol-4-yl)-1H-benzo[d]imidazol-1-yl)-2',4'-difluoro-[1,1'-biphenyl]-3-yl)ethanesulfonamide A solution of the compound of Example 200(b) (2.5 g, 5.08 mmol) in 1,2-dimethoxyethane (75 ml) was degassed by N$_2$ bubbling for 5 min. 4-(4,4,5,5-Tetramethyl-[1,3,2]dioxaborolan-2-yl)-1H-pyrazole (1.18 g, 6.1 mmol, 1.2 eq.) was added and the mixture was degassed for another 5 min. Pd(PPh$_3$)$_4$ (0.28 g, 0.254 mmol, 0.05 eq.) and aqueous sodium carbonate (1.0 g, 9.48 mmol, 2.0 eq.) were added and the procedure of Example 1(d) was followed. The crude residue of the product was purified by column chromatography (60-120 silica gel, 80% ethyl acetate in hexane) to give the product in 30% yield (0.7 g). $^1$H-NMR (300 MHz, DMSO-D6) δ=8.20 (bs, 2H), 8.08 (bs, 1H), 7.75 (m, 3H), 7.62 (s, 2H), 7.50 (m, 2H), 7.30 (m, 1H), 3.31 (q, 2H), 1.27 (t, 3H) LC-MS (ESI): Calculated mass: 479.5; Observed mass: 480.1 [M+H]⁺ (rt: 1.22 min).

d) N-(5-(5-(1-(cyclopropylsulfonyl)-1H-pyrazol-4-yl)-1H-benzo[d]imidazol-1-yl)-2',4'-difluoro-[1,1'-biphenyl]-3-yl)ethanesulfonamide To a solution of the compound of Example 200(c) (50 mg, 0.104 mmol) in DCM was added pyridine (0.5 ml, 6.32 mmol) followed by cyclopropane sulfonyl chloride (22 mg, 0.139 mmol, 1.5 eq.). The reaction was stirred for 1 h and quenched and extracted as in Example 2(b). The solvent was distilled off to afford the crude residue which was purified by preparative HPLC to give the product in 89% yield (40 mg). $^1$H-NMR (400 MHz, DMSO-D6) δ=10.36 (s, 1H), 8.89 (d, 1H), 8.61 (s, 1H), 8.28 (s, 1H), 7.86 (d, 1H), 7.77-7.74 (m, 2H), 7.60 (s, 2H), 7.48-7.46 (m, 2H), 7.29 (t, 1H), 3.30 (q, 2H), 3.20-3.18 (m, 1H), 1.33-1.32 (m, 2H), 1.26-1.23 (m, 7H) LC-MS (ESI): Calculated mass: 583.63; Observed mass: 584.1 [M+H]⁺ (rt: 1.62 min).

Example 201

N-(2',4'-difluoro-5-(5-(pyrimidin-5-yl)-1H-benzo[d]imidazol-1-yl)-[1,1'-biphenyl]-3-yl)ethanesulfonamide The compound was prepared from the compound of Example 200(b) using the procedures of Example 200(c).

H-NMR (300 MHz, CD3OD) δ=9.10 (bs, 4H), 8.14-8.10 (m, 1H), 7.97-7.82 (m, 1H), 7.80 (d, 1H), 7.60-7.52 (m, 3H), 7.46 (s, 1H), 7.06-7.04 (m, 2H), 3.25 (m, 2H), 1.28 (t, 3H); LC-MS (ESI): Calculated mass: 419.51; Observed mass: 492.1 [M+H]+ (rt: 1.43 min).

Example 202

N-(2',4'-difluoro-5-(5-(pyridin-4-yl)-1H-benzo[d] imidazol-1-yl)-[1,1'-biphenyl]-3-yl)ethanesulfonamide The compound was prepared from the compound of Example 200(b) using the procedures of Example 200(c). H-NMR (300 MHz, CD3OD) δ=8.95 (s, 1H), 8.84 (d, 2H), 8.44 (d, 3H), 8.04 (d, 1H), 7.79 (d, 1H), 7.64-7.56 (m, 1H), 7.51 (d, 2H), 7.11-7.04 (dt, 1H), 3.21 (q, 2H), 1.33 (t, 3H); LC-MS (ESI): Calculated mass: 490.52; Observed mass: 490.9 [M+H]+ (rt: 0.37 min).

Example 203

N-(5-(5-(1H-pyrazol-4-yl)-1H-benzo[d]imidazol-1-yl)-2',4'-difluoro-[1,1'-biphenyl]-3-yl)cyclopropanesulfonamide The compound was prepared from the compound of Example 200(a) (15 g, 37.5 mmoles) using the procedure of Example 186(b) and cyclopropane sulfonyl chloride (10 ml, 56.25 mmol, 1.5 eq.) followed by the procedure of Example 200(c) to give the product in 40% yield (36 mg). $^1$H-NMR (400 MHz, DMSO-D6) δ=10.33 (s, 1H), 8.88 (s, 1H), 8.20 (s, 2H), 8.09 (s, 1H), 7.80-7.77 (m, 1H), 7.73 (s, 2H), 7.63 (d, 2H), 7.53 (d, 1H), 7.52-7.49 (m, 1H), 7.32-7.31 (m, 1H), 1.05 (d, 5H) ppm. LC-MS (ESI): Calculated mass: 491.51; Observed mass: 492.4 [M+H]+ (rt: 1.34 min).

Example 204

N-(2',4'-difluoro-5-(5-(1-isopropyl-1H-pyrazol-4-yl)-1H-benzo[d]imidazol-1-yl)-[1,1'-biphenyl]-3-yl)cyclopropanesulfonamide The compound was prepared from the compound of Example 167 using the procedures of Example 2 and cyclopropane sulfonyl chloride. H-NMR (300 MHz, DMSO-D6) δ=8.64 (s, 1H), 8.30 (s, 1H), 8.01 (s, 1H), 7.95 (s, 1H), 7.80-7.72 (m, 1H), 7.65 (d, 2H), 7.55-7.52 (m, 3H), 7.45 (m, 2H), 7.32-7.22 (m, 1H), 4.52 (m, 1H), 2.82 (m, 1H), 1.48 (s, 3H), 1.46 (s, 3H), 1.01-0.99 (m, 4H); LC-MS (ESI): Calculated mass: 533.59; Observed mass: 534.1 [M+H]+ (rt: 1.59 min).

Example 205

N-(2',4'-difluoro-5-(5-(1-isopropyl-1H-pyrazol-4-yl)-1H-benzo[d]imidazol-1-yl)-[1,1'-biphenyl]-3-yl)-2-methoxyacetamide a) N-(5-(5-bromo-1H-benzo[d]imidazol-1-yl)-2',4'-difluoro-[1,1'-biphenyl]-3-yl)-2-methoxyacetamide To a solution of the compound of Example 200(a) (250 mg, 0.625 mmol) in DCM was added TEA (0.5 ml, 3.46 mmol, 5.5 eq.) followed by 2-methoxyacetyl chloride (81 mg, 0.75 mmol, 1.2 eq.). The mixture was stirred for 2 h and quenched and extracted as in Example 1(d). The solvent was distilled off to afford the crude residue which was purified by column chromatography (60-120 silica gel, 20% Ethyl acetate in hexane, 68% yield (200 mg).

b) N-(2',4'-difluoro-5-(5-(1-isopropyl-1H-pyrazol-4-yl)-1H-benzo[d]imidazol-1-yl)-[1,1'-biphenyl]-3-yl)-2-methoxyacetamide The compound was prepared from the compound of Example 205(a) (100 mg, 0.212 mmol) using the procedure of Example 200(c) and 1-isopropyl-4-(4,4,5,5-tetramethyl-1,3,2-dioxaborolan-2-yl)-1H-pyrazole (70 mg, 0.297 mmol, 1.4 eq.) to give the title product in 57% yield (60 mg). H-NMR (300 MHz, DMSO-D6) δ=8.64 (s, 1H), 8.30 (s, 1H), 8.01 (s, 1H), 7.95 (s, 1H), 7.80-7.72 (m, 1H), 7.65 (d, 2H), 7.55-7.52 (m, 3H), 7.45 (m, 2H), 7.32-7.22 (m, 1H), 4.52 (m, 1H), 2.82 (m, 1H), 1.48 (s, 3H), 1.46 (s, 3H), 1.01-0.99 (m, 4H); LC-MS (ESI): Calculated mass: 501.53; Observed mass: 502.1 [M+H]+ (rt: 1.55 min).

Example 206

N-(5-(5-(1-acetyl-1H-pyrazol-4-yl)-1H-benzo[d]imidazol-1-yl)-2',4'-difluoro-[1,1'-biphenyl]-3-yl)cyclopropanesulfonamide To a solution of the compound of Example 203 (50 mg, 0.101 mmol) in DCM (1 ml) was added TEA (0.1 ml, 0.69 mmol, 6.9 eq.) followed by acetyl chloride (12 mg, 0.142 mmol, 1.4 eq.). The mixture was stirred for 2 h and quenched and extracted as in Example 1(d). The solvent was distilled off to afford the crude residue which was purified by preparative HPLC to yield the product in 74% yield (40 mg). H-NMR (300 MHz, DMSO-D6) δ=8.93 (bs, 1H), 8.72 (s, 1H), 8.50 (s, 1H), 8.24 (s, 1H), 7.83 (d, 1H), 7.76-7.70 (m, 2H), 7.58 (bs, 2H), 7.50-7.40 (m, 2H), 7.30-7.20 (m, 1H), 3.15 (s, 3H), 2.90-2.80 (m, 1H), 2.67 (s, 3H), 1.01 (d, 4H); LC-MS (ESI): Calculated mass: 533.55; Observed mass: 534.1 [M+H]+ (rt: 1.55 min).

Example 207

N-(2',4'-difluoro-5-(5-(1-(methylsulfonyl)-1H-pyrazol-4-yl)-1H-benzo[d]-imidazol-1-yl)-[1,1'-biphenyl]-3-yl)cyclopropanesulfonamide To a solution of the compound of Example 203 (50 mg, 0.101 mmol) in DCM was added pyridine (16 mg, 0.202 mmol, 2.0 eq.) followed by methanesulfonyl chloride (14 mg, 0.122 mmol, 1.2 eq.). The mixture was stirred for 1 h and quenched and extracted as in Example 2(b). The solvent was distilled off to afford the crude residue which was purified by preparative HPLC to give the product in 60% yield (40 mg). H-NMR (400 MHz, DMSO-D6) δ=10.32 (s, 1H), 8.95 (s, 1H), 8.90 (s, 1H), 8.62 (s, 1H), 8.29 (s, 1H), 7.88 (d, 1H), 7.76 (dd, 2H), 7.63 (d, 2H), 7.52 (s, 1H), 7.50-7.47 (m, 1H), 7.30-7.29 (dt, 1H), 3.61 (s, 3H), 2.90-2.86 (m, 1H), 1.04-1.02 (d, 4H); LC-MS (ESI): Calculated mass: 569.6; Observed mass: 569.9 [M+H]+ (rt: 0.64 min).

Example 208

N-(5-(5-(1-cyclopentyl-1H-pyrazol-4-yl)-1H-benzo[d]imidazol-1-yl)-2',4'-difluoro-[1,1'-biphenyl]-3-yl)methanesulfonamide a) N-(5-(5-bromo-1H-benzo[d]imidazol-1-yl)-2',4'-difluoro-[1,1'-biphenyl]-3-yl)-methanesulfonamide To a solution of the compound was prepared from the compound of Example 200(a) (3.0 g, 7.5 mmol) in DCM was added pyridine (5 ml, 63.2 mmol, 8.4 eq.) followed by methanesulfonyl chloride (1.3 g, 11.25 mmol, 1.5 eq.). The mixture was stirred for 1 h and quenched and extracted as in Example 2(b). The solvent was distilled off to afford the crude residue which was purified by preparative HPLC to give the product in 95% yield (3.5 g).

b) N-(5-(5-(1-cyclopentyl-1H-pyrazol-4-yl)-1H-benzo[d]imidazol-1-yl)-2',4'-difluoro-[1,1'-biphenyl]-3-yl)methanesulfonamide The compound was prepared from the compound of Example 208(a) (100 mg, 0.209 mmol) using the procedure of Example 200(c) and 1-cyclopentyl-4-(4,4,5,5-tetramethyl-1,3,2-dioxaborolan-2-yl)-1H-pyrazole (82 mg, 0.313 mmol, 1.5 eq.) to give the title product in 33% yield (30 mg). H-NMR (300 MHz, DMSO-D6) δ=10.28 (s, 1H), 8.63 (s, 1H), 8.28 (s, 1H), 8.00 (s, 1H), 7.94 (s, 1H), 7.80-7.70 (m, 1H), 7.70-7.60 (m, 2H), 7.54 (d, 2H), 7.50-7.40 (m, 2H), 7.30-7.20 (dt, 1H), 4.72-4.65 (m, 1H), 3.94 (s, 1H), 3.16 (s, 3H), 2.15-2.05 (m, 2H), 2.00-1.90 (m, 2H), 1.85-1.75 (m, 2H), 1.70-1.60 (m, 2H); LC-MS (ESI): Calculated mass: 533.59; Observed mass: 534.3 [M+H]$^+$ (rt: 1.12 min).

Example 209

N-(2',6'-difluoro-5-(6-(1-methyl-1H-pyrazol-4-yl)-3H-imidazo[4,5-b]pyridin-3-yl)-[1,1'-biphenyl]-3-yl) cyclopropanecarboxamide a) N-(5-((5-bromo-3-nitropyridin-2-yl)amino)-2',6'-difluoro-[1,1'-biphenyl]-3-yl)acetamide A solution of N-(5-amino-2',6'-difluoro-[1,1'-biphenyl]-3-yl)acetamide (1.4 g, 6.1 mmol), 5-bromo-2-chloro-3-nitropyridine (1.6 g, 6.1 mmol, 1.0 eq.) and potassium fluoride (0.53 g, 9.0 mmol, 1.5 eq.) in DMF (8 ml) was heated at 110° C. for 4 h. The mixture was quenched and extracted as in Example 1(d). The solvent was distilled off to afford the crude product which was purified by column chromatography (60-120 silica gel, 30% Ethyl acetate in hexane) to give the title product in 28% yield (0.8 g).

b) N-(5-((5-bromo-3-nitropyridin-2-yl)amino)-2',6'-difluoro-[1,1'-biphenyl]-3-yl)acetamide To a solution of the compound of Example 209(a) (0.8 g, 1.73 mmol) in THF (25 ml) and methanol (5 ml) were added a solution of ammonium chloride (0.37 g, 6.92 mmol, 4 eq.) in water (5 ml) and zinc (0.45 g, 6.92 mmol, 4 eq). The mixture was stirred at RT for 1 h and filtered. The filtrate was diluted with water and extracted as in Example 1(d). The solvent was distilled off to afford the product in 80% yield (0.6 g).

c) N-(5-(6-bromo-3H-imidazo[4,5-b]pyridin-3-yl)-2',6'-difluoro-[1,1'-biphenyl]-3-yl)acetamide A mixture of the compound of Example 209(b) (0.6 g, 1.38 mmol) and formic acid (3 ml) was heated at 80° C. for 1 h. Formic acid was then distilled off and the crude was dissolved in ethyl acetate. The ethyl acetate layer was washed with water, brine and dried over sodium sulphate. The solvent was distilled off and hexane washings were given to the crude material to afford the title product in 98% yield (0.5 g).

d) N-(2',6'-difluoro-5-(6-(1-methyl-1H-pyrazol-4-yl)-3H-imidazo[4,5-b]pyridin-3-yl)-[1,1'-biphenyl]-3-yl)acetamide The compound was prepared from the compound of Example 209(c) (1.3 g, 2.94 mmol) using the procedure of Example 200(c) and 1-methyl-4-(4,4,5,5-tetramethyl-1,3,2-dioxaborolan-2-yl)-1H-pyrazole (0.91 g, 4.41 mmol, 1.5 eq.) to give the title product in 61% yield (0.8 g).

e) 2',6'-difluoro-5-(6-(1-methyl-1H-pyrazol-4-yl)-3H-imidazo[4,5-b]pyridin-3-yl)-[1,1'-biphenyl]-3-amine To a solution of the compound of Example 209(d) (0.8 g, 1.8 mmol) in ethanol (10 ml) was added aqueous solution of NaOH (0.2 g, 5.4 mmol, 3 eq.) and the mixture was heated at 80° C. for 12 h. The mixture was quenched with water when solid precipitated. This was purified using basic alumina column chromatography using 2% methanol in chloroform as eluant to give the product in 20% yield (0.15 g).

f) N-(2',6'-difluoro-5-(6-(1-methyl-1H-pyrazol-4-yl)-3H-imidazo[4,5-b]pyridin-3-yl)-[1,1'-biphenyl]-3-yl) cyclopropanecarboxamide To a solution of the compound of Example 209(e) (15 mg, 0.37 mmol) in DMF (2 ml) was added cyclopropane carboxylic acid (40 mg, 0.55 mmol). HATU (200 mg, 0.55 mmol) was added and stirred at RT for 4 h. The mixture was quenched with chilled water and the precipitate was collected and purified by preparative HPLC to afford the title product in 10% yield (17 mg). $^1$H NMR (400 MHz, DMSO-d$_6$): δ 10.7 (s, 1H), 8.89 (s, 1H), 8.73-8.72 (d, 1H), 8.42 (d, 1H), 8.35-8.34 (t, 1H), 8.31 (s, 1H), 8.04 (s, 1H), 7.82 (s, 1H), 7.69 (s, 1H), 7.57-7.51 (m 1H), 7.31-7.27 (t, 2H), 3.89 (s, 3H), 1.86-1.83 (m, 1H), 0.85-0.84 (d, 4H); LC-MS (ESI): Calculated mass: 470.47; Observed mass: 471.2 [M+H]$^+$ (rt: 1.43 min).

Example 210

3-(2',4'-difluoro-5-(5-(1-isopropyl-1H-pyrazol-4-yl)-1H-benzo[d]imidazol-1-yl)-[1,1'-biphenyl]-3-yl)-N,N'-dimethylsulfuric diamide a) 3-(5-(5-bromo-1H-benzo[d]imidazol-1-yl)-2',4'-difluoro-[1,1'-biphenyl]-3-yl)-N,N'-dimethylsulfuric diamide To a solution of the compound of Example 200(a) (4.0 g, 10.0 mmol) in DCM (50 ml) was added pyridine (5 ml, 63.29 mmol, 6.3 eq.) followed by dimethylsulfamoyl chloride (2.0 g, 14.0 mmol, 1.4 eq.). The mixture was stirred for 16 h and quenched and extracted as in Example 1(d). The solvent was distilled off to afford the crude product which was purified by column chromatography (60-120 silica gel, 2% methanol in DCM) to give the desired title product in 81% yield (4.1 g).

b) 3-(2',4'-difluoro-5-(5-(1-isopropyl-1H-pyrazol-4-yl)-1H-benzo[d]imidazol-1-yl)-[1,1'-biphenyl]-3-yl)-N,N'-dimethylsulfuric diamide The compound was prepared from the compound of Example 210(a) (200 mg, 0.394 mmol) using the procedure of Example 200(c) and 1-isopropyl-4-(4,4,5,5-tetramethyl- 1,3,2-dioxaborolan-2-yl)-1H-pyrazole (121 mg, 0.383 mmol, 1.3 eq.) to give the title product in 23% yield (50 mg). H-NMR (300 MHz, DMSO-D6) δ=10.45 (s, 1H), 8.95 (s, 1H), 8.35 (s, 1H), 8.04 (s, 1H), 7.98 (s, 1H), 7.78-7.68 (m, 3H), 7.57 (s, 2H), 7.47 (m, 2H), 7.34-7.24 (dt, 1H), 2.80 (s, 6H), 1.47 (d, 6H); LC-MS (ESI); Calculated mass: 536.6: Observed mass: 537.1 [M+H]+ (rt: 1.57 min).

Example 211

3-(5-(5-(6-(benzyloxy)pyridin-3-yl)-1H-benzo[d]imidazol-1-yl)-2',4'-difluoro-[1,1'-biphenyl]-3-yl)-N,N'-dimethylsulfuric diamide The compound was prepared from the compound of Example 210(a) using the procedures of Example 200(c) and 2-(benzyloxy)-5-(4,4,5,5-tetramethyl-1,3,2-dioxaborolan-2-yl)pyridine. $^1$H NMR (300 MHz, DMSO-d$_6$): δ 10.29 (s, 1H), 8.81 (s, 1H), 8.22 (s, 1H), 7.99 (s, 1H), 7.95 (s, 1H), 7.75-7.56 (m, 5H), 7.48-7.43 (m, 2H), 7.27 (m, 1H), 3.88 (s, 3H), 3.48-3.44 (m, 1H), 1.3 (d, 6H); LC-MS (ESI): Calculated mass: 611.66; Observed mass: 612.1 [M+H]+ (rt: 1.87 min).

Example 212

3-(2',4'-difluoro-5-(5-(6-oxo-1,6-dihydropyridin-3-yl)-1H-benzo[d]imidazol-1-yl)-[1,1'-biphenyl]-3-yl)-N,N'-dimethylsulfuric diamide To a solution of the compound of Example 211 (250 mg, 0.391 mmoles) in 1,4-dioxane (10 ml), TFA (0.2 ml) was added and heated to 70° C. for 2 h. The reaction mass was completely concentrated and the crude material was purified by preparative HPLC to give the title product in 70% yield (80 mg)$^1$H-NMR (300 MHz, DMSO-D6) δ=8.96 (s, 1H), 8.02 (s, 1H), 7.80 (dd, 1H), 7.82 (d, 1H), 7.80-7.70 (m, 2H), 7.70-7.62 (d, 1H), 7.57 (s, 2H), 7.51-7.44 (m, 2H), 7.29 (dt, 1H), 6.47 (d, 1H), 2.80 (s, 6H); LC-MS (ESI): Calculated mass: 521.54; Observed mass: 522.2 [M+H]+ (rt: 0.87 min).

Example 213

N-(5-(6-(1-(cyclopropylsulfonyl)-1H-pyrazol-4-yl)-3H-imidazo[4,5-b]pyridin-3-yl)-2',4'-difluoro-[1,1'-biphenyl]-3-yl)acetamide a) N-(5-(6-(1H-pyrazol-4-yl)-3H-imidazo[4,5-b]pyridin-3-yl)-2',4'-difluoro-[1,1'-biphenyl]-3-yl)acetamide The compound was prepared from N-(5-(6-bromo-3H-imidazo[4,5-b]pyridin-3-yl)-2',4'-difluorobiphenyl-3-yl)acetamide (2.1 g, 4.74 mmol) using the procedure of Example 200(c) to give the desired title product in 95% yield (1.9 g).

b) N-(5-(6-(1-(cyclopropylsulfonyl)-1H-pyrazol-4-yl)-3H-imidazo[4,5-b]pyridin-3-yl)-2',4'-difluoro-[1,1'-biphenyl]-3-yl)acetamide The compound was prepared from the compound of Example 213(a) (50 mg, 0.125 mmol) using the procedure of Example 200(d) to give the product in 33% yield (20 mg). H-NMR (400 MHz, CD3OD) δ=8.80 (dd, 2H), 8.73 (s, 1H), 8.44 (d, 1H), 8.40 (s, 1H), 8.27 (t, 1H), 7.81 (d, 1H), 7.76 (s, 1H), 7.66-7.64 (m, 1H), 7.14-7.09 (m, 2H), 3.03-2.99 (m, 1H), 2.20 (s, 3H), 1.47-1.44 (m, 2H), 1.25-1.23 (m, 2H) ppm: Calculated mass: 534.54; Observed mass: 534.8 [M+H]+ (rt: 1.55 min).

Example 214

N-(2',4'-difluoro-5-(6-(1-(methylsulfonyl)-1H-pyrazol-4-yl)-3H-imidazo[4,5-b]pyridin-3-yl)-[1,1'-biphenyl]-3-yl)acetamide The compound was prepared from the compound of Example 213(a) using the procedures of Example 200(d). H-NMR (400 MHz, DMSO-D6+D2O) δ=9.01 (s, 1H), 8.99 (s, 1H), 8.92 (d, 1H), 8.69-8.68 (m, 2H), 8.31 (t, 1H), 7.90 (m, 1H), 7.73 (m, 2H), 7.46 (dt, 1H), 7.29 (dt, 1H), 3.63 (s, 3H), 2.14 (s, 3H); LC-MS (ESI): Calculated mass: 508.5; Observed mass: 508.7 [M+H]+ (rt: 1.46 min).

Example 215

N-(5-(6-(1-(ethylsulfonyl)-1H-pyrazol-4-yl)-3H-imidazo[4,5-b]pyridin-3-yl)-2',4'-difluoro-[1,1'-biphenyl]-3-yl)acetamide The compound was prepared from the compound of Example 213(a) using the procedures of Example 200(d). $^1$H NMR (400 MHz, DMSO-D6) δ=10.41 (s, 1H), 9.03 (s, 1H), 8.98 (s, 1H), 8.92 (d, 1H), 8.69 (s, 1H), 8.31 (s, 1H), 7.88 (s, 1H), 7.71 (m, 2H), 7.47 (dt, 1H), 7.28 (dt, 1H), 3.77 (q, 2H), 1.16 (t, 3H), 2.12 (s, 3H); LC-MS (ESI): Calculated mass: 522.53; Observed mass: 523.2 [M+H]+ (rt: 1.56 min).

Example 216

N-(2',4'-difluoro-5-(6-(1-methyl-1H-pyrazol-4-yl)-3H-imidazo[4,5-b]pyridin-3-yl)-[1,1'-biphenyl]-3-yl)-N,N'-dimethylsulfuric diamide a) N-(2',4'-difluoro-5-((6-bromo)-3H-imidazo[4,5-b]pyridin-3-yl)-[1,1'-biphenyl]-3-yl)-N,N'-dimethylsulfuric diamide To a solution of N-(2',4'-difluoro-5-((6-bromo)-3H-imidazo[4,5-b]pyridin-3-yl)-[1,1'-biphenyl]-3-yl)amine (3.0 g, 7.48 mmol) in DCM (10 ml) was added pyridine (3 ml, 37.9 mmol, 2 eq.) followed by dimethylsulfamoyl chloride (1.6 g, 11.22 mmol, 1.5 eq.). The mixture was stirred for 16 h and quenched and extracted as in Example 1(d). The solvent was distilled off to afford the crude product which was purified by preparative HPLC to give the title product in 55% yield (2.1 g).

b) N-(2',4'-difluoro-5-(6-(1-methyl-1H-pyrazol-4-yl)-3H-imidazo[4,5-b)]pyridin-3-yl)-[1,1'-biphenyl]-3-yl)-N,N'-dimethylsulfuric diamide The compound was prepared from the compound of Example 216(a) (150 mg, 0.295 mmol) using the procedure of Example 200(c) and 1-methyl-4-(4,4,5,5-tetramethyl-1,3,2-dioxaborolan-2-yl)-1H-pyrazole to give the title product in 41% yield (45 mg). $^1$H NMR (300 MHz, DMSO-d$_6$): δ=8.95 (s, 1H), 8.72 (s, 1H), 7.41 (d, 1H), 8.32 (s, 1H), 8.05 (s, 1H), 7.98 (m, 1H), 7.72 (m, 1H), 7.50-7.42 (m, 2H), 7.32-7.24 (m, 2H), 3.90 (s, 3H), 2.81 (s, 6H); LC-MS (ESI); Calculated mass: 509.53: Observed mass: 510.1 [M+H]+ (rt: 1.49 min).

Example 217

N-(2',4'-difluoro-5-(6-(1-isopropyl-1H-pyrazol-4-yl)-3H-imidazo[4,5-b]pyridin-3-yl)-[1,1'-biphenyl]-3-yl)-N,N'-dimethylsulfuric diamide The compound was prepared from the compound of Example 216(a) using the procedures of Example 200(c) and 1-isopropyl-4-(4,4,5,5-tetramethyl-1,3,2-dioxaborolan-2-yl)-1H-pyrazole. $^1$H-NMR (300 MHz, DMSO-D6) δ=10.40 (s, 1H), 8.94 (s, 1H), 8.75 (d, 1H), 8.40 (m, 2H), 8.06 (s, 1H), 7.99 (t, 1H), 7.76-7.68 (m, 2H), 7.50-7.40 (m, 2H), 7.32-7.24 (dt, 1H), 4.60-4.50 (m, 1H), 2.81 (s, 6H), 1.48 (s, 6H); LC-MS (ESI): Calculated mass: 537.58; Observed mass: 538.1 [M+H]$^+$ (rt: 1.62 min).

Example 218

N-(2',4'-difluoro-5-(6-oxo-1,6-dihydropyridin-3-yl)-3H-imidazo[4,5-b]pyridin-3-yl)-[1,1'-biphenyl]-3-yl)-N,N'-dimethylsulfuric diamide a) N-(2',4'-difluoro-5-(6-(benzyloxy)pyridin-3-yl)-3H-imidazo[4,5-b]pyridin-3-yl)-[1,1'-biphenyl]-3-yl)-N,N'-dimethylsulfuric diamide A solution of the compound of Example 216(a) (300 mg, 0.59 mmol) in 1,2-dimethoxyethane (10 ml) was degassed by $N_2$ bubbling for 5 min. 2-(Benzyloxy)-5-(4,4,5,5-tetramethyl-1,3,2-dioxaborolan-2-yl)pyridine (220 mg, 0.708 mmol, 1.2 eq.) was added and the mixture was degassed for another 5 min. Pd(PPh$_3$)$_4$ (34 mg, 0.0295 mmol, 0.05 eq.) and aqueous sodium carbonate (125 mg, 1.179 mmol, 2.0 eq.) were added and the procedure of Example 1(d) was followed. The crude residue of the product was purified by preparative HPLC to give the title product in 69% yield (250 mg). $^1$H NMR (300 MHz, DMSO-d$_6$): δ 10.39 (s, 1H), 9.03 (s, 1H), 8.78 (s, 1H), 8.64 (s, 1H), 8.55 (s, 1H), 8.25-8.2 (m, 1H), 7.98 (s, 1H), 7.74 (m, 2H), 7.7-7.5 (m, 2H), 7.5-7.25 (m, 1H), 7.08-7.0 (d, 1H), 5.43 (s, 2H), 2.81 (s, 6H); LC-MS (ESI); Calculated mass: 614.2: Observed mass: 613.2 [M−H]$^+$ (rt: 1.4 min).

b) N-(2',4'-difluoro-5-(6-oxo-1,6-dihydropyridin-3-yl)-3H-imidazo[4,5-b]pyridin-3-yl)-[1,1'-biphenyl]-3-yl)-N,N'-dimethylsulfuric diamide To a solution of the compound of Example 218(a) (240 mg, 0.391 mmoles) in 1,4-dioxane (10 ml), TFA (0.8 ml) was added and heated to 70° C. for 2 h. The reaction mass was completely concentrated and the crude material was purified by preparative HPLC to give the title product in 50% yield (80 mg). H-NMR (300 MHz, DMSO-D6) δ=10.40 (s, 1H), 8.99 (s, 1H), 8.67 (d, 1H), 8.42 (d, 1H), 8.00-7.95 (m, 2H), 7.88 (s, 1H), 7.73 (m, 2H), 7.50-7.43 (m, 2H), 7.32-7.26 (dt, 1H), 6.48 (d, 1H), 2.81 (s, 6H); LC-MS (ESI); Calculated mass: 522.53: Observed mass: 523.1 [M+H]$^+$ (rt: 1.39 min).

Example 219

N-(2',4'-difluoro-5-(5-(1-(3-hydroxy-3-methylbutyl)-1H-pyrazol-4-yl)-1H-benzo[d]imidazol-1-yl)-[1,1'-biphenyl]-3-yl)acetamide The compound was prepared from the compound of Example 1(h) (0.2 g, 0.452 mmol) using the procedure of Example 200(c) and 2-methyl-4-(3-(4,4,5,5-tetramethyl-1,3,2-dioxaborolan-2-yl)-1H-pyrazol-1-yl)butan-2-ol to give the title product in 55.79% yield (0.13 g). $^1$H NMR (300 MHz, DMSO-d6): δ 10.42 (s, 1H), 8.96 (s, 1H), 8.11 (s, 1H), 8.01 (s, 2H), 7.82 (s, 1H), 7.71 (m, 3H), 7.54-7.41 (m, 2H), 7.29-7.25 (m, 1H), 4.24-4.18 (t, 2H), 2.155 (s, 3H), 1.98-1.92 (s, 2H), Calculated mass: 515.55; Observed mass: 516.3 [M+H]$^+$ (rt: 1.2 min).

Example 220

N-(4'-fluoro-5-(5-(1-(3-hydroxy-3-methylbutyl)-1H-pyrazol-4-yl)-1H-benzo[d]-imidazol-1-yl)-[1,1'-biphenyl]-3-yl) acetamide The compound was prepared from N-(5-(5-bromo-1H-benzo[d]imidazol-1-yl)-4'-fluoro-[1,1'-biphenyl]-3-yl)acetamide (0.07 g, 0.164 mmol) using the procedure of Example 200(c) and 2-methyl-4-(3-(4,4,5,5-tetramethyl-1,3,2-dioxaborolan-2-yl)-1H-pyrazol-1-yl)butan-2-ol (0.092 g, 0.329 mmol, 2.0 eq.) to give the title product in 22.2% yield (0.018 g). $^1$H NMR (300 MHz, DMSO-d$_6$): δ 10.42 (s, 1H), 8.68 (s, 1H), 8.25 (s, 1H), 7.99 (d, 2H), 7.93 (s, 1H), 7.83 (s, 1H), 7.69 (m, 2H), 7.65 (m, 1H), 7.61 (m, 2H), 7.36 (t, 2H), 4.48 (s, 1H); 4.26 (m, 2H); 2.12 (s, 3H); 1.91 (m, 2H); 1.15 (s, 6H); LC-MS (ESI): Calculated mass: 497.56 Observed mass: 497.9 [M+H]$^+$ (rt: 0.9 min).

Example 221

N-(2',4'-difluoro-5-(5-(3-fluoropyridin-4-yl)-1H-benzo[d]imidazol-1-yl)-[1,1'-biphenyl]-3-yl)acetamide The compound was prepared from the compound of Example 1(h) using the procedures of Example 200(c). $^1$H NMR (400 MHz, DMSO-d$_6$): δ 10.42 (s, 1H), 8.85 (s, 1H), 8.70 (s, 1H), 8.541-8.53 (d, 1H), 8.14-8.11 (d, 2H), 7.88-7.84 (m, 2H), 7.79-7.69 (m, 3H), 7.56 (s, 1H), 7.48-7.46 (t, 1H), 2.155 (s, 3H), 2.12 (s, 3H), Calculated mass: 458.43; Observed mass: 459.2[M+H]$^+$ (rt: 1.55 min).

Example 222

N-(2',4'-difluoro-5-(5-(3-methyl-1H-pyrazol-4-yl)-1H-benzo[d]imidazol-1-yl)-[1,1'-biphenyl]-3-yl) acetamide The compound was prepared from the compound of Example 1(h) using the procedures of Example 220. $^1$H NMR (300 MHz, DMSO-d6): δ 10.32 (s, 1H) 8.80 (s, 1H), 8.40 (s, 1H), 8.37 (s, 1H), 8.16 (s, 1H), 7.97-7.91 (d, 1H), 7.90-7.76 (m, 3H), 7.56 (d, 1H), 7.47 (m, 1H), 7.30 (m, 1H), 2.25 (s, 3H), 2.10 (s, 3H); LC-MS (ESI): Calculated mass: 443.45; Observed mass: 444.2 [M+H]$^+$ (rt: 0.69 min).

Example 223

Ethyl 3-((2',4'-difluoro-5-(5-(1-methyl-1H-pyrazol-4-yl)-1H-benzo[d]imidazol-1-yl)-[1,1'-biphenyl]-3-yl)amino)-3-oxopropanoate To a solution of the compound of Example 2(a) (80 mg, 0.1995 mmol) in DCM was added TEA (40 mg, 0.399 mmol, 2.0 eq.) followed by ethyl 3-chloro-3-oxopropanoate (32.9 mg, 0.219 mmol, 1.1 eq). The mixture was stirred for 2 h and quenched and extracted as in Example 1(d). The solvent was distilled off to afford the crude residue which was purified by preparative HPLC to give the pure product in 20% yield (20 mg) $^1$H NMR (400 MHz, DMSO-d$_6$): δ 10.7 (s, 1H), 8.77 (s, 1H), 8.23 (s, 1H), 8.10 (s, 1H), 8.01 (s, 1H), 7.97 (s, 1H), 7.83 (s, 1H), 7.78 (d, 1H), 7.73 (d, 1H), 7.65 (d, 1H), 7.59 (s, 1H), 7.49 (t, 1H), 7.3 (t, 1H), 3.90 (s, 3H), 3.82 (q, 2H), 1.4 (t, 3H), 3.45 (s, 2H); LC-MS (ESI): Calculated mass: 515.51; Observed mass: 516.4 [M+H]$^+$ (rt: 0.96 min).

Example 224

3-((2',4'-difluoro-5-(5-(1-methyl-1H-pyrazol-4-yl)-1H-benzo[d]imidazol-1-yl)-[1,1'-biphenyl]-3-yl) amino)-3-oxopropanoic acid To a solution of the compound of Example 223 (20 mg, 0.0388 mmol) in THF (10 ml) was added aqueous solution of lithium hydroxide (4 mg, 0.0776 mmol, 2 eq) and the mixture was stirred at RT for 2 h. The mixture was quenched and extracted as in Example 1(d). The solvent was distilled off to afford the crude residue which was purified by preparative HPLC to give the pure product in 90% yield (25 mg). $^1$H NMR (400 MHz, DMSO-d$_6$): δ 10.7 (s, 1H), 8.77 (s, 1H), 8.23 (s, 1H), 8.10 (s, 1H), 8.01 (s, 1H), 7.97 (s, 1H), 7.83 (s, 1H), 7.78 (d, 1H), 7.73 (d, 1H), 7.65 (d, 1H), 7.59 (s, 1H), 7.49 (t, 1H), 7.3 (t, 1H), 3.90 (s, 3H), 3.45 (s, 2H); LC-MS (ESI): Calculated mass: 487.15; Observed mass: 488.0 [M+H]$^+$ (rt: 0.638 min).

Example 225

N-(2',4'-difluoro-5-(5-(1-methyl-1H-pyrazol-4-yl)-1H-benzo[d]imidazol-1-yl)-[1,1'-biphenyl]-3-yl)-2-(1H-1,2,4-triazol-1-yl) acetamide To a solution of the compound of Example 2(a) (100 mg, 0.249 mmol) in DMF was added 2-(1H-1,2,4-triazol-1-yl) acetic acid (47 mg, 0.374, mmol, 1.5 eq.) followed by HATU (189 mg, 0.498 mmol, 2.0 eq) and DIPEA (96.5 mg, 0.74 mmol, 3.0 eq). The mixture was stirred for 16 h and quenched and extracted as in Example 1(d). The solvent was distilled off to afford the crude residue which was purified by preparative HPLC to give the product in 71.4% yield (90 mg). $^1$H NMR (400 MHz, DMSO-d$_6$): δ 10.9 (s, 1H), 8.66 (s, 1H), 8.59 (s, 1H), 8.19 (s, 1H), 8.06 (s, 1H), 8.02 (s, 1H), 8.00 (d, 1H), 7.93 (s, 1H), 7.80-7.75 (m, 2H), 7.7 (d, 1H), 7.61-7.59 (m, 2H), 7.48-7.42 (m, 1H), 7.3 (m, 1H) 4.12 (s, 1H), 3.87 (s, 3H); LC-MS (ESI): Calculated mass: 510.17; Observed mass: 511.2 [M+H]$^+$ (rt: 0.386 min).

Example 226

N-(2',4'-difluoro-5-(5-(1-methyl-1H-pyrazol-4-yl)-1H-benzo[d]imidazol-1-yl)-[1,1'-biphenyl]-3-yl)-2-(2H-tetrazol-5-yl) acetamide a) 2-Cyano-N-(2',4'-difluoro-5-(5-(1-methyl-1H-pyrazol-4-yl)-1H-benzo[d]-imidazol-1-yl)-[1,1'-biphenyl]-3-yl) acetamide To a solution of the compound of Example 2(a) (100 mg, 0.249 mmol) in DMF was added cyanoacetic acid (25.6 mg, 0.299 mmol, 1.2 eq) followed by HATU (184 mg, 0.485 mmol, 2.0 eq) and DIPEA (0.15 ml, 0.74 mmol, 3.0 eq). The mixture was stirred for 16 h and quenched and extracted as in Example 1(d). The solvent was distilled off to afford the crude residue which was purified by column chromatography to give the product in 19% yield (80 mg). LC-MS (ESI): Calculated mass: 468; Observed mass: 469.3 [M+H]$^+$ (rt: 0.88 min).

b) N-(2',4'-difluoro-5-(5-(1-methyl-1H-pyrazol-4-yl)-1H-benzo[d]imidazol-1-yl)-[1,1'-biphenyl]-3-yl)-2-(2H-tetrazol-5-yl) acetamide To a solution of the compound of Example 226(a) (80 mg, 0.170 mmol) in DMF was added sodium azide (11 mg, 0.170 mmol, 1. eq) followed by ammonium chloride (10 mg, 0.188 mmol, 1.1 eq). The mixture was stirred at 80° C. for 16 h and quenched and extracted as in Example 1(d). The solvent was distilled off to afford the crude residue which was purified by preparative HPLC to give the product in 6.8% yield (6 mg). $^1$H NMR (400 MHz, CD$_3$OD): δ 8.51 (s, 1H), 8.16 (s, 1H), 8.02 (s, 1H), 7.92 (s, 1H), 7.88 (s, 1H), 7.80 (s, 1H), 7.73-7.60 (m, 3H), 7.53 (s, 1H), 7.16-7.10 (m, 2H), 4.12 (s, 2H), 3.96 (s, 3H); LC-MS (ESI): Calculated mass: 511.17; Observed mass: 512.1 [M+H]$^+$ (rt: 0.874 min).

Example 227

(3S,5R)—N-(2',4'-difluoro-5-(5-(1-methyl-1H-pyrazol-4-yl)-1H-benzo[d]imidazol-1-yl)-[1,1'-biphenyl]-3-yl)-3,5-dimethylpiperazine-1-carboxamide To a solution of the compound of Example 2(a) (80 mg, 0.2 mmol) in DCM was added 20% phosgene in toluene (0.2 ml, 0.4 mmol, 2 eq.) at 0° C. The mixture was stirred for 1 h and excess phosgene was removed by purging with nitrogen, followed by the addition of 2,6-dimethylpiperazine (34 mg, 0.3 mmol, 1.5 eq.). The mixture was stirred overnight and quenched and extracted as in Example 1(d). The solvent was distilled off to afford the crude residue which was purified by preparative HPLC to give the pure product in 7% yield (7 mg). $^1$H NMR (300 MHz, CD$_3$OD): δ 8.48 (s, 1H), 8.0 (s, 1H), 7.9 (s, 1H), 7.86-7.85 (m, 2H), 7.72-7.65 (d, 1H), 7.65-7.59 (m, 4H), 7.43 (s, 1H), 7.11 (m, 1H), 4.2 (d, 2H), 3.1-3.0 (br, 2H), 2.7-2.6 (t, 1H), 1.23-1.17 (d, 6H); LC-MS (ESI): Calculated mass: 541.59; Observed mass: 542.2 [M+H]$^+$ (rt: 0.632 min).

Example 228

N-(2',4'-difluoro-5-(5-(1-methyl-1H-pyrazol-4-yl)-1H-benzo[d]imidazol-1-yl)-[1,1'-biphenyl]-3-yl)-4-methylpiperazine-1-carboxamide The compound was prepared from the compound of Example 2(a) using the procedure of Example 227. $^1$H NMR (300 MHz, CD$_3$OD): δ 8.48 (s, 1H), 8.0 (s, 1H), 7.9 (s, 1H), 7.86-7.85 (m, 2H), 7.72-7.65 (d, 1H), 7.65-7.59 (m, 4H), 7.43 (s, 1H), 7.11-7.09 (m, 2H), 3.94 (s, 3H), 3.63-3.60 (m, 4H), 2.55-2.53 (m, 4H), 2.36 (s, 3H); LC-MS (ESI): Calculated mass: 527.57; Observed mass: 528.1 [M+H]$^+$ (rt: 0.632 min).

Example 229

N-(2',4'-difluoro-5-(5-(1-methyl-1H-pyrazol-4-yl)-1H-benzo[d]imidazol-1-yl)-[1,1'-biphenyl]-3-yl)-2-((3S,5R)-3,5-dimethylpiperazin-1-yl)acetamide The compound was prepared from the compound of Example 2(a) using the procedure of Example 226. $^1$H NMR (300 MHz, DMSO-d$_6$): δ 8.4 (br s, 1H), 8.14 (m, 1H), 8.01

(s, 1H), 7.92 (s, 1H), 7.86 (s, 1H), 7.83 (m, 1H), 7.72-7.70 (d, 1H), 7.66-7.59 (m, 2H), 7.55 (s, 1H), 7.15-7.11 (m, 2H), 3.94 (s, 3H), 3.37 (m, 2H), 2.269 (m, 2H), 1.27 (s, 3H), 1.25 (s, 3H); LC-MS (ESI): Calculated mass: 555.62; Observed mass: 556.2 [M+H]$^+$ (rt: 0.75 min).

Example 230

1-(2',4'-difluoro-5-(5-(1-methyl-1H-pyrazol-4-yl)-1H-benzo[d]imidazol-1-yl)-[1,1'-biphenyl]-3-yl)-3-(furan-2-ylmethyl)urea To a solution of the compound of Example 2(a) (20 mg, 0.049 mmol) in DCM was added furfuryl isocyanate (7 mg, 0.059 mmol, 1.2 eq.) followed by DIPEA (0.01 ml, 0.0747 mmol, 1.5 eq.). The mixture was stirred overnight and quenched and extracted as in Example 1(d). The solvent was distilled off to afford the crude residue which was purified by preparative HPLC to give the product in 92% yield (24 mg). $^1$H NMR (400 MHz, DMSO-d$_6$): δ 9.07 (s, 1H), 8.95 (brS, 1H), 8.24 (s, 1H), 7.99 (s, 1H), 7.97-7.96 (m, 2H), 7.75-7.59 (m, 5H), 7.40 (m, 2H), 7.26 (m, 1H), 6.82 (t, 1H), 6.4 (m, 1H), 6.27 (m, 1H), 4.32-4.31 (d, 2H), 3.88 (s, 3H); LC-MS (ESI): Calculated mass: 524.52; Observed mass: 525.1 [M+H]$^+$ (rt: 0.75 min).

Example 231

N-(2',4'-difluoro-5-(5-(1-methyl-1H-pyrazol-4-yl)-1H-benzo[d]imidazol-1-yl)-[1,1'-biphenyl]-3-yl)-2-(piperazin-1-yl)acetamide a) tert-butyl 4-(2-((2',4'-difluoro-5-(5-(1-methyl-1H-pyrazol-4-yl)-1H-benzo[d]-imidazol-1-yl)-[1,1'-biphenyl]-3-yl)amino)-2-oxoethyl)piperazine-1-carboxylate To a solution of the compound of Example 2(a) (100 mg, 0.249 mmol) in DMF was added 2-(4-(tert-butoxycarbonyl)piperazin-1-yl)acetic acid (121 mg, 0.498 mmol, 2 eq.) followed by HATU (190 mg, 0.498 mmol, 2 eq.) and DIPEA (0.17 ml, 0.996 mmol, 4 eq.). The mixture was stirred for 16 h and quenched and extracted as in Example 1(d). The solvent was distilled off to give the crude residue which was purified by preparative HPLC to give the product in 25% yield (25 mg).

b) N-(2',4'-difluoro-5-(5-(1-methyl-1H-pyrazol-4-yl)-1H-benzo[d]imidazol-1-yl)-[1,1'-biphenyl]-3-yl)-2-(piperazin-1-yl)acetamide To a solution of the compound of Example 231(a) (23 mg, 0.038 mmol) in DCM (1 ml) at 0° C. was added TFA (1 ml) and the mixture was stirred at RT overnight. The solvent was distilled off to afford the crude residue which was recrystallized from diethyl ether to give the product in 70% yield (18 mg). $^1$H NMR (400 MHz, DMSO-d6): δ 10.29 (s, 1H), 8.75 (s, 1H), 8.62 (br s, 1H), 8.21 (s, 1H), 8.14 (s, 1H), 8.0 (s, 1H), 7.95 (s, 1H), 7.9 (s, 1H), 7.75-7.7 (m, 2H), 7.63-7.58 (m, 2H), 7.48-7.44 (t, 1H), 7.3-7.26 (t, 1H); LC-MS (ESI): Calculated mass: 527.22; Observed mass: 528.1 [M+H]$^+$ (rt: 0.632 min).

Example 232

Methyl(2',4'-difluoro-5-(5-(1-methyl-1H-pyrazol-4-yl)-1H-benzo[d]imidazol-1-yl)-[1,1'-biphenyl]-3-yl)carbamate To a solution of the compound of Example 2(a) (60 mg, 0.15 mmol) in chloroform (5 ml) at 0° C. were added methyl chloroformate (14 mg, 0.15 mmol, 1 eq.) and pyridine (0.024 ml, 0.3 mmol, 2 eq.). The mixture was stirred at RT for 1 h and then quenched with water and extracted with chloroform (3×50 ml). The combined organic layer was washed with water, brine and dried over sodium sulphate. The solvent was distilled off to afford the title compound in 37% yield (25 mg). $^1$H NMR (300 MHz, DMSO-d$_6$): δ 10.13 (s, 1H), 8.63 (s, 1H), 8.20 (s, 1H), 7.98-7.92 (m, 3H), 7.70-7.67 (m, 3H), 7.60 (m, 1H), 7.46 (m, 2H), 7.27 (m, 1H), 3.87 (m, 3H), 3.72 (s, 3H); LC-MS (ESI): Calculated mass: 459.15; Observed mass: 460.2 [M+H]$^+$ (rt: 0.94 min).

Example 233

N-(2',4'-difluoro-5-(5-(1-methyl-1H-pyrazol-4-yl)-1H-benzo[d]imidazol-1-yl)-[1,1'-biphenyl]-3-yl)-2-morpholinoacetamide The compound was prepared from the compound of Example 2(a) (100 mg, 0.249 mmol) using the procedure of Example 225 and 2-morpholinoacetic acid (54 mg, 0.373, mmol, 1.5 eq.) to give the product in 19% yield (25 mg). $^1$H NMR (300 MHz, DMSO-d$_6$): δ 10.42 (s, 1H), 8.91 (s, 1H), 8.20 (s, 1H), 8.08 (s, 1H), 8.00 (s, 1H), 7.95 (s, 1H), 7.82 (s, 1H), 7.77-7.71 (m, 2H), 7.66-7.64 (m, 2H), 7.46-7.40 (m, 1H), 7.29-7.25 (m, 1H); 4.25 (s, 2H), 3.9 (s, 3H), 3.87-3.15 (m, 8H); LC-MS (ESI): Calculated mass: 528.55 Observed mass: 529.3 [M+H]$^+$ (rt: 0.38 min).

Example 234

N-(2',4'-difluoro-5-(5-(1-methyl-1H-pyrazol-4-yl)-1H-benzo[d]imidazol-1-yl)-[1,1'-biphenyl]-3-yl)-2-(piperidin-1-yl)acetamide The compound was prepared from the compound of Example 2(a) using the procedure of Example 225. $^1$H NMR (400 MHz, DMSO-d$_6$): δ 8.91 (s, 1H), 8.18 (s, 1H), 8.05 (s, 1H), 7.99 (s, 1H), 7.94 (s, 1H), 7.81 (s, 1H), 7.75-7.70 (m, 2H), 7.67-7.63 (m, 2H), 7.42-7.37 (t, 1H), 7.27-7.23 (t, 1H), 4.12 (s, 2H), 3.86 (s, 3H), 3.50-3.35 (m, 2H), 3.05-2.99 (t, 2H), 1.79-1.68 (m, 5H), 1.40 (s, 1H); LC-MS (ESI): Calculated mass: 526.58; Observed mass: 527.1 [M+H]$^+$ (rt: 0.36 min).

Example 235

N-(2',4'-difluoro-5-(5-(1-methyl-1H-pyrazol-4-yl)-1H-benzo[d]imidazol-1-yl)-[1,1'-biphenyl]-3-yl)-2-(pyrrolidin-1-yl) acetamide The compound was prepared from the compound of Example 2(a) using the procedure of Example 225. $^1$H NMR (400 MHz, DMSO-d$_6$): δ 11.02 (s, 1H), 10.31 (s, 1H), 8.80 (s, 1H), 8.22. (s, 1H), 8.10 (s, 1H), 8.01 (s, 1H), 7.96 (s, 1H), 7.79-7.73 (m, 2H), 7.70 (d, 1H), 7.63-7.61 (m, 2H), 7.49-7.47 (t, 1H), 7.31-7.29 (t, 1H), 4.34-4.32 (d, 2H), 3.88 (s, 3H), 3.16 (m, 1H), 2.03-1.91 (m, 4H); Calculated mass: 512.55; Observed mass: 513.5 [M+H]$^+$ (rt: 0.28 min).

Example 236

N-(2',4'-difluoro-5-(5-(1-methyl-1H-pyrazol-4-yl)-1H-benzo[d]imidazol-1-yl)-2',3'-dihydro-[1,1'=biphenyl]-3-yl)-4-ethylpiperazine-1-carboxamide The compound was prepared from the compound of Example 2(a) using the procedure of Example 227. NMR (400 MHz, DMSO-D6): δ 9.53 (brs, 1H), 9.22 (s, 1H), 8.75 (s, 1H), 8.22 (s, 1H), 7.98 (t, 2H). 7.77-7.72 (m, 3H), 7.63 (dd, 1H), 7.49-7.44 (m, 2H), 7.283 (dt, 1H), 4.35 (d, 2H), 3.89 (s, 3H), 3.57 (d, 3H), 3.24-3.18 (m, 3H), 3.07-3.02 (m, 2H), 1.26 (t, 3H): LC-MS (ESI): Calculated mass: 543.6; Observed mass: 543.2 M+H]$^+$ (rt: 0.224 min).

Example 237

N-(2',4'-difluoro-5-(6-(1-methyl-1H-pyrazol-4-yl)-3H-imidazo[4,5-b]pyridin-3-yl)-[1,1'-biphenyl]-3-yl)-2-(pyrrolidin-1-yl)acetamide The compound was prepared from the compound of Example 132(a) (100 mg, 0.248 mmol) using the procedure of Example 225 and 2-(pyrrolidin-1-yl)acetic acid (35 mg, 0.273 mmol, 1.1 eq) to give the product in 7.08% yield (9 mg). $^1$H NMR (400 MHz, DMSO-d$_6$): δ 8.89 (s, 1H), 8.6 (s, 1H), 8.29 (s, 2H), 8.10 (s, 1H), 7.93 (s, 1H), 7.85 (s, 1H), 7.78 (s, 1H), 7.67-7.61 (m, 1H), 7.14-7.08 (m, 2H), 4.29 (s, 2H), 3.95 (s, 3H), 3.80 (s, 2H), 3.29 (t, 2H), 2.14 (t, 4H); LC-MS (ESI): Calculated mass: 513.21; Observed mass: 514.4 [M+H]$^+$ (rt: 0.27 min).

Example 238

N-(2',4'-difluoro-5-(6-(1-methyl-1H-pyrazol-4-yl)-3H-imidazo[4,5-b]pyridin-3-yl)-[1,1'-biphenyl]-3-yl)-2-morpholinoacetamide The compound was prepared from the compound of Example 132(a) using the procedure of Example 225. $^1$H NMR (400 MHz, DMSO-d$_6$): δ 11.1 (s, 1H), 8.99 (s, 1H), 8.70 (s, 1H), 8.42 (d, 2H), 8.31 (s, 1H), 8.05 (s, 1H), 7.90 (s, 1H), 7.83 (s, 1H), 7.77-7.75 (m, 1H), 7.47 (t, 1H), 7.30 (t, 1H), 4.27 (s, 2H), 3.90 (s, 3H), 3.82 (t, 4H), 2.50 (t, 4H); LC-MS (ESI): Calculated mass: 529.20; Observed mass: 530.4 [M+H]$^+$ (rt: 0.23 min).

Example 239

N-(2',4'-difluoro-5-(6-(1-methyl-1H-pyrazol-4-yl)-3H-imidazo[4,5-b]pyridin-3-yl)-[1,1'-biphenyl]-3-yl)-2-(piperidin-1-yl)acetamide The compound was prepared from the compound of Example 132(a) using the procedure of Example 225. $^1$H NMR (400 MHz, DMSO-d$_6$): δ 11.0 (s, 1H), 9.73 (s, 1H), 8.99 (s, 1H), 8.70 (d, 1H), 8.43 (t, 2H), 8.31 (s, 1H), 8.05 (s, 1H), 7.90 (s, 1H), 7.83 (s, 1H), 7.79-7.73 (m, 1H), 7.49-7.44 (m, 1H), 7.30 (t, 1H), 4.20 (s, 2H), 3.90 (s, 3H), 3.37 (t, 4H), 1.80-1.69 (m, 6H); LC-MS (ESI): Calculated mass: 527.57; Observed mass: 528.6 [M+H]$^+$ (rt: 0.32 min).

Example 240

N-(2',4'-difluoro-5-(6-(1-methyl-1H-pyrazol-4-yl)-3H-imidazo[4,5-b]pyridin-3-yl)-[1,1'-biphenyl]-3-yl) piperidine-4-carboxamide a) tert-butyl 4-((2',4'-difluoro-5-(6-(1-methyl-1H-pyrazol-4-yl)-3H-imidazo[4,5-b]pyridin-3-yl)-[1,1'-biphenyl]-3-yl) carbamoyl) piperidine-1-carboxylate The compound was prepared from the compound of Example 132(a) (100 mg, 0.248 mmol) using the procedure of Example 225 and 1-(tert-butoxycarbonyl)piperidine-4-carboxylic acid (56 mg, 0.248 mmol, 2 eq) to give the product in 26.3% yield (40 mg). LC-MS (ESI): Calculated mass: 513.21; Observed mass: 514.4 [M+H]$^+$ (rt: 0.68 min).

b) N-(2',4'-difluoro-5-(6-(1-methyl-1H-pyrazol-4-yl)-3H-imidazo[4,5-b]pyridin-3-yl)-[1,1'-biphenyl]-3-yl) piperidine-4-carboxamide To a solution of the compound of Example 240(a) (30 mg, 0.0489 mmol) in DCM was added TFA (1 ml) and stirred at RT for 16 h. The mixture was concentrated to give the product in 98% yield (25 mg). $^1$H NMR (400 MHz, DMSO-d$_6$): δ 10.50 (s, 1H), 8.94 (s, 1H), 8.72-8.66 (m, 2H), 8.40-8.35 (m, 3H), 8.29 (s, 1H), 8.03 (s, 1H), 7.90-7.89 (d, 1H), 7.73-7.67 (m, 2H), 7.46-7.41 (m, 1H), 7.28-7.23 (m, 1H), 3.88 (s, 3H), 3.37-3.34 (d, 2H), 2.99-2.90 (m, 2H), 2.73-2.68 (m, 1H), 2.01-1.98 (d, 2H), 1.85-1.77 (m, 2H); LC-MS (ESI): Calculated mass: 513.21; Observed mass: 514.4 [M+H]$^+$ (rt: 0.68 min).

Example 241

N-(2',4'-difluoro-5-(5-(1-methyl-1H-pyrazol-4-yl)-1H-benzo[d]imidazol-1-yl)-[1,1'-biphenyl]-3-yl)-2-(1H-1,2,4-triazol-1-yl) acetamide The compound was prepared from the compound of Example 132(a) using the procedure of Example 225. $^1$H NMR (400 MHz, DMSO-d$_6$): δ 10.9 (s, 1H), 9.0 (s, 1H), 8.73 (s, 1H), 8.6 (s, 1H), 8.3 (s, 1H), 8.4 (d, 1H), 8.03 (d, 1H), 7.87 (s, 1H), 7.75 (m, 1H), 7.48 (m, 1H), 7.29 (m, 1H), 5.23 (s, 1H), 3.95 (s, 3H); LC-MS (ESI): Calculated mass: 511.49; Observed mass: 512.1 [M+H]$^+$ (rt: 1.01 min).

Example 242

N-(2',4'-difluoro-5-(6-(1-methyl-1H-pyrazol-4-yl)-3H-imidazo[4,5-b]pyridin-3-yl)-[1,1'-biphenyl]-3-yl)-3,5-dimethylpiperazine-1-carboxamide To a solution of the compound of Example 132(a) (100 mg, 0.248 mmol) in DCM was added 20% phosgene (73.4 mg, 0.748 mmol, 3 eq) followed by 1-ethylpiperazine (28.3 mg, 0.248 mmol, 1 eq.). The mixture was stirred for 16 h and quenched and extracted as in Example 2(b). The solvent was distilled off to afford the crude residue which was purified by preparative HPLC to give the product in 5.9% yield (8 mg). $^1$H NMR (400 MHz, DMSO-d$_6$): δ 9.13 (s, 2H), 8.90 (1, 1H), 8.70-8.69 (d, 1H), 8.40-8.39 (d, 1H), 8.29 (s, 1H), 8.18 (t, 1H), 8.03 (s, 1H), 7.74-7.63 (m, 3H), 7.46-7.40 (m, 1H), 7.28-7.22 (m 1H), 4.32-4.29 (d, 2H), 3.88 (s, 3H), 3.34 (m, 2H), 2.80 (t, 2H), 1.24 (s, 3H), 1.22 (s, 3H); LC-MS (ESI): Calculated mass: 542.24; Observed mass: 543.3 [M+H]$^+$ (rt: 0.67 min).

Example 243

N-(2',4'-difluoro-5-(5-(1-methyl-1H-pyrazol-4-yl)-1H-benzo[d]imidazol-1-yl)-[1,1'-biphenyl]-3-yl) acryl amide To a solution of the compound of Example 132(a) (60 mg, 0.1492 mmol) in DCM was added TEA (30 mg, 0.298 mmol, 2.0 eq) followed by acryloyl chloride (16.1 mg, 0.179 mmol, 1.2 eq). The mixture was stirred for 4 h and quenched and extracted as in Example 2(b). The solvent was distilled off to afford the crude residue which was purified by preparative HPLC to give the product in 41% yield (28 mg). ¹H NMR (400 MHz, DMSO-d₆): δ 10.7 (s, 1H), 8.97 (s, 1H), 8.754 (d, 1H), 8.44 (t, 1H), 8.33 (s, 1H), 8.069 (d, 2H), 7.79-7.75 (m, 2H), 7.48 (t, 1H), 7.30 (t, 1H), 6.55-6.51 (m, 1H), 6.32 (d, 1H), 5.84 (d, 1H), 3.92 (s, 3H); LC-MS (ESI): Calculated mass: 456.15; Observed mass: 457.1 [M+H]⁺ (rt: 1.456 min).

Example 244

N-cyclopropyl-N'-(2',4'-difluoro-5-(6-(1-methyl-1H-pyrazol-4-yl)-3H-imidazo[4,5-b]pyridin-3-yl)-[1,1'-biphenyl]-3-yl)-sulfuric diamide To a solution of the compound of Example 132(a) (60 mg, 0.149 mmol) in pyridine was added N-cyclopropyl-2-oxooxazolidine-3-sulfonamide (49 mg, 0.238 mmol, 1.6 eq). The mixture was stirred at 50° C. for 16 h, and quenched and extracted as in Example 1(d). The solvent was distilled off to afford the crude residue which was purified by preparative HPLC to give the product in 19.4% yield (15 mg). ¹H NMR (400 MHz, CD₃OD): δ 8.89 (s, 1H), 8.71 (s, 1H), 8.32 (s, 1H), 8.14 (s, 1H), 7.96 (s, 1H), 7.77 (t, 1H), 7.71 (d, 1H), 7.71-7.63 (m, 1H), 7.47 (t, 1H), 7.15-7.09 (m, 2H), 3.98 (s, 3H), 2.48-2.44 (m, 1H), 0.65-0.55 (m, 4H); LC-MS (ESI): Calculated mass: 521.14; Observed mass: 522.1 [M+H]⁺ (rt: 1.480 min).

Example 245

N-(2',4'-difluoro-5-(6-(1-methyl-1H-pyrazol-4-yl)-3H-imidazo[4,5-b]pyridin-3-yl)-[1,1'-biphenyl]-3-yl)-N-(furan-2-ylmethyl)sulfuric diamide To a solution of the compound of Example 132(a) (100 mg, 0.248 mmol) in pyridine was added N-(furan-2-ylmethyl)-2-oxooxazolidine-3-sulfonamide (97 mg, 0.398 mmol, 1.6 eq). The mixture was stirred at 50° C. for 16 h, and quenched and extracted as in Example 1(d). The solvent was distilled off to afford the crude residue which was purified by preparative HPLC to give the product in 18% yield (25 mg). ¹H NMR (400 MHz, DMSO-d₆): δ 10.24 (s, 1H), 8.89 (s, 1H), 8.70 (d, 1H), 8.40 (d, 1H), 8.31-8.28 (m, 2H), 8.03 (d, 1H), 7.71-7.64 (m, 3H), 7.46-7.43 (m, 2H), 7.32 (d, 1H), 7.29-7.24 (m, 1H), 6.28-6.27 (m, 1H), 6.23 (d 1H), 4.10-4.09 (d, 2H), 3.88 (s, 3H); LC-MS (ESI): Calculated mass: 561.14; Observed mass: 562.1 [M+H]⁺ (rt: 1.513 min).

Example 246

N-(5-(6-(2-aminopyridin-4-yl)-3H-imidazo[4,5-b]pyridin-3-yl)-2',4'-difluoro-[1,1'-biphenyl]-3-yl)acetamide a) tert-butyl(4-(3-(5-acetamido-2',4'-difluoro-[1,1'-biphenyl]-3-yl)-3H-imidazo-[4,5-b]pyridin-6-yl)pyridin-2-yl)carbamate The compound was prepared from compound of Example 131(c) using the procedure of Example 131(d).

b) N-(5-(6-(2-aminopyridin-4-yl)-3H-imidazo[4,5-b]pyridin-3-yl)-2',4'-difluoro-[1,1'-biphenyl]-3-yl)acetamide To a solution of the compound of Example 246(a) (0.2 g, 0.359 mmol) in DCM (5 ml) was added (1.2 ml) of TFA at 0° C. The mixture was stirred at RT for 16 h. The mixture was concentrated on vacuo, quenched with sodiumbicarbonate and extracted as in Example 1(d). The solvent was distilled off to afford the product in 17.7% yield (0.29 g). ¹H NMR (400 MHz, DMSO-d₆): δ 10.41 (s, 1H), 9.09 (s, 1H), 8.87 (d, 1H), 8.70-8.69. (d, 2H), 8.34 (s, 1H), 8.10-8.08 (d, 1H), 8.12 (s, 1H), 7.86 (s, 1H), 7.71 (m, 2H), 7.52 (m, 1H), 7.41-7.39 (d, 1H), 7.31 (m, 2H), 2.12 (s, 3H); Calculated mass: 456.48; Observed mass: 457.3 [M+H]⁺ (rt: 0.19 min).

Example 247

N-(2',4'-difluoro-5-(6-(thiazol-2-yl)-3H-imidazo[4,5-b]pyridin-3-yl)-[1,1'-biphenyl]-3-yl)acetamide The compound was prepared from the compound of Example 131(c) (100 mg, 0.225 mmol) in THF (6 ml) using the procedure of Example 200(c) and thiazol-2-ylzinc (II) bromide (155 mg, 0.677 mmol, 3.0 eq.) to give the product in 25% yield (25 mg). ¹H NMR (400 MHz, DMSO-D6): δ 10.42 (s, 1H), 9.08 (d, 2H), 8.72 (d, 1H), 8.30 (s, 1H), 8.01 (d, 1H), 7.93 (s, 1H), 7.90 (d, 1H), 7.75-7.72 (m, 2H), 7.46 (t, 1H), 7.28 (t, 1H), 2.13 (s, 3H); LC-MS (ESI): Calculated mass: 447.46; Observed mass: 448.0 [M+H]⁺

Example 248

N-(5-(6-(6-aminopyridin-3-yl)-3H-imidazo[4,5-b]pyridin-3-yl)-2',4'-difluoro-[1,1'-biphenyl]-3-yl)acetamide The compound was prepared from the compound of Example 131(c) using the procedure of Example 246. ¹H NMR (300 MHz, DMSO-d₆): δ 10.43 (s, 1H), 9.02 (s, 1H), 8.76 (d, 1H), 8.55 (d, 1H), 8.44-8.34 (m, 3H), 8.04 (br s, 2H), 7.84 (s, 1H), 7.75-7.67 (m, 2H), 7.49-7.42 (m, 1H), 7.30-7.25 (m, 1H), 7.10-7.07 (m, 1H), 2.12 (s, 3H); LC-MS (ESI): Calculated mass: 456.15; Observed mass: 457.2 [M+H]⁺ (rt: 0.20 min).

Example 249

N-(5-(5-(4-aminophenyl)-1H-benzo[d]imidazol-1-yl)-2',4'-difluoro-[1,1'-biphenyl]-3-yl)acetamide The compound was prepared from the compound of Example 131(c) using the procedure of Example 246. ¹H NMR (300 MHz, DMSO-d₆): δ 10.41 (s, 1H), 8.98 (s, 1H), 8.68 (s, 1H), 8.37 (s, 1H), 8.31 (s, 1H), 7.89 (s, 1H), 7.71-7.68 (m, 1H), 7.62-7.59 (m, 2H), 7.48-7.42 (m, 1H), 7.29-7.24 (m, 2H), 7.12 (s, 1H), 6.95-6.90 (m, 3H), 2.12 (s, 3H); LC-MS (ESI): Calculated mass: 455.16; Observed mass: 456.3 [M+H]⁺ (rt: 0.78 min).

Example 250

N-(5-(5-(2-aminopyridin-4-yl)-1H-benzo[d]imidazol-1-yl)-2',4'-difluoro-[1,1'-biphenyl]-3-yl)acetamide The compound was prepared from the compound of Example 1(h) using the procedure of Example 246 to afford the product in 97.6% yield (0.40 g). ¹H NMR (400 MHz CD₃OD): 8.68 (s, 1H), 8.21-8.20 (d, 2H7.91-7.88. (t, 2H), 7.84-7.81 (dd, 1H), 7.70-7.68 (d, 1H), 7.66-7.64 (m, 1H), 7.54 (d, 1H), 7.34-7.30 (m, 2H), 7.15-7.10 (m, 2H), 3.33 (s, 1H), 2.19 (s, 3H); Calculated mass: 455.46; Observed mass: 456.3 [M+H]$^+$ (rt: 0.29 min).

Example 251

N-(2',4'-difluoro-5-(5-(thiazol-2-yl)-1H-benzo[d]imidazol-1-yl)-[1,1'-biphenyl]-3-yl)acetamide The compound was prepared from the compound of Example 1(h) (200 mg, 0.452 mmol) in THF (6 ml) using the method of Example 200(c) and thiazol-2-yl-zinc(II) bromide (310 mg, 1.35 mmol, 3.0 eq) to give the product in 25% yield (50 mg).

Example 252

N-(5-(5-(6-aminopyridin-3-yl)-1H-benzo[d]imidazol-1-yl)-2',4'-difluoro-[1,1'-biphenyl]-3-yl)acetamide The compound was prepared from the compound of Example 1(h) using the method of Example 1(i). $^1$H NMR (300 MHz, CD$_3$OD): δ 8.25 (d, 1H), 8.08 (s, 2H), 7.96 (s, 1H), 7.82 (s, 1H), 7.59-7.51 (m, 3H), 7.42 (s, 1H), 7.05-6.99 (m, 4H), 2.1 (s, 3H); LC-MS (ESI): Calculated mass: 455.16; Observed mass: 456.1 [M+H]$^+$ (rt: 0.21 min).

Example 253

N-(5-(5-(3-amino-1-methyl-1H-pyrazol-4-yl)-1H-benzo[d]difluoro-[1,1'-biphenyl]-3-yl)acetamide a) tert-butyl(4-(1-(5-acetamido-2',4'-difluoro-[1,1'-biphenyl]-3-yl)-1H-benzo[d]-imidazol-5-yl)-1-methyl-1H-pyrazol-5-yl)carbamate The compound was prepared from the compound of Example 1(h) using the procedure mentioned in Example 1(i).

b) N-(5-(5-(3-amino-1-methyl-1H-pyrazol-4-yl)-1H-benzo[d]imidazol-1-yl)-2',4'-difluoro-[1,1'-biphenyl]-3-yl)acetamide To a solution of the compound of Example 253(a) (15 mg, 0.02 mmol) in DCM was added TFA (1 ml). The mixture was stirred at RT for 16 h and concentrated to give the product in 50.4% yield (6 mg). $^1$H NMR (400 MHz, CD$_3$OD): δ 8.49 (s, 1H), 8.11-8.10 (d, 1H), 7.86 (s, 1H), 7.73-7.60 (m, 4H), 7.53-7.49 (m, 2H), 7.16-7.09 (m, 2H), 3.76 (s, 3H), 2.20 (s, 3H), 1.97 (s, 2H). LC-MS (ESI): Calculated mass: 458.46; Observed mass: 459.0 [M+H]$^+$ (rt: 0.43 min).

Example 254

N-(5-(5-(2-aminothiazol-5-yl)-1H-benzo[d]imidazol-1-yl)-2',4'-difluoro-[1,1'-biphenyl]-3-yl)acetamide To a solution of N-(5-(5-(2-bromoacetyl)-1H-benzo[d]imidazol-1-yl)-2',4'-difluoro-[1,1'-biphenyl]-3-yl)acetamide (100 mg, 0.20 mmol) in ethanol was added thiourea (20 mg, 0.30 mmol, 1.5 eq). The mixture was stirred at 60° C. for 3 h. The mixture was quenched and extracted as in Example 1(d). The solvent was distilled off to give the crude residue which was purified by preparative HPLC to give the product in 14.7% yield (14 mg). $^1$H NMR (300 MHz, CD$_3$OD): δ 8.73 (s, 1H), 8.11 (s, 1H), 8.01 (s, 1H), 7.73-7.69 (m, 2H), 7.62-7.50 (m, 2H), 7.45 (d, 1H), 7.10-6.99 (m, 3H), 2.10 (s, 3H); LC-MS (ESI): Calculated mass: 461.4; Observed mass: 462.1 [M+H]$^+$ (rt: 0.80 min).

Example 255

N-(5-(5-(2-aminopyrimidin-5-yl)-1H-benzo[d]imidazol-1-yl)-2',4'-difluoro-[1,1'-biphenyl]-3-yl)acetamide The compound was prepared from the compound of Example 1(h) using the procedure of Example 246. $^1$H NMR (300 MHz, CD$_3$OD): δ 8.84 (s, 1H), 8.70 (s, 1H), 8.18 (s, 1H), 7.99 (s, 1H), 7.86-7.83 (m, 1H), 7.72-7.61 (m, 3H), 7.53 (d, 1H), 7.13-7.01 (m, 2H), 2.13 (s, 3H); LC-MS (ESI): Calculated mass: 456.4; Observed mass: 457.1 [M+H]$^+$ (rt: 0.56 min).

Example 256

N-(5-(5-(1H-pyrazol-1-yl)-1H-benzo[d]imidazol-1-yl)-2',4'-difluoro-[1,1'-biphenyl]-3-yl)-1-methylpiperidine-4-carboxamide The compound was prepared from the compound of Example 29(a) (50 mg, 0.128 mmol) using the procedure of Example 225 using 1-methylpiperidinecarboxylic acid (22 mg, 0.154 mmol, 1.2 eq.) to give the product in 30% yield (20 mg). $^1$H NMR (300 MHz, CD$_3$OD): δ 8.59 (s, 1H), 8.27 (d, 1H), 8.15-8.14 (t, 1H), 8.11 (m, 1H), 7.82-7.75 (m, 4H), 7.66-7.56 (m, 1H), 7.56 (m, 1H), 7.13-7.11 (m, 1H), 6.56 (t, 1H), 3.53-3.47 (m, 2H), 3.0 (m, 2H), 2.82 (s, 3H), 2.7 (m, 1H), 2.14-2.0 (m, 4H). LC-MS (ESI): Calculated mass: 512.55; Observed mass: 513.1 [M+H]$^+$ (rt: 1.245 min).

Example 257

N-(5-(5-(1H-pyrazol-1-yl)-1H-benzo[d]imidazol-1-yl)-2',4'-difluoro-[1,1'-biphenyl]-3-yl)-2-(4-methylpiperazin-1-yl) acetamide The compound was prepared from the compound of Example 29(a) using the procedure of Example 225. $^1$H NMR (400 MHz, DMSO-d$_6$): δ 10.12 (s, 1H), 8.73 (s, 1H), 8.58 (d, 1H), 8.22 (d, 1H), 8.13 (t, 1H), 7.95-7.9 (m, 2H), 7.82-7.71 (m, 3H), 7.55 (s, 1H), 7.47-7.41 (m, 1H), 7.28-7.23 (dt, 1H), 6.55-6.54 (m, 1H), 3.45 (s, 2H), 3.17 (s, 3H), 2.48-2.32 (m, 8H); LC-MS (ESI): Calculated mass: 527.57; Observed mass: 528.2 [M+H]$^+$ (rt: 0.36 min).

Example 258

N-(5-(5-(1H-pyrazol-1-yl)-1H-benzo[d]imidazol-1-yl)-2',4'-difluoro-[1,1'-biphenyl]-3-yl)-2-(1H-1,2,4-triazol-1-yl)acetamide The compound was prepared from the compound of Example 29(a) using the procedure of Example 225. $^1$H NMR (400 MHz, DMSO-d$_6$): δ 11.2 (s, 1H), 8.75 (s, 1H), 8.57 (s, 1H), 8.22 (d, 1H), 8.07 (t, 1H), 8.0 (s, 1H), 7.92-7.85 (m, 2H), 7.8-7.73 (m, 3H), 7.59 (s, 1H), 7.47-7.41 (dt, 1H), 7.28-7.23 (dt, 1H), 6.54 (m, 1H), 5.24 (s, 2H): LC-MS (ESI): Calculated mass: 496.47; Observed mass: 497.0 [M+H]$^+$ (rt: 0.17 min).

Example 259

N-(5-(5-(1H-pyrazol-1-yl)-1H-benzo[d]imidazol-1-yl)-2',4'-difluoro-[1,1'-biphenyl]-3-yl)-2-(piperidin-1-yl)acetamide The compound was prepared from the compound of Example 29(a) using the procedure of Example 225 and 2-(piperidin-1-yl)acetic acid (41 mg, 0.290 mmol, 1.5 eq.) to give the product in 10.1% yield (10 mg). $^1$H NMR (400 MHz, DMSO-$d_6$): δ 10.11 (s, 1H), 8.75 (s, 1H), 8.60 (d, 1H), 8.24-8.21 (d, 1H), 8.15 (s, 1H), 7.98 (s, 1H), 7.94-7.92 (dd, 1H), 7.84-7.82 (d, 1H), 7.79-7.77 (m, 2H), 7.56 (s, 1H), 7.49-7.43 (t, 1H), 6.57-6.56 (t, 1H), 3.14 (s, 2H); 2.67 (s, 1H); 2.33 (s, 1H); 1.90 (s, 1H); 1.60-1.59 (t, 5H); 1.40 (s, 2H) LC-MS (ESI): Calculated mass: 512.55; Observed mass: 513.2[M+H]$^+$ (rt: 0.3 min).

Example 260

N-(5-(5-(1H-pyrazol-1-yl)-1H-benzo[d]imidazol-1-yl)-2',4'-difluoro-[1,1'-biphenyl]-3-yl)-2-(pyrrolidin-1-yl)acetamide The compound was prepared from the compound of Example 29(a) using the procedure of Example 225. $^1$H NMR (600 MHz, CD$_3$OD): δ 8.62 (s, 1H), 8.29-8.28 (d, 1H), 8.17-8.16 (t, 1H), 8.12 (s, 1H), 7.85-7.83 (dd, 3H), 7.77-7.76 (d, 1H), 7.68-7.67 (m, 1H), 7.59 (s, 1H), 7.15-7.12 (m, 2H), 6.58-6.57 (t, 1H), 3.73 (s, 2H); 3.02 (t, 4H); 2.00-1.94 (m, 7H); LC-MS (ESI): Calculated mass: 498.53, Observed mass: 499.6 [M+H]$^+$ (rt: 0.6 min).

Example 261

N-(2',4'-difluoro-5-(5-(1-methyl-1H-pyrazol-4-yl)-1H-benzo[d]imidazol-1-yl)-[1,1'-biphenyl]-3-yl)-1-ethylpiperidine-3-carboxamide The compound was prepared from the compound of Example 2(a) using the procedure of Example 225. $^1$H NMR (300 MHz, DMSO): δ 10.6 (d, 1H), 9.50 (s, 1H), 8.79 (d, 1H), 8.22 (s, 1H), 8.10 (s, 1H), 8.00-7.96 (d, 2H), 7.80-7.70 (m, 3H), 7.64-7.59 (m, 1H), 7.46 (m, 1H), 7.28 (m, 1H), 3.81 (s, 3H), 3.60-3.56 (d, 3H), 3.43-3.37 (m, 1H), 3.14-3.04 (d, 2H), 3.0-2.89 (t, 2H), 2.13 (d, 1H), 2.00-1.95 (d, 1H), 1.73-1.69 (d, 1H), 1.55 (d, 1H); LC-MS (ESI): Calculated mass: 540.6; Observed mass: 541.2 [M+H]$^+$ (rt: 0.22 min).

Example 262

N-(2',4'-difluoro-5-(5-(1-methyl-1H-pyrazol-4-yl)-1H-benzo[d]imidazol-1-yl)-[1,1'-biphenyl]-3-yl)-1-methylpiperidine-3-carboxamide The compound was prepared from the compound of Example 2(a) using the procedure of Example 255. $^1$H NMR (300 MHz, DMSO): δ 10.6 (d, 1H), 9.50 (s, 1H), 8.79 (d, 1H), 8.22 (s, 1H), 8.10 (s, 1H), 8.00-7.96 (d, 2H), 7.80-7.70 (m, 3H), 7.64-7.59 (m, 1H), 7.46 (m, 1H), 7.28 (m, 1H), 3.81 (s, 3H), 3.60-3.56 (d, 3H), 3.43-3.37 (m, 1H), 3.14-3.04 (d, 2H), 3.0-2.89 (t, 2H), 2.13 (d, 1H), 2.00-1.95 (d, 1H), 1.73-1.69 (d, 1H), 1.55 (d, 1H); LC-MS (ESI): Calculated mass: 526.58; Observed mass: 527.2 [M+H]$^+$ (rt: 0.15 min).

Example 263

N-(2',4'-difluoro-5-(5-(1-(tetrahydro-2H-pyran-4-yl)-1H-1,2,3-triazol-4-yl)-1H-benzo[d]imidazol-1-yl)-[1,1'-biphenyl]-3-yl)acetamide A mixture the compound of Example 17(e) (250 mg, 0.644 mmol), 4-azidotetrahydro-2H-pyran (90 mg, 0.77 mmol, 1.2 eq.), copper iodide (12 mg, 0.06 mmol, 0.1 eq.) in DMF was stirred at 90° C. for 16 h. The mixture was quenched with water and the precipitate formed was filtered and dried to give the crude product which was purified by preparative HPLC to give the product in 45% yield (150 mg). $^1$H NMR (300 MHz, DMSO): δ 10.4 (s, 1H) 8.77 (s, 1H), 8.69 (s, 1H), 8.25 (s, 1H), 8.06 (d, 1H), 7.94-7.90 (m, 1H), 7.83-7.76 (m, 3H), 7.53 (s, 1H), 7.40-7.52 (m, 1H), 7.34-7.22 (m, 1H), 4.80 (m, 1H), 4.02 (m, 2H), 3.50-3.52 (m, 2H), 2.10 (s, 3H), 2.0-2.12 (m, 4H); LC-MS (ESI): Calculated mass: 514.5; Observed mass: 514.8 [M+H]$^+$ (rt: 1.32 min).

Example 264

N-(5-(5-(1H-1,2,3-triazol-4-yl)-1H-benzo[d]imidazol-1-yl)-2',4'-difluoro-[1,1'-biphenyl]-3-yl)acetamide A mixture of the compound of Example 17(e) (300 mg, 0.77 mmol), sodium azide (150 mg, 2.32 mmol, 3.0 eq.), copper iodide (14 mg, 0.07 mmol, 0.1 eq.) in DMF was stirred for 16 h at RT. The mixture was quenched with water and the precipitate formed was filtered and dried to give the crude product which was purified by preparative HPLC to give the product in 64.3% yield (200 mg). $^1$H NMR (300 MHz, DMSO): δ 10.4 (s, 1H) 8.80 (s, 1H), 8.40 (s, 1H), 8.32 (s, 1H), 8.11 (s, 1H), 7.97-7.94 (d, 1H), 7.85-7.76 (m, 3H), 7.56 (d, 1H), 7.47 (m, 1H), 7.30 (m, 1H), 2.10 (s, 3H); LC-MS (ESI): Calculated mass: 430.4; Observed mass: 431.2 [M+H]$^+$ (rt: 0.69 min).

Example 265

N-(5-(5-(1-(cyclopropylmethyl)-1H-1,2,3-triazol-4-yl)-1H-benzo[d]imidazol-1-yl)-2',4'-difluoro-[1,1'-biphenyl]-3-yl)acetamide A mixture of the compound of Example 17(e) (100 mg, 0.25 mmol), sodium azide (25 mg, 0.387 mmol, 1.5 eq.), (bromomethyl)cyclopropane (41 mg, 0.310 mmol, 1.2 eq.), copper iodide (5 mg, 0.025 mmol, 0.1 eq.) in DMF was stirred for 16 h at RT. The mixture was quenched with water and the precipitate formed was filtered and dried to give the crude product which was purified by preparative HPLC to give the product in 80.6% yield (100 mg). $^1$H NMR (300 MHz, CD$_3$OD): δ 10.4 (s, 1H) 8.68 (d, 1H), 8.05 (s, 1H), 7.90-7.88 (m, 2H), 7.81-7.69 (m, 3H), 7.51-7.39 (m, 3H), 7.28-7.22 (m, 1H), 4.25 (d, 2H), 2.10 (s, 3H), 1.34 (m, 1H), 0.63-0.56 (2H, d), 0.50-0.46 (2H, d); LC-MS (ESI): Calculated mass: 484.5; Observed mass: 484.8 [M+H]$^+$ (rt: 1.42 min).

Example 266

N-(2',4'-difluoro-5-(5-(1-(tetrahydro-2H-pyran-4-yl)-1H-1,2,3-triazol-4-yl)-1H-benzo[d]imidazol-1-yl)-[1,1'-biphenyl]-3-yl)ethanesulfonamide To a solution of 2',4'-difluoro-5-(5-(1-(tetrahydro-2H-pyran-4-yl)-1H-1,2,3-triazol-4-yl)-1H-benzo[d]imidazol-1-yl)-[1,1'-biphenyl]-3-amine (60 mg, 0.126 mmol) in DCM was added pyridine (19 mg, 2.52 mmol, 2.0 eq.) followed by ethanesulfonyl chloride (19 mg, 0.152 mmol, 1.2 eq). After completion of the reaction the solvent was distilled off and the crude product was purified by preparative HPLC to give the product in 42% yield (30 mg). $^1$H NMR (300 MHz, CD$_3$OD): δ 8.92 (s, 1H), 8.3 (d, 1H), 8.06 (s, 1H), 8.0 (s, 1H), 7.95 (s, 1H), 7.88 (s, 1H), 7.77-7.69 (m, 5H), 7.45 (m, 1H), 6.56 (m, 1H), 3.92 (s, 3H), 3.28-3.27 (m, 4H), 1.6-1.49 (m, 6H); LC-MS (ESI): Calculated mass: 564.6; Observed mass: 565.4 [M+H]$^+$ (rt: 1.46 min).

Example 267

N-(5-(5-(1H-1,2,3-triazol-4-yl)-1H-benzo[d]imidazol-1-yl)-2',4'-difluoro-[1,1'-biphenyl]-3-yl)ethanesulfonamide To a solution of 5-(6-(1H-1,2,3-triazol-4-yl)-3H-imidazo[4,5-b]pyridin-3-yl)-2',4'-difluoro-[1,1'-biphenyl]-3-amine (70 mg, 0.18 mmol) in DCM was added pyridine (42 mg, 0.54 mmol, 3.0 eq.) followed by ethanesulfonyl chloride (27 mg, 0.216 mmol, 1.2 eq.). The reaction was monitored by LCMS. After completion of the reaction the solvent was distilled off and the crude product was purified by preparative HPLC to give the product in 2.3% yield (2 mg).

Example 268

N-(5-(6-(1-(cyclopropylmethyl)-1H-1,2,3-triazol-4-yl)-3H-imidazo[4,5-b]-pyridin-3-yl)-2',4'-difluoro-[1,1'-biphenyl]-3-yl)acetamide A mixture N-(5-(6-ethynyl-3H-imidazo[4,5-b]pyridin-3-yl)-2',4'-difluoro-[1,1'-biphenyl]-3-yl)acetamide (300 mg, 0.77 mmol), sodium azide (76 mg, 1.15 mmol, 1.5 eq.), (bromomethyl)cyclopropane (125 mg, 0.92 mmol, 1.2 eq.), copper iodide (14 mg, 0.07 mmol, 0.1 eq.) in DMF was stirred for 16 h at RT. The mixture was quenched with water and the precipitate formed was filtered and dried to give the crude product which was purified by preparative HPLC to give the product in 82.6% yield (310 mg). $^1$H NMR (300 MHz, DMSO): δ 10.4 (s, 1H) 8.99 (d, 2H), 8.80 (s, 1H), 8.63 (d, 1H), 8.30 (s, 1H), 7.91 (d, 1H), 7.76-7.68 (m, 2H), 7.49-7.41 (m, 1H), 7.30-7.25 (m, 1H), 4.21 (m, 2H), 2.12 (s, 3H), 1.23 (m, 1H), 0.63-0.60 (2H, d) 0.50-0.48 (2H, d); LC-MS (ESI): Calculated mass: 485.4; Observed mass: 486.1 [M+H]$^+$ (rt: 1.52 min).

Example 269

N-(2',4'-difluoro-5-(6-(1-(tetrahydro-2H-pyran-4-yl)-1H-1,2,3-triazol-4-yl)-3H-imidazo[4,5-b]pyridin-3-yl)-[1,1'-biphenyl]-3-yl)acetamide A mixture N-(5-(6-ethynyl-3H-imidazo[4,5-b]pyridin-3-yl)-2',4'-difluoro-[1,1'-biphenyl]-3-yl)acetamide (250 mg, 0.644 mmol), 4-azidotetrahydro-2H-pyran (90 mg, 0.77 mmol, 1.2 eq.), copper iodide (12 mg, 0.06 mmol, 0.1 eq.) in DMF was stirred at 90° C. for 16 h. The mixture was quenched with water and the precipitate formed was filtered and dried to give the crude product which was purified by preparative HPLC to give the product in 45% yield (150 mg). $^1$H NMR (300 MHz, DMSO): δ 10.4 (s, 1H), 8.99-8.97 (m, 2H), 8.88 (s, 1H), 8.61-8.60 (m, 1H), 8.32-8.29 (m, 1H), 7.91 (d, 1H), 7.76-7.68 (m, 2H), 7.48-7.41 (m, 1H), 7.3-7.24 (m, 1H), 4.80 (m, 1H), 4.02 (m, 2H), 3.50-3.60 (m, 2H), 2.10 (s, 3H), 2.0-2.12 (m, 4H); LC-MS (ESI): Calculated mass: 515.5; Observed mass: 516.5 [M+H]$^+$ (rt: 1.37 min).

Example 270

Ethyl 2-(4-(3-(5-acetamido-2',4'-difluoro-[1,1'-biphenyl]-3-yl)-3H-imidazo[4,5-b]pyridin-6-yl)-1H-1,2,3-triazol-1-yl)acetate A mixture of N-(5-(5-ethynyl-1H-benzo[d]imidazol-1-yl)-2',4'-difluorobiphenyl-3-yl)acetamide (200 mg, 0.51 mmol), sodium azide (90 mg, 1.5 mmol, 3.0 eq.), ethyl 2-bromoacetate (100 mg, 0.61 mmol, 1.2 eq.), sodium ascorbate (100 mg, 0.51 mmol, 1.0 eq.) and copper sulfate pentahydrate (45.9 mg, 0.255 mmol, 0.5 eq.) in DMSO, THF and water (1:1:1, 3 ml) was stirred for 12 h at RT. The mixture was quenched with water and the precipitate formed was filtered and dried to give the crude product which was purified by preparative HPLC to give the product in 76% yield (200 mg). $^1$H NMR (300 MHz, DMSO): δ 10.4 (s, 1H) 9.02-8.99 (d, 2H), 8.75 (s, 1H), 8.64 (d, 1H), 8.29 (s, 1H), 7.92 (d, 1H), 7.71-7.70 (m, 2H), 7.50-7.40 (m, 1H), 7.27 (m, 1H), 5.55 (s, 2H), 4.22 (q, 2H), 2.10 (s, 3H), 1.24 (t, 3H); LC-MS (ESI): Calculated mass: 517.45; Observed mass: 517.8 [M+H]$^+$ (rt: 1.47 min).

Example 271

2-(4-(3-(5-acetamido-2',4'-difluoro-[1,1'-biphenyl]-3-yl)-3H-imidazo[4,5-b]pyridin-6-yl)-1H-1,2,3-triazol-1-yl) acetamide To a mixture of the compound of Example 270 (100 mg, 0.19 mmol) in methanol was added methonalic ammonia at 0° C. and the mixture was stirred at RT for 16 h. The mixture was distilled completely and the crude product was purified by preparative HPLC to give the product in 13% yield (12 mg). δ 10.5 (s, 1H) 9.14-8.97 (d, 2H), 8.82 (s, 1H), 8.76 (d, 1H), 8.35 (s, 1H), 7.89 (d, 1H), 7.81-7.80 (m, 2H), 7.65-7.55 (m, 1H), 7.27 (m, 1H), 5.55 (s, 2H), 2.8 (s, 2H), 2.10 (s, 3H); LC-MS (ESI): Calculated mass: 515.5; Observed mass: 516.5 [M+H]$^+$ (rt: 1.37 min).

Example 272

N-(5-(6-(1H-1,2,3-triazol-4-yl)-3H-imidazo[4,5-b]pyridin-3-yl)-2',4'-difluoro-[1,1'-biphenyl]-3-yl)acetamide A mixture N-(5-(6-ethynyl-3H-imidazo[4,5-b]pyridin-3-yl)-2',4'-difluoro-[1,1'-biphenyl]-3-yl)acetamide (300 mg, 0.77 mmol), sodium azide (75 mg, 1.15 mmol, 1.5 eq.), copper iodide (14 mg, 0.07 mmol, 0.1 eq.) in DMF was stirred for 16 h at RT. The mixture was quenched with water and the precipitate formed was filtered and dried to give the crude product which was purified by preparative HPLC to give the product in 90% yield (300 mg).

Example 273

N-(5-(6-(1H-1,2,3-triazol-4-yl)-3H-imidazo[4,5-b]pyridin-3-yl)-2',4'-difluoro-[1,1'-biphenyl]-3-yl)ethanesulfonamide To a solution of 5-(6-(1H-1,2,3-triazol-4-yl)-3H-imidazo[4,5-b]pyridin-3-yl)-2',4'-difluoro-[1,1'-biphenyl]-3-amine (70 mg, 0.179 mmol) in DCM was added pyridine (42 mg, 0.53 mmol, 3.0 eq.) followed by ethanesulfonyl chloride (20 mg, 0.179 mmol, 1.0 eq.). The reaction was monitored by LCMS. After completion of the reaction the solvent was distilled off and the crude product was purified by preparative HPLC to give the product in 9.3% yield (8 mg). $^1$H NMR (300 MHz, DMSO): δ 10.4 (s, 1H) 9.0-8.97 (m, 2H), 8.64 (d, 1H), 7.92 (s, 1H), 7.75-7.64 (m, 3H), 7.47-7.43 (m, 3H), 3.31-3.24 (q, 2H), 1.39-1.34 (t, 3H); LC-MS (ESI): Calculated mass: 481.4; Observed mass: 481.8 [M+H]$^+$ (rt: 1.36 min).

Example 274

N-(2',4'-difluoro-5-(6-(1-(tetrahydro-2H-pyran-4-yl)-1H-1,2,3-triazol-4-yl)-3H-imidazo[4,5-b]pyridin-3-yl)-[1,1'-biphenyl]-3-yl)ethanesulfonamide To a solution of 2',4'-difluoro-5-(6-(1-(tetrahydro-2H-pyran-4-yl)-1H-1,2,3-triazol-4-yl)-3H-imidazo[4,5-b]pyridin-3-yl)-[1,1'-biphenyl]-3-amine (65 mg, 0.136 mmol) in DCM was added pyridine (21 mg, 2.72 mmol, 2.0 eq.) followed by ethanesulfonyl chloride (21 mg, 0.164 mmol, 1.2 eq.). After completion of the reaction the solvent was distilled off and the crude product was purified by preparative HPLC to give the product in 42% yield (30 mg). $^1$H NMR (300 MHz, DMSO): δ 10.4 (s, 1H) 9.04 (s, 1H), 8.99-8.98 (d, 1H), 8.90 (d, 1H), 8.63-8.61 (d, 1H) 7.95 (d, 1H), 7.76-7.70 (m, 2H), 7.49 (m, 2H), 7.35 (d, 1H), 4.82 (m, 1H), 3.95 (d, 2H), 3.58-3.55 (t, 2H), 3.36-3.28 (m, 2H), 2.12 (m, 2H), 1.29-1.24 (t, 3H), 1.08-1.06 (t, 2H); LC-MS (ESI): Calculated mass: 565.5; Observed mass: 565.9 [M+H]$^+$ (rt: 1.44 min).

Example 275

N-(5-(6-(1-(cyclopropylmethyl)-1H-1,2,3-triazol-4-yl)-3H-imidazo[4,5-b]-pyridin-3-yl)-2',4'-difluoro-[1,1'-biphenyl]-3-yl)ethanesulfonamide To a solution of 5-(6-(1-(cyclopropylmethyl)-1H-1,2,3-triazol-4-yl)-3H-imidazo-[4,5-b]pyridin-3-yl)-2',4'-difluoro-[1,1'-biphenyl]-3-amine (50 mg, 0.112 mmol) in DCM was added pyridine (26 mg, 0.33 mmol, 3.0 eq.) and ethanesulfonyl chloride (17 mg, 0.135 mmol, 1.2 eq.). After completion of the reaction the solvent was distilled off and the crude product was purified by preparative HPLC to give the product in 33% yield (20 mg). $^1$H NMR (300 MHz, DMSO): δ 10.3 (s, 1H) 9.02-8.99 (m, 2H), 8.81 (d, 1H), 8.63-8.61 (d, 1H) 7.95 (d, 1H) 7.77-7.69 (m, 2H), 7.49-7.42 (m, 2H), 7.31-7.25 (d, 1H), 4.33 (d, 2H), 3.42-3.26 (m, 2H), 1.34-1.24 (t, 3H), 0.63-0.60 (t, 2H), 0.49-0.48 (t, 2H); LC-MS (ESI): Calculated mass: 535.5; Observed mass: 535.8 [M+H]$^+$ (rt: 0.1.33 min).

Example 276

N-(5-(6-(1-(cyclopropylmethyl)-1H-1,2,3-triazol-4-yl)-3H-imidazo[4,5-b]pyridin-3-yl)-2',4'-difluoro-[1,1'-biphenyl]-3-yl)cyclopropanecarboxamide To a solution of 5-(6-(1-(cyclopropylmethyl)-1H-1,2,3-triazol-4-yl)-3H-imidazo-[4,5-b]pyridin-3-yl)-2',4'-difluoro-[1,1'-biphenyl]-3-amine (50 mg, 0.11 mmol) in DMF was added cyclopropanecarboxylic acid (11 mg, 0.13, mmol, 1.2 eq.) followed by HATU (91 mg, 0.24 mmol, 2.0 eq.) and DIPEA (43 mg, 0.33 mmol, 3.0 eq). The mixture was stirred for 16 h and quenched extracted as in Example 1(d). The solvent was distilled off to afford the crude residue which was purified by column chromatography to give the product in 51% yield (25 mg). $^1$H NMR (300 MHz, DMSO): δ 10.6 (s, 1H) 8.99 (d, 2H), 8.88 (d, 1H), 8.62 (d, 1H), 8.31 (d, 1H), 7.92 (d, 1H), 7.76-7.71 (m, 2H), 7.47-7.40 (m, 1H), 7.29-7.24 (m, 1H), 4.33-4.30 (d, 2H), 3.64-3.62 (m, 2H), 3.12-3.09 (m, 2H), 1.87-1.83 (m, 1H), 0.63-0.61 (t, 2H), 0.49-0.48 (t, 2H); LC-MS (ESI): Calculated mass: 511.5; Observed mass: 511.8 [M+H]$^+$ (rt: 1.63 min).

Example 277

N-(3-(3-fluoropyridin-4-yl)-5-(5-(1-methyl-1H-pyrazol-4-yl)-1H-benzo[d]-imidazol-1-yl)phenyl)acetamide a) N-(3-bromo-5-((4-(1-methyl-1H-pyrazol-4-yl)-2-nitrophenyl)amino)phenyl) acetamide A solution of 4-(4-fluoro-3-nitrophenyl)-1-methyl-1H-pyrazole (1.6 g, 7.239 mmol), N-(3-amino-5-bromophenyl) acetamide (1.98 g, 8.687 mmol) and potassium fluoride (0.503 g, 8.687 mmol) in DMF was heated at 130° C. for 48 h. The mixture was quenched and extracted as in Example 1(d). The solvent was distilled off to afford the crude residue which was purified by column chromatography (60-120 silica gel, 50% ethyl acetate in hexane) to yield the title product in 35% yield (1.1 g); LC-MS (API): Calculated mass: 430.1; Observed mass: 432 [M+H]$^+$ (rt: 1.50 min).

b) N-(3-((2-amino-4-(1-methyl-1H-pyrazol-4yl)-phenyl)amino)-5-bromophenyl) acetamide To a solution of the compound of Example 277(a) (1.0 g, 2.32 mmol) in THF (20 ml) and methanol (20 ml) were added a solution of ammonium chloride (1.24 g, 23.20 mmol, 10 eq.) in water (15 ml) and zinc (1.5 g, 23.20 mmol, 10 eq.). The mixture was stirred at RT for 4 h and filtered. The filtrate was diluted with water and extracted as in Example 1(d). The solvent was distilled off to give the title product in 90% yield (0.9 g); LC-MS (API): Calculated mass: 399.1; Observed mass: 400.0 [M+H]$^+$ (rt: 0.61 min).

c) N-(3-bromo-5-(5-(1-methyl-1H-pyrazol-4-yl)-1H-benzo[d]imidazol-1-yl)-phenyl)acetamide A mixture of the compound of Example 277(b) (1.0 g, 2.50 mmol) and formic acid (10 ml) was heated at 90° C. for 2 h. The formic acid was distilled off and the residue was dissolved in ethyl acetate. The ethyl acetate layer was washed with water, brine and dried over sodium sulphate. The solvent was distilled off to give the product in 85% yield (0.9 g); LC-MS (ESI): Calculated mass: 410.1; Observed mass: 412.1 [M+H]$^+$ (rt: 0.403 min).

d) N-(3-(3-fluoropyridin-4-yl)-5-(5-(1-methyl-1H-pyrazol-4-yl)-1H-benzo[d]-imidazol-1-yl)phenyl) acetamide A solution of the compound of Example 277(c) (0.1 g, 0.243 mmol) in 1,2-dimethoxyethane (4 ml) was degassed by N$_2$ bubbling for 5 min. (3-Fluoropyridin-4-yl)-boronic acid (0.041 g, 0.292 mmol, 1.2 eq.) was added and the mixture was degassed for another 5 min. Pd(dppf)Cl$_2$ (0.020 g, 0.024 mmol, 0.1 eq.) and aqueous sodium carbonate (0.077 g, 0.731 mmol, 3.0 eq.) were added and the procedure of Example 1(d) was followed. The crude residue of the product was purified by preparative HPLC to give the product in 21% yield. $^1$H NMR (300 MHz, DMSO-d$_6$): δ 10.5 (s, 1H), 8.97 (s, 1H), 8.75 (s, 1H), 8.59 (d, 1H), 8.24 (s, 1H), 8.20 (s, 1H), 8.01 (s, 1H), 7.97 (d, 2H), 7.80-7.65 (m, 4H), 3.89 (s, 3H), 2.13 (s, 3H); LC-MS (ESI): Calculated mass: 426.16; Observed mass: 427.1 [M+H]$^+$ (rt: 0.20 min).

Example 278

N-(3-(3-fluoropyridin-4-yl)-5-(5-(1-methyl-1H-pyrazol-4-yl)-1H-benzo[d]-imidazol-1-yl)phenyl)ethanesulfonamide The compound was prepared from the compound of Example 277 (0.9 g, 2.11 mmol, 1 eq.) using the procedure of Example 2 and ethanesulfonyl chloride (60 mg, 0.46 mmol, 1.2 eq.) to give the product in 15.13% yield (28 mg). $^1$H NMR (400 MHz, DMSO-d$_6$): δ 8.69-8.68 (d, 1H), 8.58 (s, 1H), 8.54-8.52 (d, 1H), 8.18 (s, 1H), 7.97 (s, 1H), 7.93 (s, 1H), 7.74-7.71 (t, 1H), 7.67-7.64 (d, 1H), 7.58-7.56 (d, 1H), 7.44-7.43 (t, 1H), 7.36-7.33 (d, 2H), 3.87 (s, 3H), 3.07-3.02 (quartet, 2H), 1.22-1.18 (t, 3H); LC-MS (ESI): Calculated mass: 476.14; Observed mass: 476.9 [M+H]$^+$ (rt: 0.36 min).

Example 279

N-(3-(3-chloropyridin-4-yl)-5-(5-(1-methyl-1H-pyrazol-4-yl)-1H-benzo[d]-imidazol-1-yl)phenyl)acetamide The compound was prepared from the compound of Example 277(c) using the procedure of Example 277(d). $^1$H NMR (400 MHz, DMSO-d$_6$): δ 10.5 (s, 1H), 8.80 (m, 2H), 8.66-8.63 (m, 2H), 8.20 (s, 1H), 8.13 (s, 1H), 7.99 (s, 1H), 7.94 (s, 1H), 7.81 (s, 1H), 7.72 (d, 1H), 7.65 (d, 1H), 7.60 (d, 1H), 7.53 (s, 1H), 3.88 (s, 3H), 2.13 (s, 3H); LC-MS (ESI): Calculated mass: 442.13; Observed mass: 443.1 [M+H]$^+$ (rt: 0.28 min).

Example 280

N-(2',4'-difluoro-5-(5-(1-methyl-1H-pyrazol-4-yl)-1H-benzo[d]imidazol-1-yl)-[1,1'-biphenyl]-3-yl)pyrimidin-2-amine A solution of 1-(5-bromo-2',4'-difluoro-[1,1'-biphenyl]-3-yl)-5-(1-methyl-1H-pyrazol-4-yl)-1H-benzo[d]imidazole (0.075 g, 0.161 mmol) in 1,4-dioxane (3 ml) was degassed by N$_2$ bubbling for 5 min. Pyrimidin-2-amine (0.018 g, 0.193 mmol, 1.2 eq.) was added and the mixture was degassed for another 5 min. Pd$_2$(dba)$_3$ (0.014 g, 0.016 mmol, 0.1 eq.) and xantphos (0.037 g, 0.064 mmol, 0.4 eq.) and Cs$_2$CO$_3$ (0.209 g, 0.644 mmol, 4.0 eq) were added sequentially and the mixture was further degassed for 5 min. and then heated at 110° C. for 16 h. The mixture was filtered on celite bed, quenched and extracted as in Example 1(d). The solvent was distilled off to afford the crude residue which was purified by column chromatography (60-120 silica gel, 2% methanol in ethyl acetate) to yield the title product in 11.6% yield (0.09 g). $^1$H NMR (400 MHz, DMSO-d$_6$): δ 10.15 (s, 1H), 8.83 (S, 1H), 8.57-8.56 (D, 2H), 8.35 (s, 1H), 8.24 (s, 1H), 8.01-7.97 (s, 3H), 7.84-7.81 (m, 2H), 7.70-7.68 (m, 2H), 7.46-7.432 (m, 2H), 7.280-7.286 (m, 1H), 6.95-6.32 (t, 1H), 3.88 (s, 1H), LC-MS (ESI): Calculated mass: 479.48; Observed mass: 480.1 [M+H]$^+$ (rt: 1.52 min).

Example 281

N-(2',4'-difluoro-5-(5-(1-methyl-1H-pyrazol-4-yl)-1H-benzo[d]imidazol-1-yl)-[1,1'-biphenyl]-3-yl)thiazol-2-amine The compound was prepared from 1-(5-bromo-2',4'-difluoro-[1,1'-biphenyl]-3-yl)-5-(1-methyl-1H-pyrazol-4-yl)-1H-benzo[d]imidazole (0.05 g, 0.107 mmol) using the procedure of Example 280 and thiazol-2-amine (0.01 g, 0.10 mmol, 1.0 eq.) to yield the title product in 11.7% yield (0.06 g). $^1$H NMR (400 MHz CD$_3$OD): δ 9.45 (s, 1H), 8.39 (s, 1H), 8.11 (s, 1H), 8.01 (s, 1H), 7.94 (s, 1H), 7.86-7.83 (m, 2H), 7.74 (s, 1H), 7.67-7.65 (m, 1H), 7.45 (s, 1H), 7.28-7.27 (d, 1H), 7.16-7.11 (m, 2H), 6.89 (d, 1H), 3.95 (s, 3H) LC-MS (ESI): Calculated mass: 484.52; Observed mass: 485.2 [M+H]$^+$ (rt: 1.01 min).

Example 282

N-(2',4'-difluoro-5-(5-(1-methyl-1H-pyrazol-4-yl)-1H-benzo[d]imidazol-1-yl)-[1,1'-biphenyl]-3-yl)-1-methyl-1H-pyrazol-3-amine The compound was prepared from 1-(5-bromo-2',4'-difluoro-[1,1'-biphenyl]-3-yl)-5-(1-methyl-1H-pyrazol-4-yl)-1H-benzo[d]imidazole using the procedure of Example 280. $^1$H NMR (400 MHz CD$_3$OD): δ 8.72 (s, 1H), 8.19 (s, 1H), 7.97-7.90 (m, 3H), 7.79-7.77 (d, 1H), 7.70 (m, 1H), 7.63-7.61 (d, 1H), 7.56-7.55 (d, 1H), 7.45-7.40 (m, 2H), 7.23 (m, 1H), 7.13 (s, 1H), 5.86-5.85 (d, 1H), 3.87 (s, 3H), 3.74 (s, 3H) LC-MS (ESI): Calculated mass: 481.50; Observed mass: 482.1 [M+H]$^+$ (rt: 1.45 min).

Example 283

N-(2',4'-difluoro-5-(5-(1-methyl-1H-pyrazol-4-yl)-1H-benzo[d]imidazol-1-yl)-[1,1'-biphenyl]-3-yl)-1-methyl-1H-pyrazol-4-amine The compound was prepared from 1-(5-bromo-2',4'-difluoro-[1,1'-biphenyl]-3-yl)-5-(1-methyl-1H-pyrazol-4-yl)-1H-benzo[d]imidazole using the procedure of Example 280. $^1$H NMR (400 MHz, DMSO-d$_6$): δ 9.13 (s, 1H), 8.27 (s, 1H), 8.11 (s, 1H), 8.02-8.00. (d, 2H), 7.821 (s, 1H), 7.74-7.70 (m, 3H), 7.48 (m, 2H), 7.29 (m, 1H), 7.09-7.04 (m, 3H), 3.92 (s, 3H), 3.84 (s, 3H), Calculated mass: 481.50 observed mass: 482.1 [M+H]$^+$ (rt: 1.36 min).

Example 284

N-(2',4'-difluoro-5-(5-(1-(3-hydroxy-3-methylbutyl)-1H-pyrazol-4-yl)-1H-benzo[d]imidazol-1-yl)-[1,1'-biphenyl]-3-yl)ethanesulfonamide The compound was prepared from 4-(4-(1-(5-amino-2',4'-difluoro-[1,1'-biphenyl]-3-yl)-1H-benzo[d]imidazol-5-yl)-1H-pyrazol-1-yl)-2-methylbutan-2-ol (88 mg, 0.185 mmol) using the procedure of Example 2(b) and ethanesulfonyl chloride (28.6 mg, 0.370 mmol, 1.2 eq.) to give the product in 33.6% yield (35 mg)$^1$H NMR (300 MHz, DMSO-d$_6$): δ 10.42 (s, 1H), 8.92 (s, 1H), 8.30 (s, 1H), 8.01-7.97 (d, 2H), 7.69 (m, 3H), 7.59 (d, 2H), 7.56 (m, 2H), 7.32 (m, 1H), 4.30 (m, 2H), 3.31-3.28 (m, 4H), 1.8 (m, 2H), 1.28-1.24 (t, 3H), 1.15 (s, 6H), Calculated mass: 565.63; Observed mass: 566.2 [M+H]$^+$ (rt: 1.40 min).

Example 285

N-(2',4'-difluoro-5-(6-(6-oxo-1,6-dihydropyridin-3-yl)-3H-imidazo[4,5-b]pyridin-3-yl)[1,1'-biphenyl]-3-yl)acetamide A solution of N-(5-(6-(6-(benzyloxy)pyridin-3-yl)-3H-imidazo[4,5-b]pyridin-3-yl)-2',4'-difluoro-[1,1'-biphenyl]-3-yl)acetamide (0.10 g, 0.182 mmol) in TFA (4 ml) was stirred at RT for 16 h. The mixture was concentrated on vacuo, quenched with sodium bicarbonate and extracted as in Example 1(d). The solvent was distilled off to give the product in 84.3% yield (0.70 g) $^1$H NMR (400 MHz, DMSO-$d_6$): δ 10.42 (s, 1H), 8.98 (s, 1H), 8.68-8.67 (D, 1H), 8.43 (d, 1H), 8.31 (s, 1H), 7.99-7.96 (dd, 1H), 7.89 (s, 2H), 7.76-7.70 (m, 2H), 7.49-7.43 (m, 1H), 7.31-7.26 (m, 1H), 6.51-6.48 (d, 1H), 2.13 (s, 3H); LC-MS (ESI): Calculated mass 457.43: Observed mass: 458.1[M+H]$^+$ (rt: 0.68 min).

Example 286

N-(2',4'-difluoro-5-(6-(6-oxo-1,6-dihydropyridin-3-yl)-3H-imidazo[4,5-b]-pyridin-3-yl)-[1,1'-biphenyl]-3-yl)ethanesulfonamide A solution of N-(5-(6-(6-(benzyloxy)pyridin-3-yl)-3H-imidazo[4,5-b]pyridin-3-yl)-2',4'-difluoro-[1,1'-biphenyl]-3-yl)ethanesulfonamide (0.140 g, 0.234 mmol) in TFA (5 ml) was stirred at RT for 16 h. The mixture was concentrated on vacuo, quenched with sodium bicarbonate and extracted as in Example 1(d). The solvent was distilled off to give the product in 23.7% yield (0.028 g). $^1$H NMR (400 MHz, DMSO-$d_6$): δ 10.35 (s, 1H), 9.07 (s, 1H), 8.70 (s, 1H), 8.44 (s, 1H), 8.01 (d, 1H), 7.93 (s, 2H), 7.78-7.72 (m, 2H), 7.48-7.45 (d, 2H), 7.30-7.26 (t, 1H), 6.52-6.50 (d, 1H), 3.30-3.28 (q, 2H), 1.28-1.25 (t, 3H); LC-MS (ESI): Calculated mass: 507.51; Observed mass: 508.1 [M+H]$^+$ (rt: 0.1 min).

Example 287

N-(2',4'-difluoro-5-(5-(6-oxo-1,6-dihydropyridin-3-yl)-1H-benzo[d]imidazol-1-yl)-[1,1'-biphenyl]-3-yl)acetamide The compound was prepared from N-(5-(5-(6-(benzyloxy)pyridin-3-yl)-1H-benzo[d]imidazol-1-yl)-2',4'-difluoro-[1,1'-biphenyl]-3-yl)acetamide (0.15 g, 0.274 mmol) using the procedure of Example 286 to afford the product in 11.2% yield (0.014 g). $^1$H NMR (400 MHz, CD$_3$OD): δ 8.92 (s, 1H), 8.20-8.19 (s, 1H), 8.05-8.02 (dd, 1H), 7.94 (s, 1H), 7.83-7.78 (m, 2H), 7.74 (s, 1H), 7.67-7.61 (m, 2H), 7.55 (s, 1H), 7.16-7.09 (m, 2H), 6.69-6.67 (d, 1H), 2.65 (s, 5H), 2.19 (s, 3H); LC-MS (ESI): Calculated mass 456.44: Observed mass: 457.1[M+H]$^+$ (rt: 0.68 min).

Example 288

N-(2',4'-difluoro-5-(5-(6-oxo-1,6-dihydropyridin-3-yl)-1H-benzo[d]imidazol-1-yl)-[1,1'-biphenyl]-3-yl)ethane sulfonamide The compound was prepared from N-(5-(5-(6-(benzyloxy)pyridin-3-yl)-1H-benzo[d]imidazol-1-yl)-2',4'-difluoro-[1,1'-biphenyl]-3-yl)ethanesulfonamide (0.25 g, 0.419 mmol) using the procedure of Example 286 to afford the product in 82.5% yield (0.175 g). $^1$H NMR (400 MHz, DMSO-$d_6$): δ 10.38 (s, 1H), 9.06 (S, 1H), 8.025-7.954 (m, 2H), 7.83-7.84 (d, 1H), 7.82-7.72 (m, 2H), 7.68-7.66 (d, 1H), 7.61 (s, 2H), 7.50-7.43 (m, 2H), 7.31-7.26 (t, 1H), 6.50-6.47 (d, 1H), 3.33-3.27 (q, 2H), 1.28-1.24 (t, 3H), LC-MS (ESI): Calculated mass: 506.52; Observed mass: 507.0 [M+H]$^+$ (rt: 0.085 min).

Example 289

N-(2',4'-difluoro-5-(5-(6-oxo-1,6-dihydropyridin-3-yl)-1H-benzo[d]imidazol-1-yl)-[1,1'-biphenyl]-3-yl)cyclopropanesulfonamide The compound was prepared from N-(5-(5-(6-(benzyloxy)pyridin-3-yl)-1H-benzo[d]imidazol-1-yl)-2',4'-difluoro-[1,1'-biphenyl]-3-yl)cyclopropanesulfonamide (0.145 g, 0.238 mmol) using the procedure of Example 286 to afford the product in 6.1% yield (0.09 g). $^1$H NMR (400 MHz, CD$_3$OD): δ 9.19 (s, 1H), 8.07-8.04 (dd, 1H), 7.99 (s, 1H), 7.85-7.82 (dd, 2H), 7.76-7.71 (m, 2H), 7.90 (m, 2H), 7.64-7.59 (m, 1H), 7.15-7.13 (m, 2H), 6.71-7.68 (d, 1H), 2.76-2.72 (m, 1H), 1.17-1.12 (m, 2H), 1.06-1.02 (m, 2H), Calculated mass: 518.53; Observed mass: 519.3 [M+H]$^+$ (rt: 0.8 min).

Example 290

N-(5-(6-(2-aminopyridin-4-yl)-3H-imidazo[4,5-b]pyridin-3-yl)-2',4'-difluoro-[1,1'-biphenyl]-3-yl)cyclopropanesulfonamide To a solution of tert-butyl(5-(3-(5-(cyclopropanesulfonamido)-2',4'-difluoro-[1,1'-biphenyl]-3-yl)-3H-imidazo[4,5-b]pyridin-6-yl)pyridin-2-yl)carbamate (0.2 g, 0.32 mmol) in DCM (5 ml) was added TFA (1.2 ml) at 0° C. The mixture was stirred at RT for 16 h. The mixture was concentrated on vacuo, quenched with sodiumbicarbonate and extracted as in Example 1(d). The solvent was distilled off to afford the product in 17.9% yield (0.30 g). $^1$H NMR (400 MHz, DMSO-$d_6$): δ 10.15 (s, 1H), 9.09 (S, 1H), 8.90 (s, 1H), 8.69 (s, 1H), 8.04-8.03 (d, 1H), 7.93 (s, 1H), 7.79 (s, 1H), 7.74-7.72 (d, 1H), 7.50 (s, 1H), 7.45-7.38 (m, 2H), 7.34 (s, 1H), 7.30-7.26 (t, 1H), 2.76-2.72 (m, 1H), 1.17-1.12 (m, 2H), 1.06-1.02 (m, 2H); LC-MS (ESI): Calculated mass: 518.54; Observed mass: 519.2 [M+H]$^+$ (rt: 0.71 min).

Example 291

N-(5-(5-(2-aminopyridin-4-yl)-1H-benzo[d]imidazol-1-yl)-2',4'-difluoro-[1,1'-biphenyl]-3-yl)cyclopropanesulfonamide The compound was prepared from tert-butyl(5-(1-(5-(cyclopropanesulfonamido)-2',4'-difluoro-[1,1'-biphenyl]-3-yl)-1H-benzo[d]imidazol-5-yl)pyridin-2-yl)-carbamate (0.2 g, 0.32 mmol) using the procedure of Example 290 to afford the product in 9.0% yield (0.18 g). $^1$H NMR (400 MHz, DMSO-$d_6$): δ 10.32 (s, 1H), 8.84 (s, 1H), 8.30 (s, 1H), 8.05-8.03. (s, 3H), 7.88-7.86 (d, 1H), 7.82-7.79 (m, 2H), 7.62-7.60 (d, 2H), 7.52-7.47 (m, 2H), 7.39-7.38 (d, 1H), 7.31-7.29 (m, 2H), 1.03-1.01 (d, 4H), Calculated mass: 517.55; Observed mass: 518.1 [M+H]$^+$ (rt: 0.41 min).

Example 292

N-(2',4'-difluoro-5-(5-(5-methyl-1,3,4-thiadiazol-2-yl)-1H-benzo[d]imidazol-1-yl)-[1,1'-biphenyl]-3-yl) cyclopropanesulfonamide A solution of N-(2',4'-difluoro-5-(5-(4,4,5,5-tetramethyl-1,3,2-dioxaborolan-2-yl)-1H-benzo[d]imidazol-1-yl)-[1,1'-biphenyl]-3-yl)cyclopropanesulfonamide (0.15 g, 0.272 mmol) in 1,2-dimethoxyethane (5 ml) was degassed by $N_2$ bubbling for 5 min. 2-Bromo-5-methyl-1,3,4-thiadiazole (0.058 g, 0.326 mmol, 1.2 eq.) was added and the mixture was degassed for another 5 min. Pd(dppf)Cl$_2$ (0.011, 0.013 mmol, 0.05 eq.) and aqueous sodium carbonate (0.072, 0.680 mmol, 2.5 eq.) were added and the procedure of Example 1(d) was followed. The crude residue of the product was purified by column chromatography (60-120 silica gel, 80% ethyl acetate in hexane) to yield the desired title product in 4.2% yield (0.006 g). $^1$H NMR (400 MHz, DMSO-d$_6$): δ 10.21 (s, 1H), 8.81 (s, 1H), 8.34-8.33 (s, 1H), 8.00-7.98 (dd, 1H), 7.84 (d, 1H), 7.79-7.73 (m, 1H), 7.54 (s, 1H), 7.49-7.42 (m, 2H), 7.29-7.24 (m, 1H), 3.17-3.16 (d, 2H), 2.85-2.84 (m, 1H), 2.79 (s, 3H), 1.01-0.99 (m, 4H); LC-MS (ESI): Calculated mass: 523.58; Observed mass: 523.7 [M+H]$^+$ (rt: 1.50 min).

Example 293

N-(2',4'-difluoro-5-(5-(5-fluoropyridin-2-yl)-1H-benzo[d]imidazol-1-yl)-[1,1'-biphenyl]-3-yl)cyclopropanesulfonamide A solution of N-(2',4'-difluoro-5-(5-(4,4,5,5-tetramethyl-1,3,2-dioxaborolan-2-yl)-1H-benzo[d]imidazol-1-yl)-[1,1'-biphenyl]-3-yl)cyclopropanesulfonamide (0.15 g, 0.272 mmol) in 1,2-dimethoxyethane (5 ml) was degassed by $N_2$ bubbling for 5 min. 2-Bromo-5-fluoropyridine (0.057 g, 0.326 mmol, 1.2 eq.) was added and the mixture was degassed for another 5 min. Pd(dppf)Cl$_2$ (0.011, 0.013 mmol, 0.05 eq.) and aqueous sodium carbonate (0.072, 0.680 mmol, 2.5 eq.) were added and the procedure of Example 1(d) was followed. The crude residue of the product was purified by column chromatography (60-120 silica gel, 80% ethyl acetate in hexane) to yield the title product in 14.1% yield (0.02 g). $^1$H NMR (400 MHz, DMSO-d$_6$): δ 10.23 (s, 1H), 8.75 (s, 1H), 8.68-8.67 (d, 1H), 8.48 (d, 1H), 8.20-8.13 (m, 2H), 7.86-7.743 (m, 3H), 7.61-7.60 (d, 2H), 7.51-7.43 (m, 2H), 7.30-7.25 (m, 1H), 2.89-2.86 (t, 1H), 1.03-1.02 (d, 4H); LC-MS (ESI): Calculated mass: 520.53; Observed mass: 521.2 [M+H]$^+$ (rt: 1.64 min).

Example 294

N-(3-(3-fluoropyridin-2-yl)-5-(5-(1-(2-morpholinoethyl)-1H-pyrazol-4-yl)-1H-benzo[d]imidazol-1-yl) phenyl)methane sulphonamide a) N-(3-nitro-5-(4,4,5,5-tetramethyl-1,3,2-dioxaborolan-2-yl)phenyl)acetamide To a degassed (N$_2$ bubbling) solution of N-(3-bromo-5-nitrophenyl)acetamide (25 g, 96.89 mmol) in 1,4-dioxane (150 ml) were added 4,4,4',4',5,5,5',5'-octamethyl-2,2'-bi(1,3,2-dioxaborolane) (29.5 g, 116.27 mmol, 1.2 eq), Pd(dppf) Cl$_2$ (7.9 g, 9.68 mmol, 0.1 eq.) and potassium acetate (28.5 g, 290.69 mmol, 3 eq.). The mixture was heated at 100° C. in a sealed tube for 6 h. The mixture was diluted with ethyl acetate and filtered over a pad of celite. The solvent was distilled off to afford the product (24 g). $^1$H NMR (300 MHz, DMSO-d$_6$): δ 10.44 (s, 1H), 8.72 (t, 1H), 8.18-8.15 (m, 1H), 8.03 (d, 1H), 2.08 (s, 1H), 1.30 (s, 9H).

b) N-(3-(3-fluoropyridin-2-yl)-5-nitrophenyl)acetamide

A solution of N-(3-nitro-5-(4,4,5,5-tetramethyl-1,3,2-dioxaborolan-2-yl)phenyl-acetamide (10 g, 32.67 mmol) in 1,2-dimethoxyethane (100 ml) was degassed by N$_2$ bubbling for 5 min. 2-Chloro-3-fluoro pyridine (4.29 g, 32.67 mmol) was added and the mixture was degassed for another 5 min. Pd(dppf)cl$_2$ (2.6 g, 3.26 mmol) and aqueous sodium carbonate (10.39 g, 98.03 mmol) were added and the procedure of Example 1(d) was followed. The crude residue of the product was purified by column chromatography (60-120 silica gel, 3% methanol in chloroform) to yield the title product in 70% yield (6.3 g). $^1$H NMR (300 MHz, DMSO-d$_6$): δ10.64 (s, 1H), 8.74 (m, 1H), 8.62 (m, 1H), 8.55, (brs, 1H), 8.44 (brs, 1H), 7.93 (m, 1H), 7.60 (m, 1H), 2.12 (s, 3H).

c) N-(3-amino-5-(3-fluoropyridin-2-yl)phenyl)acetamide

To a solution of N-(3-(3-fluoropyridin-2-yl)-5-nitrophenyl)acetamide (5 g, 18.18 mmol) in THF (50 ml), Zn (11.8 g, 181.18 mmol) was added followed by slow addition of solution of NH$_4$Cl (9.7 g, 181.18 mmol) in 20 ml water. The mixture was stirred at RT for 1 h. The mixture was filtered through celite and bed washed with ethyl acetate. The mixture was diluted with ethyl acetate and washed with water and brine solution, dried over sodium sulphate and distilled to give the product in 90% yield (4.2 g). LC-MS (ESI): Calculated mass: 245; Observed mass: 246.1 [M+H]$^+$ (rt: 0.21 min).

d) N-(3-((4-bromo-2-nitrophenyl)amino)-5-(3-fluoropyridin-2-yl)phenyl)acetamide

Solution of 4-bromo-1-fluoro-2-nitrobenzene (3.0 g, 13.63 mmol), N-(3-amino-5-(3-fluoropyridin-2-yl)phenyl) acetamide (4.0 g, 16.36 mmol), and potassium fluoride (0.95 g, 16.36 mmol) in DMF was heated at 130° C. for 16 h. The mixture was quenched and extracted as in Example 1(d). The solvent was distilled off to afford the crude residue which was purified by column chromatography (60-120 silica gel, 30% ethyl acetate in hexane) to yield the title product in 50% yield (3.4 g). $^1$H NMR (300 MHz, DMSO-d$_6$): δ 8.55 (brs, 1H), 8.23 (brs, 1H), 7.96 (m, 2H), 7.85 (m, 2H), 7.67 (d, 1H), 7.51 (m, 2H), 7.21 (d, 1H), 2.07 (s, 3H).

e) N-(3-((2-amino-4-bromophenyl)amino)-5-(3-fluoropyridin-2-yl)phenyl)acetamide

To a solution of the compound of Example 294(d) (3.4 g, 7.64 mmol) in THF (35 ml) were added a solution of ammonium chloride (4.08 g, 76.40 mmol, 10 eq.) in water (15 ml) and zinc (4.98 g, 76.40 mmol, 10 eq.). The mixture was stirred at RT for 4 h and filtered. The filtrate was diluted with water and extracted as in Example 1(d). The solvent was distilled off to afford the title product in 75% yield (2.4 g). LC-MS (API): Calculated mass: 415.2, Observed mass: 417.1 [M+H]$^+$ (rt: 1.35 min).

f) N-(3-(5-bromo-1H-benzo[d]imidazol-1-yl)-5-(3-fluoropyridin-2-yl)phenyl)-acetamide A mixture of the compound of Example 294(e) (2.4 g, 5.78 mmol) and formic acid (24 ml) was heated at 90° C. for 6 h. The formic acid was distilled off and the crude was dissolved in ethyl acetate. The ethyl acetate layer was washed with water, brine and dried over sodium sulphate. The solvent was distilled off to afford the title product in 73% yield (1.8 g). LC-MS (ESI): Calculated mass: 425.2; Observed mass: 426.7 [M+H]$^+$ (rt: 1.38 min).

g) 3-(5-bromo-1H-benzo[d]imidazol-1-yl)-5-(3-fluoropyridin-2-yl)aniline

To a solution of the compound of Example 294(f) (0.6 g, 1.41 mmol) in ethanol (20 ml) was added solution of NaOH (0.56 g, 14.11 mmol) in 5 ml of water and the mixture was heated at 90° C. for 2 h. The mixture was concentrated and the crude residue was quenched with water and extracted as in Example 1(d). The solvent was distilled off to afford the product in 55% yield (0.3 g). LC-MS (API): Calculated mass: 382.0; Observed mass: 385.1 [M+H]$^+$ (rt: 1.32 min).

h) N-(3-(5-bromo-1H-benzo[d]imidazol-1-yl)-5-(3-fluoropyridin-2-yl)phenyl methane sulphonamide To a solution of the compound of Example 294(g) (0.15 g, 0.39 mmol) in DCM was added pyridine (0.093 g, 1.17 mmol) followed by methane sulfonyl chloride (0.054 g, 0.47 mmol). The mixture was stirred for 3 h, quenched with water and extracted as in Example 2(b). The solvent was distilled off to afford the crude residue which was purified by 60-120 mesh silicagel, to give the product in 60% yield (120 mg). LC-MS (ESI): Calculated mass: 460.1; Observed mass: 460.2 [M+H]$^+$ (rt: 1.54 min).

i) N-(3-(3-fluoropyridin-2-yl)-5-(5-(1-(2-morpholinoethyl)-1H-pyrazol-4-yl)-1H-benzo[d]imidazol-1-yl)phenyl)methane sulfonamide A solution of the compound of Example 294(h) (0.12 g, 0.260 mmol) in 1,2-dimethoxyethane (8 ml) was degassed by N$_2$ bubbling for 5 min. 4-(2-(4-(4,4,5,5-Tetramethyl-1,3,2-dioxaborolan-2-yl)-1H-pyrazol-1-yl)ethyl) morpholine (0.096 g, 0.313 mmol) was added and the mixture was degassed for another 5 min. Aqueous sodium carbonate (0.083 g, 0.782 mmol) and Pd(dppf)Cl$_2$ (0.021 g, 0.026 mmol) were added and the procedure of Example 1(d) was followed. The crude residue of the product was purified by preparative HPLC to give the title product in 10% yield (15 mg). $^1$H NMR (400 MHz, CD$_3$OD): δ 8.56 (d, 2H), 8.11 (s, 1H), 7.94-7.90 (m, 4H), 7.80-7.72 (m, 2H), 7.66-7.62 (m, 2H), 7.52-7.50 (m, 1H), 4.33 (t, 2H), 3.68-3.64 (m, 4H), 3.12 (s, 3H), 2.85 (m, 2H), 2.52 (m, 4H); LC-MS (ESI): Calculated mass: 561.2; Observed mass: 561.8 [M+H]$^+$ (rt: 0.10 min).

Example 295

N-(3-(3-fluoropyridin-2-yl)-5-(5-(1-methyl-1H-pyrazol-4-yl)-1H-benzo[d]-imidazol-1-yl)phenyl)cyclopropanesulfonamide The compound was prepared from N-(3-(5-bromo-1H-benzo[d]imidazol-1-yl)-5-(3-fluoropyridin-2-yl)phenyl)cyclopropanesulfonamide (150 mg, 0.30 mmol) using the method of Example 1(i) to give the product in 15% yield (10 mg). $^1$H NMR (400 MHz, CDCl3): δ 8.53 (d, 1H), 7.92 (d, 3H), 7.80 (s, 1H), 7.72 (d, 2H), 7.6.3-7.55 (m, 4H), 7.41-7.28 (m, 1H), 3.92 (s, 3H), 2.85-2.80 (m, 1H), 1.31-1.17 (m, 2H) 1.03-1.01 (m, 2H); LC-MS (ESI): Calculated mass: 488.5; Observed mass: 489.0 [M+H]$^+$ (rt: 0.59 min).

Example 296

N-(3-(3-methoxypyridin-2-yl)-5-(5-(1-methyl-1H-pyrazol-4-yl)-1H-benzo[d]-imidazol-1-yl)phenyl) cyclopropanesulfonamide The compound was prepared from N-(3-(5-bromo-1H-benzo[d]imidazol-1-yl)-5-(3-methoxypyridin-2-yl)phenyl) cyclopropanesulfonamide (200 mg, 0.40 mmol) using the procedure of Example 1(i) to give the title product in 20% yield (20 mg). $^1$H NMR (400 MHz, DMSO): δ 10.3 (s, 1H), 8.60 (d, 1H), 8.32-8.31 (d, 1H), 8.20 (s, 1H) 7.99 (d, 1H), 7.94 (s, 1H), 7.92-7.89 (d, 2H), 7.66-7.63 (m, 3H), 7.54 (d, 1H), 7.47-7.43 (m, 1H), 4.33 (d, 2H), 3.42-3.26 (m, 2H), 1.34-1.24 (t, 3H), 0.63-0.60 (t, 2H), 0.49-0.48 (t, 2H); LC-MS (ESI): Calculated mass: 500.5; Observed mass: 500.8 [M+H]$^+$ (rt: 0.45 min).

Example 297

N-(2',4'-difluoro-5-(5-(1-methyl-1H-imidazol-4-yl)-1H-benzo[d]imidazol-1-yl)-[1,1'-biphenyl]-3-yl) acetamide a) N-(2',4'-difluoro-5-(5-(4,4,5,5-tetramethyl-1,3,2-dioxaborolan-2-yl)-1H-benzo[d]imidazol-1-yl)-[1,1'-biphenyl]-3-yl)acetamide To a degassed (N$_2$ bubbling) solution of compound of Example 1(h) (0.3 g, 0.68 mmol) in 1,2-dimethoxyethane (10 ml) were added 4,4,4',4',5,5,5',5'-octamethyl-2,2'-bi(1,3,2-dioxaborolane) (0.26 g, 1.02 mmol, 1.5 eq.), Pd(dppf)Cl$_2$ (55 mg, 0.068 mmol, 0.1 eq.) and potassium acetate (0.2 g, 2.04 mmol, 3 eq.) and the mixture was heated at 80° C. in a sealed tube for 3 h. The mixture was diluted with ethyl acetate and filtered over a pad of celite. The solvent was distilled off to afford the crude residue which was purified by column chromatography (60-120 silica gel, 70% ethyl acetate in hexane) to yield the title product in 60% yield (0.2 g). LC-MS (ESI): Calculated mass: 489.32; Observed mass: 490.5 [(M+H]$^+$ (rt: 1.83 min).

b) N-(2',4'-difluoro-5-(5-(1-methyl-1H-imidazol-4-yl)-1H-benzo[d]imidazol-1-yl)-[1,1'-biphenyl]-3-yl) acetamide A solution of the compound of Example 297(a) (0.1 g, 0.204 mmol) in 1,2-dimethoxyethane (15 ml) was degassed by N$_2$ bubbling for 5 min. 4-Bromo-1-methyl imidazole (49 mg, 0.306 mmol, 1.5 eq.) was added and the mixture was degassed for another 5 min. Pd(dppf)Cl$_2$ (16 mg, 0.0204 mmol, 0.1 eq.) and aqueous sodium carbonate (65 mg, 0.612 mmol, 3.0 eq.) were added and the procedure of Example 1(d) was followed. The crude residue of the product was purified by column chromatography (60-120 silica gel, 5% methanol in chloroform) to yield the title product in 11% yield (10 mg). $^1$H NMR (400 MHz, DMSO-d6): δ 10.5 (s, 1H), 9.05-9.0 (br S, 1H), 8.8 (s, 1H), 8.26 (s, 1H), 8.18 (s, 1H), 8.13 (s, 1H), 7.87-7.76 (m, 5H), 7.56 (s, 1H), 7.48 (dt, 1H), 7.3-7.29 (dt, 1H), 3.9 (s, 3H), 2.15 (s, 3H); LC-MS (ESI): Calculated mass: 443.45; Observed mass: 444.1 [M+H]+ (rt: 0.632 min).

Example 298

1-(2',4'-difluoro-5-(5-(1-methyl-1H-imidazol-4-yl)-1H-benzo[d]imidazol-1-yl)-[1,1'-biphenyl]-3-yl)-3-(furan-2-ylmethyl)urea a) 2',4'-difluoro-5-(5-(1-methyl-1H-imidazol-4-yl)-1H-benzo[d]imidazol-1-yl)-[1,1'-biphenyl]-3-amine The compound was prepared from the compound of Example 297 (0.4 g, 2.26 mmol) using the procedure of Example 2(a) to afford the product in 27% yield (0.1 g). LC-MS (ESI): Calculated mass: 401.41; Observed mass: 402.1 [M+H]+ (rt: 1.198 min).

b) 1-(2',4'-difluoro-5-(5-(1-methyl-1H-imidazol-4-yl)-1H-benzo[d]imidazol-1-yl)-[1,1'-biphenyl]-3-yl)-3-(furan-2-ylmethyl)urea To a solution of the compound of Example 298(a) (50 mg, 0.124 mmol) in DCM was added furfuryl isocyanate (0.01 ml, 0.149 mmol, 1.2 eq.) followed by DIPEA (0.06 ml, 0.37 mmol, 3 eq.). The mixture was stirred for overnight and quenched and extracted as in Example 1(d). The solvent was distilled off to afford the crude residue which was purified by preparative HPLC to give the product in 40% yield (20 mg). $^1$H NMR (300 MHz, DMSO-d6): δ 9.16 (s, 1H), 9.14 (s, 1H), 8.8 (s, 1H), 8.27-8.22 (d, 2H), 7.99 (s, 1H), 7.89 (s, 1H), 7.87 (s, 1H), 7.81-7.73 (m, 2H), 7.62 (s, 2H), 7.49-7.42 (m, 2H), 7.31-7.26 (dt, 1H), 6.91-6.88 (t, 1H), 6.44-6.42 (m, 1H), 6.3-6.29 (m, 1H), 4.35-4.33 (d, 2H), 3.94 (s, 3H). LC-MS (ESI): Calculated mass: 524.52; Observed mass: 525 [M+H]+ (rt: 0.632 min).

Example 299

N-(2',4'-difluoro-5-(5-(1-methyl-1H-imidazol-4-yl)-1H-benzo[d]imidazol-1-yl)-[1,1'-biphenyl]-3-yl)ethanesulfonamide The compound was prepared from the compound of Example 298(a) using the procedures of Example 294(h). $^1$H NMR (300 MHz, CD$_3$OD): δ 8.4 (s, 1H), 8.0 (s, 1H), 7.71-7.69 (dd, 1H), 7.59-7.41 (m, 6H), 7.04-7.01 (m, 2H), 3.69 (S, 3H), 3.22-3.13 (q, 2H), 1.29-1.26 (t, 3H); LC-MS (ESI): Calculated mass: 493.53; Observed mass: 494 [M+H]+ (rt: 0.632 min).

Example 300

N-(2',4'-difluoro-5-(5-(1-methyl-1H-imidazol-5-yl)-1H-benzo[d]imidazol-1-yl)-[1,1'-biphenyl]-3-yl)ethanesulfonamide The compound was prepared from the compound of Example 200(b) (0.5 g, 1.02 mmol) using the procedures of Example 297 to give the title product in 16% yield (15 mg). $^1$H NMR (300 MHz, CD$_3$OD): δ 9.01 (s, 1H), 8.73 (s, 1H), 8.01 (s, 1H), 7.88-7.86 (d, 1H), 7.71-7.70 (m, 1H), 7.65-7.56 (m, 4H), 7.51-7.5 (m, 1H), 7.13-7.09 (m, 2H), 3.91 (s, 3H), 3.28-3.22 (m, 2H), 1.38-1.35 (t, 3H); LC-MS (ESI): Calculated mass: 493.53; Observed mass: 493.9 [M+H]+ (rt: 1.232 min).

Example 301

N-(3-(3-fluoropyridin-2-yl)-5-(5-(1-(2-morpholinoethyl)-1H-pyrazol-4-yl)-1H-benzo[d]imidazol-1-yl)phenyl)methanesulfonamide The title compound was prepared from the title compound of Example 294(f) using the procedures of Example 294(i). $^1$H NMR (400 MHz, DMSO-d$_6$): δ 10.43 (s, 1H), 8.25 (s, 1H), 8.21 (s, 1H), 8.16 (s, 1H), 7.99 (s, 1H), 7.95 (s, 1H), 7.94-7.88 (m, 1H), 7.86 (s, 1H), 7.67-7.65 (m, 1H), 7.61-7.57 (m, 2H), 4.26-4.23 (t, 2H), 3.57-3.55 (t, 4H), 2.77-2.67 (t, 2H), 2.43 (m, 4H), 2.13 (s, 3H): LC-MS (ESI): Calculated mass: 525.58; Observed mass: 526.3 [M+H]+ (rt: 0.11 min).

Example 302

N-(5-(5-(4-acetamido-1H-pyrazol-1-yl)-1H-benzo[d]imidazol-1-yl)-2',4'-difluoro-[1,1'-biphenyl]-3-yl)acetamide To a solution of compound of Example 1(h) (120 mg, 0.271 mmol) in DMF (20 ml) were added N-(1H-pyrazol-4-yl)acetamide (50 mg, 0.407 mmol, 1.5 eq), copper(I) oxide (4.9 mg, 0.027 mmol, 0.1 eq) and cesium carbonate (176 mg, 0.5429 mmol, 2.0 eq) and then heated at 110° C. for 48 h. The mixture was quenched and extracted as in Example 1(d). The solvent was distilled off to afford the crude residue which was purified by preparative HPLC to yield the title product in 12.8% yield (16 mg). $^1$H NMR (400 MHz, DMSO-d$_6$): δ 10.41 (s, 1H), 10.15 (s, 1H), 8.85 (s, 1H), 8.54 (s, 1H), 8.14 (d, 1H), 8.07 (t, 1H), 7.87-7.71 (m, 5H), 7.53 (s, 1H), 7.47-7.41 (m, 1H), 7.28-7.23 (m, 1H), 2.11 (s, 3H), 2.02 (s, 3H), LC-MS (ESI): Calculated mass: 461.54; Observed mass: 462.1 [M+H]+ (rt: 0.7 min).

Example 303

Ethyl 2-(4-(3-(5-acetamido-2',4'-difluoro-[1,1'-biphenyl]-3-yl)-3H-imidazo[4,5-b]pyridin-6-yl)-1H-1,2,3-triazol-1-yl)acetate The title compound was prepared from the title compound of Example 131(c) using the procedures of Example 131(d). $^1$H NMR (400 MHz, DMSO-d$_6$): 8.71 (s, 1H), 8.64 (s, 1H), 8.26 (s, 1H), 8.07 (s, 1H), 7.93 (s, 1H), 7.91 (s, 1H), 7.84 (s, 1H), 7.78-7.73 (m, 2H), 7.54 (s, 1H), 7.48-7.42 (m, 1H), 7.29-7.24 (dt, 1H), 5.48 (s, 2H), 4.25-4.19 (q, 2H), 2.13 (s, 3H), 1.27-1.24 (t, 3H): LC-MS (ESI): Calculated mass: 517.49; Observed mass: 518.4 [M+H]+ (rt: 1.37 min).

Example 304

N-(4'-fluoro-5-(6-(thiazol-2-yl)-3H-imidazo[4,5-b]pyridin-3-yl)-[1,1'-biphenyl]-3-yl)acetamide A solution of N-(5-(6-bromo-3H-imidazo[4,5-b]pyridin-3-yl)-4'-fluoro-[1,1'-biphenyl]-3-yl)acetamide (300 mg, 0.705 mmol) in THF (8 ml) was degassed by N$_2$ bubbling for 5 min. Thiazol-2-yl zinc(II) bromide (485 mg, 2.11 mmol, 3.0 eq.) was added and the mixture was degassed for another 5 min. Pd(dppf)Cl$_2$ (57 mg, 0.070 mmol, 0.1 eq.) aqueous sodium carbonate were added and the procedure of Example 1(d) was followed. The crude residue of the product was purified by preparative HPLC to yield the title product in 40% yield (120 mg) $^1$H NMR (400 MHz, DMSO-D6): 610.43 (s, 1H), 8.78 (s, 1H), 8.45 (s, 1H), 8.08 (s, 1H), 8.01

(d, 1H), 7.94 (d, 1H), 7.85-7.73 (m, 4H), 7.55 (s, 1H), 7.45 (t, 1H), 7.27 (t, 1H), 2.13 (s, 3H), LC-MS (ESI): Calculated mass: 429.47; Observed mass: 430.00 [M+H]$^+$ (rt: 1.33 min).

Example 305

N-(2',4'-difluoro-5-(5-(thiazol-2-yl)-1H-benzo[d]imidazol-1-yl)-[1,1'-biphenyl]-3-yl)methanesulfonamide The compound was prepared using the procedure of Example 304 starting from the compound of Example 208(a) to give the product in 10.4% yield (12 mg). $^1$H NMR (400 MHz, DMSO-D6): δ10.31 (s, 1H), 8.80 (s, 1H), 8.35 (s, 1H), 8.02 (d, 1H), 7.94 (d, 1H), 7.83-7.75 (m, 3H), 7.61 (s, 1H), 7.57 (d, 1H), 7.49-7.43 (m, 2H), 7.28 (dt, 1H), 3.19 (s, 3H), LC-MS (ESI): Calculated mass: 482.53; Observed mass: 483.2.

Example 306

N-(2',4'-difluoro-5-(5-(thiazol-2-yl)-1H-benzo[d]imidazol-1-yl)-[1,1'-biphenyl]-3-yl)ethanesulfonamide The compound was prepared from the compound of Example 200(b) using the procedure of Example 304 to give the product in 9.6% yield (15 mg). $^1$H NMR (400 MHz, DMSO-D6): δ10.35 (s, 1H), 8.81 (s, 1H), 8.35 (s, 1H), 8.01 (d, 1H), 7.93 (s, 1H), 7.81-7.76 (m, 3H), 7.58 (d, 2H), 7.49-7.44 (m, 2H), 7.29 (t, 1H), 3.30 (q, 2H), 1.26 (t, 3H), LC-MS(ESI): Calculated mass: 496.55; Observed mass: 497.0 [M+H]$^+$ (rt: 1.12 min).

Example 307

N-(2',4'-difluoro-5-(5-(1-isopropyl-1H-pyrazol-4-yl)-1H-benzo[d]imidazol-1-yl)-[1,1'-biphenyl]-3-yl)methane sulfonamide The compound was prepared from the compound of Example 208(a) using the procedure of Example 208(b) and 1-isopropyl-4-(4,4,5,5-tetramethyl-1,3,2-dioxaborolan-2-yl)-1H-pyrazole to afford the product in 9% yield (18 mg). $^1$H NMR (300 MHz, DMSO-d$_6$): δ 10.28 (s, 1H), 8.63 (s, 1H), 8.28 (s, 1H), 7.99 (s, 1H), 7.92 (s, 1H), 7.77 (d, 1H), 7.70-7.61 (m, 2H), 7.60-7.51 (m, 2H), 7.50-7.38 (m, 2H), 7.30-7.29 (m, 1H), 4.60-4.40 (m, 1H), 3.15 (s, 3H), 1.44 (d, 6H); LC-MS (API): Calculated mass: 507.15; Observed mass: 508.0 [M+H]$^+$ (rt: 1.00 min).

Example 308

N-(2',4'-difluoro-5-(5-(1-isopropyl-1H-pyrazol-4-yl)-1H-benzo[d]imidazol-1-yl)-[1,1'-biphenyl]-3-yl)ethane sulfonamide The compound was prepared from the compound of Example 200(b) using the procedure of Example 200(c). $^1$H NMR (400 MHz, DMSO-d$_6$): δ 10.31 (s, 1H), 8.64 (s, 1H), 8.30 (s, 1H), 8.01 (s, 1H), 7.95 (s, 1H), 7.75 (q, 1H), 7.65 (q, 2H), 7.56 (m, 2H), 7.46 (m, 2H), 7.27 (m, 1H), 4.51 (m, 1H), 3.28 (q, 2H), 1.46 (d, 6H), 1.25 (t, 3H). LC-MS (ESI): Calculated mass: 521.17; Observed mass: 522.1 [M+H]$^+$ (rt: 1.55 min).

Example 309

N-(2',4'-difluoro-5-(6-(1-isopropyl-1H-pyrazol-4-yl)-3H-imidazo[4,5-b]pyridin-3-yl)-[1,1'-biphenyl]-3-yl)ethanesulfonamide A solution of N-(5-(6-bromo-3H-imidazo[4,5-b]pyridin-3-yl)-2',4'-difluoro-[1,1'-biphenyl]-3-yl)ethanesulfonamide (0.2 g, 0.405 mmol) in 1,2-dimethoxyethane (5 ml) was degassed by N$_2$ bubbling for 5 min. 1-Isopropyl-3-(4,4,5,5-tetramethyl-1,3,2-dioxaborolan-2-yl)-1H-pyrazole (0.191 g, 0.810 mmol, 2.0 eq.) was added and the mixture was degassed for another 5 min. Pd(dppf)Cl$_2$ (0.032 g, 0.040 mmol, 0.1 eq.) and aqueous sodium carbonate (0.17 g, 1.012 mmol, 2.5 eq.) were added and the procedure of Example 1(d) was followed. The crude residue of the product was purified by column chromatography (60-120 silica gel, 80% ethyl acetate in hexane) to yield the product in 52.1% yield (0.11 g). $^1$H NMR (400 MHz, DMSO-d$_6$): δ 10.42 (s, 1H), 8.94 (s, 1H), 8.75 (d, 1H), 8.44-8.42 (dd, 2H), 8.05 (s, 1H), 7.95 (s, 1H), 7.77-7.70 (m, 2H), 7.48-7.43 (m, 2H), 7.30-7.26 (m, 1H), 4.54-4.51 (m, 1H), 4.13-4.11 (m, 1H); 3.28-3.26 (m, 2H), 3.17-3.16 (d, 1H), 1.48-1.46 (d, 6H), 1.28-1.25 (t, 3H), LC-MS (ESI): Calculated mass: 522.57 Observed mass: 523.0 [M+H]$^+$ (rt: 1.52 min).

Example 310

N-(5-(5-(6-aminopyridin-3-yl)-1H-benzo[d]imidazol-1-yl)-2',4'-difluoro-[1,1'-biphenyl]-3-yl)methanesulfonamide The title compound was prepared from the title compound of Example 208(a) using the procedures of Example 246. $^1$H NMR (300 MHz, DMSO-d$_6$): δ 10.43 (s, 1H), 9.05 (s, 1H), 8.42 (s, 2H), 8.17 (s, 2H), 7.84 (s, 1H), 7.78-7.73 (m, 3H), 7.62 (m, 2H), 7.49 (m, 2H), 7.31-7.27 (m, 1H), 7.15-7.12 (m, 1H), 3.19 (s, 3H); LC-MS (ESI): Calculated mass: 491.12; Observed mass: 492.2 [M+H]$^+$ (rt: 0.28 min).

Example 311

N-(5-(5-(6-aminopyridin-3-yl)-1H-benzo[d]imidazol-1-yl)-2',4'-difluoro-[1,1'-biphenyl]-3-yl)ethanesulfonamide The compound was prepared from the compound of Example 200(b) using the procedures of Example 246. $^1$H NMR (300 MHz, DMSO-d$_6$): δ 10.43 (s, 1H), 8.75 (s, 1H), 8.38-8.36 (m, 2H), 8.12 (s, 1H), 7.80-7.42 (m, 3H), 7.72-7.66 (m, 2H), 7.58-7.57 (m, 2H), 7.49-7.42 (m, 2H), 7.31-7.27 (m, 1H), 7.06-7.02 (m, 1H), 3.29 (quartet, 2H), 1.26 (s, 3H); LC-MS (ESI): Calculated mass: 505.14; Observed mass: 506.3 [M+H]$^+$ (rt: 0.37 min).

Example 312

1-(5-Acetamido-2',4'-difluoro-[1,1'-biphenyl]-3-yl)-1H-benzo[d]imidazole-5-carboxamide a) 1-(5-Amino-2',4'-difluoro-[1,1'-biphenyl]-3-yl)-1H-benzo[d]imidazole-5-carboxamide To a solution of N-(5-(5-cyano-1H-benzo[d]imidazol-1-yl)-2',4'-difluoro-[1,1'-biphenyl]-3-yl)acetamide (0.5 g, 1.28 mmol, 1 eq.) in ethanol (10 ml) was added 20% aqueous solution of potassium hydroxide (0.721 g, 12.88 mmol, 10 eq.) and the mixture was heated at 85° C. for 5 h. The mixture was quenched and extracted as in Example 1(d). The solvent was distilled off to afford title product in 71% yield (0.32 g). LC-MS (ESI): Calculated mass: 364.11; Observed mass: 365.1 [M+H]$^+$ (rt: 0.59 min).

b) 1-(5-Acetamido-2',4'-difluoro-[1,1'-biphenyl]-3-yl)-1H-benzo[d]imidazole-5-carboxamide Acetic anhydride (0.1 ml, 1 vol.) was added dropwise at 0° C. to the compound of Example 312(a) (0.1 g). The mixture was stirred for 30 min at RT and subsequently quenched by the addition of crushed ice. The precipitate formed was filtered and was washed with cold water to obtain off-white solid. The solid was dried under vacuum to give the product in 28.8% yield (32 mg). $^1$H NMR (400 MHz, DMSO-d$_6$): δ 10.48 (s, 1H), 8.80 (s, 1H), 8.42 (s, 1H), 8.10 (s, 1H), 7.99-7.97 (d, 1H), 7.88 (s, 1H), 7.80-7.76 (m, 2H), 7.57 (s, 1H), 7.49 (t, 1H), 7.41 (s, 1H), 7.31-7.29 (t, 1H), 2.18 (s, 3H); LC-MS (ESI): Calculated mass: 406.12; Observed mass: 407.2 [M+H]$^+$ (rt: 0.47 min).

Example 313

N-(2',4'-difluoro-5-(5-(5-methyl-1,2,4-oxadiazol-3-yl)-1H-benzo[d]imidazol-1-yl)-[1,1'-biphenyl]-3-yl) acetamide a) N-(5-((4-cyano-2-nitrophenyl)amino)-2',4'-difluoro-[1,1'-biphenyl]-3-yl)acetamide A solution of N-(5-aminobiphenyl-3-yl)acetamide (1.5 g, 5.72 mmol), 4-fluoro-3-nitrobenzonitrile (0.95 g, 5.72 mmol, 1.0 eq.) and potassium fluoride (0.33 g, 5.72 mmol, 1.0 eq.) in DMF (15 ml) was heated at 130° C. for 12 h. The mixture was quenched and extracted as in Example 1(d). The solvent was distilled off to afford the crude residue which was purified by column chromatography (60-120 silica gel, 50% ethyl acetate in hexane) to yield the title product in 43% yield (1 g).

b) N-(5-((2-amino-4-cyanophenyl)amino)-2',4'-difluoro-[1,1'-biphenyl]-3-yl)-acetamide To a solution of the compound of Example 313(a) (1.0 g, 2.45 mmol) in THF (15 ml) were added a solution of ammonium chloride (0.52 g, 9.8 mmol, 4 eq.) in water (5 ml) and zinc (0.64 g, 9.8 mmol, 4 eq.). The mixture was stirred at 45° C. for 2 h and filtered. The filtrate was diluted with water and extracted as in Example 1(d). The solvent was distilled off to afford the title product in 86% yield (0.8 g).

c) N-(5-(5-cyano-1H-benzo[d]imidazol-1-yl)-2',4'-difluoro-[1,1'-biphenyl]-3-yl)-acetamide A mixture of the compound of Example 313(b) (0.8 g, 2.11 mmol) and formic acid (10 ml) was heated at 100° C. for 4 h. The formic acid was distilled off and the crude was dissolved in ethyl acetate. The ethyl acetate layer was washed with water, brine and dried over sodium sulphate. The solvent was distilled off to afford the crude residue in 97% yield (0.8 g).

d) N-(2',4'-difluoro-5-(5-(N-hydroxycarbamimidoyl)-1H-benzo[d]imidazol-1-yl)-[1,1'-biphenyl]-3-yl)acetamide To a solution of the compound of Example 313(c) (0.1 g, 0.25 mmol) in ethanol was added hydroxylamine hydrochloride (20 mg, 0.28 mmol, 1.1 eq.) and Et$_3$N (0.1 ml, 0.75 mmol, 3 eq.) and the mixture was heated at 80° C. for 3 h. The volatiles were distilled off and the crude solid obtained was washed several times with diethyl ether to afford the title compound in 100% yield (0.11 g).

e) N-(2',4'-difluoro-5-(5-(5-methyl-1,2,4-oxadiazol-3-yl)-1H-benzo[d]imidazol-1-yl)-[1,1'-biphenyl]-3-yl)acetamide To a solution of the compound of Example 313(d) (0.1 g, 0.237 mmol) in TFA (1 ml) was added trimethylortho acetate (5 ml) and the mixture was heated at 100° C. for 4 h. The volatiles were distilled off and the crude product obtained was extracted with ethyl acetate and water and dried over sodium sulphate and the residue was purified by preparative HPLC to give the pure product in 6.6% yield (6.6 mg). LC-MS (ESI): Calculated mass: 445.14; Observed mass: 446.1 [M+H]$^+$ (rt: 1.15 min).

Example 314

N-(2',4'-difluoro-5-(6-(1-methyl-1H-pyrazol-4-yl)-3H-imidazo[4,5-b]pyridin-3-yl)-[1,1'-biphenyl]-3-yl)-2-(3,5-dimethylpiperazin-1-yl) acetamide The compound was prepared from the compound of Example 132(a) (60 mg, 0.149 mmol) using the procedure of Example 225 and 2-(3,5-dimethylpiperazin-1-yl)acetic acid (30 mg, 0.179 mmol, 1.2 eq) to give the product in 21.9% yield (18 mg). LC-MS (ESI): Calculated mass: 556.25; Observed mass: 557.2 [M+H]$^+$ (rt: 0.67 min).

Example 315

N-(2',4'-difluoro-5-(6-(1-methyl-1H-pyrazol-4-yl)-3H-imidazo[4,5-b]pyridin-3-yl)-2',3'-dihydro-[1,1'-biphenyl]-3-yl)-2-(4-ethylpiperazin-1-yl)acetamide The compound was prepared from N-(5-(6-bromo-3H-imidazo[4,5-b]pyridin-3-yl)-2',4'-difluoro-[1,1'-biphenyl]-3-yl)-2-(4-ethylpiperazin-1-yl)acetamide (300 mg, 0.540 mmol) using the method of Example 1(i) to give the product in 11.6% yield (35 mg). NMR (400 MHz, DMSO-D6): δ 9.40 (brs, 1H), 8.96 (s, 1H), 8.740 (d, 1H), 8.44 (d, 1H), 8.38 (s, 1H), 8.33 (s, 1H), 8.07 (s, 1H), 8.97 (s, 1H), 7.794-7.713 (m, 2H), 7.48 (t, 1H), 7.31 (t, 1H), 3.93 (s, 3H), 3.44 (s, 2H), 3.19-3.12 (m, 8H), 2.71 (q, 2H), 1.24 (t, 3H), LC-MS (ESI): Calculated mass: 558.6; Observed mass: 557.0 [M−H]$^-$ (rt: 0.21 min).

Example 316

N-(2',4'-difluoro-5-(6-(1-methyl-1H-pyrazol-4-yl)-3H-imidazo[4,5-b]pyridin-3-yl)-[1,1'-biphenyl]-3-yl)-2-(4-methylpiperazin-1-yl)acetamide The compound was prepared from the compound of Example 132(a) (75 mg, 0.186 mmol) using the procedure of Example 225 and 2-(4-methylpiperazin-1-yl)acetic acid (44.2 mg, 0.279 mmol, 1.5 eq) to give the product in 34.6% yield (35 mg). $^1$H NMR (400 MHz, DMSO-d$_6$): δ 10.29 (s, 1H), 8.94 (s, 1H), 8.72 (d, 1H), 8.42-8.31 (d, 3H), 8.05 (s, 1H), 7.93 (s, 1H), 7.77-7.71 (m, 2H), 7.49-7.43 (m, 1H), 7.29 (t, 1H), 3.90 (s, 3H), 3.17-3.11 (m, 4H), 2.80 (s, 3H), 2.67 (m, 2H), 2.50 (m, 4H); LC-MS (ESI): Calculated mass: 542.58; Observed mass: 543.1 [M+H]$^+$ (rt: 0.252 min).

Example 317

1-Cyclopentyl-3-(2',4'-difluoro-5-(6-(1-methyl-1H-pyrazol-4-yl)-3H-imidazo-[4,5-b]pyridin-3-yl)-[1,1'-biphenyl]-3-yl)urea To a solution of the compound of Example 132(a) (65 mg, 0.1616 mmol) in DCM was added diisopropylamine (89 mg, 0.485 mmol, 3 eq) and cyclopentyl isocyanate (19.7 mg, 0.1778 mmol, 1.1 eq). The mixture was stirred for 16 h, and quenched and extracted as in Example 2(b). The solvent was distilled off to give the crude residue which was purified by preparative HPLC to give the product in 12% yield (10 mg). $^1$H NMR (400 MHz, DMSO-d$_6$): δ8.92 (s, 1H), 8.71 (t, 1H), 8.41 (d, 1H), 8.30 (s, 1H), 8.05 (t, 1H), 7.72-7.66 (m, 1H), 7.56 (s, 1H), 7.46-7.40 (m, 1H), 7.27-7.24 (m, 2H), 6.30 (s, 1H), 3.93 (s, 3H), 3.10 (m, 1H), 1.87-1.81 (m, 2H), 1.65-1.53 (m, 4H), 1.43-1.37 (m, 2H); LC-MS (ESI): Calculated mass: 513.54; Observed mass: 514.5 [M+H]$^+$ (rt: 1.56 min).

Example 318

N-(2',4'-difluoro-5-(6-(1-methyl-1H-pyrazol-4-yl)-3H-imidazo[4,5-b]pyridin-3-yl)-[1,1'-biphenyl]-3-yl)-2-(piperazin-1-yl)acetamide a) tert-butyl 4-(2-((2',4'-difluoro-5-(6-(1-methyl-1H-pyrazol-4-yl)-3H-imidazo[4,5-b]pyridin-3-yl)-[1,1'-biphenyl]-3-yl)amino)-2-oxoethyl)piperazine-1-carboxylate The compound was prepared from the compound of Example 132(a) (120 mg, 0.298 mmol) using the method of Example 225 and 2-(4-(tert-butoxycarbonyl)piperazin-1-yl)acetic acid (145 mg, 0.597 mmol, 2 eq) to give the product in 10.6% yield (20 mg). LC-MS (ESI): Calculated mass: 628; Observed mass: 629.1 [M+H]$^+$ (rt: 1.056 min).

b) N-(2',4'-difluoro-5-(6-(1-methyl-1H-pyrazol-4-yl)-3H-imidazo[4,5-b]pyridin-3-yl)-[1,1'-biphenyl]-3-yl)-2-(piperazin-1-yl)acetamide To a solution of the compound of Example 318(a) (12 mg, 0.0191 mmol) in DCM was added TFA (1 ml) and the mixture was stirred at RT for 16 h. The mixture was concentrated to give the product in 98% yield (10 mg). $^1$H NMR (400 MHz, DMSO-d$_6$): δ 10.3 (s, 1H), 8.93 (s, 1H), 8.70 (d, 2H), 8.41-8.07 (d, 1H), 8.35 (t, 1H), 8.29 (s, 1H), 8.03 (s, 1H), 7.94-7.93 (d, 1H), 7.76-7.68 (m, 2H), 7.47-7.42 (m, 1H), 7.30-7.25 (m, 1H), 3.89 (s, 3H), 3.50 (s, 2H), 3.21 (s, 4H), 2.92 (s, 4H); LC-MS (ESI): Calculated mass: 528.22; Observed mass: 529.2[M+H]$^+$ (rt: 0.182 min).

Example 319

N-(2',4'-difluoro-5-(6-(1-methyl-1H-pyrazol-4-yl)-3H-imidazo[4,5-b]pyridin-3-yl)-[1,1'-biphenyl]-3-yl)-1-methylpiperidine-4-carboxamide The compound was prepared from the compound of Example 132(a) (75 mg, 0.1865 mmol) using the method of Example 225 and 1-methylpiperidine-4-carboxylic acid (40 mg, 0.27 mmol, 1.5 eq) to give the product in 15% yield (15 mg). $^1$H NMR (400 MHz, CD$_3$OD): δ 8.97 (s, 1H), 8.67 (s, 1H), 8.31 (t, 1H), 8.28 (s, 1H), 8.10 (s, 1H), 7.93 (s, 1H), 7.81 (t, 1H), 7.74 (s, 1H), 7.65-7.59 (m, 1H), 7.13-7.07 (m, 2H), 3.96 (s, 3H), 3.66-3.63 (m, 2H), 3.14-3.07 (m, 2H), 2.92 (s, 3H), 2.79-2.73 (m, 1H), 2.24-2.01 (m, 4H); LC-MS (ESI): Calculated mass: 527.22; Observed mass: 528.0 [M+H]$^+$ (rt: 0.20 min).

Example 320

N-(2',4'-difluoro-5-(5-(1-methyl-1H-pyrazol-4-yl)-1H-benzo[d]imidazol-1-yl)-2',3'-dihydro-[1,1'-biphenyl]-3-yl)-2-(4-ethylpiperazin-1-yl)acetamide The compound was prepared from the compound of Example 132(a) (100 mg, 0.249 mmol) using the procedure of Example 225 and 2-(4-ethylpiperazin-1-yl)acetic acid (85 mg, 0.498, mmol, 2.0 eq.) to give the product in 38% yield (40 mg).

Example 321

N-(5-(5-(4-ethylpiperazin-1-yl)-1H-benzo[d]imidazol-1-yl)-2',4'-difluoro-[1,1'-biphenyl]-3-yl)cyclopropanesulfonamide To a solution of the compound of N-(5-(5-bromo-1H-benzo[d]imidazol-1-yl)-2',4'-difluoro-[1,1'-biphenyl]-3-yl)cyclopropanesulfonamide (110 mg, 0.198 mmol) in DMSO was added potassium carbonate (54 mg, 0.391 mmol, 2.0 eq.). The mixture was degassed by N$_2$ bubbling for 10 min followed by addition of 1-ethylpiperazine (68 mg, 0.595 mmol, 3.0 eq.) and L-proline (4.5 mg) and CuI (3 mg). Then seal tube was closed and the mixture was kept at 95° C. for 24 h. The mixture was quenched and extracted as in Example 1(d). The solvent was distilled off to afford the crude residue which was purified by preparative HPLC to give the product in 18% yield (20 mg). $^1$H NMR (400 MHz, DMSO-D6): δ10.3 (s, 1H), 8.98 (s, 1H), 7.77 (m, 1H), 7.66 (s, 1H), 7.60 (brs, 2H), 7.50 (brs, 2H), 7.41 (s, 1H), 7.33-7.27 (m, 2H), 3.60 (m, 4H), 3.29-3.20 (m, 4H), 3.02 (q, 2H), 2.90 (t, 1H), 1.30 (t, 3H), 1.04 (q, 4H), LC-MS (ESI): Calculated mass: 537.62; Observed mass: 538.1 [M+H]$^+$

Example 322

N-(2',4'-difluoro-5-(5-(3-hydroxypyrrolidin-1-yl)-1H-benzo[d]imidazol-1-yl)-2',3'-dihydro-[1,1'-biphenyl]-3-yl)cyclopropanesulfonamide The compound was prepared as in Example 321 using (S)-pyrrolidin-3-ol to give the pure product in 12% yield (12 mg). NMR (400 MHz, DMSO-D6): δ 8.52 (s, 1H), 7.77 (q, 1H), 7.56 (d, 3H), 7.51-7.46 (m, 2H), 7.29 (t, 1H), 6.82 (s, 1H), 6.73 (d, 1H), 5.01 (d, 1H), 4.45 (s, 1H), 3.52 (q, 1H), 3.35 (s, 1H), 3.14 (d, 1H), 2.87 (q, 1H), 2.12-2.09 (m, 1H), 1.96-1.94 (m, 1H), 1.03 (d, 4H), LC-MS (ESI): Calculated mass: 512.1; Observed mass: 510 [M−H]$^−$ (rt: 0.42 min).

Example 323

N-(5-(5-(1-cyclopentyl-1H-pyrazol-4-yl)-1H-benzo[d]imidazol-1-yl)-2',4'-difluoro-[1,1'-biphenyl]-3-yl)ethane sulfonamide The title compound was prepared from the title compound of Example 200(b) using the procedures of Example 1(i). $^1$H NMR (400 MHz, CD$_3$OD): δ 8.51 (s, 1H), 8.09 (s, 1H), 7.92

(s, 1H), 7.88 (s, 1H), 7.68-7.62 (m, 3H), 7.58 (d, 1H), 7.51 (dd, 2H), 7.15-7.10 (m, 2H), 4.75-4.72 (m, 1H), 3.24 (quartet, 2H), 2.23-2.19 (m, 2H), 2.06-2.01 (m, 2H), 1.94-1.90 (m, 2H), 1.77-1.73 (m, 2H), 1.36 (t, 2H); LC-MS (ESI): Calculated mass: 547.19; Observed mass: 548.1 [M+H]$^+$ (rt: 1.66 min).

Example 324

N-(5-(6-(1-cyclopentyl-1H-pyrazol-4-yl)-3H-imidazo[4,5-b]pyridin-3-yl)-2',4'-difluoro-[1,1'-biphenyl]-3-yl)ethanesulfonamide a) N-(5-(6-bromo-3H-imidazo[4,5-b]pyridin-3-yl)-2',4'-difluoro-[1,1'-biphenyl]-3-yl)ethanesulfonamide To a solution of 5-(6-bromo-3H-imidazo[4,5-b]pyridin-3-yl)-2',4'-difluoro-[1,1'-biphenyl]-3-amine (133 mg, 0.33 mmol) in DCM was added pyridine (52 mg, 0.66 mmol, 2.0 eq.) followed by ethanesulfonyl chloride (76 mg, 0.66 mmol, 2.0 eq.). The mixture was stirred for 1 h, and quenched and extracted as in Example 2(b). The solvent was distilled off to afford the crude residue which was taken to the next step without further purification, yield 76.68% (125 mg); LC-MS (ESI): Calculated mass: 492.01; Observed mass: 493.0 [M+H]$^+$ (rt: 1.72 min).

b) N-(5-(6-(1-cyclopentyl-1H-pyrazol-4-yl)-3H-imidazo[4,5-b]pyridin-3-yl)-2',4'-difluoro-[1,1'-biphenyl]-3-yl)ethanesulfonamide The compound was prepared from the compound of Example 324(a) (125 mg, 0.25 mmol) using the method of Example 200(c) and 1-cyclopentyl-4-(4,4,5,5-tetramethyl-1,3,2-dioxaborolan-2-yl)-1H-pyrazole (136 mg, 0.50 mmol, 2.0 eq.) to give the product in 21.73% yield (30 mg). $^1$H NMR (400 MHz, DMSO-d6): δ 10.32 (s, 1H), 8.96 (s, 1H), 8.76-8.75 (d, 1H), 8.45-8.42 (t, 2H), 8.06 (s, 1H), 7.95-7.94 (t, 1H), 7.77-7.70 (m, 2H), 7.49-7.43 (m, 2H), 7.28 (t, 1H), 4.74-4.70 (t, 1H), 3.31-3.26 (q, 2H), 2.14-2.09 (m, 2H), 2.00-1.95 (m, 2H), 1.84-1.81 (m, 2H), 1.68-1.65 (m, 2H), 1.28-1.24 (t, 3H); LC-MS (ESI): Calculated mass: 548.18; Observed mass: 549.1 [M+H]$^+$ (rt: 1.70 min).

Example 325

2-(4-(1-(5-amino-2',4'-difluoro-[1,1'-biphenyl]-3-yl)-1H-benzo[d]imidazol-5-yl)-1H-pyrazol-1-yl)ethanol To a solution of N-(2',4'-difluoro-5-(5-(1-(2-((tetrahydro-2H-pyran-2-yl)oxy)-ethyl)-1H-pyrazol-4-yl)-1H-benzo[d]imidazol-1-yl)-[1,1'-biphenyl]-3-yl)acetamide (0.12 g, 0.125 mmol) in methanol (5 ml) was added (1 ml) acetyl chloride at 0° C. The mixture was stirred at RT for 16 h. The mixture was quenched and extracted as in Example 1(d). The solvent was distilled off to afford the product in 28% yield (0.026 g). $^1$H NMR (400 MHz, DMSO-d$_6$): δ 8.53 (s, 1H), 8.20 (s, 1H), 7.97-7.95 (d, 2H), 7.69-7.64 (m, 2H), 7.59-7.56 (dd, 1H), 7.39-7.36 (m, 1H), 6.88 (s, 2H), 6.82 (d, 1H), 5.70 (s, 2H), 4.95 (s, 1H), 4.19-4.16 (t, 2H), 3.81-3.78 (t, 2H); LC-MS (ESI): Calculated mass: 431.44; Observed mass: 432.2 [M+H]$^+$ (rt: 0.4 min).

Example 326

N-(5-(5-(1H-pyrazol-4-yl)-1H-benzo[d]imidazol-1-yl)-2',4'-difluoro-[1,1'-biphenyl]-3-yl)acetamide The compound was prepared from the title compound of Example 1(h) using the procedures of Example 1(i). $^1$H NMR (400 MHz, DMSO-d$_6$): δ 10.43 (s, 1H), 9.0 (s, 1H), 8.17 (s, 2H), 8.13 (m, 1H), 8.06 (s, 1H), 7.82 (s, 1H), 7.74-7.73 (m, 3H), 7.55 (s, 1H), 7.5-7.42 (m, 1H), 7.3-7.26 (dt, 1H), 2.12 (s, 3H); LC-MS (ESI): Calculated mass: 429.42; Observed mass: 429.8 [M+H]$^+$ (rt: 0.6 min).

Example 327

N-(5-(5-(1H-pyrazol-3-yl)-1H-benzo[d]imidazol-1-yl)-2',4'-difluoro-[1,1'-biphenyl]-3-yl)acetamide The title compound was prepared from the title compound of Example 1(h) using the procedures of Example 1(i).

Example 328

N-(2',4'-difluoro-5-(5-(6-oxo-1,6-dihydropyridin-3-yl)-1H-benzo[d]imidazol-1-yl)-[1,1'-biphenyl]-3-yl)-2-(1H-1,2,4-triazol-1-yl) acetamide a) N-(5-(5-(6-(benzyloxy)-1,6-dihydropyridin-3-yl)-1H-benzo[d]imidazol-1-yl)-2',4'-difluoro-[1,1'-biphenyl]-3-yl)acetamide The compound was prepared from the compound of Example 1(h) (2 g, 4.5 mmol) using the procedures of Example 200(c) and 2-(benzyloxy)-5-(4,4,5,5-tetramethyl-1,3,2-dioxaborolan-2-yl)-1,2-dihydropyridine (1.68 g, 5.4 mmol, 1.2 eq) to yield the product in 50% yield (1.2 g). LC-MS (ESI): Calculated mass: 548.2; Observed mass: 549.4 [M+H]$^+$ (rt: 0.302 min).

b) 5-(5-(6-(benzyloxy)-1,6-dihydropyridin-3-yl)-1H-benzo[d]imidazol-1-yl)-2',4'-difluoro-[1,1'-biphenyl]-3-amine The compound was prepared from the compound of Example 328(a) (1.1 g, 2.00 mmol) using the procedure of Example 2(a) to afford the product in 50% yield (0.7 g).

c) N-(5-(5-(6-(benzyloxy)-1,6-dihydropyridin-3-yl)-1H-benzo[d]imidazol-1-yl)-2',4'-difluoro-[1,1'-biphenyl]-3-yl)-2-(1H-1,2,4-triazol-1-yl)acetamide The compound was prepared from the compound of Example 328(b) (100 mg, 0.1984 mmol) using the procedure of Example 225 to give the product in 65% yield (80 mg). LC-MS (ESI): Calculated mass: 613; Observed mass: 614 [M+H]$^+$ (rt: 1.681 min).

d) N-(2',4'-difluoro-5-(5-(6-oxo-1,6-dihydropyridin-3-yl)-1H-benzo[d]imidazol-1-yl)-[1,1'-biphenyl]-3-yl)-2-(1H-1,2,4-triazol-1-yl) acetamide The solution of the compound of Example 328(c) (60 mg, 0.0975 mmol) in TFA was heated at 50° C. for 16 h. The mixture was concentrated to give the product in 50% yield (30 mg). $^1$H NMR (400 MHz, DMSO-d$_6$): δ 8.94 (s, 1H), 8.61 (s, 1H), 8.11 (s, 1H), 8.04-7.94 (m, 3H), 7.81-7.75 (m, 4H), 7.63 (d, 2H), 7.49-7.44 (m, 1H), 7.28 (t, 1H), 6.46 (d, 1H), 5.24 (s, 2H), LC-MS (ESI): Calculated mass: 523.16; Observed mass: 524.1 [M+H]$^+$ (rt: 0.343 min).

Example 329

1-(2',4'-difluoro-5-(5-(6-oxo-1,6-dihydropyridin-3-yl)-1H-benzo[d]imidazol-1-yl)-[1,1'-biphenyl]-3-yl)-3-(furan-2-ylmethyl)urea a) 1-(5-(5-(6-(benzyloxy)pyridin-3-yl)-1H-benzo[d]imidazol-1-yl)-2',4'-difluoro-[1,1'-biphenyl]-3-yl)-3-(furan-2-ylmethyl)urea To a solution of 5-(5-(6-(benzyloxy)-1,6-dihydropyridin-3-yl)-1H-benzo[d]imidazol-1-yl)-2',4'-difluoro-[1,1'-biphenyl]-3-amine (75 mg, 0.148 mmol) in DCM was added furfuryl isocyanate (19 mg, 0.163 mmol, 1.1 eq.). The mixture was stirred overnight and quenched and extracted as in Example 2(b). The solvent was distilled off to afford the crude residue which was recrystallized in ether to afford the title compound in 86% yield (80 mg).

b) 1-(2',4'-difluoro-5-(5-(6-oxo-1,6-dihydropyridin-3-yl)-1H-benzo[d]imidazol-1-yl)-[1,1'-biphenyl]-3-yl)-3-(furan-2-ylmethyl)urea To a solution of the compound of Example 329(a) (80 mg) in THF (5 ml) and ethanol (5 ml) was added 10% palladium on carbon (10 mg) followed by 20% palladium hydroxide (10 mg). The mixture was stirred under hydrogen atmosphere for 2 h. The reaction mass was filtered through a bed of celite and concentrated to afford the crude product which was purified by silica gel (60-120) column chromatography using 6% MeOH in chloroform as eluant to afford the product in 58% yield (40 mg).

Example 330

N-(2',4'-difluoro-5-(5-(1-(2-hydroxyethyl)-1H-pyrazol-4-yl)-1H-benzo[d]-imidazol-1-yl)-[1,1'-biphenyl]-3-yl) methane sulfonamide To a solution of N-(2',4'-difluoro-5-(5-(1-(2-((tetrahydro-2H-pyran-2-yl)oxy)-ethyl)-1H-pyrazol-4-yl)-1H-benzo[d]imidazol-1-yl)-[1,1'-biphenyl]-3-yl)methanesulfonamide (0.15 g, 0.252 mmol) in methanol (5 ml) was added acetyl chloride (1 ml) at 0° C. as in Example 1(d). The solvent was distilled off to afford the product (0.063 g). $^1$H NMR (300 MHz, DMSO-d$_6$): δ 8.64 (s, 1H), 8.22 (s, 1H), 8.00-7.97 (d, 2H), 7.80-7.69 (m, 2H), 7.67-7.61 (m, 1H), 7.59-7.60 (d, 1H), 7.53 (s, 2H), 7.47-7.41 (m, 2H), 7.29-7.25 (t, 1H), 4.97-4.95 (t, 1H), 4.18-4.15 (m, 2H), 3.80-3.78 (m, 2H), 3.14 (s, 3H) Calculated mass: 509.1; Observed mass: 510.3 [M+H]$^+$ (rt: 1.18 min).

Example 331

N-(2',6'-difluoro-5-(6-(1-(piperidin-4-yl)-1H-pyrazol-4-yl)-3H-imidazo[4,5-b]-pyridin-3-yl)-[1,1'-biphenyl]-3-yl)acetamide a) tert-butyl 4-(4-(3-(5-acetamido-2',6'-difluoro-[1,1'-biphenyl]-3-yl)-3H-imidazo[4,5-b]pyridin-6-yl)-1H-pyrazol-1-yl)piperidine-1-carboxylate The title compound was prepared from the title compound of Example 209(c) using the procedures of Example 209(d).

b) N-(2',6'-difluoro-5-(6-(1-(piperidin-4-yl)-1H-pyrazol-4-yl)-3H-imidazo[4,5-b]pyridin-3-yl)-[1,1'-biphenyl]-3-yl)acetamide A solution of the compound of Example 331(a) (180 mg, 0.293 mmol) in TFA was stirred at RT for 16 h. The mixture was concentrated to give the crude product which was purified by preparative HPLC to afford the product in 13% yield (20 mg). $^1$H NMR (400 MHz, DMSO-d$_6$): δ 10.41 (s, 1H), 8.87 (s, 1H), 8.77-8.76 (d, 1H), 8.7-8.5 (br, 1H), 8.42 (s, 1H), 8.36 (m, 1H), 8.14 (s, 1H), 7.75 (s, 1H), 7.69 (s, 1H), 7.55 (m, 1H), 7.31-7.27 (t, 2H), 4.58-4.44 (m, 1H), 3.17-3.09 (m, 4H), 2.32-2.16 (m, 4H), 2.11 (s, 3H) Calculated mass: 513.54; Observed mass: 514.3 [M+H]$^+$ (rt: 1.32 min).

Example 332

1-(5-Acetamido-2',4'-difluoro-[1,1'-biphenyl]-3-yl)-1H-benzo[d]imidazole-5-carboxylic acid a) Methyl 4-((5-acetamido-2',4'-difluoro-[1,1'-biphenyl]-3-yl)amino)-3-nitrobenzoate A solution of N-(5-amino-2',4'-difluoro-[1,1'-biphenyl]-3-yl)acetamide (1.0 g, 3.813 mmol), methyl 4-fluoro-3-nitrobenzoate (0.835 g, 4.194 mmol, 1.1 eq.) and potassium fluoride (0.265 g, 4.457 mmol, 1.2 eq.) in DMF was heated at 130° C. for 16 h. The mixture was quenched and extracted as in Example 1(d). The solvent was distilled off to give the crude residue which was purified by column chromatography (60-120 silica gel, 40% ethyl acetate in hexane) to give the product in 48.78% yield (0.82 g).

b) Methyl 1-(5-acetamido-2',4'-difluoro-[1,1'-biphenyl]-3-yl)-1H-benzo[d]-imidazole-5-carboxylate The compound was prepared from the compound of Example 332(a) using the methods of Example 1(g) and 1(h) to give the product in 91.3% yield (0.58 g). $^1$H NMR (300 MHz, DMSO-d$_6$): δ 10.21 (s, 1H), 8.89 (s, 1H), 8.38 (s, 1H), 8.14 (s, 1H), 8.03 (s, 1H), 7.86-7.83 (d, 2H), 7.79-7.75 (m, 2H), 7.53 (s, 2H), 7.26-7.25 (m, 1H), 2.10 (s, 3H); LC-MS (ESI): Calculated mass: 421.4; Observed mass: 422 [M+H]$^+$ (rt: 1.52 min).

c) 1-(5-Acetamido-2',4'-difluoro-[1,1'-biphenyl]-3-yl)-1H-benzo[d]imidazole-5-carboxylic acid To a solution of the compound of Example 332(b) (0.1 g, 0.24 mmol, 1 eq.) in THF (10 ml), methanol (6 ml) and water (4 ml) was added LiOH (0.049 g, 1.18 mmol, 5 eq.) The mixture was stirred at RT overnight. The reaction mass was diluted with water and extracted as in Example 1(d). The solvent was distilled off to afford the product in 26% yield (0.025 g). $^1$H NMR (400 MHz, DMSO-d$_6$): δ 12.92 (s, 1H), 10.38 (s, 1H), 8.79 (s, 1H), 8.34 (s, 1H), 8.07 (s, 1H), 7.98-7.96 (d, 1H), 7.87 (s, 1H), 7.78-7.73 (m, 2H), 7.52-7.41 (m, 2H), 7.28-7.24 (t, 1H), 2.11 (s, 3H); LC-MS (ESI): Calculated mass: 407.11; Observed mass: 408.4 [M+H]$^+$ (rt: 1.01 min).

Example 333

N-(5-(5-(4-bromo-1H-pyrazol-1-yl)-1H-benzo[d]imidazol-1-yl)-4'-fluoro-[1,1'-biphenyl]-3-yl)acetamide To a solution of the compound of Example 70 (4 g, 9.73 mmol) in acetic acid (40 ml) bromine (1.53 g, 9.73 mmoles)

in acetic acid (10 ml) was added dropwise at RT. The reaction was stirred at RT for 1 h, cold water was added and the solid obtained was filtered and dried to afford the title product in 63.15% yield (3 g). $^1$H NMR (300 MHz, DMSO-d$_6$): δ 10.42 (s, 1H), 8.88 (s, 2H), 8.24 (s, 1H), 8.23 (s, 1H), 8.0 (s, 1H), 7.92-7.85 (m, 3H), 7.85-7.78 (m, 3H), 7.66 (s, 1H), 7.4-7.3 (m, 2H), 2.13 (s, 3H); LC-MS (ESI): Calculated mass: 490.33; Observed mass: 491.7 [M+H]$^+$ (rt: 1.66 min).

Example 334

N-(5-(6-(1-cyclopentyl-1H-pyrazol-4-yl)-3H-imidazo[4,5-b]pyridin-3-yl)-2',4'-difluoro-[1,1'-biphenyl]-3-yl)methanesulfonamide a) N-(5-(6-bromo-3H-imidazo[4,5-b]pyridin-3-yl)-2',4'-difluoro-[1,1'-biphenyl]-3-yl)methanesulfonamide To a solution of 5-(6-bromo-3H-imidazo[4,5-b]pyridin-3-yl)-2',4'-difluoro-[1,1'-biphenyl]-3-amine (133 mg, 0.33 mmol) in DCM was added pyridine (52 mg, 0.66 mmol, 2.0 eq.) followed by methanesulfonyl chloride (76 mg, 0.66 mmol, 2 eq.). The reaction was stirred for 1 h, and quenched and extracted as in Example 2(b). The solvent was distilled off to afford the crude residue which was taken next step without further purification. Yield 75.0% (120 mg). $^1$H NMR (300 MHz, DMSO-d$_6$): δ 10.30 (s, 1H), 9.30 (s, 1H), 8.56 (s, 1H), 7.83 (s, 1H), 7.45 (s, 1H), 7.44 (s, 2H), 3.16 (s, 3H); LC-MS (ESI): Calculated mass: 479.5; Observed mass: 480.2 [M+H]$^+$ (rt: 1.59 min).

b) N-(5-(6-(1-cyclopentyl-1H-pyrazol-4-yl)-3H-imidazo[4,5-b]pyridin-3-yl)-2',4'-difluoro-[1,1'-biphenyl]-3-yl)methanesulfonamide The compound was prepared from the compound of Example 334(a) (0.120 g, 0.25 mmol) using the procedure of Example 200(c) and 1-cyclopentyl-4-(4,4,5,5-tetramethyl-1,3,2-dioxaborolan-2-yl)-1H-pyrazole (0.253 g, 0.50 mmol, 2.0 eq) to afford the crude residue which was purified by preparative HPLC to give the product 19% yield (0.026 g). $^1$H NMR (400 MHz, DMSO-d$_6$): δ 10.29 (s, 1H), 8.96 (s, 1H), 8.75 (d, 1H), 8.44-8.41 (d, 2H), 8.05 (s, 1H), 7.93 (s, 1H), 7.79 (s, 1H), 7.74-7.72 (m, 1H), 7.46-7.41 (m, 2H), 7.28 (t, 1H), 4.74-4.70 (t, 1H), 3.17 (s, 3H), 2.14-2.09 (m, 2H), 2.00-1.95 (m, 2H), 1.84-1.80 (m, 2H), 1.68-1.65 (m, 2H); LC-MS (ESI): Calculated mass: 534.16; Observed mass: 535.1 [M+H]$^+$ (rt: 1.70 min)

Example 335

N-(5-(6-(1-cyclopentyl-1H-pyrazol-4-yl)-3H-imidazo[4,5-b]pyridin-3-yl)-2',4'-difluoro-[1,1'-biphenyl]-3-yl)cyclopropanesulfonamide The compound was prepared using the procedures of Example 334 starting from 5-(6-bromo-3H-imidazo[4,5-b]pyridin-3-yl)-2',4'-difluoro-[1,1'-biphenyl]-3-amine (133 mg, 0.33 mmol) and using cyclopropanesulfonyl chloride (20 mg, 0.66 mmol, 2.0 eq.) and 1-cyclopentyl-4-(4,4,5,5-tetramethyl-1,3,2-dioxaborolan-2-yl)-1H-pyrazole (0.115 g, 0.43 mmol, 2.0 eq.) to give the crude residue which was purified by preparative HPLC to give the product in 27.86% yield (34 mg). $^1$H NMR (400 MHz, DMSO-d$_6$): δ 10.26 (s, 1H), 8.96 (s, 1H), 8.76-8.75 (d, 1H), 8.45-8.42 (t, 2H), 8.06 (s, 1H), 8.00-7.99 (d, 1H), 7.78-7.70 (m, 2H), 7.49-7.43 (m, 2H), 7.31-7.26 (t, 1H), 4.74-4.70 (t, 1H), 2.84 (m, 1H), 2.14-2.08 (m, 2H), 2.00-1.96 (m, 2H), 1.84-1.81 (m, 2H), 1.69-1.65 (m, 2H), 1.09-1.02 (m, 4H); LC-MS (ESI): Calculated mass: 560.18; Observed mass: 561.2 [M+H]$^+$ (rt: 1.70 min).

Example 336

N-(2',4'-difluoro-5-(5-(1-methyl-1H-pyrazol-4-yl)-1H-benzo[d]imidazol-1-yl)-[1,1'-biphenyl]-3-yl)-2-methoxyacetamide The title compound was prepared from the compound of Example 2(a) using the procedures of Example 205. $^1$H NMR (300 MHz, DMSO-d$_6$): δ 10.28 (s, 1H), 8.99 (s, 1H), 8.23 (d, 2H), 8.03-7.98 (m, 3H), 7.80-7.67 (m, 3H), 7.60 (s, 1H), 7.47 (t, 1H), 7.29 (t, 1H), 4.09 (s, 3H), 3.89 (s, 3H), 3.42 (s, 2H); LC-MS (API): Calculated mass: 473.17; Observed mass: 474.1 [M+H]$^+$ (rt: 0.90 min).

Example 337

N-(5-(5-(1H-pyrazol-3-yl)-1H-benzo[d]imidazol-1-yl)-2',4'-difluoro[1,1'-biphenyl]-3-yl)ethanesulfonamide a) N-(2',4'-difluoro-5-((2-nitro-4-(1H-pyrazol-3-yl)phenyl)amino)-[1,1'-biphenyl]-3-yl)acetamide To a solution of the compound of Example 168(b) (0.8 g, 1.66 mmol) in ethanol (15 ml) was added hydrazine (7 ml) and stirred at RT overnight. The mixture was purified by silica gel chromatography using 1% MeOH in chloroform as eluant to afford the product in 62% yield (0.46 g).

b) N-(5-((2-amino-4-(1H-pyrazol-3-yl)phenyl)amino)-2',4'-difluoro-[1,1'-biphenyl]-3-yl)acetamide To a solution of the compound of Example 337(a) (0.46 g, 1.02 mmol) in THF (3 ml) and methanol (3 ml) was added 10% palladium on carbon. The mixture was stirred under hydrogen atmosphere for 4 h. The mixture was filtered through a bed of celite and concentrated to afford the product in 66% yield (0.28 g).

c) N-(5-(5-(1H-pyrazol-3-yl)-1H-benzo[d]imidazol-1-yl)-2',4'-difluoro-[1,1'-biphenyl]-3-yl)acetamide A mixture of the compound of Example 337(b) (0.3 g, 0.69 mmol) and formic acid (3 ml) was heated at 80° C. for 2 h. The formic acid was distilled off and the crude product was extracted with DCM. The solvent was distilled off to afford the product in 95% yield (0.3 g).

d) 5-(5-(1H-pyrazol-3-yl)-1H-benzo[d]imidazol-1-yl)-2',4'-difluoro-[1,1'-biphenyl]-3-amine A solution of the compound of Example 337(c) (0.26 g, 0.465 mmol) in ethanol (3 ml) was added 1:1 HCl solution and heated at 80° C. for 1 h. The mixture was basified with saturated NaHCO$_3$ solution and extracted with DCM (2×15 ml). The DCM layer was concentrated to afford the product in 80% yield (0.28 g).

e) N-(5-(5-(1H-pyrazol-3-yl)-1H-benzo[d]imidazol-1-yl)-2',4'-difluoro-[1,1'-biphenyl]-3-yl)ethanesulfonamide To a solution of the compound of Example 337(d) (100 mg, 0.25 mmol) in DCM was added pyridine 0.2 ml followed by ethanesulfonyl chloride (33 mg, 0.25 mmol, 1.0 eq.). The mixture was stirred for 1 h, quenched with water and extracted with DCM (3×10 ml). The combined organic layer was concentrated and the crude material was stirred with 10% NaOH solution (3 ml) for 1 h and washed with water, brine and dried over sodium sulphate. The aqueous layer was extracted with DCM (2×10 ml). The solvent was distilled to afford the crude material which was purified by preparative HPLC to afford the title product. $^1$H NMR (400 MHz, DMSO-$d_6$): δ 13-12.5 (brs, 1H), 10.4-10.2 (brs, 1H), 8.69 (s, 1H), 8.21 (s, 1H), 7.87-7.86 (m, 1H), 7.79-7.71 (m, 3H), 7.56 (m, 2), 7.42-7.42 (m, 2H), 7.3-7.25 (dt, 1H), 6.81 (d, 1H), 3.35-3.25 (q, 2H), 1.27-1.24 (t, 3H); LC-MS (API): Calculated mass: 479.5; Observed mass: 480.3 [M+H]$^+$ (rt: 1.32 min).

Example 338

N-(5-(5-(1H-pyrazol-3-yl)-1H-benzo[d]imidazol-1-yl)-2',4'-difluoro-[1,1'-biphenyl]-3-yl)methanesulfonamide The compound was prepared from the compound of Example 208(a) using the procedures of Example 208(b). $^1$H NMR (400 MHz, DMSO-$d_6$): δ 8.68 (s, 1H), 8.2 (s, 1H), 7.87-7.85 (m, 1H), 7.76-7.72 (m, 3H), 7.51-7.49 (m, 2H), 7.44-7.4 (m, 2H), 7.3-7.22 (dt, 1H), 6.81-6.8 (d, 1H), 3.11 (s, 3H); LC-MS (API): Calculated mass: 465.48; Observed mass: 466.32 [M+H]$^+$ (rt: 1.4 min).

Example 339

N-(5-(6-(6-aminopyridin-3-yl)-3H-imidazo[4,5-b]pyridin-3-yl)-2',4'-difluoro-[1,1'-biphenyl]-3-yl)methanesulfonamide The compound was prepared from the compound of Example 334(a) using the procedures of Example 246. $^1$H NMR (300 MHz, CD$_3$OD): δ 8.73 (s, 1H), 8.56 (s, 1H), 8.17 (d, 2H), 7.79-7.71 (m, 3H), 7.59-7.57 (m, 1H), 7.42 (m, 1H), 7.08-7.03 (m, 2H), 6.65-6.62 (m, 1H), 3.04 (s, 3H); LC-MS (ESI): Calculated mass: 492.12; Observed mass: 493.0 [M+H]$^+$ (rt: 0.20 min).

Example 340

N-(2',5'-difluoro-5-(5-(1-methyl-1H-pyrazol-4-yl)-1H-benzo[d]imidazol-1-yl)-[1,1'-biphenyl]-3-yl)ethanesulfonamide The compound was prepared from 2',5'-difluoro-5-(5-(1-methyl-1H-pyrazol-4-yl)-1H-benzo[d]imidazol-1-yl)-[1,1'-biphenyl]-3-amine (70 mg, 0.175 mmol) using the procedure of Example 2(b) and ethanesulfonyl chloride (26 mg, 0.21 mmol, 1.2 eq.) to give the pure product in 16.2% yield (14 mg). NMR (400 MHz, DMSO-D6): δ10.35 (s, 1H), 8.80 (s, 1H), 8.23 (s, 1H), 8.00 (s, 1H), 7.96 (s, 1H), 7.70 (d, 1H), 7.65-7.60 (m, 4H), 7.51 (s, 2H), 7.49-7.39 (m, 1H), 3.88 (s, 3H), 3.30 (q, 2H), 1.26 (t, 3H), LC-MS (ESI): Calculated mass: 493.53; Observed mass: 494.2 [M+H]+ (rt: 0.1.33 min).

Example 341

N-(5-(6-(2-aminopyridin-4-yl)-3H-imidazo[4,5-b]pyridin-3-yl)-2',4'-difluoro-[1,1'-biphenyl]-3-yl)methane sulfonamide To a solution of tert-butyl(5-(3-(2',4'-difluoro-5-(methylsulfonamido)-[1,1'-biphenyl]-3-yl)-3H-imidazo[4,5-b]pyridin-6-yl)pyridin-2-yl)carbamate (0.2 g, 0.33 mmol) in DCM (5 ml) was added TFA (1.2 ml) at 0° C. The mixture was stirred at RT for 16 h. The mixture was concentrated in vacuum, quenched with sodium bicarbonate and extracted as in Example 1(d). The solvent was distilled off to afford the product in 16.9% yield (0.28 g). $^1$H NMR (300 MHz, DMSO-$d_6$): δ 10.30 (s, 1H), 9.04 (s, 1H), 8.73 (s, 1H), 8.46 (s, 1H), 8.00 (d, 1H), 7.91 (s, 1H), 7.79 (m, 2H), 7.44 (m, 2H), 7.30 (m, 1H), 6.95 (d, 1H), 6.82 (s, 1H), 6.06 (s, 2H), 3.17 (s, 3H); LC-MS (ESI): Calculated mass: 492.50; Observed mass: 493.1 [M+H]$^+$ (rt: 0.39 min).

Example 342

N-(5-(5-(1H-pyrazol-1-yl)-1H-benzo[d]imidazol-1-yl)-2',4'-difluoro-[1,1'-biphenyl]-3-yl)-2-(pyrrolidin-1-yl) acetamide The compound was prepared from the compound of Example 29(a) (75 mg, 0.193 mmol) using the procedure of Example 225 and 2-(pyrrolidin-1-yl)acetic acid (37.3 mg, 0.289 mmol, 1.5 eq.) to give the product in 31.18% yield (30 mg). $^1$H NMR (600 MHz, CD$_3$OD): δ 8.62 (s, 1H), 8.29-8.28 (d, 1H), 8.17-8.16 (t, 1H), 8.12 (s, 1H), 7.85-7.83 (dd, 3H), 7.77-7.76 (d, 1H), 7.68-7.67 (m, 1H), 7.59 (s, 1H), 7.15-7.12 (m, 2H), 6.58-6.57 (t, 1H), 3.73 (s, 2H); 3.02 (t, 4H); 2.00-1.94 (m, 4H); LC-MS (ESI): Calculated mass: 498.53, Observed mass: 499.6 [M+H]$^+$ (rt: 0.6 min).

Example 343

N-(5-(5-(2-aminopyridin-4-yl)-1H-benzo[d]imidazol-1-yl)-2',4'-difluoro-[1,1'-biphenyl]-3-yl) methane sulfonamide The compound was prepared from 5-(1-(5-amino-2',4'-difluoro-[1,1'-biphenyl]-3-yl)-1H-benzo[d]imidazol-5-yl)pyridin-2-amine (50 mg, 0.121 mmol) using the method of Example 2(b) and methanesulfonyl chloride (27.7 mg, 0.242 mmol, 2.0 eq) to give the product in 37.2% yield (22 mg). $^1$H NMR (400 MHz, DMSO-$d_6$): δ 10.42 (s, 1H), 8.84 (s, 1H), 8.29 (s, 1H), 8.04-8.20 (d, 3H), 7.89-7.87 (d, 1H), 7.81-7.74 (m, 2H), 7.61 (s, 1H), 7.57 (s, 1H), 7.47-7.44 (d, 2H), 7.39-7.38 (d, 1H), 7.31-7.26 (m, 1H), 3.19 (s, 3H); LC-MS (ESI): Calculated mass: 491.51 Observed mass: 492.2 [M+H]$^+$ (rt: 0.24 min).

Example 344

N-(5-(5-(4-amino-3-fluorophenyl)-1H-benzo[d]imidazol-1-yl)-2',4'-difluoro-[1,1'-biphenyl]-3-yl)acetamide The compound was prepared from the compound of Example 1(h) using the procedures of Example 246. $^1$H NMR (300 MHz, DMSO-$d_6$): δ 10.46 (s, 1H), 8.86 (s, 1H), 8.07 (s, 1H), 7.95 (s, 1H), 7.81-7.71 (m, 3H), 7.59 (d, 1H), 7.51-7.40 (m, 3H), 7.33-7.24 (m, 2H), 6.88-6.82 (m, 1H), 5.25 (brs, 2H), 2.12 (s, 3H); LC-MS (ESI): Calculated mass: 472.15; Observed mass: 473.5 [M+H]$^+$ (rt: 1.47 min).

Example 345

N-(5-(5-(2-aminopyridin-4-yl)-1H-benzo[d]imidazol-1-yl)-2',4'-difluoro-[1,1'-biphenyl]-3-yl) ethane sulfonamide The compound was prepared as in Example 343 using ethanesulfonyl chloride (46.8 mg, 0.363 mmol, 2.0 eq.) to give the product in 36.1% yield (33 mg). $^1$H NMR (400 MHz, DMSO-d$_6$): δ 10.35 (s, 1H), 8.84 (s, 1H), 8.29 (s, 1H), 8.04-7.99 (t, 3H), 7.88-7.86 (d, 1H), 7.81-7.73 (m, 2H), 7.59-7.58 (d, 1H), 7.48-7.44 (m, 2H), 7.39-7.31 (d, 1H), 7.31-7.26 (m, 2H), 3.32-3.27 (q, 2H), 1.28-1.24 (t, 3H), LC-MS (ESI): Calculated mass: 505.54; Observed mass: 506.3 [M+H]$^+$ (rt: 0.2 min).

Example 346

N-(5-(6-(2-aminopyridin-4-yl)-3H-imidazo[4,5-b]pyridin-3-yl)-2',4'-difluoro-[1,1'-biphenyl]-3-yl) ethanesulfonamide The compound was prepared from tert-butyl(5-(3-(5-(ethylsulfonamido)-2',4'-difluoro-[1,1'-biphenyl]-3-yl)-3H-imidazo[4,5-b]pyridin-6-yl)pyridin-2-yl)carbamate (0.2 g, 0.33 mmol) following the procedure of Example 290 to afford the product in 17.9% yield (0.30 g). $^1$H NMR (300 MHz, DMSO-d$_6$): δ 10.42 (s, 1H), 9.01 (s, 1H), 8.85 (s, 1H), 8.64. (s, 1H), 7.96 (d, 1H), 7.81-7.73 (m, 3H), 7.44-7.32 (m, 4H), 7.21 (m, 2H), 3.25-3.23 (q, 2H), 1.26-1.23 (t, 3H), Calculated mass: 506.53; Observed mass: 507.3 [M+H]$^+$ (rt: 0.2 min).

Example 347

N-(5-(6-(6-aminopyridin-3-yl)-3H-imidazo[4,5-b]pyridin-3-yl)-2',4'-difluoro-[1,1'-biphenyl]-3-yl)ethanesulfonamide The title compound was prepared as in Example 340 starting from N-(5-(6-bromo-3H-imidazo[4,5-b]pyridin-3-yl)-2',4'-difluoro-[1,1'-biphenyl]-3-yl)ethanesulfonamide. $^1$H NMR (300 MHz, CD$_3$OD): δ 8.73 (s, 1H), 8.56 (s, 1H), 8.17 (d, 2H), 7.79-7.71 (m, 3H), 7.59-7.57 (m, 1H), 7.42 (m, 1H), 7.08-7.03 (m, 2H), 6.65-6.62 (m, 1H), 3.04 (s, 3H); LC-MS (ESI): Calculated mass: 492.12; Observed mass: 493.0 [M+H]$^+$ (RT: 0.20 min).

Example 348

1-(2',4'-difluoro-5-(6-(1-methyl-1H-pyrazol-4-yl)-3H-imidazo[4,5-b]pyridin-3-yl)-[1,1'-biphenyl]-3-yl)-3-(furan-2-ylmethyl)urea To a solution of the compound of Example 132(a) (60 mg, 0.149 mmol) in DCM was added DIPEA (0.1 ml, 0.447 mmol, 3 eq.) followed by 2-(isocyanatomethyl)furan (22 mg, 0.179 mmol, 1.2 eq). The mixture was stirred for 16 h, and quenched and extracted as in Example 2(b). The solvent was distilled off to afford the crude residue which was purified by preparative HPLC to give the product in 44.87% yield (35 mg). $^1$H NMR (400 MHz, DMSO-d$_6$): δ 9.02 (s, 1H), 8.92 (s, 1H), 8.71 (s, 1H), 8.4 (s, 1H), 8.30 (s, 1H), 8.10 (s, 1H), 8.04 (s, 1H), 7.72-7.67 (m, 2H), 7.60 (d, 2H), 7.43 (t, 1H), 7.25 (t, 1H), 6.73 (t, 1H), 6.41 (s, 1H), 6.3 (d, 2H), 4.3 (d, 2H), 3.90 (s, 3H); LC-MS (ESI): Calculated mass: 525.17; Observed mass: 526.3 [M+H]$^+$ (rt: 1.49 min).

Example 349

N-(2',4'-difluoro-5-(5-(1-methyl-1H-imidazol-4-yl)-1H-benzo[d]imidazol-1-yl)-[1,1'-biphenyl]-3-yl)cyclopropanesulfonamide The compound was prepared from the compound of Example 203(a) using the procedures of Example 203(b). $^1$H NMR (400 MHz, DMSO-d6): δ 10.3 (s, 1H), 8.96 (s, 1H), 8.25 (s, 1H), 8.02 (s, 1H), 7.98 (s, 1H), 7.77-7.66 (m, 2H), 7.62 (s, 2H), 7.52-7.44 (m, 2H), 1.0 (s, 4H); LC-MS (ESI): Calculated mass: 505.14; Observed mass: 506.0 [M+H]$^+$ (rt: 0.632 min).

Example 350

N-(2',4'-difluoro-5-(5-(pyridin-4-yl)-1H-benzo[d]imidazol-1-yl)-[1,1'-biphenyl]-3-yl)cyclopropanesulfonamide The compound was prepared from the title compound of Example 203(a) using the procedures of Example 203(b). $^1$H NMR (300 MHz, DMSO-d$_6$): δ 8.62-8.59 (m, 3H), 8.18 (s, 1H), 7.84-7.81 (m, 4H), 7.67-7.56 (m, 4H), 7.15-7.1 (m, 2H), 2.7 (m, 1H), 1.2-1.1 (m, 4H); LC-MS (API): Calculated mass: 502.54; Observed mass: 503.2 [M+H]$^+$ (rt: 1.15 min).

Example 351

1-(5-(Cyclopropanesulfonamido)-2',4'-difluoro-[1,1'-biphenyl]-3-yl)-1H-benzo-[d]imidazole-5-carboxamide The compound was prepared from the compound of Example 312(a) (100 mg, 0.27 mmol) using the procedure of Example 2(b) and cyclopropanesulfonyl chloride (42 mg, 0.30 mmol, 2.0 eq.) to give the product in 27.34% yield (35 mg). $^1$H NMR (400 MHz, DMSO-d6): δ 10.35 (s, 1H), 8.82 (s, 1H), 8.37 (s, 1H), 8.08 (s, 1H), 7.96-7.94 (d, 1H), 7.77-7.72 (m, 2H), 7.60-7.58 (d, 2H), 7.51 (s, 1H), 7.48-7.43 (m, 1H), 7.38 (s, 1H), 7.29-7.24 (m, 1H), 2.89-2.86 (t, 1H), 1.02-1.01 (d, 4H); LC-MS (ESI): Calculated mass: 468.11; Observed mass: 469.1 [M+H]$^+$ (rt: 1.23 min).

Example 352

N-(2',4'-difluoro-5-(5-(1-(2-hydroxyethyl)-1H-pyrazol-4-yl)-1H-benzo[d]-imidazol-1-yl)-[1,1'-biphenyl]-3-yl)cyclopropanesulfonamide The compound was prepared from N-(2',4'-difluoro-5-(5-(1-(2-((tetrahydro-2H-pyran-2-yl)oxy)ethyl)-1H-pyrazol-4-yl)-1H-benzo[d]imidazol-1-yl)-[1,1'-biphenyl]-3-yl)cyclopropanesulfonamide (0.15 g, 0.242 mmol) using the procedure of Example 330 to give the product in 78% yield (0.063 g). $^1$H+NMR (400 MHz, DMSO-d$_6$): δ 10.15 (s, 1H), 8.65 (S, 1H), 8.22 (s, 1H), 8.00-7.97 (d, 2H), 7.75 (s, 1H), 7.76-7.62 (d, 2H), 7.56 (m, 2H), 7.47 (s, 3H), 7.27 (s, 1H), 4.95 (s, 1H), 4.17 (s, 1H), 3.79 (s, 1H), 1.01 (m, 5H); LC-MS (ESI): Calculated mass: 535.57; Observed mass: 536.4[M+H]$^+$ (rt: 1.0 min).

Example 353

N-(2',4'-difluoro-5-(5-(1-methyl-1H-pyrazol-4-yl)-1H-benzo[d]imidazol-1-yl)-[1,1'-biphenyl]-3-yl)-N,N'-dimethylsulfuric diamide The compound was prepared from the title compound of Example 210(a) using the procedures of Example 210(b). $^1$H NMR (300 MHz, CD$_3$OD): δ 9.4 (s, 1H), 8.02 (s, 1H), 7.92 (s, 1H), 7.85 (s, 1H), 7.78-7.67 (m, 3H), 7.55-7.46 (m, 4H), 7.06-7.03 (d, 2H), 3.86 (s, 3H), 2.77 (s, 6H); LC-MS (ESI): Calculated mass: 508.54; Observed mass: 509.0 [M+H]$^+$ (rt: 0.96 min).

Example 354

N-(2',4'-difluoro-5-(6-(1-isopropyl-1H-pyrazol-4-yl)-3H-imidazo[4,5-b]pyridin-3-yl)-[1,1'-biphenyl]-3-yl)acetamide The compound was prepared from the title compound of Example 131(c) using the procedures of Example 131(d). $^1$H NMR (400 MHz, DMSO-d$_6$): δ 13.0 (br, 1H), 10.2 (br, 1H), 8.69 (s, 1H), 8.20 (s, 1H), 7.87-7.71 (m, 4H), 7.56 (m, 2H), 7.48-7.42 (s, 1H), 7.3-7.25 (dt, 1H), 6.81 (d, 1H), 3.35-3.25 (q, 2H), 1.27-1.24 (t, 3H): LC-MS (ESI): Calculated mass: 479.5; Observed mass: 480.2 [M+H]$^+$ (rt: 1.42 min).

Example 355

N-(2'-fluoro-4'-methoxy-5-(5-(1-methyl-1H-pyrazol-4-yl)-1H-benzo[d]imidazol-1-yl)-[1,1'-biphenyl]-3-yl)-N,N'-dimethylsulfuric diamide The compound was prepared from the compound of Example 191(c) using the methods of Example 210 (a) and (b). $^1$H NMR, 400 MHz: (DMSO-d$_6$): δ 10.42 (s, 1H), 8.95 (s, 1H), 8.25 (s, 1H), 8.02 (s, 1H), 7.98 (s, 1H), 7.68 (s, 2H), 7.6 (t, 1H), 7.52-7.47 (m, 3H), 7.04-7.00 (dd, 1H), 6.97-6.94 (s, 1H), 3.88 (s, 3H), 3.84 (s, 3H), 2.8 (s, 6H); LC-MS (ESI): Calculated mass: 520.58; Observed mass: 521 [M+H]$^+$ (rt: 1.38 min).

Example 356

N-(2',4'-difluoro-5-(6-(1-isopropyl-1H-pyrazol-4-yl)-3H-imidazo[4,5-b]pyridin-3-yl)-[1,1'-biphenyl]-3-yl)methane sulfonamide The compound was prepared from the compound Example 334(a) (0.2 g, 0.417 mmol) using the method of Example 200(c) and 1-isopropyl-3-(4,4,5,5-tetramethyl-1,3,2-dioxaborolan-2-yl)-1H-pyrazole (0.196 g, 0.834 mmol, 2.0 eq.) to give the product in 45% yield (0.095 g). $^1$H NMR (400 MHz, DMSO-d$_6$): δ 10.30 (s, 1H), 8.97 (s, 1H), 8.766-8.762 (d, 1H), 8.44-8.42 (dd, 2H), 8.06 (s, 1H), 7.942-7.93 (s, 1H), 7.80-7.71 (m, 2H), 7.49-7.42 (m, 2H), 7.31-7.27 (m, 1H), 4.53 (m, 1H), 3.18 (s, 1H), 1.48-1.47 (d, 6H); LC-MS (ESI): Calculated mass: 508.54; Observed mass: 509.1 [M+H]$^+$ (rt: 1.55 min)

Example 357

N-(5-(5-(4-aminophenyl)-1H-benzo[d]imidazol-1-yl)-2',4'-difluoro-[1,1'-biphenyl]-3-yl)acetamide The compound was prepared from the compound of Example 1(h) using the procedures of Example 246. $^1$H NMR (300 MHz, DMSO-d$_6$): δ 10.41 (s, 1H), 8.83 (s, 1H), 8.11 (s, 1H), 7.98 (s, 1H), 7.79-7.75 (m, 3H), 7.65.7.63 (m, 4H), 7.52 (s, 1H), 7.49-7.39 (m, 2H), 7.29-7.22 (m, 1H), 7.04-7.02 (m, 2H), 2.1 (s, 3H); Calculated mass: 454.16; Observed mass: 454.8 [M+H]$^+$ (rt: 0.58 min).

Example 358

N-(5-(6-(4-amino-3-fluorophenyl)-3H-imidazo[4,5-b]pyridin-3-yl)-2',4'-difluoro-[1,1'-biphenyl]-3-yl)acetamide The compound was prepared from the compound of Example 131(c) using the procedures of Example 246. $^1$H NMR (300 MHz, DMSO-d$_6$): δ 10.39 (s, 1H), 8.94 (s, 1H), 8.68 (s, 1H), 8.37 (d, 1H), 8.29 (s, 1H), 7.89 (s, 1H), 7.71 (m, 2H), 7.55-7.25 (m, 4H), 6.85 (m, 1H), 5.35 (brs, 2H), 2.12 (s, 3H); LC-MS (ESI): Calculated mass: 473.15; Observed mass: 474.4 [M+H]$^+$ (rt: 1.51 min).

Example 359

1-Cyclopropyl-3-(2',4'-difluoro-5-(5-(6-oxo-1,6-dihydropyridin-3-yl)-1H-benzo[d]imidazol-1-yl)-[1,1'-biphenyl]-3-yl)sulfuric diamide a) 1-(5-(5-(6-(benzyloxy)pyridin-3-yl)-1H-benzo[d]imidazol-1-yl)-2',4'-difluoro-[1,1'-biphenyl]-3-yl)-3-cyclopropyl sulfuric diamide To a solution of 5-(5-(6-(benzyloxy)-1,6-dihydropyridin-3-yl)-1H-benzo[d]imidazol-1-yl)-2',4'-difluoro-[1,1'-biphenyl]-3-amine (120 mg, 0.2380 mmol) in pyridine was added N-cyclopropyl-2-oxooxazolidine-3-sulfonamide (78 mg, 0.380 mmol, 1.6 eq.). The mixture was stirred at 50° C. for 16 h, quenched with water and extracted with ethyl acetate (3×50 ml). The combined organic layer was washed with 1 N HCl and 1N NaOH, water, brine and dried over sodium sulphate. The solvent was distilled off to afford the crude residue which was purified by preparative HPLC to give the product in 10% yield (15 mg).

b) 1-Cyclopropyl-3-(2',4'-difluoro-5-(5-(6-oxo-1,6-dihydropyridin-3-yl)-1H-benzo[d]imidazol-1-yl)-[1,1'-biphenyl]-3-yl)sulfuric diamide The solution of the compound of Example 359(a) (14 mg, 0.0224 mmol) in TFA (1 ml) was heated at 50° C. for 16 h. The mixture was concentrated to give the product in 83% yield (10 mg). $^1$H NMR (400 MHz, CD$_3$OD): δ 11.8 (s, 1H), 10.37 (s, 1H), 8.73 (s, 1H), 8.16 (d, 1H), 7.97-7.91 (m, 2H), 7.76-7.68 (m, 3H), 7.58-7.55 (m, 1H), 7.50 (t, 1H), 7.46-7.38 (m, 3H), 7.28-7.22 (m, 1H), 6.44 (d, 1H), 2.31 (m, 1H), 0.56-0.53 (m, 2H), 0.45-0.42 (m, 2H); LC-MS (ESI): Calculated mass: 533.13; Observed mass: 534.1 [M+H]$^+$ (rt: 1.195 min).

Example 360

1-Cyclopropyl-3-(2',4'-difluoro-5-(5-(1-methyl-1H-pyrazol-4-yl)-1H-benzo[d]-imidazol-1-yl)-[1,1'-biphenyl]-3-yl)sulfuric diamide The compound was prepared from the compound of Example 2(a) (50 mg, 0.1246 mmol) using the procedure of Example 359(a) to give the product in 9.3% yield (6 mg). $^1$H NMR (400 MHz, CD$_3$OD): δ 9.06 (s, 1H), 8.09 (s, 1H), 7.99 (s, 1H), 7.93 (s, 1H), 7.77 (s, 2H), 7.69-7.49 (m, 4H), 7.18-7.11 (m, 2H), 3.97 (s, 3H), 2.48-2.44 (m, 1H), 0.66-0.53 (m, 4H); LC-MS (ESI): Calculated mass: 520.0; Observed mass: 521.2 [M+H]$^+$ (rt: 0.94 min).

Example 361

N-(2',4'-difluoro-5-(6-(3-fluoropyridin-4-yl)-3H-imidazo[4,5-b]pyridin-3-yl)-[1,1'-biphenyl]-3-yl)acetamide The compound was prepared from the title compound of Example 131(c) using the procedures of Example 131(d). $^1$H NMR (400 MHz, DMSO-d$_6$): δ 10.41 (s, 1H), 9.08 (s, 1H), 8.75 (s, 2H), 8.57 (s, 2H), 8.31 (s, 1H), 7.91 (s, 1H), 7.83 (s, 1H), 7.71 (s, 2H), 7.47-7.42 (t, 1H), 7.29-7.25 (t, 1H), 2.12 (s, 3H); LC-MS (ESI): Calculated mass: 459.13; Observed mass: 460.1 [M+H]$^+$ (rt: 1.50 min).

Example 362

N-(5-(5-(3-amino-1-methyl-1H-pyrazol-4-yl)-1H-benzo[d]imidazol-1-yl)-2',4'-difluoro-[1,1'-biphenyl]-3-yl)cyclopropanesulfonamide A solution of N-(2',4'-difluoro-5-(5-(4,4,5,5-tetramethyl-1,3,2-dioxaborolan-2-yl)-1H-benzo[d]imidazol-1-yl)-[1,1'-biphenyl]-3-yl)cyclopropanesulfonamide (100 mg, 0.181 mmol) in THF/EtOH/Water (5:5:2) was degassed by $N_2$ bubbling for 5 min. 4-Bromo-1-methyl-1H-pyrazol-3-amine (35 mg, 0.19 mmol, 1.1 eq.) was added and the mixture was degassed for another 5 min. Bis(tri-tert-butylphosphine)palladium(0) (5 mg, 0.009 mmol, 0.05 eq.) and cesium carbonate (170 mg, 0.54 mmol, 3.0 eq.) were added sequentially and the mixture was further degassed for 5 min and heated at 90° C. for 16 h. The mixture was quenched and extracted as in Example 1(d). The solvent was distilled off to give the crude residue which was purified by preparative HPLC to give the product in 27% yield (25 mg). $^1$H NMR (300 MHz, DMSO): δ 10.3 (s, 1H) 8.79 (s, 1H), 7.95-7.92 (m, 2H), 7.77-7.07 (m, 2H), 7.59 (s, 2H), 7.53-7.47 (m, 3H), 7.29 (m, 1H), 3.75 (s, 3H), 2.91 (m, 1H), 1.5-1.49 (d, 2H), 1.30-1.26 (t, 2H), 1.03-1.01 (t, 2H); LC-MS (ESI): Calculated mass: 520.5; Observed mass: 521.0 [M+H]$^+$ (rt: 0.676 min).

Example 363

N-(5-(5-(3-amino-1-methyl-1H-pyrazol-4-yl)-1H-benzo[d]imidazol-1-yl)-2',4'-difluoro-[1,1'-biphenyl]-3-yl)ethanesulfonamide The compound was prepared from the compound of Example 200(b) using the procedure of Example 200(c) to give the title product in 12% yield (8 mg). 1H NMR (300 MHz, CD3OD): δ 8.89 (s, 1H), 7.90 (s, 1H), 7.78-7.74 (m, 2H), 7.65-7.54 (m, 4H), 7.51 (d, 1H), 7.15-7.05 (m, 2H), 3.81 (s, 3H), 3.31-3.24 (q, 2H), 1.39-1.34 (t, 3H); LC-MS (ESI): Calculated mass: 508.54; Observed mass: 509.0 [M+H]+ (rt: 0.85 min).

Example 364

(Z)—N-(2',4'-difluoro-5-(5-(1-(hydroxyimino)ethyl)-1H-benzo[d]imidazol-1-yl)-[1,1'-biphenyl]-3-yl)cyclopropanesulfonamide To a solution of N-(5-(5-acetyl-1H-benzo[d]imidazol-1-yl)-2',4'-difluoro-[1,1'-biphenyl]-3-yl)cyclopropanesulfonamide (110 mg, 0.235 mmol) in ethanol was added hydroxyl amine hydrochloride (24.7 mg, 0.353 mmol) and the mixture was heated at 80° C. for 2 h. The mixture was concentrated under vacuum and washed with ether to afford the product in 49% yield (55 mg). $^1$H NMR (400 MHz, DMSO-$d_6$): δ 9.00 (s, 1H), 8.03 (s, 1H), 7.82-7.70 (m, 3H), 7.60-7.58 (d, 2H), 7.52 (s, 1H), 7.46-7.40 (m, 1H), 7.27-7.24 (m, 1H), 2.86-2.83 (m, 1H), 2.25 (s, 3H), 1.01-1.00 (m, 4H); LC-MS (ESI): Calculated mass: 482.5; Observed mass: 483.1 [M+H]$^+$ (rt: 1.475 min).

Example 365

2-(5-(1-(5-Acetamido-2',4'-difluoro-[1,1'-biphenyl]-3-yl)-1H-benzo[d]imidazol-5-yl)-1H-1,2,3-triazol-1-yl)acetamide a) Ethyl 2-(5-(1-(5-acetamido-2',4'-difluoro-[1,1'-biphenyl]-3-yl)-1H-benzo[d]-imidazol-5-yl)-1H-1,2,3-triazol-1-yl)acetate A mixture of N-(5-(5-ethynyl-1H-benzo[d]imidazol-1-yl)-2',4'-difluorobiphenyl-3-yl)acetamide (258 mg, 0.6 mmol), ethyl-2-azidoacetate (180 mg, 0.8 mmol, 1.3 eq.), sodium ascorbate (125 mg, 0.6 mmol, 1.0 eq.) and copper sulfate pentahydrate (80 mg, 0.32 mmol, 0.5 eq.) in t-butanol and water (1:1, 3 ml) was stirred for 12 h at RT. The mixture was quenched with water and the precipitate formed was filtered and dried to give the product in 75% yield (250 mg).

b) 2-(5-(1-(5-acetamido-2',4'-difluoro-[1,1'-biphenyl]-3-yl)-1H-benzo[d]imidazol-5-yl)-1H-1,2,3-triazol-1-yl)acetic acid To a solution of the compound of Example 365(a) (250 mg, 0.48 mmol) in THF/methanol/water (1:1:0.5, 5 ml) was added LiOH $H_2O$ (40 mg, 0.968 mmol, 2 eq.) and the mixture was stirred at RT for 12 h. The mixture was concentrated and the crude product obtained was extracted with ethyl acetate and water and dried over sodium sulphate to give the product in 42% yield (100 mg).

c) 2-(5-(1-(5-acetamido-2',4'-difluoro-[1,1'-biphenyl]-3-yl)-1H-benzo[d]imidazol-5-yl)-1

To a solution of the compound of Example 365(b) (100 mg, 0.2 mmol) in DMF was added HOBt (30 mg, 0.224 mmol, 1.1 eq.) followed by EDC (40 mg, 0.224 mmol, 1.1 eq.). The mixture was stirred at RT for 12 h, then 25% ammonia solution was added to the precooled reaction mass and stirred for 4 h. The mixture was then quenched and extracted as in Example 1(d). The solvent was distilled off to afford the crude residue which was purified by preparative TLC to give the product in 5% yield (5 mg).

Example 366

N-(2',4'-Difluoro-5-(5-(1-methyl-1H-pyrazol-4-yl)-1H-benzo[d]imidazol-1-yl)-[1,1'-biphenyl]-3-yl)ethenesulfonamide The compound was prepared from the compound of Example 2(a) (50 mg, 0.125 mmol) in THF using the procedure of Example 2(b) and 2-chloroethanesulfonyl chloride (30 mg, 0.187 mmol, 1.5 eq.) to afford the product in 29% yield (18 mg). $^1$H NMR (400 MHz, CD$_3$OD): δ 9.1 (s, 1H), 8.08 (s, 1H), 7.98 (s, 1H), 7.92 (s, 1H), 7.76-7.74 (m, 2H), 7.63-7.59 (m, 3H), 7.50 (s, 1H), 7.14-7.12 (m, 2H), 6.80-6.78 (m, 1H), 6.31-6.27 (d, 1H), 6.09-6.06 (d, 1H), 3.95 (s, 3H); LC-MS (ESI): Calculated mass: 491.5; Observed mass: 492.1 [M+H]$^+$ (rt: 1.413 min).

Example 367

N-(2',4'-difluoro-5-(5-(1-methyl-1H-pyrazol-4-yl)-1H-benzo[d]imidazol-1-yl)-[1,1'-biphenyl]-3-yl)-2-hydroxyethanesulfonamide a) 2-(Benzyloxy)-N-(2',4'-difluoro-5-(5-(1-methyl-1H-pyrazol-4-yl)-1H-benzo-[d]imidazol-1-yl)-[1,1'-biphenyl]-3-yl)ethanesulfonamide The compound was prepared from the compound of Example 2(a) (100 mg, 0.249 mmol) in THF using the method of Example 2(b) and 2-(benzyloxy)ethanesulfonyl chloride (87 mg, 0.374 mmol, 1.5 eq.) to give the product in 69% yield (100 mg). LC-MS (ESI): Calculated mass: 512.55; Observed mass: 513.1 [M+H]+ (rt: 0.632 min).

b) N-(2',4'-difluoro-5-(5-(1-methyl-1H-pyrazol-4-yl)-1H-benzo[d]imidazol-1-yl)-[1,1'-biphenyl]-3-yl)-2-hydroxyethanesulfonamide To a solution of the compound of Example 367(a) (100 mg, 0.17 mmol) in methanol (2 ml) and THF (1 ml) was added 10% Pd/C (10 mg, 0.1 eq.) and palladium hydroxide on carbon (10 mg, 0.1 eq). The reaction vessel was purged with $N_2$ for 5 min. The mixture was then hydrogenated with $H_2$ for 12 h. The mixture was filtered through a pad of celite and the filtrate was concentrated to give the compound in 13% yield (11 mg). $^1$H NMR (400 MHz, DMSO-$d_6$): δ 10.3 (s, 1H), 8.9 (s, 1H), 8.23 (s, 1H), 8.00-7.97 (d, 2H), 7.76-7.58 (m, 5H), 7.48 (s, 2H), 7.29 (d, 1H), 3.88 (s, 3H), 3.81 (t, 4H). LC-MS (ESI): Calculated mass: 509.53; Observed mass: 510.1 [M+H]+ (rt: 0.853 min).

Example 368

N-(2',4'-difluoro-5-(5-(1-methyl-1H-pyrazol-4-yl)-1H-benzo[d]imidazol-1-yl)-[1,1'-biphenyl]-3-yl)piperidine-4-carboxamide The title compound was prepared from the compound of Example 2(a) using the procedures of Example 240. $^1$H NMR (400 MHz, CD$_3$OD): δ 8.49 (s, 1H), 8.11 (s, 1H), 8.0 (s, 1H), 7.91 (s, 1H), 7.86 (s, 1H), 7.75 (s, 1H), 7.71 (s, 1H), 7.69 (s, 1H), 7.65-7.59 (m, 2H), 7.52 (m, 1H), 7.14-7.1 (m, 2H), 3.94 (s, 1H), 2.89 (t, 4H), 2.7 (m, 1H), 2.04-1.84 (m, 4H): LC-MS (ESI): Calculated mass: 512.55; Observed mass: 513.2 [M+H]+ (rt: 1.0 min).

Example 369

N-(5-(5-(4,5-dihydrooxazol-2-yl)-1H-benzo[d]imidazol-1-yl)-2',4'-difluoro-[1,1'-biphenyl]-3-yl)acetamide a) N-(5-((4-(4,5-dihydrooxazol-2-yl)-2-nitrophenyl)amino)-2',4'-difluoro-[1,1'-biphenyl]-3-yl)acetamide To a solution of the compound of Example 22(a) (0.25 g, 0.608 mmol) in tert-butanol was added 2-amino ethanol (0.05 ml, 0.912 mmol, 1.5 eq.) and stirred at RT for 30 min. Iodine (0.25 g, 1.82 mmol, 3 eq.) and K$_2$CO$_3$ (0.25 g, 1.82 mmol, 3 eq.) were added and the mixture was stirred at 75° C. for 24 h. The mixture was quenched with sodium thiocyanate solution and extracted with ethyl acetate (3×50 ml). The solvent was distilled off to give the crude residue which was purified by combiflash chromatography (5% methanol in chloroform) to give the product in 60% yield (0.15 g).

b) N-(5-((2-amino-4-(4,5-dihydrooxazol-2-yl)phenyl)amino)-2',4'-difluoro-[1,1'-biphenyl]-3-yl)acetamide To a solution of the compound of Example 369(a) (150 mg, 0.33 mmol) in THF (3 ml) were added a solution of ammonium chloride (70 mg, 1.32 mmol, 4 eq.) in water (1 ml) and zinc (86 mg, 1.32 mmol, 4 eq.). The mixture was stirred at RT for 2 h and filtered. The filtrate was diluted with water and extracted as in Example 1(d). The solvent was distilled off to afford the product in 78% yield (0.11 g).

c) N-(5-(5-(4,5-dihydrooxazol-2-yl)-1H-benzo[d]imidazol-1-yl)-2',4'-difluoro-[1,1'-biphenyl]-3-yl)acetamide The compound was prepared from the compound of Example 369(b) using the procedure of Example 22(d) to give the product in 78% yield (0.11 g). $^1$H NMR (400 MHz, DMSO-$d_6$): δ 10.5 (s, 1H), 8.84 (s, 1H), 8.7 (d, 1H), 8.13 (t, 1H), 8.10-8.05 (m, 3H), 7.85-7.72 (m, 3H), 7.54 (s, 1H), 7.49-7.43 (m, 1H), 4.47 (t, 2H), 3.31 (t, 2H), 2.12 (s, 3H). LC-MS (ESI): Calculated mass: 432.4; Observed mass: 432.8 [M+H]+ (rt: 0.288 min).

Example 370

N-(5-(5-(1,2,4-oxadiazol-3-yl)-1H-benzo[d]imidazol-1-yl)-2',4'-difluoro-[1,1'-biphenyl]-3-yl)acetamide The compound was prepared from the compound of Example 313(d) using the procedures of Example 313(e). $^1$H NMR (400 MHz, DMSO-$d_6$): δ 10.49 (s, 1H), 9.73 (s, 1H), 8.83 (s, 1H), 8.43 (s, 1H), 8.06 (t, 2H), 7.88 (t, 2H), 7.79-7.73 (m, 1H), 7.55 (s, 1H), 7.49-7.43 (m, 1H), 7.29-7.25 (m, 1H), 2.12 (s, 3H); LC-MS (ESI): Calculated mass: 431.4; Observed mass: 432.8 [M+H]+ (rt: 1.485 min)

Example 371

N-(5-(5-(4,5-dihydrooxazol-2-yl)-1H-benzo[d]imidazol-1-yl)-2',4'-difluoro-[1,1'-biphenyl]-3-yl)ethanesulfonamide The compound was prepared from the compound of Example 369 using the procedures of Example 2. $^1$H NMR (300 MHz, CD$_3$OD): δ 8.59 (s, 1H), 8.27 (d, 1H), 8.15-8.14 (t, 1H), 8.11 (m, 1H), 7.82-7.75 (m, 4H), 7.66-7.56 (m, 1H), 7.56 (m, 1H), 7.13-7.11 (m, 1H), 6.56 (t, 1H), 3.53-3.47 (m, 2H), 3.0 (m, 2H), 2.82 (s, 3H), 2.7 (m, 1H), 2.14-2.0 (m, 4H). LC-MS (ESI): Calculated mass: 512.55; Observed mass: 513.1 [M+H]+ (rt: 0.632 min).

Example 372

1-(2',4'-Difluoro-5-(5-(1-methyl-1H-pyrazol-4-yl)-1H-benzo[d]imidazol-1-yl)-[1,1'-biphenyl]-3-yl)-3-(furan-2-ylmethyl)sulfuric diamide The compound was prepared from the compound of Example 2(a) using the procedure of Example 245 to give the pure product in 10% yield (7 mg). $^1$H NMR (300 MHz, DMSO-$d_6$): δ 10.26 (s, 1H), 8.66 (s, 1H), 8.2 (s, 1H), 7.98

(s, 1H), 7.94 (s, 1H), 7.75-7.67 (m, 2H), 7.57 (t, 3H), 7.45-7.43 (m, 2H), 7.29-7.25 (m, 2H), 7.22 (m, 2H), 3.87 (s, 3H), 3.17 (s, 2H); LC-MS (ESI): Calculated mass: 479.5; Observed mass: 480.2 [M+H]$^+$ (rt: 1.34 min).

Example 373

N-(2',4'-difluoro-5-(5-(1-methyl-1H-pyrazol-4-yl)-1H-benzo[d]imidazol-1-yl)-[1,1'-biphenyl]-3-yl)-1-methylpiperidine-4-carboxamide The compound was prepared from the compound of Example 2(a) using the procedures of Example 233. $^1$H NMR (400 MHz, CD$_3$OD): δ 9.11 (s, 1H), 8.23 (t, 1H), 8.07 (s, 1H), 7.98 (s, 1H), 7.91 (s, 1H), 7.80-7.77 (m, 3H), 7.65-7.61 (m, 2H), 7.14-7.12 (m, 2H), 3.96 (s, 3H), 3.63-3.60 (m, 2H), 3.088-3.082 (m, 2H), 2.90 (s, 3H), 2.79-2.73 (m, 1H), 2.24-2.01 (m, 4H); LC-MS (ESI): Calculated mass: 526.58; Observed mass: 527.2 [M+H]$^+$ (rt: 0.183 min).

Example 374

2',4'-difluoro-5-(5-(1-methyl-1H-pyrazol-4-yl)-1H-benzo[d]imidazol-1-yl)-[1,1'-biphenyl]-3-ol a) 1-bromo-3-methoxy-5-nitrobenzene To a solution of 1-bromo-3,5-dinitrobenzene (5 g, 20.2 mmol) in methanol (50 ml) was added sodium methoxide (1.3 g, 24.3 mmol, 1.2 eq.) and the mixture was heated to reflux for 12 h and then quenched with 10% HCl. The solid formed was filtered and dried to afford the compound in 65% yield (3 g).

b) 3-bromo-5-methoxyaniline

To a solution of 1-bromo-3-methoxy-5-nitrobenzene (1 g, 4.33 mmol) in THF (10 ml) were added a solution of ammonium chloride (1.83 g, 34.6 mmol, 8 eq.) in water (5 ml) and zinc (1.93 g, 34.6 mmol, 8 eq.). The mixture was stirred at RT for 30 min and filtered. The filtrate was diluted with water and extracted as in Example 1(d). The solvent was distilled off to afford the product in 92% yield (0.8 g).

c) N-(3-bromo-5-methoxyphenyl)-4-(1-methyl-1H-pyrazol-4-yl)-2-nitroaniline

A solution of the compound of Example 374(b) (1 g, 4.78 mmol, 1.2 eq.), 3-bromo-5-methoxyaniline (0.8 g, 3.98 mmol) and potassium fluoride (0.23 g, 3.98 mmol, 1 eq.) in DMF was heated at 120° C. for 12 h. The mixture was quenched and extracted as in Example 1(d). The solvent was distilled off to afford the crude residue which was purified by column chromatography (60-120 silica gel, 50% ethyl acetate in hexane) to give the product in 42% yield (0.81 g).

d) 1-(3-Bromo-5-methoxyphenyl)-5-(1-methyl-1H-pyrazol-4-yl)-1H-benzo[d]-imidazole The compound was prepared using the procedures of Example 1(g) and 1(h) starting from the compound of Example 374(c) (0.81 g, 2.02 mmol) to afford the product in 52% yield (0.35 g).

e) 1-(2',4'-Difluoro-5-methoxy-[1,1'-biphenyl]-3-yl)-5-(1-methyl-1H-pyrazol-4-yl)-1H-benzo[d]imidazole The compound was prepared from the compound of Example 374(d) (0.35 g, 0.92 mmol) using the procedure of Example 277(d) and 2,4-difluorophenyl boronic acid (0.17 g, 1.09 mmol, 1.2 eq.) to yield the product in 25% yield (95 mg).

f) 2',4'-difluoro-5-(5-(1-methyl-1H-pyrazol-4-yl)-1H-benzo[d]imidazol-1-yl)-[1,1'-biphenyl]-3-ol To a slurry of aluminium chloride (77 mg, 0.576 mmol) and thiourea (15 mg, 0.192 mmol) in DCM (5 ml) was added a solution of the compound of Example 374(e) (80 mg, 0.192 mmol) in DCM (3 ml). The mixture was heated at 50° C. for 5 h. The mixture was quenched and extracted as in Example 2(d) and dried over anhydrous Na$_2$SO$_4$ and concentrated to afford the product in 17% yield (15 mg). $^1$H NMR (400 MHz, CD$_3$OD): δ 9.2 (s, 1H), 8.07 (s, 1H), 7.99 (s, 1H), 7.91 (s, 1H), 7.77 (s, 2H), 7.64-7.58 (m, 1H), 7.30 (s, 1H), 7.17-7.07 (m, 4H), 3.95 (s, 3H). LC-MS (ESI): Calculated mass: 402.4; Observed mass: 403.1 [M+H]$^+$ (rt: 1.282 min).

Example 375

N-(2',4'-difluoro-5-(5-(1-methyl-1H-pyrazol-4-yl)-1H-benzo[d]imidazol-1-yl)-[1,1'-biphenyl]-3-yl)pyrazin-2-amine A solution of the compound of Example 2(a) (100 mg, 0.24 mmol) in toluene (6 ml) was degassed by N$_2$ bubbling for 5 min. 2-Chloro pyrazine (34 g, 0.29 mmol, 1.2 eq.) was added and the mixture was degassed for another 5 min. Pd$_2$(dba)$_3$ (22 mg, 0.02 mmol, 0.1 eq.) and xantphos (28 mg, 0.04 mmol, 0.2 eq.) and Cs$_2$CO$_3$ (242 mg, 0.74 mmol, 3.0 eq) were added sequentially and the mixture was further degassed for 5 min and then heated at 110° C. for 16 h. The mixture was filtered on celite bed and quenched and extracted as in Example 1(d). The solvent was distilled off to afford the crude residue which was purified by preparative HPLC to yield the product in 10% yield (11 mg). $^1$H NMR (400 MHz, DMSO-d$_6$): δ 9.99 (s, 1H), 8.65 (s, 1H), 8.31 (s, 1H), 8.26-8.25 (m, 1H), 8.19 (m, 2H), 8.00-7.98 (m, 3H), 7.93 (s, 1H), 7.85 (d, 1H), 7.79-7.34 (m, 2H), 7.62-7.59 (dd, 1H), 7.47-7.4 (m, 2H), 7.28-7.24 (dt, 1H), 3.87 (s, 3H). LC-MS (ESI): Calculated mass: 479.48; Observed mass: 480.1 [M+H]$^+$ (rt: 1.54 min).

Example 376

N-(2',4'-difluoro-5-(5-(1-methyl-1H-pyrazol-4-yl)-1H-benzo[d]imidazol-1-yl)-[1,1'-biphenyl]-3-yl)isoxazol-3-amine a) 1-(5-Bromo-2',4'-difluoro-[1,1'-biphenyl]-3-yl)-5-(1-methyl-1H-pyrazol-4-yl)-1H-benzo[d]imidazole To a solution of the compound of Example 2(a) (0.80 g, 1.995 mmol) in HBr (8 ml) was added aqueous solution of NaNO$_2$ (0.26 g in 2 ml of water) and the mixture was stirred at 0° C. for 20 min. Then CuBr in HBr (0.572 g, 3.99 mmol, 2.0 eq in 3 ml of HBr) was added at 0° C. and the mixture was stirred at 50° C. for 10 min. The mixture was quenched and extracted as in Example 1(d). The solvent was distilled off under reduced pressure to afford the product in 80.9% yield (0.750 g). LC-MS (ESI): Calculated mass: 465.2; Observed mass: 467.0 [M+H]$^+$ (rt: 1.75 min).

b) N-(2',4'-difluoro-5-(5-(1-methyl-1H-pyrazol-4-yl)-1H-benzo[d]imidazol-1-yl)-[1,1'-biphenyl]-3-yl)isoxazol-3-amine The compound was prepared from the compound of Example 376(a) following the method of Example 280. $^1$H NMR (400 MHz, CD$_3$OD): δ 8.53 (s, 1H), 8.43-8.42 (d, 1H), 8.03 (s, 1H), 7.95-7.93 (m, 2H), 7.89 (s, 1H), 7.76-7.45 (d, 1H), 7.68-7.62 (m, 3H), 7.33-7.32 (d, 1H), 7.16-7.11 (m, 2H), 6.23-6.22 (d, 1H), 6.23-6.27 (m, 1H), 3.97 (s, 3H). LC-MS (ESI): Calculated mass: 468.46; Observed mass: 468.46 [M+H]$^+$ (rt: 1.282 min).

Example 377

N-(2',4'-difluoro-5-(5-(1-methyl-1H-pyrazol-4-yl)-1H-benzo[d]imidazol-1-yl)-[1,1'-biphenyl]-3-yl)pyridazin-3-amine The compound was prepared from the compound of Example 376(a) following the procedure described in the Example 280. $^1$H NMR (400 MHz, DMSO-d$_6$): δ 9.75 (s, 1H), 8.74-8.73 (d, 2H), 8.65 (s, 1H), 8.34-8.33 (m, 1H), 8.19 (s, 1H), 7.98 (s, 1H), 7.94 (m, 2H), 7.78-7.75 (m, 2H), 7.6-7.57 (dd, 1H), 7.53-7.4 (m, 3H), 7.4-7.2 (m, 2H), 3.87 (s, 3H). LC-MS (ESI): Calculated mass: 479.48; Observed mass: 403.1 [M+H]$^+$ (rt: 1.282 min).

Example 378

N-(4'-cyano-5-(5-(1-methyl-1H-pyrazol-4-yl)-1H-benzo[d]imidazol-1-yl)-[1,1'-biphenyl]-3-yl)cyclopropanesulfonamide a) 3-bromo-5-(5-(1-methyl-1H-pyrazol-4-yl)-1H-benzo[d]imidazol-1-yl)aniline To a solution of the compound of Example 277(c) (1.6 g, 3.89 mmol) in ethanol (15 ml) was added aqueous solution of NaOH (1.56 g, 38.9 mmol, 10.0 eq.) and the mixture was heated at 85° C. for 5 h. The mixture was quenched and extracted as in Example 1(d). The solvent was distilled off under reduced pressure to afford the product in 90% yield (1.3 g).

b) N-(3-bromo-5-(5-(1-methyl-1H-pyrazol-4-yl)-1H-benzo[d]imidazol-1-yl)-phenyl)cyclopropanesulfonamide To a solution of the compound of Example 378(a) (200 mg, 0.54 mmol) in DCM was added pyridine (86 mg, 1.08 mmol, 2.0 eq.) followed by cyclopropane sulfonyl chloride (93 mg, 0.65 mmol, 1.2 eq.). The mixture was stirred for 1 h, and quenched and extracted as in Example 2(b). The solvent was distilled off under reduced pressure to afford the product in 59% yield (75 mg).

c) N-(4'-cyano-5-(5-(1-methyl-1H-pyrazol-4-yl)-1H-benzo[d]imidazol-1-yl)-[1,1'-biphenyl]-3-yl)cyclopropanesulfonamide The compound was prepared from the compound of Example 378(b) (100 mg, 0.21 mmol) using the procedure of Example 200(c) and 4-cyano phenyl boronic acid (38 mg, 0.32 mmol, 2.5 eq.) to give the product in 24% yield (25 mg). $^1$H NMR (400 MHz, DMSO-d$_6$): δ 10.2-10.3 (brS, 1H), 8.71 (s, 1H), 8.19 (s, 1H), 8.02-7.94 (m, 6H), 7.77 (s, 1H), 7.69-7.67 (d, 1H), 7.6-7.58 (m, 3H), 3.87 (s, 3H), 2.91-2.88 (m, 1H), 1.0 (d, 4H). LC-MS (ESI): Calculated mass: 494.59; Observed mass: 495.15 [M+H]$^+$ (rt: 1.4 min).

Example 379

N-(2',4'-difluoro-5-(5-(4-methylpiperazine-1-carbonyl)-1H-benzo[d]imidazol-1-yl)-[1,1'-biphenyl]-3-yl)acetamide To a solution of the compound of Example 332(b) (100 mg, 0.23 mmol, 1.0 eq.) in 1,4-dioxane (5 ml) was added trimethyl aluminium (49 mg, 0.59 mmol, 2.5 eq). The mixture was stirred for 10 min and then N-methyl piperazine (35 mg, 0.35 mmol, 1.5 eq.) was added and the mixture was heated at 110° C. in a sealed tube for 12 h. The mixture was cooled to RT and filtered through celite and the filtrate was concentrated to afford the crude product which was purified by preparative HPLC to afford the product in 21% yield (24 mg). $^1$H NMR (400 MHz, CD$_3$OD): δ 8.61 (s, 1H), 8.1 (s, 1H), 7.86 (s, 1H), 7.79.7.77 (d, 1H), 7.75 (d, 1H), 7.68-7.6 (m, 1H), 7.51 (d, 1H), 7.48-7.46 (d, 1H), 7.14-7.08 (m, 2H), 3.8-3.5 (br, 4H), 2.6-2.4 (br, 4H), 2.35 (s, 3H), 2.18 (s, 3H). LC-MS (ESI): Calculated mass: 489.52; Observed mass: 489.8 [M+H]$^+$ (rt: 0.15 min).

Example 381

N-(5-(5-cyano-1H-benzo[d]imidazol-1-yl)-2',4'-difluoro-[1,1'-biphenyl]-3-yl)ethanesulfonamide a) 1-(5-amino-2',4'-difluoro-[1,1'-biphenyl]-3-yl)-1H-benzo[d]imidazole-5-carbonitrile To a solution of the compound of Example 313(c) (1.0 g, 2.88 mmol, 1.0 eq.) in ethanol (20 ml) was added KOH (0.486 g, 8.66 mmol, 3.0 eq.) as a 20% aqueous solution and the mixture was heated at 80° C. for 6 h. The solvent was distilled off under reduced pressure and the crude material was stirred with water and ethyl acetate. The ethyl acetate was dried over sodium sulphate and concentrated to afford the product in 78% yield (0.7 g).

b) N-(5-(5-cyano-1H-benzo[d]imidazol-1-yl)-2',4'-difluoro-[1,1'-biphenyl]-3-yl)ethanesulfonamide The compound was prepared from the compound of Example 380(a) (100 mg, 0.28 mmol) and ethanesulfonyl chloride (40 mg, 0.31 mmol, 1.1 eq.) using the procedure of Example 2(b) to give the product in 16% yield (22 mg). $^1$H NMR (400 MHz, DMSO-d$_6$): δ 8.91 (s, 1H), 8.4 (s, 1H), 7.86-7.73 (m, 3H), 7.58-7.45 (m, 4H), 7.29-7.25 (t, 1H), 3.3 (m, 2H), 1.27-1.24 (t, 3H). LC-MS (ESI): Calculated mass: 438.45; Observed mass: 438.9 [M+H]$^+$ (rt: 1.5 min).

Example 381

1-(2',4'-difluoro-5-methyl-[1,1'-biphenyl]-3-yl)-5-(1-methyl-1H-pyrazol-4-yl)-1H-benzo[d]imidazole a) 2,4-Difluoro-5'-methyl-3'-nitrobiphenyl

The compound was prepared from 1-bromo-3-methyl-5-nitro-benzene (1.5 g, 6.94 mmol) and difluorophenyl boronic acid (1.3 g, 8.33 mmol, 1.2 eq.) using the procedure of Example 1(d) to afford the product in 27% yield (0.65 g).

b) 2',4'-difluoro-5-methyl-[1,1'-biphenyl]-3-amine

To a solution of the compound of Example 381(a) (1.4 g, 5.62 mmol) in THF (20 ml) were added a solution of ammonium chloride (2.4 g, 44.9 mmol, 8 eq.) in water (8 ml) and zinc (2.92 g, 44.9 mmol, 8 eq.). The mixture was stirred at RT for 2 h and filtered. The filtrate was diluted with water and extracted as in Example 1(d). The solvent was distilled off to afford the product in 92% yield (1.3 g).

c) 1-(2',4'-difluoro-5-methyl-[1,1'-biphenyl]-3-yl)-5-(1-methyl-1H-pyrazol-4-yl)-1H-benzo[d]imidazole The compound was prepared from the compound of Example 381(b) (1.3 g, 5.93 mmol) using the procedures of Example 1 steps (f) to (i) to give the product in 10% yield (20 mg). $^1$H NMR (400 MHz, DMSO-$d_6$): δ 8.96 (s, 1H), 8.24 (s, 1H), 8.00-7.97 (d, 2H), 7.77-7.72 (m, 2H), 7.67-7.62 (m, 3H), 7.53 (s, 1H), 7.5-7.4 (t, 1H), 7.3-7.2 (t, 1H), 3.9 (s, 6H). LC-MS (ESI): Calculated mass: 400.42; Observed mass: 401.1 [M+H]$^+$ (rt: 1.6 min).

Example 382

N-(5-(5-(1-methyl-1H-pyrazol-4-yl)-1H-benzo[d]imidazol-1-yl)-3'-(1H-pyrazol-1-yl)-[1,1'-biphenyl]-3-yl)acetamide The compound was prepared from the compound of Example 277(c) using the procedure described in Example 277(d). $^1$H NMR (400 MHz, DMSO-$d_6$): δ 9.1 (s, 1H), 8.65 (d, 1H), 8.25 (s, 1H), 8.22 (s, 1H), 8.17 (s, 1H), 8.03 (s, 1H), 7.98 (s, 2H), 7.94-7.92 (d, 1H), 7.81-7.8 (d, 1H), 7.77-7.5 (d, 1H), 7.7-7.64 (m, 4H), 6.59 (s, 1H), 2.1 (s, 1H). LC-MS (ESI): Calculated mass: 473.53; Observed mass: 474.2 [M+H]$^+$ (rt: 0.47 min).

Example 383

N-(5-(5-(1-methyl-1H-pyrazol-4-yl)-1H-benzo[d]imidazol-1-yl)-4'-(1H-pyrrol-1-yl)-[1,1'-biphenyl]-3-yl)acetamide The compound was prepared from the compound of Example 277(c) using the procedure described in Example 277(d). $^1$H NMR (400 MHz, DMSO-$d_6$): δ 8.71 (s, 1H), 8.2 (s, 1H), 8.03 (s, 1H), 7.99 (s, 1H), 7.94-7.93 (m, 2H), 7.86-7.83 (m, 2H), 7.76-7.68 (m, 4H), 7.6-7.48 (m, 3H), 6.3 (d, 1H), 3.88 (s, 3H), 2.14 (s, 3H): LC-MS (ESI): Calculated mass: 472.54; Observed mass: 473.1 [M+H]$^+$ (rt: 1.39 min).

Example 384

N-(2',4'-difluoro-5-(5-morpholino-1H-benzo[d]imidazol-1-yl)-[1,1'-biphenyl]-3-yl)cyclopropanesulfonamide The compound was prepared from N-(5-(5-bromo-1H-benzo[d]imidazol-1-yl)-2',4'-difluoro-[1,1'-biphenyl]-3-yl)cyclopropanesulfonamide using the procedure of Example 321. $^1$H NMR (400 MHz, DMSO-$d_6$): δ 10.38 (s, 1H), 9.0 (s, 1H), 7.79-7.73 (m, 1H), 7.67 (s, 1H), 7.64 (s, 1H), 7.61 (s, 1H), 7.53-7.46 (m, 2H), 7.33-7.26 (m, 3H), 3.9 (s, 4H), 3.2 (s, 4H), 2.9 (m 1H), 1.05 (d, 4H): LC-MS (ESI): Calculated mass: 510.56; Observed mass: 473.1 [M+H]$^+$ (rt 1.39 min).

Example 385

(E)-N-(2',4'-difluoro-5-(5-(1-(methoxyimino)ethyl)-1H-benzo[d]imidazol-1-yl)-[1,1'-biphenyl]-3-yl)cyclopropanesulfonamide The compound was prepared from N-(5-(5-acetyl-1H-benzo[d]imidazol-1-yl)-2',4'-difluoro-[1,1'-biphenyl]-3-yl)cyclopropanesulfonamide using the method described in Example 364. $^1$H NMR (400 MHz, DMSO-$d_6$): δ 8.69 (s, 1H), 9.0 (s, 1H), 8.03 (d, 1H), 7.76-7.67 (m, 3H), 7.54 (m, 2H), 7.47 (m, 1H), 7.45-7.42 (m, 2H), 7.28-7.22 (m, 3H), 7.25-7.24 (dt, 1H), 3.92 (s, 3H), 2.84-2.81 (m, 1H), 2.26 (s, 3H), 1.0 (d, 4H): LC-MS (ESI): Calculated mass: 496.53; Observed mass: 497.0 [M+H]$^+$ (rt: 1.68 min).

Example 386

N-(5-(5-(1-cyclopentyl-1H-pyrazol-4-yl)-1H-benzo[d]imidazol-1-yl)-2',4'-difluoro-[1,1'-biphenyl]-3-yl)cyclopropanesulfonamide The compound was prepared from N-(5-(5-bromo-1H-benzo[d]imidazol-1-yl)-2',4'-difluoro-[1,1'-biphenyl]-3-yl)cyclopropanesulfonamide using the procedure described in Example 200(c). $^1$H NMR (400 MHz, DMSO-$d_6$): δ 8.4 (s, 1H), 8.33 (s, 1H), 8.03 (s, 1H), 7.98 (s, 1H), 7.8-7.7 (m, 1H), 7.69 (s, 1H), 7.61 (m, 2H), 7.5-7.4 (m, 2H), 7.32-7.25 (dt, 1H), 4.8-4.65 (m, 1H), 2.95-2.15-1.6 (m, 8H), 1.02 (d, 4H): LC-MS (ESI): Calculated mass: 559.63; Observed mass: 560.3 [M+H]$^+$ (rt: 1.19 min).

Example 387

N-(2',4'-difluoro-5-(5-(2-oxopyrrolidin-1-yl)-1H-benzo[d]imidazol-1-yl)-[1,1'-biphenyl]-3-yl)cyclopropanesulfonamide A solution of N-(5-(5-bromo-1H-benzo[d]imidazol-1-yl)-2',4'-difluoro-[1,1'-biphenyl]-3-yl)cyclopropanesulfonamide (50 mg, 0.099 mmol, 1 eq.) in DMSO (2 ml) was degassed by nitrogen bubbling for 10 min. Copper(I)iodide (11.3 mg, 0.059 mmol, 0.6 eq.), K$_2$CO$_3$ (42 mg, 0.298 mmol, 3 eq.), N,N-dimethyl glycine HCl (11 mg, 0.079 mmol) and 2-pyrrolidone (42 mg, 0.49 mmol, 5 eq.) were added and the mixture was further degassed for 10 min and then heated to 110° C. for 16 h. The mixture was cooled to RT and diluted with ethyl acetate, filtered through a celite bed and washed with water and brine solution. The ethyl acetate layer was dried over sodium sulphate. The solvent was distilled off to afford the crude residue which was purified by preparative HPLC to afford the product in 90% yield (45 mg). $^1$H NMR (400 MHz, DMSO-$d_6$): δ 8.65 (s, 1H), 7.96 (d, 1H), 7.78-7.65 (m, 3H), 7.54 (m, 2H), 7.45-7.42 (m, 2H), 7.28-7.24 (dt, 1H), 3.9 (t, 2H), 2.88-2.8 (m, 1H), 2.12-2.02 (m, 2H), 1.0 (m, 4H): LC-MS (ESI): Calculated mass: 508.54; Observed mass: 508.7 [M+H]$^+$ (rt: 1.46 min).

Example 388

N-(3-(5-(1-methyl-1H-pyrazol-4-yl)-1H-benzo[d]imidazol-1-yl)-5-(1H-pyrazol-4-yl)phenyl)acetamide The compound was prepared from the compound of Example 277(c) using the procedure described in Example 277(d). $^1$H NMR (400 MHz, DMSO-$d_6$): δ 10.3 (s, 1H), 8.61 (s, 1H), 8.2 (s, 1H), 8.11 (br, 1H), 7.98 (s, 1H), 7.94 (s, 1H), 7.88 (s, 1H), 7.76 (s, 1H), 7.66-7.57 (m, 3H), 3.88 (s, 3H), 1.84 (s, 3H): LC-MS (ESI): Calculated mass: 397.43; Observed mass: 398.22 [M+H]+ (rt: 1.46 min).

Example 389

N-(3-(3-fluoropyridin-4-yl)-5-(5-(1-methyl-1H-pyrazol-4-yl)-1H-benzo[d]-imidazol-1-yl)phenyl)acetamide The compound was prepared from the compound of Example 277(c) using the procedure described in Example 277(d). $^1$H NMR (400 MHz, DMSO-$d_6$): δ 10.5 (s, 1H), 8.97 (s, 1H), 8.76 (s, 1H), 8.59 (s, 1H), 8.58 (s, 1H), 8.24 (s, 1H), 8.2 (s, 1H), 8.02 (s, 1H), 7.97-7.96 (m, 2H), 7.8-7.65 (m, 4H), 3.89 (s, 3H), 2.13 (s, 3H); LC-MS (ESI): Calculated mass: 426.45; Observed mass: 427.1 [M+H]+ (rt: 0.26 min).

Example 390

N-(5-(5-(1-(cyclopropylsulfonyl)-1H-pyrazol-4-yl)-1H-benzo[d]imidazol-1-yl)-2',4'-difluoro-[1,1'-biphenyl]-3-yl)acetamide To a solution of the compound of Example 326 (50 mg, 0.116 mmol) in DCM was added pyridine (0.5 ml) followed by cyclopropanesulfonyl chloride (20 mg, 0.139 mmol, 1.2 eq.). The mixture was stirred for 1 h, and quenched and extracted as in Example 2(b). The solvent was distilled off to afford the crude residue which was purified by preparative HPLC to give the product in 90% yield (42 mg). $^1$H NMR (400 MHz, CD$_3$OD): δ 8.58 (s, 1H), 8.52 (s, 1H), 8.33 (s, 1H), 8.09 (s, 1H), 8.05 (s, 1H), 7.74-7.62 (m, 4H), 7.49 (s, 1H), 7.17-7.08 (m, 2H), 3.0 (m, 1H), 2.2 (s, 3H), 1.1 (d, 4H); LC-MS (ESI): Calculated mass: 533.5; Observed mass: 534.1 [M+H]+ (rt: 1.61 min).

Example 391

N-(2'-fluoro-5-(5-(1-methyl-1H-pyrazol-4-yl)-1H-benzo[d]imidazol-1-yl)-[1,1'-biphenyl]-3-yl)cyclopropanesulfonamide The compound was prepared from N-(2'-fluoro-5-nitro-[1,1'-biphenyl]-3-yl)-acetamide using the procedures of Example 1, 2 and 200(c) to afford the product in 26.6% yield (20 mg). $^1$H NMR (400 MHz, CD$_3$OD): δ 8.52 (s, 1H), 8.03 (s, 1H), 7.94 (s, 1H), 7.89 (s, 1H), 7.71-7.69 (m, 1H), 7.65-7.6 (m, 5H), 7.53-7.49 (m, 2H), 7.35-7.25 (m, 2H), 3.96 (s, 3H), 2.78-2.73 (m, 1H), 1.17-1.0 (m, 4H); LC-MS (ESI): Calculated mass: 487.55; Observed mass: 488.6 [M+H]+ (rt: 1.45 min).

Example 392

N-(2',4'-difluoro-5-(5-(1-(piperidin-4-yl)-1H-pyrazol-4-yl)-1H-benzo[d]-imidazol-1-yl)-[1,1'-biphenyl]-3-yl)cyclopropanesulfonamide a) tert-butyl 4-(4-(1-(5-(cyclopropanesulfonamido)-2',4'-difluoro-[1,1'-biphenyl]-3-yl)-1H-benzo[d]imidazol-5-yl)-1H-pyrazol-1-yl)piperidine-1-carboxylate The compound was prepared from N-(5-(5-bromo-1H-benzo[d]imidazol-1-yl)- 2',4'-difluoro-[1,1'-biphenyl]-3-yl) cyclopropane sulfonamide (100 mg, 0.19 mmol) using the procedure of Example 200(c) to afford the title product in 26.6% yield (20 mg).

b) N-(2',4'-difluoro-5-(5-(1-(piperidin-4-yl)-1H-pyrazol-4-yl)-1H-benzo[d]-imidazol-1-yl)-[1,1'-biphenyl]-3-yl)cyclopropanesulfonamide The compound was prepared from the compound of Example 392(a) (60 mg, 0.08 mmol) using the procedure of 331(b) to afford the product in 40% yield (0.020 g). $^1$H NMR (400 MHz, DMSO-$d_6$): δ 8.64 (s, 1H), 8.30 (s, 1H), 8.03 (s, 1H), 7.90 (s, 1H), 7.76-7.74 (m, 1H), 7.69-7.62 (m, 2H), 7.54-7.53 (t, 1H), 7.49 (s, 1H), 7.46-7.43 (m, 1H), 7.27 (t, 3H), 4.23 (m, 1H), 3.12-3.09 (d, 2H), 2.81 (m, 1H), 2.70-2.64 (t, 2H), 2.04-2.01 (d, 2H), 1.88-1.84 (m, 2H), 1.23 (s, 2H), 1.00-0.99 (m, 2H), 0.97 (s, 1H); LC-MS (ESI): Calculated mass: 574.20; Observed mass: 574.8 [M+H]+ (rt: 0.27 min).

Example 393

N-(2',4'-difluoro-5-(5-(1-(pyrrolidin-3-yl)-1H-pyrazol-4-yl)-1H-benzo[d]-imidazol-1-yl)-[1,1'-biphenyl]-3-yl)cyclopropanesulfonamide The compound was prepared using the procedures of Example 392. $^1$H NMR (400 MHz, DMSO-$d_6$): δ 8.64 (s, 1H), 8.33 (s, 1H), 8.03 (s, 1H), 7.98 (s, 1H), 7.78-7.72 (q, 1H), 7.69-7.62 (q, 2H), 7.55-7.52 (d, 2H), 7.48-7.42 (m, 2H), 7.30-7.25 (m, 1H), 4.87-4.82 (m, 1H), 3.34-3.16 (m, 2H), 3.14-2.94 (m, 3H), 2.93-2.80 (m, 2H), 2.26-2.21 (m, 1H), 2.14-2.07 (m, 1H), 1.01-0.98 (d, 4H); LC-MS (ESI): Calculated mass: 560.62; Observed mass: 561.3 [M+H]+ (rt: 0.39 min).

Example 394

N-(5-(5-(4-amino-3-fluorophenyl)-1H-benzo[d]imidazol-1-yl)-2',4'-difluoro-[1,1'-biphenyl]-3-yl)acetamide The compound was prepared from the compound of Example 1(h) using the procedure of Example 253. $^1$H NMR (300 MHz, DMSO-$d_6$): δ 10.46 (s, 1H), 8.86 (s, 1H), 8.07 (s, 1H), 7.95 (s, 1H), 7.81-7.71 (m, 3H), 7.59 (d, 1H), 7.51-7.40 (m, 3H), 7.33-7.24 (m, 2H), 6.88-6.82 (m, 1H), 5.25 (brs, 2H), 2.12 (s, 3H); LC-MS (ESI): Calculated mass: 472.15; Observed mass: 473.5 [M+H]+ (rt: 1.47 min).

Example 395

N-(2',4'-difluoro-5-(5-(1-methyl-1H-pyrazol-4-yl)-1H-benzo[d]imidazol-1-yl)-[1,1'-biphenyl]-3-yl)-2-(4-methylpiperazin-1-yl)acetamide The compound was prepared from the compound of Example 2(a) using the procedure of Example 233. $^1$H NMR (300 MHz, DMSO-$d_6$): δ 10.37 (s, 1H), 8.89 (s, 1H), 8.23 (s, 1H), 8.14 (s, 1H), 8.01 (s, 1H), 7.97 (s, 1H), 7.89 (s, 1H), 7.76-7.72 (m, 2H), 7.66-7.64 (m, 2H), 7.6 (s, 1H), 7.49-7.44 (m, 1H), 7.31-7.26 (dt, 1H), 3.88 (s, 3H), 3.46 (s, 3H), 3.5-3.4 (br, 2H), 3.16 (s, 4H), 2.8 (s, 4H); LC-MS (ESI): Calculated mass: 541.59; Observed mass: 542.1 [M+H]+ (rt: 0.1 min).

Example 396

N-(3-(5-fluoropyridin-2-yl)-5-(5-(1-methyl-1H-pyrazol-4-yl)-1H-benzo[d]-imidazol-1-yl)phenyl)cyclopropanesulfonamide a) N-(3-(5-(1-methyl-1H-pyrazol-4-yl)-1H-benzo[d]imidazol-1-yl)-5-(4,4,5,5-tetramethyl-1,3,2-dioxaborolan-2-yl)phenyl)acetamide A solution of the compound of Example 277(c) (0.9 g, 2.2 mmol) in 1,4-dioxane (20 ml) was degassed by $N_2$ bubbling for 5 min. Bis(pinacolato)diboron (0.67 g, 0.1855 mmol, 1.2 eq.) was added and the mixture was degassed for another 5 min. Pd(dppf)Cl$_2$ (0.0107 g, 0.0131 mmol, 0.05 eq.) and potassium acetate (0.539 g, 5.49 mmol, 2.5 eq.) were added sequentially and the mixture was further degassed for 5 min and then heated at 100° C. for 12 h. The mixture was quenched and extracted as in Example 1(d). The solvent was distilled off to afford the crude residue, which was washed with hexane to afford the title crude product (1.1 g). $^1$H NMR (300 MHz, DMSO-d6): δ 10.31 (s, 1H), 8.58 (s, 1H), 8.19-8.18 (m, 1H), 7.98-7.94 (m, 3H), 7.58 (m, 2H), 7.49 (m, 1H), 3.89 (s, 3H), 2.10 (s, 3H), 1.33 (s, 6H), 1.17 (s, 6H); LC-MS (ESI): Calculated mass: 457.23; Observed mass: 457.90 [M+H]$^+$ (rt: 0.480-0.493 min).

b) N-(3-(5-fluoropyridin-2-yl)-5-(5-(1-methyl-1H-pyrazol-4-yl)-1H-benzo[d]-imidazol-1-yl)phenyl)acetamide A solution of 2-bromo-5-fluoropyridine (0.2 g, 1.136 mmol) in 1,2-dimethoxyethane (16 ml) was degassed by $N_2$ bubbling for 5 min. The compound of Example 396(a) (1.03 g, 2.253 mmol, 2.0 eq.) was added and the mixture was degassed for another 5 min. Pd(dppf)Cl$_2$ (0.0463 g, 0.0567 mmol, 0.05 eq.) and aqueous sodium carbonate (0.3 g, 2.83 mmol, 2.5 eq.) were added sequentially and the mixture was further degassed for 5 min and then heated at 90° C. for 3 h. The mixture was quenched and extracted as in Example 1(d). The solvent was distilled off to afford the crude residue which was purified by column chromatography (60-120 silica gel, 3% methanol in DCM) to afford the title product in 52% yield (250 mg). $^1$H NMR (400 MHz, DMSO-d6): δ 8.59 (m, 1H), 8.53 (s, 1H), 8.19 (m, 1H), 8.13 (m, 1H), 8.03-8.01 (m, 1H), 7.96-7.91 (m, 1H), 7.88 (m, 1H), 7.76-7.71 (m, 1H), 7.65-7.57 (m, 3H), 7.56-7.48 (m, 1H), 3.89 (s, 3H), 2.10 (s, 3H). LC-MS (ESI): Calculated mass: 426.16; Observed mass: 427.1 [M+H]$^+$ (rt: 0.491 min).

c) 3-(5-Fluoropyridin-2-yl)-5-(5-(1-methyl-1H-pyrazol-4-yl)-1H-benzo[d]-imidazol-1-yl) aniline To a solution of the compound of Example 396(b) (250 mg, 0.586 mmol) in ethanol (30 ml) was added aqueous solution of NaOH (230 mg, 5.75 mmol, 10 eq.) and the mixture was heated at 85° C. for 16 h. The mixture was quenched and extracted as in Example 1(d). The solvent was distilled off to afford the crude residue which was taken to the next step without further purification. Yield 250 mg. LC-MS (API): Calculated mass: 384.15; Observed mass: 385.2 [M+H]$^+$ (rt: 0.312 to 0.413 min).

d) N-(3-(5-fluoropyridin-2-yl)-5-(5-(1-methyl-1H-pyrazol-4-yl)-1H-benzo[d]imidazol-1-yl)phenyl)cyclopropanesulfonamide To a solution of the compound of Example 396(c) (250 mg, 0.651 mmol) in THF (15 ml) was added pyridine (0.154 g, 1.946 mmol, 3.0 eq.) followed by cyclopropanesulfonyl chloride (0.11 g, 0.7746 mmol, 1.2 eq.). The reaction was stirred at RT for 12 h, and quenched and extracted as in Example 1(d). The solvent was distilled off to afford the crude residue which was purified by preparative HPLC to afford the product in 5% yield (15.6 mg). $^1$H NMR (400 MHz, DMSO-d$_6$): δ 10.25 (s, 1H), 8.74-8.73 (d, 1H), 8.70 (s, 1H), 8.22-8.18 (m, 2H), 8.07-8.00 (m, 3H), 7.94-7.91 (m, 2H), 7.67-7.65 (m, 1H), 7.61-7.59 (m, 2H), 3.87 (s, 3H), 2.84 (m, 1H), 1.01-0.996 (m, 4H); LC-MS (ESI): Calculated mass: 488.14; Observed mass: 489.1 [M+H]$^+$ (rt: 0.847 to 1.048 min).

ABBREVIATIONS

RT—Room temperature
rt—Retention time
BINAP—2,2'-bis(diphenylphosphino)-1,1'-binaphthyl
DMF—N,N-dimethylformamide
THF—Tetrahydrofuran
TEA—Triethyl amine
DCM Dichloromethane
DMSO—Dimethylsulfoxide
EDC—1-Ethyl-3-(3-dimethylaminopropyl) carbodiimide hydrochloride
HATU—2-(1H-7-azabenzotriazol-1-yl)-1,1,3,3-tetramethyl uronium hexafluorophosphate methanaminium
HOBt—Hydroxybenzotriazole
DIPEA—N,N-diisopropylethylamine
TBAF—tetra-n-butylammonium fluoride
Pd(dppf)Cl$_2$—1,1'-Bis(diphenylphosphino)ferrocene-palladium(II)dichloride
Pd(PPh$_3$)$_4$—Tetrakis(triphenylphosphine)palladium(0)
Pd$_2$(dba)$_3$—Tris(dibenzylideneacetone)dipalladium(0)

The invention claimed is:
1. A compound of formula (I)

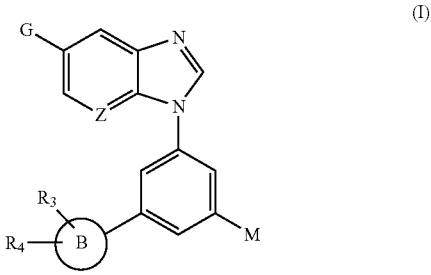

wherein
Z is CH or N;
G is a group of formula

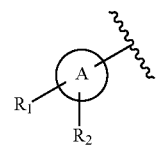

wherein ring A is a phenyl ring or a 5-12 membered heterocyclic ring, and
R$_1$ is H, C$_{1-7}$ alkyl, C$_{3-7}$ cycloalkyl, C$_{3-7}$ cycloalkyl C$_{1-7}$ alkyl, C$_{1-7}$ alkoxy, C$_{1-7}$ alkyl carbonyl, amino, hydroxy, hydroxy $C_{1-7}$ alkyl, $C_{1-7}$ alkylamino $C_{1-7}$ alkyl, phenyl $C_{1-7}$ alkoxy, —NHC(O)—$R_{21}$, —$R_{12}$—C(O)—$R_{13}$, —$SO_2$—$R_{14}$ or -E-$R_6$, and $R_2$ is H, halogen, $C_{1-7}$ alkyl or oxo;

ring B is a 5-12 membered carbocyclic or heterocyclic ring;

$R_3$ is H, halogen, $C_{1-7}$ alkyl, $C_{1-7}$ alkoxy, cyano or an optionally substituted 5-6 membered heterocyclic ring;

$R_4$ is H, halogen, $C_{1-7}$ alkyl or oxo;

M is —$NHR_5$;

$R_5$ is H, —C(O)$R_7$, —$SO_2R_8$, —C(O)-D-$R_9$ or an optionally substituted 5-6 membered heterocyclic ring;

$R_6$ is an optionally substituted 5-6 membered heterocyclic ring;

$R_7$ is $C_{1-7}$ alkyl, $C_{2-7}$ alkenyl, $C_{3-7}$ cycloalkyl, $C_{1-7}$ alkoxy, $C_{1-7}$ alkoxy $C_{1-7}$ alkyl, carboxy $C_{1-7}$ alkyl, $C_{1-7}$ alkoxy carbonyl $C_{1-7}$ alkyl, $C_{1-7}$ alkylamino $C_{1-7}$ alkyl, —NH—$R_{10}$ or —NH—$X_1$—$R_{11}$;

$R_8$ is $C_{1-7}$ alkyl, $C_{2-7}$ alkenyl, $C_{3-7}$ cycloalkyl, hydroxy $C_{1-7}$ alkyl, —$NR_{18}R_{19}$, —NH—$X_2$—$R_{20}$, phenyl or an optionally substituted 5-6 membered heterocyclic ring;

$R_9$ is phenyl or an optionally substituted 5-6 membered heterocyclic ring;

$R_{10}$ is $C_{1-7}$ alkyl or $C_{3-7}$ cycloalkyl;

$R_{11}$ is phenyl or an optionally substituted 5-6 membered heterocyclic ring;

$R_{12}$ and $R_{21}$ are $C_{1-7}$ alkyl;

$R_{13}$ is $C_{1-7}$ alkoxy, amino or hydroxy;

$R_{14}$ is $C_{1-7}$ alkyl or $C_{3-7}$ cycloalkyl;

$R_{18}$ and $R_{19}$ are, independently, H, $C_{1-7}$ alkyl or $C_{3-7}$ cycloalkyl;

$R_{20}$ is phenyl or an optionally substituted 5-6 membered heterocyclic ring;

E is a bond or a $C_{1-7}$ alkyl;

D is a bond or a $C_{1-7}$ alkyl;

$X_1$ and $X_2$ are, independently, a bond or $C_{1-7}$ alkyl;

or a pharmaceutically acceptable salt thereof.

2. The compound according to claim 1, wherein ring A is a 5-12 membered heterocyclic ring selected from the following groups or tautomers thereof

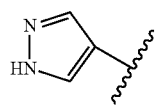
(1')

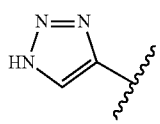
(2')

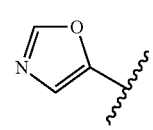
(3')

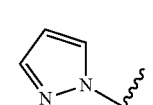
(4')

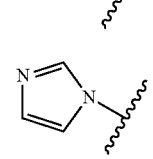
(5')

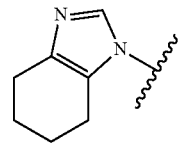
(6')

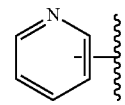
(7')

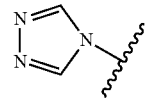
(8')

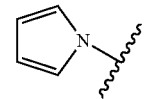
(9')

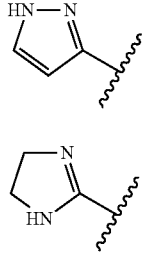
(10')

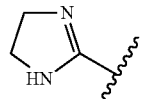
(11')

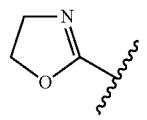
(12')

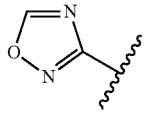
(13')

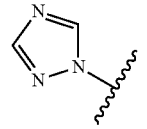
(14')

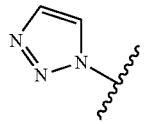
(15')

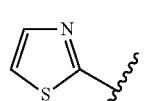
(16')

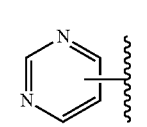
(17')

-continued

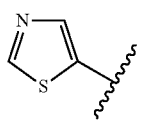 (18')

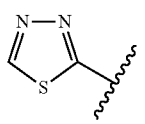 (19')

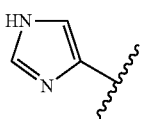 (20')

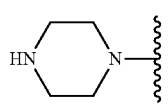 (21')

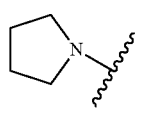 (22')

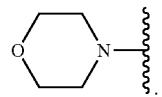 (23')

3. The compound according to claim 1, wherein ring B is a 5-12 membered carbocyclic or heterocyclic ring selected from the following groups or tautomers thereof

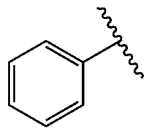 (1″)

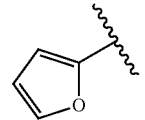 (2″)

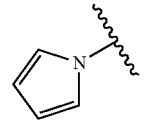 (3″)

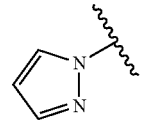 (4″)

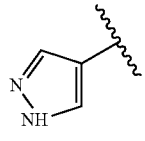 (5″)

-continued

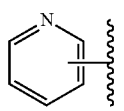 (6″)

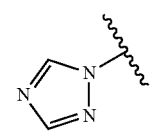 (7″)

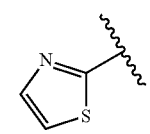 (8″)

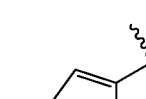 (9″)

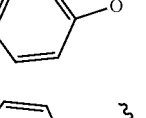 (10″)

4. The compound according to claim 1, wherein Z is CH.
5. The compound according to claim 1, wherein Z is N.
6. The compound according to claim 1, wherein G is a group of formula

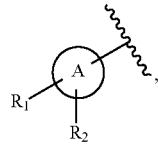

wherein ring A is a 5-12 membered heterocyclic ring selected from the following groups or tautomers thereof

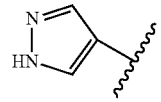 (1')

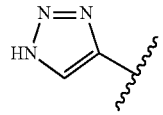 (2')

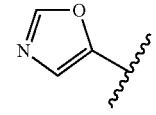 (3')

-continued

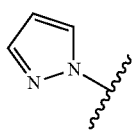 (4')

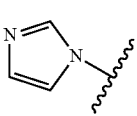 (5')

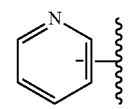 (7')

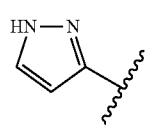 (10')

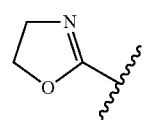 (12')

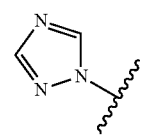 (14')

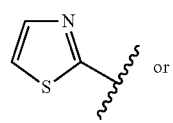 (16') or

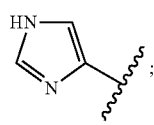 (20');

$R_1$ is H, $C_{1-7}$ alkyl, $C_{1-7}$ alkoxy, hydroxy $C_{1-7}$ alkyl, $C_{1-7}$ alkylamino $C_{1-7}$ alkyl or -E-$R_6$;

$R_2$ is H;

ring B is a 5-12 membered carbocyclic or heterocyclic ring of formula

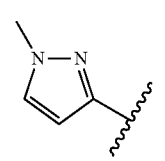 (1″)

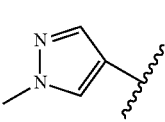 (2″)

-continued

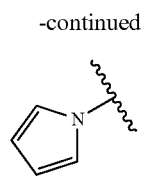 (3″)

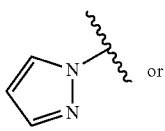 (4″) or

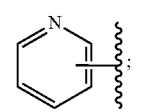 (6″);

E is a bond or $C_{1-7}$ alkyl;

$R_6$ is a 5-6 membered heterocyclic ring selected from the following groups:

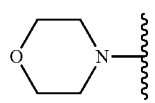 (a)

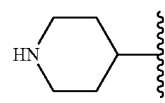 (b)

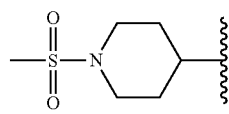 (c)

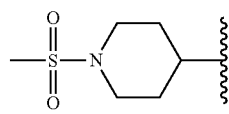 (d)

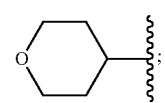 (e);

$R_3$ is H, halogen, $C_{1-7}$ alkyl, $C_{1-7}$ alkoxy or cyano;

$R_4$ is H or halogen;

M is —$NHR_5$;

$R_5$ is —$C(O)R_7$, —$SO_2R_8$ or —$C(O)$-D-$R_9$ or a 5-6 membered heterocyclic ring selected from the following groups:

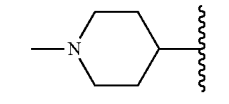 (a″)

(b″)

-continued

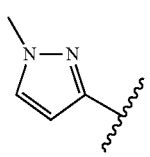
(c″)

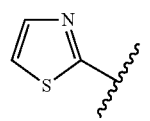
(d″)

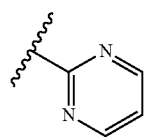
(e″)

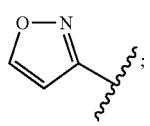
(f″);

R₇ is $C_{1-7}$ alkyl, $C_{2-7}$ alkenyl, —NH—$R_{10}$ or —NH—$X_1$—$R_{11}$;

R₈ is $C_{1-7}$ alkyl, $C_{2-7}$ alkenyl, $C_{3-7}$ cycloalkyl, hydroxy $C_{1-7}$ alkyl, —$NR_{18}R_{19}$, —NH—$X_2$—$R_{20}$, phenyl or the 5-6 membered heterocyclic ring:

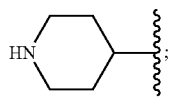
(b)

R₉ is phenyl or a 5-6 membered heterocyclic ring selected from the following groups or tautomers thereof:

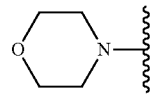
(a)

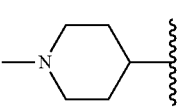
(d)

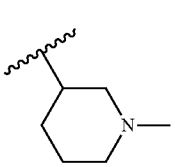
(f)

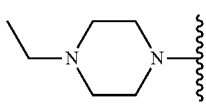
(g)

-continued

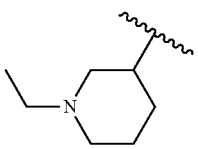
(h)

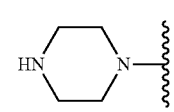
(i)

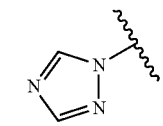
(j)

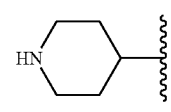
(k)

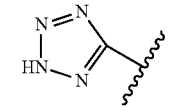
(l)

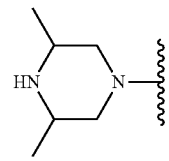
(m)

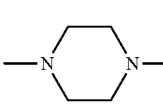
(n)

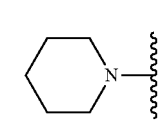
(o)

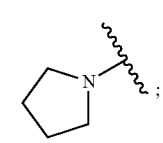
(p);

R₁₀ is $C_{1-7}$ alkyl or $C_{3-7}$ cycloalkyl;

R₁₁ is phenyl, 4-fluorophenyl, or a 5-6 membered heterocyclic ring selected from the following groups:

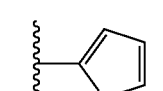
(a′)

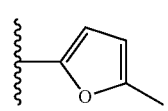
(b′)

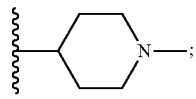
(c')

$R_{18}$ and $R_{19}$ are, independently, H, $C_{1-7}$ alkyl or $C_{3-7}$ cycloalkyl;

$R_{20}$ is the 5-6 membered heterocyclic ring:

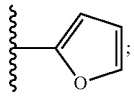
(a')

$X_1$ and $X_2$ are, independently, a bond or $C_{1-7}$ alkyl, and D is a bond or $C_{1-7}$ alkyl.

7. The compound according to claim 1, wherein ring B is a 5-12 membered carbocyclic or heterocyclic ring of formula

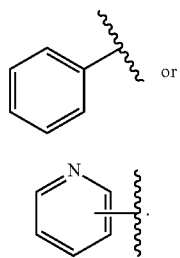
(1″) or (6″)

8. The compound according to claim 1, wherein ring A is a 5-12 membered heterocyclic ring selected from the following groups or tautomers thereof

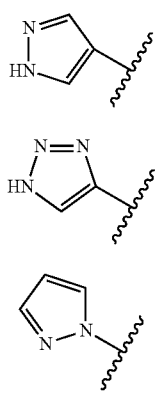
(1'), (2'), (4')

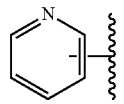
(7')

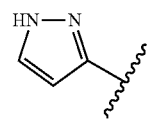
(10')

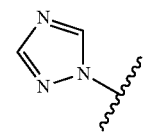
(14')

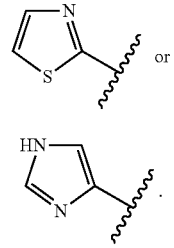
(16') or (20')

9. The compound according to claim 1, wherein ring B is phenyl, $R_3$ is halogen, and $R_4$ is H or halogen.

10. The compound according to claim 1, wherein M is —NHC(O)$R_7$, wherein $R_7$ is $C_{1-7}$ alkyl, $C_{2-7}$ alkenyl, $C_{3-7}$ cycloalkyl, —NH—$R_{10}$ or —NH—$X_1$—$R_{11}$, wherein $R_{10}$ is $C_{1-7}$ alkyl or $C_{3-7}$ cycloalkyl, $X_1$ is a bond or $C_{1-7}$ alkyl, and $R_{11}$ is a 5-6 membered heterocyclic ring optionally substituted by one or two $C_{1-7}$ alkyl groups.

11. The compound according to claim 1, wherein M is —NHSO$_2$R$_8$, wherein $R_8$ is $C_{1-7}$ alkyl, $C_{2-7}$ alkenyl, $C_{3-7}$ cycloalkyl, phenyl, or NR$_{18}$R$_{19}$, wherein $R_{18}$ and $R_{19}$ are, independently, H, $C_{1-7}$ alkyl or $C_{3-7}$ cycloalkyl.

12. The compound according to claim 1, wherein or M is —NHC(O)-D-R$_9$, wherein D is bond or $C_{1-7}$ alkyl, and $R_9$ is a 5-6 membered heterocyclic ring optionally substituted by one or two $C_{1-7}$ alkyl groups.

13. The compound according to claim 1, wherein or $R_5$ is a 5-6 membered heterocyclic ring optionally substituted by one or two $C_{1-7}$ alkyl groups.

14. A pharmaceutical composition comprising a compound of according to claim 1 and a pharmaceutically acceptable carrier.

15. A method for inhibiting FGFR kinase comprising administering to a subject an effective amount of a compound according to claim 1.

* * * * *

UNITED STATES PATENT AND TRADEMARK OFFICE
CERTIFICATE OF CORRECTION

| | | |
|---|---|---|
| PATENT NO. | : 9,447,091 B2 | Page 1 of 1 |
| APPLICATION NO. | : 14/350718 | |
| DATED | : September 20, 2016 | |
| INVENTOR(S) | : Tero Linnanen et al. | |

It is certified that error appears in the above-identified patent and that said Letters Patent is hereby corrected as shown below:

In the Claims

Claim 12, Column 204, Line 43, "wherein or M is" should read -- wherein M is --.

Claim 13, Column 204, Line 48, "wherein or $R_5$ is" should read -- wherein $R_5$ is --.

Claim 14, Column 204, Lines 51-52, "a compound of according to claim 1" should read -- a compound according to claim 1 --.

Signed and Sealed this
Third Day of January, 2017

Michelle K. Lee
*Director of the United States Patent and Trademark Office*